US008604173B2

(12) United States Patent
Ono et al.

(10) Patent No.: US 8,604,173 B2
(45) Date of Patent: Dec. 10, 2013

(54) DOPAMINERGIC NEURON PROGENITOR CELL MARKER 187A5

(75) Inventors: Yuichi Ono, Kobe (JP); Yoshimasa Sakamoto, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/492,733

(22) Filed: Jun. 8, 2012

(65) Prior Publication Data

US 2012/0252021 A1 Oct. 4, 2012

Related U.S. Application Data

(62) Division of application No. 12/296,915, filed as application No. PCT/JP2007/058009 on Apr. 11, 2007, now Pat. No. 8,198,081.

(30) Foreign Application Priority Data

Apr. 11, 2006 (JP) .................................. 2006-108786

(51) Int. Cl.
 *C12N 5/16* (2006.01)
 *C07K 16/28* (2006.01)
 *C12Q 1/68* (2006.01)

(52) U.S. Cl.
 USPC .................. 530/387.9; 536/24.31; 536/24.33; 435/6.11; 530/810

(58) Field of Classification Search
 None
 See application file for complete search history.

(56) References Cited

U.S. PATENT DOCUMENTS

2001/0053519 A1  12/2001  Fodor et al.
2010/0120628 A1*  5/2010  Belouchi et al. .................. 506/9

FOREIGN PATENT DOCUMENTS

| EP | 1447413 A2 | 8/2004 |
|---|---|---|
| WO | WO 2004/005458 A2 | 1/2004 |
| WO | WO 2004/038018 A1 | 5/2004 |
| WO | WO 2004/048511 A2 | 6/2004 |
| WO | WO 2004/048938 A2 | 6/2004 |
| WO | WO 2004/065599 A1 | 8/2004 |
| WO | WO 2004/094598 A2 | 11/2004 |
| WO | WO 2004/094651 A2 | 11/2004 |
| WO | WO 2005/052190 A1 | 6/2005 |
| WO | WO 2006/009241 A1 | 1/2006 |
| WO | WO 2007/021003 A1 | 2/2007 |
| WO | WO 2007/021004 A1 | 2/2007 |

OTHER PUBLICATIONS

"Affymetrix GeneChip Human Genome U95 Version [1 or 2] Set HG-U95A," GEO Expression, 2 pgs. (Mar. 11, 2002).

(Continued)

*Primary Examiner* — Jeffrey Stucker
*Assistant Examiner* — Aurora M Fontainhas
(74) *Attorney, Agent, or Firm* — Kilpatrick Townsend & Stockton LLP

(57) ABSTRACT

An object of the present invention is to provide a probe, a primer, a primer set and an antibody for use in the detection or selection of a dopaminergic neuron progenitor cell. The present invention provides a probe, a primer and a primer set for use in the detection or selection of a mesencephalon dopaminergic neuron progenitor cell, and preferably a dopaminergic neuron proliferative progenitor cell, which can hybridize with a nucleotide sequence of a 187A5 gene, or a complementary sequence thereto, and an antibody for use in the detection or selection of a mesencephalon dopaminergic neuron progenitor cell, and preferably a dopaminergic neuron progenitor cell, which is capable of binding to a 187A5 protein.

4 Claims, 13 Drawing Sheets

(56) References Cited

OTHER PUBLICATIONS

"Affymetrix GeneChip Human Genome U133 Array Set HG-U133A," GEO Expression, 2 pgs. (Mar. 11, 2002).
Bentwich, I., Database Geneseq [Online] "Viral regulatory miRNA SEQ ID No. 116234," Database Accession No. AJI63913, 1 pg. (Dec. 28, 2007).
Stamatoyannopoulos, JA, et al., Database Geneseq [Online], "Diagnosis and therapy associated functional site SEQ ID 11873,", Database Accession No. AGH79117, 1 pg. (Oct. 18, 2007).
Office Action issued Jan. 10, 2012, for Japanese Application No. 2008-510971, 12 pgs.
Office Action issued Apr. 3, 2012, for Japanese Application No. 2008-510971, 6 pgs.
International Preliminary Report on Patentability from PCT/JP2007/058009 dated Nov. 27, 2008, 9 pages.
Piccini, et al., "Dopamine release from nigral transplants visualized in vivo in a Parkinson's patient," *Nature Neuroscience* vol. 2(12), pp. 1137-1140 (Dec. 1999).
Office Action for Canadian Patent Application No. 2649250, 4 pages, issued on May 17, 2013.

* cited by examiner

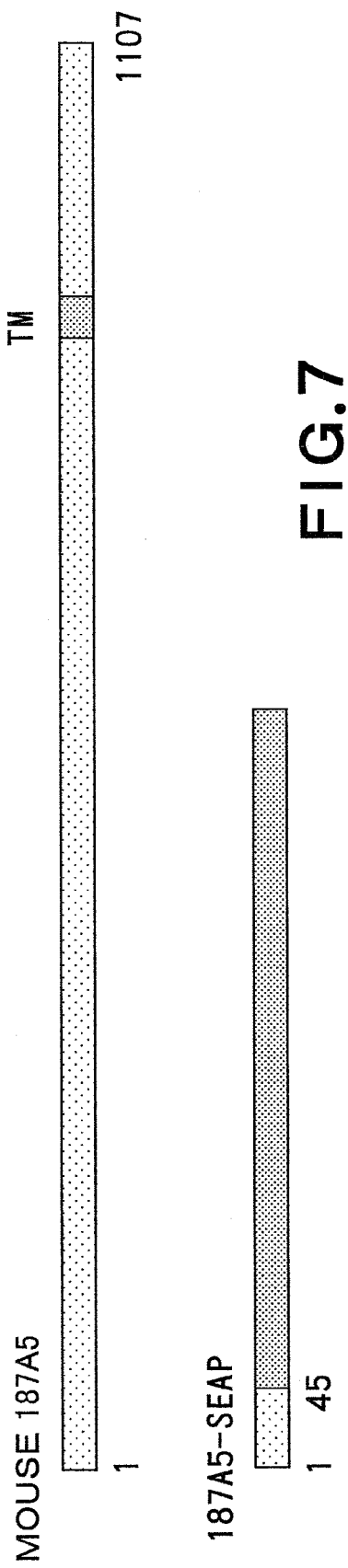
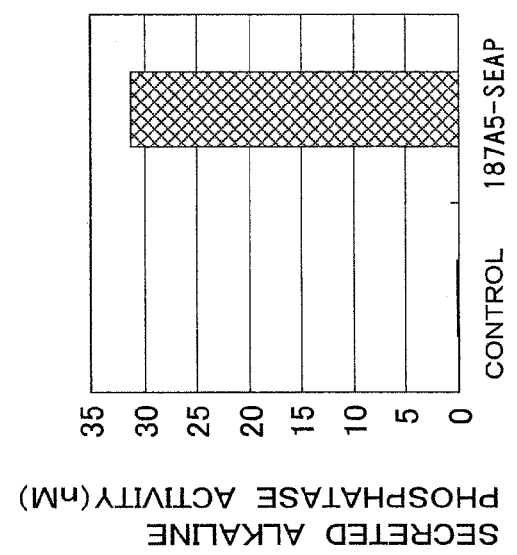
FIG.7
FIG.8

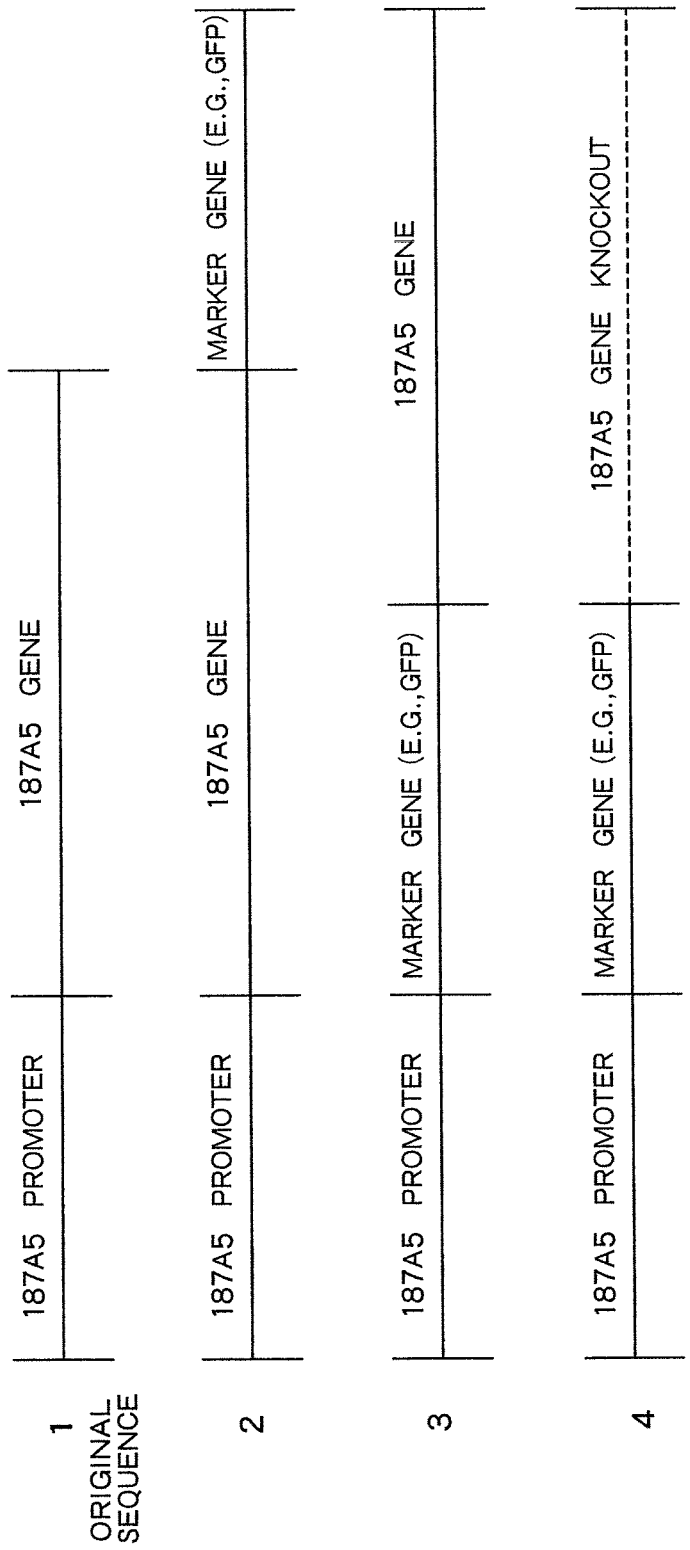
F I G. 15

DOPAMINERGIC NEURON PROGENITOR CELL MARKER 187A5

CROSS REFERENCE TO RELATED APPLICATIONS

This application is a divisional of U.S. patent application Ser. No. 12/296,915, filed Oct. 10, 2008 which is a U.S. National Phase of PCT/JP2007/058009, filed Apr. 11, 2007, which claims priority to Japanese Patent Application No. 2006-108786, filed Apr. 11, 2006. The contents of all of the aforementioned applications are herein incorporated by reference in their entirety.

REFERENCE TO A SEQUENCE LISTING

This application includes a Sequence Listing as a text file named "91787-000310US-843197_SEQLIST.txt" created Jun. 7, 2012, and containing 349,291 bytes. The material contained in this text file is incorporated by reference in its entirety for all purposes.

TECHNICAL FIELD

The present invention relates to a 187A5 gene, which is a dopaminergic neuron progenitor cell marker. More particularly, the present invention relates to a means for detecting a dopaminergic neuron progenitor cell, a method for detecting the cell, and a kit for detecting the cell.

BACKGROUND ART

The dopamine system is a very important system involved in movement control, hormone secretion control, affectivity control, and so forth, which are important in the mammalian brain. Therefore, abnormalities in dopaminergic neurotransmission cause various disorders of the neural system. For example, the Parkinson's disease is a neurodegenerative disease of the extrapyramidal system which is caused by specific degeneration of dopaminergic neurons in the mesencephalon substantia nigra (HARRISON'S PRINCIPLES OF INTERNAL MEDICINE Vol. 2 23$^{rd}$ ed., Isselbacher et al. edited by McGraw-Hill Inc., NY (1994) pp. 2275-7).

As a method for treating the Parkinson's disease, a method of orally administering L-DOPA (3,4-dihydroxy-phenylalanine) has been mainly adopted for compensating the decrease in the amount of the produced dopamine, but it is known that the duration of the effect is not good.

Accordingly, as a method for compensating the loss of dopaminergic neurons, recently, there has been attempted a therapeutic method of transplanting a mesencephalon ventral region of a 6-9 week aborted fetus containing dopaminergic neuron precursors (U.S. Pat. No. 5,690,927; Spencer et al. (1992) N. Engl. J. Med. 327:1541-8; Freed et al. (1992) N. Engl. J. Med. 327:1549-55; Widner et al. (1992) N. Engl. J. Med. 327:1556-63; Kordower et al. (1995) N. Engl. J. Med. 332:1118-24; Defer et al. (1996) Brain 119:41-50; and Lopez-Lozano et al. (1997) Transp. Proc. 29:977-80). However, at the present time, in addition to cell supply and ethical issues (Rosenstain (1995) Exp. Neurol. 33:106; Turner et al. (1993) Neurosurg. 33:1031-7), various other problems have been indicated, for example, risk of infectious contamination, immunologic transplant rejection (Lopez-Lozano et al. (1997) Transp. Proc. 29:977-80 and Widner and Brudin (1988) Brain Res. Rev. 13:287-324), low survival rate due to the fetus tissue's mainly dependence on lipid metabolism rather than glycolysis (Rosenstein (1995) Exp. Neurol. 33:106), and so forth.

As a method for solving the problem of the ethical issues or supply shortage, for example, a method by using a cortex, a striatum, and mesencephalon cells, derived from a pig, and so forth have been proposed (for example, Japanese Patent Laid-Open Publication No. 10-508487, No. 10-508488, and No. 10-509034). However, in this method, a complex procedure for modifying an antigen on the cell surface (MHC class I antigen) is required to suppress rejection. As a method for solving the transplant rejection, for example, a method involving local immunosuppression by simultaneously transplanting Sertoli cells has been proposed (Japanese Patent Laid-Open Publication No. 11-509170 and No. 11-501818; and Selawly and Cameron (1993) Cell Transplant 2:123-9). It is possible that transplant cells are obtained from a relative whose MHC matches, bone marrow of another person, a bone marrow bank, a cord blood bank, and so forth. However, if patient's own cells can be used, the problems of rejection can be solved without extra procedures and trouble.

Accordingly, it has been expected that, instead of cells derived from an aborted fetus, a differentiation system of dopaminergic neurons in vitro from non-neural cells such as embryo-stem (ES) cell and bone marrow stromal cells are utilized as a transplant material. Actually, it is confirmed that a dopaminergic neuron derived from ES cell is functional for transplantation into lesion striatum of a rat Parkinson's disease model (Kim et al. (2002) Nature 418:50-56). It is thought that in the future, importance of regenerative medicine from ES cells or the patient's own neural stem cells will increase.

On the other hand, in the treatment of damage of neural tissue, restructuring of brain function is required, and for forming appropriate linkage with surrounding cells (network formation), not mature cells but progenitor cells that can differentiate into neurons in vivo are required to be transplanted. However, in the transplantation of neuron progenitor cells, in addition to the above-described problem regarding supply, there is a problem that the progenitor cells can differentiate into a nonuniform cell population. For example, in the treatment of the Parkinson's disease, it is necessary that dopaminergic neurons are selectively transplanted among catecholamine-containing neurons. Before now, as transplant cells for use in the treatment of the Parkinson's disease, there has been proposed a striatum (Lindvall et al. (1989) Arch. Neurol. 46:615-31 and Widner et al. (1992) N. Engl. J. Med. 327:1556-63), an immortalized cell line derived from human embryonic nerve (Japanese Patent Laid-Open Publication No. 8-509215, No. 11-506930, and No. 2002-522070), a post-mitotic human neuron of NT2Z cells (Japanese Patent Laid-Open Publication No. 9-5050554), a neuron primordial cell (Japanese Patent Laid-Open Publication No. 11-509729), a cell transfected with an exogenous gene so as to produce catecholamine such as dopamine, a bone marrow stromal cell (Japanese Patent Laid-Open Publication No. 2002-504503 and No. 2002-513545), an ES cell in which a gene is modified (Kim et al. (2002) Nature 418:50-56), and so forth. However, none of these contain only dopaminergic neurons or cells to differentiate into dopaminergic neurons.

As a method for selectively condensing or isolating dopaminergic neurons from undifferentiated cell population, there has been proposed a method of, introducing a reporter gene expressing a fluorescent protein under control of promoter/enhancer of a gene such as tyrosine hydroxylase (TH) expressed in dopaminergic neurons into each cell of the cell population, isolating the cells emitting fluorescence, and thereby visualizing the alive dopaminergic neurons to condense, segregate or identify (Japanese Patent Laid-Open Publication No. 2002-51775). However, this method requires a complex step of introduction of an exogenous gene, and furthermore, when used in gene treatment, the existence of the reporter gene causes problem of toxicity and immunogenicity.

As described above, now, one of the largest problems in transplantation treatment for the Parkinson's disease is that the either dopaminergic neuron progenitor cells derived from the mesencephalon ventral region of aborted fetus or induced to differentiate are a mixture of various cells. It is desirable that only a desired cell species is isolated and used, considering safety in neural network formation. Furthermore, considering survival or ability for correctly forming a network in a brain in which the cells are transplanted, it can be said that it is desirable from the treatment effect that earlier proliferative progenitor cells are isolated and transplanted.

Before now, as a gene that is expressed in the dopaminergic neuron proliferative progenitor cells, Lrp4 (WO 2004/065599) has been reported. Additionally, some markers of dopaminergic neuron progenitor cells have been reported (WO 2004/038018 and WO 2004/052190).

SUMMARY OF THE INVENTION

In order to isolate a gene selectively expressed in dopaminergic neuron progenitor cells, and preferably dopaminergic neuron proliferative progenitor cells, the present inventors have separated cells positive for an Lrp4 protein, a dopaminergic neuron proliferative progenitor cell marker gene, from the mesencephalon and metencephalon ventral regions of a 13.5-day rat embryo, and have searched a gene specific for the Lrp4-positive cells in the mesencephalon by a subtraction (N-RDA) method. The present inventors have consequently found a gene selectively expressed in dopaminergic neuron proliferative progenitor cells (187A5 gene (hereinafter, occasionally referred to as "187A5")) (Example 2). The present invention is based on this finding.

An object of the present invention is to provide a means for detecting a dopaminergic neuron progenitor cell (preferably, a dopaminergic neuron proliferative progenitor cell), a method for detecting a dopaminergic neuron progenitor cell (preferably, a dopaminergic neuron proliferative progenitor cell), and a kit for detecting a dopaminergic neuron progenitor cell (preferably, a dopaminergic neuron proliferative progenitor cell).

Further, an object of the present invention is to provide a method for screening for an effective substance for inducing differentiation into a dopaminergic neuron progenitor cell (preferably, a dopaminergic neuron proliferative progenitor cell).

Furthermore, an object of the present invention is to provide a method for producing a dopaminergic neuron progenitor cell (preferably, a dopaminergic neuron proliferative progenitor cell) for use in the treatment of the Parkinson's disease.

The present invention provides a polynucleotide selected from the following (i), (ii), (iii) and (iv) (hereinafter, occasionally referred to as a "187A5 gene"):
(i) a polynucleotide comprising the nucleotide sequence of SEQ ID NO: 1;
(ii) a polynucleotide encoding a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;
(iii) a polynucleotide which hybridizes under stringent conditions to a polynucleotide consisting of the nucleotide sequence of SEQ ID NO: 1, and which encodes a protein functionally equivalent to a protein consisting of the amino acid sequence of SEQ ID NO: 2; and
(iv) a polynucleotide which has 70% or more identity with a polynucleotide consisting of the nucleotide sequence of SEQ ID NO: 1, and which encodes a protein functionally equivalent to a protein consisting of the amino acid sequence of SEQ ID NO: 2.

The present invention also provides a protein selected from the following (v), (vi), (vii) and (viii) (hereinafter, occasionally referred to as a "187A5 protein"):
(v) a protein comprising the amino acid sequence of SEQ ID NO: 2;
(vi) a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;
(vii) a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and
(viii) a protein which consists of an amino acid sequence having 70% or more identity with the amino acid sequence of SEQ ID NO: 2, and which is functionally equivalent to a protein consisting of the amino acid sequence of SEQ ID NO: 2.

The present invention provides a probe or primer for use in the detection or selection of a dopaminergic neuron progenitor cell (preferably, a dopaminergic neuron proliferative progenitor cell), which can hybridize to a nucleotide sequence of a 187A5 gene, or a complementary sequence thereto (hereinafter, occasionally referred to as a "probe according to the present invention" and a "primer according to the present invention", respectively).

The present invention provides an antibody for use in the detection or selection of a dopaminergic neuron progenitor cell (preferably, a dopaminergic neuron proliferative progenitor cell), which is capable of binding to a 187A5 protein (hereinafter, occasionally referred to as an "antibody according to the present invention").

The present invention provides a method for detecting or selecting a dopaminergic neuron progenitor cell (preferably, a dopaminergic neuron proliferative progenitor cell), comprising the step of detecting expression of a 187A5 gene, or a 187A5 protein (hereinafter, occasionally referred to as a "detection method according to the present invention").

The present invention provides a kit for detecting or selecting a dopaminergic neuron progenitor cell (preferably, a dopaminergic neuron proliferative progenitor cell), comprising at least a probe according to the present invention, a primer according to the present invention, a primer set according to the present invention, or an antibody according to the present invention (hereinafter, occasionally referred to as a "detection kit according to the present invention").

The present invention provides an agent for detecting or selecting a dopaminergic neuron progenitor cell (preferably, a dopaminergic neuron proliferative progenitor cell), comprising at least a probe according to the present invention, a primer according to the present invention, a primer set according to the present invention, or an antibody according to the present invention (hereinafter, occasionally referred to as an "agent for detection according to the present invention").

The present invention provides a method for screening for an effective substance for inducing differentiation into a dopaminergic neuron progenitor cell (preferably, a dopaminergic neuron proliferative progenitor cell), comprising the step of detecting expression of a 187A5 gene, or a 187A5 protein.

The present invention provides a method for producing a dopaminergic neuron progenitor cell (preferably, a dopaminergic neuron proliferative progenitor cell) for use in the treatment of the Parkinson's disease.

The probe according to the present invention, the primer according to the present invention, the primer set according to the present invention and the antibody according to the present invention can be used as markers specific for dopaminergic neuron progenitor cells, and preferably dopaminergic neuron proliferative progenitor cells in the mesencephalon. Accordingly, the present invention is extremely useful in a purity test of a transplant material and development of a method for inducing differentiation into a dopaminergic neuron progenitor cell, and preferably a dopaminergic neuron proliferative progenitor cell in vitro, or the like, and largely contributes to the promotion of practical application of regenerative medicine. Moreover, the protein according to the present invention is not merely expressed but has a region expressed in the extracellular space. Accordingly, the extracellular region of the protein according to the present invention can be used as an index for detecting live cells with reliability and for separating and obtaining the cells. Therefore, the present invention is expected to largely contribute to the practical application of regenerative medicine.

BRIEF DESCRIPTION OF THE DRAWINGS

FIG. 7 shows mouse 187A5 and 187A5-SEAP.

FIG. 8 shows the results of analyzing signal sequence activity of 187A5.

FIG. 15 schematically shows the structure of a DNA construct that can be used for selecting dopaminergic neuron progenitor cells.

DETAILED DESCRIPTION OF THE INVENTION

Figure 1:
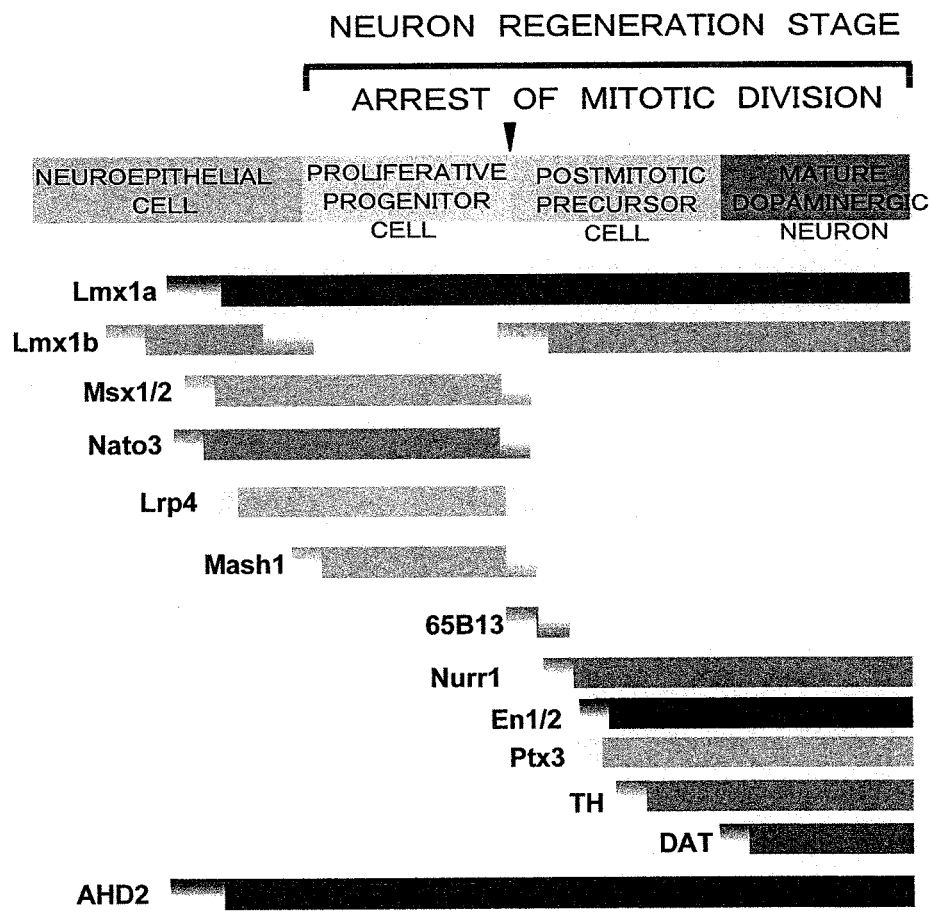
FIG. 1 shows an expression period of dopaminergic neuron-related marker genes.

Hereinafter, the present invention will be explained in detail. The following description is an example for explaining the present invention, and the present invention is not limited to the embodiments to be described. All technical terms, scientific terms and terminologies used in the present specification have the same meanings as those that are generally understood by those ordinary skilled in the art in the technical fields to which the present invention belongs, and are used merely for the purpose of explaining a specific embodiment but are not intended to make limitation. The present invention can be carried out in various embodiments as long as not departing from the spirit thereof. All the prior art documents, published publications, patent publications and other patent documents cited in the present specification are incorporated into the present specification as references, and can be used for carrying out the present invention.

[Dopaminergic Neuron Progenitor Cell]

The "dopaminergic neuron progenitor cell", which is an object to be detected or selected in the present invention, means premature dopaminergic neuron cells.

The "dopaminergic neuron proliferative progenitor cell", which is also an object to be detected or selected in the present invention, means dopaminergic neuron progenitor cells before arrest of mitotic division.

Dopaminergic neurons differentiate from neuroepithelial cells, through the differentiation stages of proliferative progenitor cells and postmitotic precursor cells, into mature dopaminergic neurons. The dopaminergic neuron progenitor cells are progenitor cells in the dopaminergic neurons. Among them, the dopaminergic neuron proliferative progenitor cell is the earliest progenitor cell in the dopaminergic neurons, and therefore, high survival rate and high ability of network formation in the brain to which the cell is transplanted can be expected. Therefore, the dopaminergic neuron progenitor cell, particularly, the dopaminergic neuron proliferative progenitor cell is useful for the transplantation treatment of diseases caused by decrease in dopamine due to degeneration of the dopaminergic neurons, such as the Parkinson's disease.

The cells selected by using the probe according to the present invention, the primer according to the present invention, the primer set according to the present invention or the antibody according to the present invention as an index are dopaminergic neuron progenitor cells, and therefore, are preferable for the transplantation treatment of neurodegenerative diseases such as the Parkinson's disease in the aspects of safety, survival rate and network formation ability, compared to a conventional mixed cell population or dopaminergic neuron progenitor cells in which an exogenous gene is introduced. Particularly, when the cells detected or selected by using the probe according to the present invention, the primer according to the present invention, the primer set according to the present invention or the antibody according to the present invention are dopaminergic neuron progenitor cells before arrest of mitotic division, namely, dopaminergic neuron progenitor cells in proliferation, the cells have the possibility of differentiating to mature in the most appropriate place in the brain, and also, the dopaminergic neuron progenitor cells have the possibility of proliferating in vivo. Therefore, a longer effect of the treatment can be expected. Therefore, it can be said that the present invention paves the way to the practical application of the effective transplantation treatment of neurodegenerative diseases such as the Parkinson's disease.

[187A5 Gene and Protein]

In the present invention, the "187A5 gene" means those encoding a 187A5 protein and includes not only cDNA but also genomic DNA. It also includes RNA corresponding thereto.

In the present invention, the "187A5 gene", which is an index for the existence of dopaminergic neuron progenitor cells, has been registered in database as a functionally unknown sequence in mice. However, in humans, rats, bovines, dogs, chimpanzees, and so forth, only predicted sequences of 187A5 genes have been obtained. GenBank Accession Numbers disclosing the respective sequences are as follows.

Human: XM_044062 (SEQ ID NO: 3 (base sequence), SEQ ID NO: 4 (amino acid sequence), hereinafter, representation will be in the same order), AK126715 (SEQ ID NO: 5, SEQ ID NO: 6), HSM803256 (SEQ ID NO: 7, SEQ ID NO: 8), HSM803467 (SEQ ID NO: 9, SEQ ID NO: 10)

Mouse: AK028289 (SEQ ID NO: 11, SEQ ID NO: 12), AK157823 (SEQ ID NO: 13 (base sequence)), AK028541 (SEQ ID NO: 14, SEQ ID NO: 15), AK035053 (SEQ ID NO: 16, SEQ ID NO: 17), XM_485684 (SEQ ID NO: 18, SEQ ID NO: 19), AK163356 (SEQ ID NO: 20 (base sequence))

Rat: XM_344107 (SEQ ID NO: 21, SEQ ID NO: 22)

Bovine: XM_590147 (SEQ ID NO: 23, SEQ ID NO: 24)

Dog: XM_543360 (SEQ ID NO: 25, SEQ ID NO: 26)

Chimpanzee: XM_522557 (SEQ ID NO: 27, SEQ ID NO: 28)

In the present invention, a cDNA sequence (SEQ ID NO: 1) of a human 187A5 gene as a gene selectively expressed in dopaminergic neuron progenitor cells (preferably, dopaminergic neuron proliferative progenitor cells) in a mesencephalon site as well as an amino acid sequence (SEQ ID NO: 2) of a human 187A5 protein (polypeptide) as a protein (polypeptide) selectively expressed in dopaminergic neuron progenitor cells (preferably, dopaminergic neuron proliferative progenitor cells) were determined.

Those skilled in the art can specify a nucleotide sequence of a 187A5 gene or an amino acid sequence of a 187A5 protein inherent in various animals based on the nucleotide sequence of the 187A5 gene of SEQ ID NO: 1 and the amino acid sequence of the 187A5 protein of SEQ ID NO: 2. For example, by homology search based on the human or mouse 187A5 gene or 187A5 protein, a 187A5 gene or a 187A5 protein of the animal can be searched and identified. In the homology search, BLAST to be described later or the like can be used. Therefore, in the present invention, the "187A5 gene" and the "187A5 protein" used is meant to include, in addition to a human-derived 187A5 gene or a human-derived 187A5 protein, a 187A5 gene or a 187A5 protein inherent in various animals (preferably, mammals).

The 187A5 gene includes:

a polynucleotide encoding a human 187A5 protein comprising the amino acid sequence of SEQ ID NO: 2, SEQ ID NO: 4, SEQ ID NO: 6, SEQ ID NO: 8 or SEQ ID NO: 10;

a polynucleotide encoding a mouse 187A5 protein comprising the amino acid sequence of SEQ ID NO: 12, SEQ ID NO: 15, SEQ ID NO: 17 or SEQ ID NO: 19;

a polynucleotide encoding a rat 187A5 protein comprising the amino acid sequence of SEQ ID NO: 22;

a polynucleotide encoding a bovine 187A5 protein comprising the amino acid sequence of SEQ ID NO: 24;

a polynucleotide encoding a dog 187A5 protein comprising the amino acid sequence of SEQ ID NO: 26; and a polynucleotide encoding a chimpanzee 187A5 protein comprising the amino acid sequence of SEQ ID NO: 28.

Moreover, the 187A5 gene includes:

a polynucleotide comprising the human 187A5 gene nucleotide sequence of SEQ ID NO: 1, SEQ ID NO: 3, SEQ ID NO: 5, SEQ ID NO: 7 or SEQ ID NO: 9;

a polynucleotide comprising the mouse 187A5 gene nucleotide sequence of SEQ ID NO: 11, SEQ ID NO: 13, SEQ ID NO: 14, SEQ ID NO: 16, SEQ ID NO: 18 or SEQ ID NO: 20;

a polynucleotide comprising the rat 187A5 gene nucleotide sequence of SEQ ID NO: 21;

a polynucleotide comprising the bovine 187A5 gene nucleotide sequence of SEQ ID NO: 23;

a polynucleotide comprising the dog 187A5 gene nucleotide sequence of SEQ ID NO: 25; and a polynucleotide comprising the chimpanzee 187A5 gene nucleotide sequence of SEQ ID NO: 27.

The 187A5 gene includes a polynucleotide selected from the following (i'), (ii'), (iii') and (iv'):

(i') a polynucleotide comprising the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27;

(ii') a polynucleotide encoding a protein which consists of an amino acid sequence encoded by a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii') a polynucleotide which hybridizes under stringent conditions to a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which encodes a protein functionally equivalent to a protein consisting of the amino acid sequence of SEQ ID NO: 2; and (iv') a polynucleotide which has 70% or more identity with a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which encodes a protein functionally equivalent to a protein consisting of the amino acid sequence of SEQ ID NO: 2.

Moreover, the 187A5 gene includes a polynucleotide encoding a protein selected from the following (v'), (vi'), (vii') and (viii'):

(v') a protein comprising the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28;

(vi') a protein which consists of an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28 in which one or more amino acids are inserted, substituted and/or deleted, and/or one or more amino acids are added to one or both of ends, and which is functionally equivalent to a protein consisting of the amino acid sequence of SEQ ID NO: 2;

(vii') a protein which is encoded by a polynucleotide which hybridizes under stringent conditions to a polynucleotide which encodes the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2; and (viii') a protein which consists of an amino acid sequence having 70% or more identity with the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2.

According to the present invention, preferably, there is provided a polynucleotide selected from the following (i"), (ii"), (iii") and (iv"):

(i") a polynucleotide comprising the nucleotide sequence of SEQ ID NO: 1;

(ii") a polynucleotide encoding a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii") a polynucleotide which hybridizes under stringent conditions to a polynucleotide consisting of the nucleotide sequence of SEQ ID NO: 1, and which encodes a protein functionally equivalent to a protein consisting of the amino acid sequence of SEQ ID NO: 2; and (iv") a polynucleotide which has 70% or more identity with a polynucleotide consisting of the nucleotide sequence of SEQ ID NO: 1, and which encodes a protein functionally equivalent to a protein consisting of the amino acid sequence of SEQ ID NO: 2.

According to the present invention, preferably, there is also provided a polynucleotide encoding a protein selected from the following (v"), (vi"), (vii") and (viii"):

(v") a protein comprising the amino acid sequence of SEQ ID NO: 2;

(vi") a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;

(vii") a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and (viii") a protein which consists of an amino acid sequence having 70% or more identity with the amino acid sequence of SEQ ID NO: 2, and which is functionally equivalent to a protein consisting of the amino acid sequence of SEQ ID NO: 2.

According to the present invention, more preferably, there is provided a human-derived polynucleotide selected from the following (i'"), (ii'"), (iii'") and (iv'"):

(i'") a polynucleotide comprising the nucleotide sequence of SEQ ID NO: 1;

(ii'") a polynucleotide encoding a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;

(iii'") a polynucleotide which hybridizes under stringent conditions to a polynucleotide consisting of the nucleotide sequence of SEQ ID NO: 1, and which encodes a protein functionally equivalent to a protein consisting of the amino acid sequence of SEQ ID NO: 2; and (iv'") a polynucleotide which has 95% or more identity with a polynucleotide consisting of the nucleotide sequence of SEQ ID NO: 1, and which encodes a protein functionally equivalent to a protein consisting of the amino acid sequence of SEQ ID NO: 2.

According to the present invention, more preferably, there is also provided a polynucleotide encoding a human-derived protein selected from the following (v'"), (vi'"), (vii'") and (viii'"):

(v'") a protein comprising the amino acid sequence of SEQ ID NO: 2;

(vi'") a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;

(vii'") a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and (viii'") a protein which consists of an amino acid sequence having 95% or more identity with the amino acid sequence of SEQ ID NO: 2, and which is functionally equivalent to a protein consisting of the amino acid sequence of SEQ ID NO: 2.

According to the present invention, further preferably, there is provided a human-derived polynucleotide comprising the nucleotide sequence of SEQ ID NO: 1.

According to the present invention, further preferably, there is also provided a polynucleotide encoding a human-derived protein comprising the amino acid sequence of SEQ ID NO: 2.

The 187A5 protein (polypeptide) includes:
a human 187A5 protein comprising the amino acid sequence of SEQ ID NO: 2, SEQ ID NO: 4, SEQ ID NO: 6, SEQ ID NO: 8 or SEQ ID NO: 10;
a mouse 187A5 protein comprising the amino acid sequence of SEQ ID NO: 12, SEQ ID NO: 15, SEQ ID NO: 17 or SEQ ID NO: 19;
a rat 187A5 protein comprising the amino acid sequence of SEQ ID NO: 22;
a bovine 187A5 protein comprising the amino acid sequence of SEQ ID NO: 24;
a dog 187A5 protein comprising the amino acid sequence of SEQ ID NO: 26; and
a chimpanzee 187A5 protein comprising the amino acid sequence of SEQ ID NO: 28.

Moreover, the 187A5 protein (polypeptide) includes:
a protein which is encoded by a nucleotide sequence comprising the human 187A5 gene nucleotide sequence of SEQ ID NO: 1, SEQ ID NO: 3, SEQ ID NO: 5, SEQ ID NO: 7 or SEQ ID NO: 9;
a protein which is encoded by a nucleotide sequence comprising the mouse 187A5 gene nucleotide sequence of SEQ ID NO: 11, SEQ ID NO: 13, SEQ ID NO: 14, SEQ ID NO: 16, SEQ ID NO: 18 or SEQ ID NO: 20;
a protein which is encoded by a nucleotide sequence comprising the rat 187A5 gene nucleotide sequence of SEQ ID NO: 21;
a protein which is encoded by a nucleotide sequence comprising the bovine 187A5 gene nucleotide sequence of SEQ ID NO: 23;
a protein which is encoded by a nucleotide sequence comprising the dog 187A5 gene nucleotide sequence of SEQ ID NO: 25; and
a protein which is encoded by a nucleotide sequence comprising the chimpanzee 187A5 gene nucleotide sequence of SEQ ID NO: 27.

The 187A5 protein (polypeptide) includes a protein selected from the following (i'), (ii'), (iii') and (iv'):
(i') a protein which is encoded by the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27;
(ii') a protein which consists of an amino acid sequence encoded by a nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27 in which one or more nucleotides are inserted, substituted and/or deleted, and/or one or more nucleotides are added to one or both of ends, and which is functionally equivalent to a protein consisting of the amino acid sequence of SEQ ID NO: 2;
(iii') a protein which is encoded by a polynucleotide which hybridizes under stringent conditions to a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which is functionally equivalent to a protein consisting of the amino acid sequence of SEQ ID NO: 2; and
(iv') a protein which is encoded by a polynucleotide which has 70% or more identity with a polynucleotide consisting of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 14, SEQ ID NO: 16, SEQ ID NO: 18, SEQ ID NO: 20, SEQ ID NO: 21, SEQ ID NO: 23, SEQ ID NO: 25 or SEQ ID NO: 27, and which is functionally equivalent to a protein consisting of the amino acid sequence of SEQ ID NO: 2.

Moreover, the 187A5 protein (polypeptide) includes a protein selected from the following (v'), (vi'), (vii') and (viii'):
(v') a protein comprising the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28;
(vi') a protein which consists of an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28 in which one or more amino acids are inserted, substituted and/or deleted, and/or one or more amino acids are added to one or both of ends, and which is functionally equivalent to a protein consisting of the amino acid sequence of SEQ ID NO: 2;
(vii') a protein which is encoded by a polynucleotide which hybridizes under stringent conditions to a polynucleotide which encodes the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2; and
(viii') a protein which consists of an amino acid sequence having 70% or more identity with the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 15, SEQ ID NO: 17, SEQ ID NO: 19, SEQ ID NO: 22, SEQ ID NO: 24, SEQ ID NO: 26 or SEQ ID NO: 28, and which is functionally equivalent to a protein consisting of the amino acid sequence of SEQ ID NO: 2.

According to the present invention, preferably, there is provided a protein (polypeptide) selected from the following (i'), (ii'), (iii') and (iv'):
(i') a protein which is encoded by the nucleotide sequence of SEQ ID NO: 1;
(ii') a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;
(iii') a protein which is encoded by a polynucleotide which hybridizes under stringent conditions to a polynucleotide consisting of the nucleotide sequence of SEQ ID NO: 1, and which is functionally equivalent to a protein consisting of the amino acid sequence of SEQ ID NO: 2; and
(iv') a protein which is encoded by a polynucleotide which has 70% or more identity with a polynucleotide consisting of the nucleotide sequence of SEQ ID NO: 1, and which is functionally equivalent to a protein consisting of the amino acid sequence of SEQ ID NO: 2.

According to the present invention, preferably, there is also provided a protein (polypeptide) selected from the following (v'), (vi'), (vii') and (viii'):
(v') a protein comprising the amino acid sequence of SEQ ID NO: 2;
(vi') a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;
(vii') a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and
(viii') a protein which consists of an amino acid sequence having 70% or more identity with the amino acid sequence of SEQ ID NO: 2, and which is functionally equivalent to a protein consisting of the amino acid sequence of SEQ ID NO: 2.

According to the present invention, more preferably, there is provided a human-derived protein (polypeptide) selected from the following (i'''), (ii'''), (iii''') and (iv'''):
(i''') a protein which is encoded by the nucleotide sequence of SEQ ID NO: 1;
(ii''') a protein which consists of an amino acid sequence encoded by a nucleotide sequence of SEQ ID NO: 1 in which one or more nucleotides are inserted, substituted and/or deleted, and/or one or more nucleotides are added to one or both of ends, and which is functionally equivalent to a protein consisting of the amino acid sequence of SEQ ID NO: 2;
(iii''') a protein which is encoded by a polynucleotide which hybridizes under stringent conditions to a polynucleotide consisting of the nucleotide sequence of SEQ ID NO: 1, and which is functionally equivalent to a protein consisting of the amino acid sequence of SEQ ID NO: 2; and
(iv''') a protein which is encoded by a polynucleotide which has 95% or more identity with a polynucleotide consisting of the nucleotide sequence of SEQ ID NO: 1, and which is functionally equivalent to a protein consisting of the amino acid sequence of SEQ ID NO: 2.

According to the present invention, more preferably, there is also provided a human-derived protein (polypeptide) selected from the following (v'''), (vi'''), (vii''') and (viii'''):
(v''') a protein comprising the amino acid sequence of SEQ ID NO: 2;
(vi''') a protein which consists of an amino acid sequence of SEQ ID NO: 2 in which one or more amino acids are inserted, substituted and/or deleted, and/or one or more amino acids are added to one or both of ends, and which is functionally equivalent to a protein consisting of the amino acid sequence of SEQ ID NO: 2;
(vii''') a protein which is encoded by a polynucleotide which hybridizes under stringent conditions to a polynucleotide which encodes the amino acid sequence of SEQ ID NO: 2, and which is functionally equivalent to a protein consisting of the amino acid sequence of SEQ ID NO: 2; and
(viii''') a protein which consists of an amino acid sequence having 95% or more identity with the amino acid sequence of SEQ ID NO: 2, and which is functionally equivalent to a protein consisting of the amino acid sequence of SEQ ID NO: 2.

According to the present invention, further preferably, there is provided a human-derived protein encoded by the nucleotide sequence of SEQ ID NO: 1.

According to the present invention, further preferably, there is also provided a human-derived protein comprising the amino acid sequence of SEQ ID NO: 2.

In the present specification, "a polynucleotide in which one or more nucleotides are inserted, substituted and/or deleted, and/or one or more nucleotides are added to one or both of ends" or "an amino acid sequence in which one or more amino acids are inserted, substituted and/or deleted, and/or one or more amino acids are added to one or both of ends" means that the modification is performed by a well-known technical method such as site-directed mutagenesis or by substitution of a plurality of nucleotides or amino acids to an extent of being naturally generated, or the like. In the case of the polynucleotide, the term is meant to include single nucleotide polymorphisms (SNPs). The number of nucleotide or amino acid modifications can be insertion, substitution, deletion, and/or addition to one or both of ends, of, for example, 1 to 30, preferably 1 to 20, more preferably 1 to 10, further preferably one to several (for example, 9 or less), particularly preferably 1 to 4, and most preferably 1 or 2 nucleotides or amino acids.

The modified nucleotide sequence can be preferably a nucleotide sequence of SEQ ID NO: 1 having one or more (for example, one or several, or 1, 2, 3 or 4) mutations without affecting the functions of a protein consisting of the amino acid sequence of SEQ ID NO: 2.

The modified amino acid sequence can be preferably an amino acid sequence of SEQ ID NO: 2 having one or more (for example, one or several, or 1, 2, 3 or 4) conservative substitutions.

The number of insertion, substitution, deletion or addition introduced into the nucleotide sequence in (ii), (ii'), (ii') or (ii''') can be preferably one or several (for example, 9 or less), more preferably 1 to 6, particularly preferably 1 to 4, most preferably 1 or 2.

The number of insertion, substitution, deletion or addition introduced into the amino acid sequence in (vi), (vi'), (vi') or (vi''') can be preferably one or several (for example, 9 or less), more preferably 1 to 6, particularly preferably 1 to 4, most preferably 1 or 2.

In the present specification, the "conservative substitutions" mean that one or more amino acid residues are substituted with other chemically analogous amino acid residues so as not to substantially change protein functions. For example, the case that a certain hydrophobic residue is substituted with another hydrophobic residue and the case that a certain polar residue is substituted with another polar residue having the same charge can be exemplified. Functionally analogous amino acids which can be substituted in such a manner are known in the technical field, with respect to every amino acid. To give specific examples, non-polar (hydrophobic) amino acids include alanine, valine, isoleucine, leucine, proline, tryptophan, phenylalanine and methionine. Polar (neutral) amino acids include glycine, serine, threonine, tyrosine, glutamine, asparagine and cysteine. Positively charged (basic) amino acids include arginine, histidine and lysine. Negatively charged (acidic) amino acids include aspartic acid and glutamic acid.

The modified nucleotide sequence includes a nucleotide sequence having substitution of guanine to adenine at nucleotide 512 of SEQ ID NO: 1, substitution of guanine to adenine at nucleotide 844 of SEQ ID NO: 1, substitution of guanine to adenine at nucleotide 1360 of SEQ ID NO: 1, substitution of adenine to guanine at nucleotide 2458 of SEQ ID NO: 1 or substitution of adenine to guanine at nucleotide 2991 of SEQ ID NO: 1. The modified nucleotide sequence may have all or some of these substitutions in combination.

The modified amino acid sequence includes an amino acid sequence having substitution of arginine to histidine at amino acid 161 of SEQ ID NO: 2, substitution of valine to isoleucine at amino acid 272 of SEQ ID NO: 2, substitution of valine to isoleucine at amino acid 444 of SEQ ID NO: 2 or substitution of arginine to glycine at amino acid 810 of SEQ ID NO: 2. The modified amino acid sequence may have all or some of these substitutions in combination.

In the present specification, "hybridize under stringent conditions" means hybridization to a target polynucleotide under stringent conditions. Specifically, there can be exemplified a polynucleotide having at least 70% or more, preferably 80% or more, more preferably 85% or more, further preferably 90% or more, further more preferably 95% or more, particularly preferably 98% or more, and most preferably 99% or more identity, with the target nucleotide sequence when calculation is performed using a parameter of default (initial setting) with homology search software such as FASTA, BLAST or Smith-Waterman (Meth. Enzym., 164, 765 (1988)). Moreover, the "stringent conditions" can be performed according to a method of performing reaction in a hybridization buffer that can be generally used by those skilled in the art so that the temperature is 40 to 70° C., and preferably 60 to 65° C., and performing rinsing in a rinse solution whose salt concentration is 15 to 300 mmol/L, and preferably 15 to 60 mmol/L. The temperature and the salt concentration can be appropriately adjusted according to a length of the probe to be used. Furthermore, the condition when the hybridized nucleotide is rinsed can be 0.2 or 2×SSC, 0.1% SDS, and a temperature of 20 to 68° C. As to control of stringent (high stringency) or mild (low stringency) conditions, the difference can be provided by a salt concentration or a temperature in rinsing. When the difference of the hybridization is provided by a salt concentration, a stringent wash buffer (high stringency wash buffer) of 0.2×SSC, 0.1% SDS, or a mild wash buffer (low stringency wash buffer) of 2×SSC, 0.1% SDS can be used. Alternatively, when the difference of the hybridization is provided by a temperature, the temperature is 68° C. in the stringent case, 42° C. in the case of moderate stringency, and room temperature (20 to 25° C.) in the mild case, and every case thereof may be performed under 0.2×SSC, 0.1% SDS.

In general, prehybridization is performed under the same conditions as the hybridization. However, hybridization and preliminary rinsing are not limited to be performed under the same conditions.

The hybridization can be performed according to a known method. Moreover, in the case of using a commercially available library, the hybridization can be performed according to the method described in the appended instruction for use.

In the present specification, the "identity" (occasionally referred to as homology) with respect to amino acid sequences means the degree of identity of the amino acid residues of the respective sequences between the sequences to be compared. In this case, existence of a gap and properties of the amino acids are considered (Wilbur, Natl. Acad. Sci. U.S.A. 80: 726-730 (1983)). For calculation of the homology, commercially available software BLAST (Altschul: J. Mol. Biol. 215: 403-410 (1990)), FASTA (Peasron: Methods in Enzymology 183: 63-69 (1990)), or the like can be used.

The "identity" may be a value calculated by using a homology search program known by those skilled in the art and can be calculated, for example, by using a parameter of default (initial setting) in the homology algorithm BLAST (Basic local alignment search tool) http://www.ncbi.nlm.nih.gov/BLAST/in NCBI (National Center for Biotechnology Information).

The nucleotide sequence having at least 70% or more identity with the nucleotide sequence of SEQ ID NO: 1 can be a nucleotide sequence having preferably 80% or more, more preferably 90% or more, further preferably 90% or more, further more preferably 95% or more, particularly preferably 98% or more, and most preferably 99% or more identity.

The amino acid sequence having at least 70% or more identity with the amino acid sequence of SEQ ID NO: 2 can be an amino acid sequence having preferably 80% or more, more preferably 90% or more, further preferably 90% or more, further more preferably 95% or more, particularly preferably 98% or more, and most preferably 99% or more identity.

In the present invention, if the amino acid sequence of SEQ ID NO: 2 is given, a nucleotide sequence encoding it can be easily determined, and thereby, various nucleotide sequences encoding the amino acid sequence of SEQ ID NO: 2 can be selected. Thus, a polynucleotide encoding a protein consisting of the amino acid sequence of SEQ ID NO: 2 means not only a part or all of a cDNA sequence of SEQ ID NO: 1 but also a cDNA sequence encoding the same amino acids, which has a codon having a degeneracy relationship therewith as a cDNA sequence. Furthermore, the polynucleotide encoding a protein consisting of the amino acid sequence of SEQ ID NO: 2 means even a genomic DNA sequence also containing introns or noncoding regions. In the present invention, it further includes an RNA sequence corresponding thereto.

In the present specification, whether or not to be "functionally equivalent to a protein consisting of the amino acid sequence of SEQ ID NO: 2" can be determined by evaluating a biological phenomenon or functions associated with the expression of the 187A5 gene. For example, it can be determined by evaluating whether or not to be selectively expressed in dopaminergic neuron progenitor cells, and preferably dopaminergic neuron proliferative progenitor cells in the mesencephalon.

The present invention provides a protein comprising a polypeptide consisting of at least 5 amino acid residues (preferably, at least 6 amino acid residues) or all of an amino acid sequence of amino acids 248-397 or 792-877 of SEQ ID NO: 2. This protein corresponds to a high discrimination part in the amino acid sequence of the 187A5 protein, and therefore, can be used as an antigen against an antibody that can discriminate the 187A5 protein with higher accuracy.

The 187A5 protein is a type I single transmembrane protein that is expressed on the cell surface in a direction wherein the N-terminal side thereof can be located in the extracellular space. Thus, by flow cytometry using an antibody capable of binding to the protein, live cells in which the protein is expressed can be separated.

The present invention provides a protein comprising a polypeptide consisting of at least 5 amino acid residues (preferably, at least 6 amino acid residues) or all of an amino acid sequence of amino acids 28 to 927 of SEQ ID NO: 2, amino acids 16 to 1267 of SEQ ID NO: 4, amino acids 1 to 550 of SEQ ID NO: 6, amino acids 1 to 542 of SEQ ID NO: 8, amino acids 1 to 418 of SEQ ID NO: 10, amino acids 76 to 964 of SEQ ID NO: 12, amino acids 40 to 928 of SEQ ID NO: 15, amino acids 1 to 540 of SEQ ID NO: 17, amino acids 40 to 1106 of SEQ ID NO: 19, amino acids 24 to 1524 of SEQ ID NO: 22, amino acids 43 to 1018 of SEQ ID NO: 24, amino acids 43 to 908 of SEQ ID NO: 26 or amino acids 1 to 866 of SEQ ID NO: 28. This protein corresponds to the extracellular region in the amino acid sequence of the 187A5 protein, and therefore, can be used as an antigen for preparing an antibody that can detect live cells as an object to be detected.

The present invention provides use of the protein according to the present invention as an index for detecting or selecting a dopaminergic neuron progenitor cell, and preferably a dopaminergic neuron proliferative progenitor cell.

[Probe, Primer and Primer Set]

The probe or primer according to the present invention for use in the detection or selection of a dopaminergic neuron progenitor cell, and preferably a dopaminergic neuron proliferative progenitor cell can specifically hybridize to a 187A5 gene. According to Example 2, in a 12.5-day mouse embryo which is in the period of generating dopaminergic neurons, mRNA of 187A5 is selectively expressed in the mesencephalon most ventral ventricular zone (ventricular zone; VZ) and the mesencephalon most dorsal roof plate zone in which Lrp4-positive dopaminergic neuron progenitor cells exist, but is not expressed in metencephalon floor plate cells positive for Lrp4. Therefore, it became revealed that mRNA of 187A5 is selectively expressed in dopaminergic neuron proliferative progenitor cells. Accordingly, the expression of the 187A5 gene is useful as an index for dopaminergic neuron progenitor cells. Therefore, the probe, the primer and the primer set according to the present invention can be used as a marker for detecting dopaminergic neuron progenitor cells, and preferably dopaminergic neuron proliferative progenitor cells.

The probe and the primer according to the present invention can be used for detecting expression of a 187A5 gene, and corresponds to a polymer consisting of a plurality of bases or base pairs such as deoxyribonucleic acid (DNA) or ribonucleic acid (RNA). It is known that double-strand cDNA can also be used in tissue in situ hybridization, and such double-strand cDNA is also included in the probe and the primer according to the present invention. As a particularly preferable probe and primer in the detection of RNA in tissue, an RNA probe (riboprobe) can be exemplified.

The probe and the primer according to the present invention include those comprising a nucleotide sequence consisting of at least 10, preferably at least 15 contiguous nucleotides of a nucleotide sequence of a 187A5 gene, or a complementary sequence thereto. Also, the probe and the primer according to the present invention include those comprising a nucleotide sequence consisting of preferably 10 to 50 or 10 to 30, more preferably 15 to 50 or 15 to 30, further preferably 20 to 50 or 20 to 30, further more preferably 25 to 50 or 25 to 30, and most preferably 26 to 39 or 26 to 35 nucleotides.

The probe and the primer according to the present invention can be at least 10 base length, preferably at least 15 base length, more preferably at least 20 base length, and further preferably at least 25 base length. The probe and the primer according to the present invention can also be preferably 10 to 50 base length or 10 to 30 base length, more preferably 15 to 50 base length or 15 to 30 base length, further preferably 20 to 50 base length or 20 to 30 base length, further more preferably 25 to 50 base length or 25 to 30 base length, and most preferably 26 to 39 base length or 26 to 35 base length.

According to preferable embodiments of the probe and the primer according to the present invention, there is provided a polynucleotide for use in the detection or selection of a dopaminergic neuron progenitor cell, and preferably a dopaminergic neuron proliferative progenitor cell in the mesencephalon, comprising a nucleotide sequence consisting of at least 10 (more preferably, at least 15) contiguous nucleotides of a nucleotide sequence of a 187A5 gene, or a complementary sequence thereto and having 15 to 50 base length or 15 to 30 base length, more preferably 25 to 50 base length or 25 to 30 base length, and most preferably 26 to 39 base length or 26 to 35 base length, which can hybridize with a 187A5 gene.

According to preferable embodiments of the probe according to the present invention, there is also provided a polynucleotide that can hybridize to a high discrimination part in the nucleotide sequence of the 187A5 gene. By using such a polynucleotide, it becomes possible to detect the progenitor cells, and preferably the proliferative progenitor cells with higher accuracy. Such a polynucleotide includes a polynucleotide that hybridizes to a nucleotide sequence comprising a part or all of a nucleotide sequence of nucleotides 774 to 1221 or 2403 to 2666 of SEQ ID NO: 1.

According to preferable embodiments of the primer according to the present invention, there is also provided those that can amplify a high discrimination part in the nucleotide sequence of the 187A5 gene by a nucleic acid amplification method, and a polynucleotide that can hybridize to the high discrimination part. By using such a polynucleotide, it becomes possible to detect the progenitor cells, and preferably the proliferative progenitor cells with higher accuracy. Such a polynucleotide includes a polynucleotide that can amplify, by a nucleic acid amplification method, a nucleotide sequence comprising a part or all of a nucleotide sequence of nucleotides 774 to 1221 or 2403 to 2666 of SEQ ID NO: 1.

The probe according to the present invention can be used as a probe according to the general methods in known methods for detecting a gene of interest, such as a northern blotting method, a southern blotting method or in situ hybridization method.

The probe according to the present invention can be chemically synthesized based on the nucleotide sequences disclosed in the present specification. The preparation of the probe is well-known and can be performed, for example, according to "Molecular Cloning, A Laboratory Manual $2^{nd}$ ed." (Cold Spring Harbor Press (1989)) or "Current Protocols in Molecular Biology" (John Wiley & Sons (1987-1997)).

The primer according to the present invention can also be used as a primer set consisting of two or more primers according to the present invention.

The primer and the primer set according to the present invention can be used as a primer and a primer set according to the general methods in known methods for detecting a gene of interest by using a nucleic acid amplification method such as a PCR method, a RT-PCR method, a real-time PCR method or in situ PCR.

The primer set according to the present invention can be selected so that the nucleotide sequence of the 187A5 gene can be amplified by a nucleic acid amplification method such as a PCR method. The nucleic acid amplification method is well-known, and selection of the primer set in the nucleic acid amplification method is understood by those skilled in the art. For example, in the PCR method, primers can be selected so that one of two primers (primer pair) is paired with the plus strand of the double-strand DNA of the 187A5 gene while the other primer is paired with the minus strand of the double-strand DNA, and with a strand extended by one primer, the other primer can be paired. Moreover, in the LAMP method (WO 00/28082), with respect to the target gene, three regions F3c, F2c and F1c and three regions B1, B2 and B3 are defined from the 3' end side and from the 5' end side, respectively, and by using these six regions, four primers can be designed.

The primer according to the present invention can be chemically synthesized based on the nucleotide sequences disclosed in the present specification. The preparation of the primer is well-known and can be performed, for example, according to "Molecular Cloning, A Laboratory Manual $2^{nd}$ ed." (Cold Spring Harbor Press (1989)) or "Current Protocols in Molecular Biology" (John Wiley & Sons (1987-1997)).

[Antibody]

The antibody according to the present invention can specifically recognize a 187A5 protein. According to Example 5, it was confirmed that the 187A5 protein exists in dopaminergic neuron progenitor cells. Accordingly, the existence of the 187A5 protein is useful as an index for dopaminergic neuron progenitor cells including dopaminergic neuron proliferative progenitor cells. Therefore, the antibody according to the present invention can be used as a marker for detecting dopaminergic neuron progenitor cells, and preferably dopaminergic neuron progenitor cells.

The 187A5 protein is expressed on the cell surface in a direction wherein the N-terminal side thereof can be located in the extracellular space (Example 4). Therefore, the antibody according to the present invention has the advantage that the dopaminergic neuron progenitor cells can be detected or selected as live cells (Example 6). Moreover, the antibody according to the present invention has the advantage that ES cell-derived cells can also be detected or selected (Example 7).

The 187A5 protein for obtaining the antibody according to the present invention may have antigenicity of 187A5 and includes the above-described protein. Moreover, it includes a protein having an amino acid sequence of the 187A5 protein in which one or more amino acid residues are deleted, inserted, substituted or added. It is known that in such a protein, the same biological activity as the original protein is maintained (Mark et al. (1984) Proc. Natl. Acad. Sci. USA 81: 5662-6; Zoller and Smith (1982) Nucleic Acids Res. 10: 6487-500; Wang et al. (1984) Science 224: 1431-3; and Dalbadie-McFarland et al. (1982) Proc. Natl. Acad. Sci. USA 79: 6409-13). A method by which in a protein, one or more amino acid residues are deleted, inserted, substituted or added in the state of maintaining the antigenicity of the original protein is known. For example, a polynucleotide encoding a mutant protein can be prepared by site-directed mutagenesis and can be appropriately expressed to obtain the protein (Molecular Cloning, A Laboratory Manual $2^{nd}$ ed., Cold Spring Harbor Press (1989); Current Protocols in Molecular Biology, John Wiley & Sons, (1987-1997), Section 8.1-8.5; Hashimoto-Goto et al. (1995) Gene 152: 271-5; Kinkel (1985) Proc. Natl. Acad. Sci. USA 82: 488-92; Kramer and Fritz (1987) Method. Enzymol 154: 350-67; and Kunkel (1988) Method. Enzymol. 85: 2763-6).

The antibody according to the present invention also includes an antibody specific for a part of a 187A5 protein. Specifically, the 187A5 protein for obtaining the antibody of the present invention includes a polypeptide having the full-length amino acid sequence of the 187A5 protein as well as a polypeptide fragment having a sequence of at least 6 amino acid residues or more (for example, 8, 10, 12 or 15 amino acid residues or more) of the 187A5 protein. The polypeptide fragment of the 187A5 protein in the present specification may be any fragment as long as having the 187A5 protein or antigenicity thereof.

Preferable fragments can include polypeptide fragments such as the amino terminal of the 187A5 protein. The antigenic determinant site of the polypeptide is estimated by a method of analyzing hydrophobicity/hydrophilicity of the amino acid sequence of the protein (Kyte-Doolittle (1982) J. Mol. Biol. 157: 105-22) or a method of analyzing the secondary structure (Chou-Fasman (1978) Ann. Rev. Biochem. 47: 251-76), and furthermore, can be confirmed by a computer program (Anal. Biochem. 151: 540-6 (1985)) or a technique such as a PEPSCAN method (Japanese Patent Laid-Open Publication No. 60-500684) of synthesizing a short peptide and confirming its antigenicity.

The antibody capable of binding to the 187A5 protein includes:
an antibody capable of binding to a protein consisting of the amino acid sequence of SEQ ID NO: 2, SEQ ID NO: 4, SEQ ID NO: 6, SEQ ID NO: 8 or SEQ ID NO: 10, or a part thereof;
an antibody capable of binding to a protein consisting of the amino acid sequence of SEQ ID NO: 12, SEQ ID NO: 15, SEQ ID NO: 17 or SEQ ID NO: 19 or, or a part thereof;
an antibody capable of binding to a protein consisting of the amino acid sequence of SEQ ID NO: 22, or a part thereof;
an antibody capable of binding to a protein consisting of the amino acid sequence of SEQ ID NO: 24, or a part thereof;
an antibody capable of binding to a protein consisting of the amino acid sequence of SEQ ID NO: 26, or a part thereof; and
an antibody capable of binding to a protein consisting of the amino acid sequence of SEQ ID NO: 28, or a part thereof.

According to preferable embodiments of the antibody according to the present invention, there is provided an antibody that recognizes a high discrimination polypeptide region in the 187A5 protein. By using such an antibody, it becomes possible to detect the progenitor cells, and preferably the proliferative progenitor cells with higher accuracy. Such an antibody includes an antibody capable of binding to a protein comprising a polypeptide consisting of at least 5 amino acid residues (preferably, at least 6 amino acid residues) or all of an amino acid sequence of amino acids 248 to 397 or 792 to 877 of SEQ ID NO: 2.

According to preferable embodiments of the antibody according to the present invention, there is also provided an antibody that recognizes a polypeptide region expressed in the extracellular space of the 187A5 protein. By using such an antibody, it becomes possible to detect the progenitor cells, and preferably the proliferative progenitor cells as live cells. Such an antibody includes an antibody capable of binding to the polypeptide region expressed in the extracellular space of the 187A5 protein, for example, an antibody capable of binding to a protein comprising a polypeptide consisting of at least 5 amino acid residues (preferably, at least 6 amino acid residues) or all of an amino acid sequence of amino acids 28 to 927 of SEQ ID NO: 2, amino acids 16 to 1267 of SEQ ID NO: 4, amino acids 1 to 550 of SEQ ID NO: 6, amino acids 1 to 542 of SEQ ID NO: 8, amino acids 1 to 418 of SEQ ID NO: 10, amino acids 76 to 964 of SEQ ID NO: 12, amino acids 40 to 928 of SEQ ID NO: 15, amino acids 1 to 540 of SEQ ID NO: 17, amino acids 40 to 1106 of SEQ ID NO: 19, amino acids 24 to 1524 of SEQ ID NO: 22, amino acids 43 to 1018 of SEQ ID NO: 24, amino acids 43 to 908 of SEQ ID NO: 26 or amino acids 1 to 866 of SEQ ID NO: 28.

The antibody according to the present invention can be obtained by using a well-known method for those skilled in the art (for example, "Current Protocols in Molecular Biology" (John Wiley & Sons (1987)) and Antibodies: A Laboratory Manual, Ed. Harlow and David Lane, Cold Spring Harbor Laboratory (1988)).

The antibody according to the present invention includes a polyclonal antibody, a monoclonal antibody, a chimeric antibody, a single-strand antibody (scFv), a humanized antibody, a polyspecific antibody and antibody fragments such as Fab, Fab', F(ab')$_2$, Fc and Fv.

In the case of the polyclonal antibody, the blood of a mammal in which an antigen is sensitized is extracted, and serum can be segregated as polyclonal antibody-containing serum from the blood by a known method.

According to need, fractions containing the polyclonal antibody can also be further isolated from this serum.

In the case of the monoclonal antibody, antibody-producing cells obtained from the spleen or lymph node of the above-described mammal in which an antigen is sensitized are extracted and cell-fused with myeloma cells or the like. The obtained hybridomas (fused cells) are cloned, and antibodies can be collected as the monoclonal antibody from the cultures thereof.

A fragment of the 187A5 protein can be used as the immunizing antigen. Alternatively, those synthesized based on the above-described amino acid sequence can be used. The antigen may be used as a complex with a carrier protein. For preparation of the complex of the antigen and the carrier protein, various condensation agents such as glutaraldehyde, carbodiimide or maleimide-activated ester can be used. The carrier protein may be one generally used such as bovine serum albumin, thyroglobulin or hemocyanin, and a method for coupling at a ratio of 1 to 5 is generally used.

The animal to be immunized includes a mouse, a rat, a hamster, a guinea pig, a rabbit, a cat, a dog, a pig, a goat, a horse and a bovine, and, preferably, includes a mouse, a rat, a rabbit, a guinea pig and a hamster. The injection method includes subcutaneous, muscular or intraperitoneal administration. In the administration, the antigen may be mixed with complete Freund's adjuvant or incomplete Freund's adjuvant. The administration is generally performed once per 2 to 5 weeks.

The antibody-producing cells obtained from the spleen or lymph node of the immunized animal are cell-fused with myeloma cells and isolated as hybridomas. The myeloma cells to be used are derived from a mouse, a rat, a human, or the like, and preferably, derived from the same species as the antibody-producing cells, but cells between different species are occasionally possible.

Operation of the hybridomas (cell fusion) can be performed according to a previously known method, for example, the method disclosed in Nature, 256, 495, 1975. Fusion accelerators include polyethylene glycol and Sendai virus. In general, the cell fusion can be performed by reaction for approximately 1 to 10 minutes so that the ratio between the number of the antibody-producing cells and the number of the myeloma cells is generally approximately 1:1 to 10:1, under a temperature of 20 to 40° C., and preferably 30 to 37° C. by using polyethylene glycol (average molecular weight 1000 to 4000) having a concentration of approximately 20 to 50%.

For screening of the antibody-producing hybridomas, various immunochemical methods can be used, which include an ELISA method by using a microplate coated with the 187A5 protein, an EIA method by using a microplate coated with an anti-immunoglobulin antibody, and an immunoblotting method by using a nitrocellulose transfer membrane after electrophoresing samples containing the 187A5 protein.

From such wells, cloning is further performed, for example, by a limiting dilution method, and thereby, clones can be obtained. Selection and culture of the hybridomas are generally performed in a medium for animal cells (for example, RPMI1640) containing 10 to 20% fetal bovine serum to which HAT (hypoxanthine, aminopterin and thymidine) is added. The clones obtained as described above are transplanted into the peritoneal cavity of an SCID mouse to which pristine is preliminarily administered, and ascitic fluid containing the monoclonal antibody at a high concentration is collected after 10 to 14 days, and can be used as a material for antibody purification. Also, the clones can be cultured, and the cultures thereof can also be used as a material for antibody purification.

For the purification of the monoclonal antibody, a previously known method as an immunoglobulin purification method may be used, and the purification can be easily achieved, for example, by a means such as an ammonium sulfate fraction method, a PEG fraction method, an ethanol fraction method, use of an anion exchanger, or affinity chromatography using the 187A5 protein.

The purification of the polyclonal antibody from the serum can be similarly performed.

[Detection Method]

The expression of the 187A5 gene serves as an index for the existence of dopaminergic neuron progenitor cells, and preferably dopaminergic neuron proliferative progenitor cells, as described above. Therefore, according to the present invention, the dopaminergic neuron progenitor cells, and preferably the dopaminergic neuron proliferative progenitor cells can be detected or selected by detecting expression of a 187A5 gene.

The method for "detecting expression of a 187A5 gene" used herein is not particularly limited as long as being capable of detecting the expression of the 187A5 gene in cell samples to be tested, and can be performed, for example, by the following steps of:

(a) contacting a cell sample to be tested, with the probe, the primer or the primer set according to the present invention; and (b) detecting the presence or absence of reactivity.

The method for "detecting the presence or absence of reactivity" used herein, for example, includes hybridization methods and nucleic acid amplification methods.

The "cell sample to be tested" used herein may be cell samples that are thought to contain the dopaminergic neuron progenitor cells, and preferably the dopaminergic neuron proliferative progenitor cells, and, preferably, cells in the mesencephalon ventral region can be used. The cells in the mesencephalon ventral region can be obtained by a known method (Studer, L., et al. Nature Neurosci (1998) 1: 290-295). For example, fetus's (preferably, human aborted fetus's) or patient's own cells of the mesencephalon ventral region can be used as the cell sample to be tested. Moreover, culture cells containing dopaminergic neuron progenitor cells, and preferably dopaminergic neuron proliferative progenitor cells induced to differentiate in vitro can be used. The induction to differentiate into the dopaminergic neuron progenitor cells or the dopaminergic neuron proliferative progenitor cells in vitro can be performed by differentiation treatment by a known method such as an SDIA method (Kawasaki et al. Neuron (2000) 28 (1): 31-40) or a 5-stage method (Lee, S H., et al. Nature Biotech (2000) 18: 675-579) using, as a starting material, cells such as known ES cells (Kawasaki et al. Neuron (2000) 28 (1): 31-40) and Lee, S H., et al. Nature Biotech (2000) 18: 675-579), bone marrow stromal cells, nerve-derived immortalized cell lines (Japanese Patent Laid-Open Publication No. 8-509215, No. 11-506930 and No. 2002-522070) or neuron primordial cells (Japanese Patent Laid-Open Publication No. 11-509729). Preferably, ES cells subjected to the differentiation treatment by the SDIA method can be used as the cell sample to be tested.

The "SDIA method" used herein can be performed by co-culturing ES cells and the stromal cell line PA6 in a serum-free medium (Kawasaki et. al. Neuron. 2000 28 (1): 31-40). Moreover, the "5-stage method" can be performed as follows. ES cells are cultured on a non-adherent culture plate in the presence of serum, and thereby, an embryoid body (EB) is formed. Sequentially, the EB is attached onto an adherent culture plate, and thereby, neuron progenitor cells are selected. Finally, a growth factor such as Shh, FGF2 or FGF8 is added thereto, and thereby, dopaminergic neuron progenitor cells are induced (Lee, S H., et al. Nature Biotech (2000) 18: 675-579).

According to the first embodiment of the detection method according to the present invention, using the probe according to the present invention, the polynucleotide for detection hybridizes to a nucleic acid sample (mRNA or a transcript thereof), and the hybridization complex, namely, the nucleotide double strand, is detected. Thus, the expression of the 187A5 gene can be detected in the cell sample.

For the detailed procedure of the hybridization method, there can be referred to "Molecular Cloning, A Laboratory Manual $2^{nd}$ ed." (Cold Spring Harbor Press (1989), particularly, Sections 9.47-9.58), "Current Protocols in Molecular Biology" (John Wiley & Sons (1987-1997), particularly, Sections 6.3-6.4), and "DNA Cloning 1: Core Techniques, A Practical Approach $2^{nd}$ ed." (Oxford University (1995), particularly, Section 2.10 for the conditions).

The detection of expression of a 187A5 gene by using the hybridization method can be performed, for example, by the following steps of:
(a-1) contacting a polynucleotide derived from a cell sample to be tested, with the probe according to the present invention; and
(b-1) detecting a hybridization complex.

In step (a-1), mRNA prepared from the cell sample that is thought to contain dopaminergic neuron progenitor cells, and preferably dopaminergic neuron proliferative progenitor cells, or a complementary DNA (cDNA) transcribed from the mRNA can be contacted, as the polynucleotide derived from the cell sample to be tested, with the probe.

In the detection method by using the probe, the probe can be labeled. The label includes a label by using radioactivity (such as $^{32}P$, $^{14}C$ and $^{35}S$), fluorescence (such as FITC and europium), an enzyme (such as peroxidase or alkaline phosphatase) reaction such as chemical coloring, or the like.

The detection of the hybridization product can be performed by using a well-known method such as northern hybridization, southern hybridization or colony hybridization.

The cells in which the hybridization complex is detected are those expressing a 187A5 gene, and therefore, can be determined as the dopaminergic neuron progenitor cells, and preferably the dopaminergic neuron proliferative progenitor cells.

According to the second embodiment of the detection method according to the present invention, using the primer or the primer set according to the present invention, a nucleic acid sample (mRNA or a transcript thereof) is amplified by a nucleic acid amplification method, and the amplification product is detected. Thus, the expression of the 187A5 gene can be detected in the cell sample.

The detection of expression of a 187A5 gene by using the nucleic acid amplification method can be performed, for example, by the following steps of:
(a-2) performing a nucleic acid amplification method by using a polynucleotide derived from a cell sample to be tested as a template and the primer or the primer set according to the present invention; and
(b-2) detecting a formed amplification product.

In step (a-2), mRNA prepared from the sample that is thought to contain dopaminergic neuron progenitor cells, and preferably dopaminergic neuron proliferative progenitor cells, or a complementary DNA (cDNA) transcribed from the mRNA can be used as the template.

The detection of the amplification product can be performed by using a nucleic acid amplification method such as a PCR method, a RT-PCR method, a real-time PCR method or a LAMP method.

The cells in which the amplification product is detected are those expressing a 187A5 gene, and therefore, can be determined as the dopaminergic neuron progenitor cells, and preferably the dopaminergic neuron proliferative progenitor cells.

The 187A5 protein serves as an index for the existence of dopaminergic neuron progenitor cells, and preferably dopaminergic neuron proliferative progenitor cells, as described above. Therefore, according to the present invention, the dopaminergic neuron progenitor cells, and preferably the dopaminergic neuron proliferative progenitor cells can be detected or selected by detecting a 187A5 protein.

The method for "detecting a 187A5 protein" used herein is not particularly limited as long as being capable of detecting the 187A5 protein in cell samples to be tested, and, for example, includes antigen-antibody reaction methods.

According to the third embodiment of the detection method according to the present invention, the antibody according to the present invention and the cell sample are contacted, and the antigen-antibody reaction is detected. Thus, the 187A5 protein can be detected in the cell sample.

The detection of a 187A5 protein by using the antigen-antibody reaction can be performed, for example, by the following steps of:
(c) contacting a protein derived from a cell sample to be tested, with the antibody according to the present invention; and
(d) detecting the presence or absence of reactivity.

The method for "detecting the presence or absence of reactivity" used herein, for example, includes antigen-antibody reaction methods.

The "cell sample to be tested" used herein can be cell samples to be tested that are thought to contain the dopaminergic neuron progenitor cells, and preferably the dopaminergic neuron proliferative progenitor cells, and are preferably cells in the mesencephalon ventral region or culture cells containing dopaminergic neuron progenitor cells, and preferably dopaminergic neuron proliferative progenitor cells induced to differentiate in vitro. For example, those derived from an embryonic mesencephalon can be used as the cell sample to be tested. The method for obtaining the cell sample to be tested is as described above.

The detection of a 187A5 protein by using the antigen-antibody reaction method can be performed, for example, by the following steps of:
(c-1) contacting a protein derived from a cell sample to be tested, with the antibody according to the present invention; and
(d-1) detecting an antigen-antibody complex.

The method for detecting the antigen-antibody reaction is well-known for those skilled in the art, and, for example, a 187A5 protein can be detected in the cell sample to be tested that is thought to contain dopaminergic neuron progenitor cells, and preferably dopaminergic neuron proliferative progenitor cells, by an immunological method. For the immunological method, a previously known method such as an immunohistologic staining method, an enzyme-linked immunosorbent assay, a western blotting method, an agglutination method, a competition method or a sandwich method, can be applied to the cell sample subjected to appropriate treatment according to need, such as cell separation or extraction operation. The immunohistologic staining method can be performed by, for example, a direct method by using a labeled antibody or an indirect method by using a labeled antibody capable of binding to the antibody. For the labeling agent, a known labeling substance such as a fluorescent substance, a radioactive substance, an enzyme, a metal or a pigment can be used.

The protein derived from a cell sample to be tested is preferably a polypeptide comprising the extracellular region (namely, the N-terminal region).

The cells in which the antigen-antibody complex is detected are those expressing a 187A5 protein, and therefore, can be determined as the dopaminergic neuron progenitor cells, and preferably the dopaminergic neuron proliferative progenitor cells.

For use in the treatment of the Parkinson's disease, it is desirable that the purity of the dopaminergic neuron progenitor cells, and preferably the dopaminergic neuron proliferative progenitor cells is high.

The accuracy of the detection or selection of the dopaminergic neuron progenitor cells, and preferably the dopaminergic neuron proliferative progenitor cells can be enhanced by performing each of the above-described detection steps not only once but repeatedly.

Therefore, according to the detection method according to the present invention, the dopaminergic neuron progenitor cells, and preferably the dopaminergic neuron proliferative progenitor cells can be detected or selected with higher accuracy by performing the above-described step twice or more.

Moreover, the accuracy of the detection or selection of the dopaminergic neuron progenitor cells, and preferably the dopaminergic neuron proliferative progenitor cells can be further enhanced by using together other marker genes, preferably a dopaminergic neuron proliferative progenitor cell marker gene other than the 187A5 gene.

Therefore, according to the detection method according to the present invention, the dopaminergic neuron progenitor cells, and preferably the dopaminergic neuron proliferative progenitor cells can be detected or selected with higher accuracy by using together a dopaminergic neuron proliferative progenitor cell marker gene other than the 187A5 gene or a protein thereof, a postmitotic dopaminergic neuron precursor cell marker gene or a protein thereof, a dopaminergic neuron progenitor cell marker gene other than the 187A5 gene or a protein thereof, or a mature dopaminergic neuron cell marker gene or a protein thereof, and detecting not only expression of the 187A5 gene, or a protein thereof but also expression of the above-described other marker genes, or the proteins thereof.

Dopaminergic neuron-related marker genes selectively expressed in each of differentiation stages are shown in FIG. 1.

In the detection method characterized in that the expression of the 187A5 gene is detected, the dopaminergic neuron progenitor cells, and preferably the dopaminergic neuron proliferative progenitor cells can be detected or selected with high accuracy by using together a dopaminergic neuron proliferative progenitor cell marker gene other than the 187A5 gene or a protein thereof, and detecting not only the 187A5 gene but also expression of the dopaminergic neuron proliferative progenitor cell marker gene other than the 187A5 gene, or the protein thereof.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the dopaminergic neuron proliferative progenitor cell marker gene other than the 187A5 gene, or the protein thereof is detected. In this case, the cells in which reactivity is detected (for example, the cells in which the hybridization complex or the amplification product is detected) in step (b) are those which express the 187A5 gene, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-1) detecting expression of a dopaminergic neuron proliferative progenitor cell marker gene other than the 187A5 gene, or a protein thereof, with respect to the cells in which reactivity is detected (for example, the cells in which the hybridization complex or the amplification product is detected) in step (b). In this case, in step (e-1), the cells in which the expression of the dopaminergic neuron proliferative progenitor cell marker gene other than the 187A5 gene, or the protein thereof is detected are those which express the 187A5 gene, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the expression of the 187A5 gene is detected, by using together a postmitotic dopaminergic neuron precursor cell marker gene or a protein thereof, it can be confirmed that the 187A5 gene is expressed but the expression of the postmitotic dopaminergic neuron precursor cell marker gene, or the protein thereof is not detected. Thus, the dopaminergic neuron progenitor cells, and preferably the dopaminergic neuron proliferative progenitor cells can be detected or selected with high accuracy.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the postmitotic dopaminergic neuron precursor cell marker gene, or the protein thereof is not detected. In this case, the cells in which reactivity is detected (for example, the cells in which the hybridization complex or the amplification product is detected) in step (b) are those which express the 187A5 gene, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-2) detecting expression of a postmitotic dopaminergic neuron precursor cell marker gene, or a protein thereof, with respect to the cells in which reactivity is detected (for example, the cells in which the hybridization complex or the amplification product is detected) in step (b). In this case, in step (e-2), the cells in which the expression of the postmitotic dopaminergic neuron precursor cell marker gene, or the protein thereof is not detected are those which express the 187A5 gene, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the expression of the 187A5 gene is detected, the dopaminergic neuron progenitor cells, and preferably the dopaminergic neuron proliferative progenitor cells can be detected or selected with high accuracy by using together a dopaminergic neuron progenitor cell marker gene other than the 187A5 gene or a protein thereof, and detecting not only the 187A5 gene but also expression of the dopaminergic neuron progenitor cell marker gene other than the 187A5 gene, or the protein thereof.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the dopaminergic neuron progenitor cell marker gene other than the 187A5 gene, or the protein thereof is detected. In this case, the cells in which reactivity is detected (for example, the cells in which the hybridization complex or the amplification product is detected) in step (b) are those which express the 187A5 gene, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-3) detecting expression of a dopaminergic neuron progenitor cell marker gene other than the 187A5 gene, or a protein thereof, with respect to the cells in which reactivity is detected (for example, the cells in which the hybridization complex or the amplification product is detected) in step (b). In this case, in step (e-3), the cells in which the expression of the dopaminergic neuron progenitor cell marker gene other than the 187A5 gene, or the protein thereof is detected are those which express the 187A5 gene, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the expression of the 187A5 gene is detected, by using together a mature dopaminergic neuron cell marker gene or a protein thereof, it can be confirmed that the 187A5 gene is expressed but the expression of the mature dopaminergic neuron cell marker gene, or the protein thereof is not detected. Thus, the dopaminergic neuron progenitor cells, and preferably the dopaminergic neuron proliferative progenitor cells can be detected or selected with high accuracy.

Specifically, in step (a), the dopaminergic neuron progenitor cells, and preferably the dopaminergic neuron proliferative progenitor cells can be detected or selected with high accuracy by using, as the cell sample to be tested, the cells in which the expression of the mature dopaminergic neuron cell marker gene, or the protein thereof is not detected. In this case, the cells in which reactivity is detected (for example, the cells in which the hybridization complex or the amplification product is detected) in step (b) are those which express the 187A5 gene, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-4) detecting expression of a mature dopaminergic neuron cell marker gene, or a protein thereof, with respect to the cells in which reactivity is detected (for example, the cells in which the hybridization complex or the amplification product is detected) in step (b). In this case, in step (e-4), the cells in which the expression of the mature dopaminergic neuron cell marker gene, or the protein thereof is not detected are those which express the 187A5 gene, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, the dopaminergic neuron progenitor cells, and preferably the dopaminergic neuron proliferative progenitor cells can be detected or selected with high accuracy by using together a dopaminergic neuron proliferative progenitor cell marker gene other than the 187A5 gene or a protein thereof, and detecting not only the 187A5 protein but also expression of the dopaminergic neuron proliferative progenitor cell marker gene other than the 187A5 gene, or the protein thereof.

Specifically, in step (c), the dopaminergic neuron progenitor cells, and preferably the dopaminergic neuron proliferative progenitor cells can be detected or selected with high accuracy by using, as the cell sample to be tested, the cells in which the expression of the dopaminergic neuron proliferative progenitor cell marker gene other than the 187A5 gene, or the protein thereof is detected. In this case, the cells in which reactivity is detected (for example, the cells in which the antigen-antibody complex is detected) in step (d) are those which have the existence of the 187A5 protein, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-1) detecting expression of a dopaminergic neuron proliferative progenitor cell marker gene other than the 187A5 gene, or a protein thereof, with respect to the cells in which reactivity is detected (for example, the cells in which the antigen-antibody complex is detected) in step (d). In this case, in step (e-1), the cells in which the expression of the dopaminergic neuron proliferative progenitor cell marker gene other than the 187A5 gene, or the protein thereof is detected are those which have the existence of the 187A5 protein, and which express the dopaminergic neuron proliferative progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, by using together a postmitotic dopaminergic neuron precursor cell marker gene or a protein thereof, it can be confirmed that the 187A5 protein is expressed but the expression of the postmitotic dopaminergic neuron precursor cell marker gene, or the protein thereof is not detected. Thus, the dopaminergic neuron progenitor cells, and preferably the dopaminergic neuron proliferative progenitor cells can be detected or selected with high accuracy.

Specifically, in step (c), the dopaminergic neuron progenitor cells, and preferably the dopaminergic neuron proliferative progenitor cells can be detected or selected with high accuracy by using, as the cell sample to be tested, the cells in which the expression of the postmitotic dopaminergic neuron precursor cell marker gene, or the protein thereof is not detected. In this case, the cells in which reactivity is detected (for example, the cells in which the antigen-antibody complex is detected) in step (d) are those which have the existence of the 187A5 protein, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-2) detecting expression of a postmitotic dopaminergic neuron precursor cell marker gene, or a protein thereof, with respect to the cells in which reactivity is detected (for example, the cells in which the antigen-antibody complex is detected) in step (d). In this case, in step (e-2), the cells in which the expression of the postmitotic dopaminergic neuron precursor cell marker gene, or the protein thereof is not detected are those which have the existence of the 187A5 protein, which do not express the postmitotic dopaminergic neuron precursor cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, the dopaminergic neuron progenitor cells, and preferably the dopaminergic neuron proliferative progenitor cells can be detected or selected with high accuracy by using together a dopaminergic neuron progenitor cell marker gene other than the 187A5 gene or a protein thereof, and detecting not only the 187A5 protein but also expression of the dopaminergic neuron progenitor cell marker gene other than the 187A5 gene, or the protein thereof.

Specifically, in step (c), the dopaminergic neuron progenitor cells, and preferably the dopaminergic neuron proliferative progenitor cells can be detected or selected with high accuracy by using, as the cell sample to be tested, the cells in which the dopaminergic neuron progenitor cell marker gene other than the 187A5 gene, or the protein thereof is detected. In this case, the cells in which reactivity is detected (for example, the cells in which the antigen-antibody complex is detected) in step (d) are those which have the existence of the 187A5 protein, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-3) detecting expression of a dopaminergic neuron progenitor cell marker gene other than the 187A5 gene, or a protein thereof, with respect to the cells in which reactivity is detected (for example, the cells in which the antigen-antibody complex is detected) in step (d). In this case, in step (e-3), the cells in which the expression of the dopaminergic neuron progenitor cell marker gene other than the 187A5 gene, or the protein thereof is detected are those which have the existence of the 187A5 protein, and which express the dopaminergic neuron progenitor cell marker gene other than the 187A5 gene or which have the existence of the protein thereof. Thus, the cells can be determined as the detected or selected dopaminergic neuron progenitor cells, and preferably the detected or selected dopaminergic neuron proliferative progenitor cells with high accuracy.

In the detection method characterized in that the 187A5 protein is detected, by using together a mature dopaminergic neuron cell marker gene or a protein thereof, it can be confirmed that the 187A5 protein is expressed but the expression of the mature dopaminergic neuron cell marker gene, or the protein thereof is not detected. Thus, the dopaminergic neuron progenitor cells, and preferably the dopaminergic neuron proliferative progenitor cells can be detected or selected with high accuracy.

Specifically, in step (c), the dopaminergic neuron progenitor cells, and preferably the dopaminergic neuron proliferative progenitor cells can be detected or selected with high accuracy by using, as the cell sample to be tested, the cells in which the expression of the mature dopaminergic neuron cell marker gene, or the protein thereof is not detected. In this case, the cells in which reactivity is detected (for example, the cells in which the antigen-antibody complex is detected) in step (d) are those which have the existence of the 187A5 protein, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

Moreover, the dopaminergic neuron progenitor cells, and preferably the dopaminergic neuron proliferative progenitor cells can be detected or selected with high accuracy by performing the method further comprising the step of (e-4) detecting expression of a mature dopaminergic neuron cell marker gene, or a protein thereof, with respect to the cells in which reactivity is detected (for example, the cells in which the antigen-antibody complex is detected) in step (d). In this case, in step (e-4), the cells in which the expression of the mature dopaminergic neuron cell marker gene, or the protein thereof is not detected are those which have the existence of the 187A5 protein, which do not express the mature dopaminergic neuron cell marker gene, and which do not have the existence of the protein thereof. Thus, the cells can be determined as the detected or selected dopaminergic neuron progenitor cells, and preferably the detected or selected dopaminergic neuron proliferative progenitor cells with high accuracy.

"The dopaminergic neuron proliferative progenitor cell marker gene other than the 187A5 gene or the protein thereof" is a "dopaminergic neuron proliferative progenitor cell marker gene other than the 187A5 gene" or a "dopaminergic neuron proliferative progenitor cell marker protein other than the 187A5 protein".

"The dopaminergic neuron proliferative progenitor cell marker gene other than the 187A5 gene" includes a dopaminergic neuron proliferative progenitor cell marker gene other than the 187A5 gene which is expressed in the mesencephalon most ventral ventricular zone (VZ region), and includes an Lrp4 gene, a Nato3 gene, an Msx1 gene, an Msx2 gene and a Mash1 gene.

The Lrp4 gene is described in WO 2004/065599. The Nato3 gene is described in WO 2007/021003. The Msx1 gene and the Msx2 gene are described in WO 2007/021004. The Mash1 gene is described in Kele J, Simplicio N, Ferri A L, Mira H, Guillemot F, Arenas E, Ang S L. Neurogenin 2 is required for the development of ventral mesencephalon dopaminergic neurons. Development. 2006 February; 133 (3): 495-505.

The detection of the dopaminergic neuron proliferative progenitor cell marker gene other than the 187A5 gene is not particularly limited as long as using a method by which expression of the known gene can be detected, and, for example, includes the hybridization method and the nucleic acid amplification method, as described above.

"The dopaminergic neuron proliferative progenitor cell marker protein other than the 187A5 protein" includes a dopaminergic neuron proliferative progenitor cell marker protein other than the 187A5 protein which is expressed in the mesencephalon most ventral ventricular zone (VZ region), and, preferably, includes a protein detected only in dopaminergic neuron proliferative progenitor cells.

Such a protein includes proteins of an Lrp4 gene, a Nato3 gene, an Msx1 gene, an Msx2 gene and a Mash1 gene.

The detection of the dopaminergic neuron proliferative progenitor cell marker protein other than the 187A5 protein is not particularly limited as long as using a method by which expression of the known protein can be detected, and, for example, includes the antigen-antibody reaction method, as described above.

"The postmitotic dopaminergic neuron precursor cell marker gene or the protein thereof" includes a gene expressed in the mesencephalon most ventral mantle layer (ML region) or a protein thereof, and includes a Nurr1 gene, an En1 gene, an En2 gene, a Ptx3 gene and a TH gene. Moreover, the marker gene includes a gene expressed in the mesencephalon most ventral ventricular zone (VZ region) or a protein thereof, and includes a 65B13 gene.

The Nurr1 gene is described in Science. 1997 11; 276 (5310): 248-50. The En1 gene is described in J. Neurosci. 2001 21 (9): 3126-34. The En2 gene is described in J. Neurosci. 2001 21 (9): 3126-34. The Ptx3 gene is described in Proc. Natl. Acad. Sci. 1997 94: 13305-10. The TH gene is described in Science. 1997 11; 276 (5310): 248-50. The 65B13 gene is described in WO 2004/038018.

The detection of the postmitotic dopaminergic neuron precursor cell marker gene or the protein thereof is not particularly limited as long as using a method by which expression of the known gene or the protein thereof can be detected, and, for example, includes the hybridization method, the nucleic acid amplification method and the antigen-antibody reaction method, as described above.

"The dopaminergic neuron progenitor cell marker gene other than the 187A5 gene or the protein thereof" is a "dopaminergic neuron progenitor cell marker gene other than the 187A5 gene" or a "dopaminergic neuron progenitor cell marker protein other than the 187A5 protein".

"The dopaminergic neuron progenitor cell marker gene other than the 187A5 gene" includes a dopaminergic neuron progenitor cell marker gene other than the 187A5 gene which is expressed in the mesencephalon most ventral region, and includes an Lmx1a gene.

The Lmx1a gene is described in WO 2005/052190.

The detection of the dopaminergic neuron progenitor cell marker gene other than the 187A5 gene is not particularly limited as using a method by which expression of the known gene can be detected, and, for example, includes the hybridization method and the nucleic acid amplification method, as described above.

"The dopaminergic neuron progenitor cell marker protein other than the 187A5 protein" includes a dopaminergic neuron progenitor cell marker protein other than the 187A5 protein which is expressed in the mesencephalon most ventral region. Such a protein includes a protein of an Lmx1a gene.

The detection of the dopaminergic neuron progenitor cell marker protein other than the 187A5 protein is not particularly limited as long as using a method by which expression of the known protein can be detected, and, for example, includes the antigen-antibody reaction method, as described above.

"The mature dopaminergic neuron cell marker gene" includes a DAT gene.

The DAT gene is described in Development 2003 131: 1145-55.

The detection of the mature dopaminergic neuron cell marker gene or the protein thereof is not particularly limited as long as using a method by which expression of the known gene or the protein thereof can be detected, and, for example, includes the hybridization method, the nucleic acid amplification method and the antigen-antibody reaction method, as described above.

Moreover, the accuracy of the detection or selection of the dopaminergic neuron progenitor cells, and preferably the dopaminergic neuron proliferative progenitor cells can be further enhanced by using together a vector comprising a gene construct in which a promoter of the 187A5 gene is operably linked to a marker gene.

Therefore, according to the detection method according to the present invention, the dopaminergic neuron progenitor cells, and preferably the dopaminergic neuron proliferative progenitor cells can be detected or selected with higher accuracy by using together a gene construct in which a promoter of the 187A5 gene is operably linked to a marker gene, and detecting not only expression of the 187A5 gene, or the protein thereof but also expression of the marker gene.

The detection of the dopaminergic neuron progenitor cells by using the vector comprising a gene construct in which a promoter of the 187A5 gene is operably linked to a marker gene can be performed, for example, according to Japanese Patent Laid-Open Publication No. 2002-51775.

A marker gene that can be detected under the control of a promoter/enhancer of the 187A5 gene expressed in dopaminergic neuron progenitor cells is introduced into each cell in a cell population, and the expression of the marker gene is detected. Thus, the dopaminergic neuron progenitor cells can be detected.

Specifically, the dopaminergic neuron progenitor cells can be detected or selected by performing the steps of transforming the cell sample to be tested, with a vector comprising a gene construct in which a promoter of the gene according to the present invention is operably linked to a marker gene, and detecting expression of the marker gene in the cell sample to be tested. In this case, in the step, the cells in which the expression of the marker gene is detected can be determined as the detected or selected dopaminergic neuron progenitor cells, and preferably the detected or selected dopaminergic neuron proliferative progenitor cell with high accuracy.

The nucleotide sequence of the "promoter of the gene according to the present invention" used herein includes a nucleotide sequence of a promoter region obtained by expression region analysis of the 187A5 gene to be described later, and also includes a modified sequence thereof having approximately equivalent promoter activity.

The "marker gene" used herein may be a marker gene that can be detected under the control of a promoter/enhancer of the 187A5 gene, and includes GFP.

The "gene construct" used herein may have a structure in which the 187A5 gene is linked upstream or downstream of the marker gene under the control of an expression control sequence (including a promoter, an enhancer, or the like) of the 187A5 gene. In addition, a gene encoding the maker can be knocked in to the 187A5 gene locus. As preferable embodiments of the gene construct, constructs having structures schematically described in 2 to 4 in FIG. 15 can be exemplified.

[Detection Kit]

The present invention provides a detection kit for performing the detection method according to the present invention.

The first embodiment of the detection kit according to the present invention includes a detection kit for performing the first embodiment of the detection method according to the present invention, and specifically, includes a kit for detecting expression of a 187A5 gene, comprising at least the probe according to the present invention. This probe may be labeled. The detection kit detects the expression of the 187A5 gene by a hybrid formation method. Therefore, the detection kit of the first embodiment can optionally further include various reagents for performing the hybrid formation method, for example, a substrate compound for use in the detection of a label, a hybridization buffer, instructions, equipment, and/or so forth.

Moreover, a detection kit for performing the detection with high accuracy includes the kit further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof The probe, the primer, the primer set or the antibody may be labeled. By any of the hybrid formation method, the nucleic acid amplification method and the antigen-antibody reaction method, the detection kit further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The second embodiment of the detection kit according to the present invention includes a detection kit for performing the second embodiment of the detection method according to the present invention, and specifically, includes a kit for detecting expression of a 187A5 gene, comprising at least the primer according to the present invention or the primer set according to the present invention. The detection kit detects the expression of the 187A5 gene by the nucleic acid amplification method. Therefore, the detection kit of the second embodiment can optionally further include various reagents for performing the nucleic acid amplification method, for example, a buffer, an internal standard indicating that the amplification reaction can normally progress, instructions, equipment, and/or so forth.

Moreover, a detection kit for performing the detection with high accuracy includes the kit further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the detection kit further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The third embodiment of the detection kit according to the present invention includes a detection kit for performing the third embodiment of the detection method according to the present invention, and specifically, includes a kit for detecting a 187A5 protein, comprising at least the antibody according to the present invention. This antibody may be labeled. The detection kit detects the expression of the 187A5 protein by detecting the antigen-antibody reaction. Therefore, the detection kit of the third embodiment can optionally further include various reagents for performing the antigen-antibody reaction, for example, a secondary antibody for use in an ELISA method or the like, a coloring reagent, a buffer, instructions, equipment, and/or so forth.

Moreover, a detection kit for performing the detection with high accuracy includes the kit further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the detection kit further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

Furthermore, a detection kit for performing the detection with high accuracy includes the detection kits of the first to third embodiment according to the present invention, further comprising a vector comprising a gene construct in which a promoter of the 187A5 gene is operably linked to a marker gene.

[Agent for Detection]

The present invention provides an agent for detection for performing the detection method according to the present invention.

The first embodiment of the agent for detection according to the present invention includes an agent for detection for performing the first embodiment of the detection method according to the present invention, and specifically, includes an agent for detecting expression of a 187A5 gene, comprising at least the probe according to the present invention. This probe may be labeled. The agent for detection detects the expression of the 187A5 gene by a hybrid formation method. Therefore, the agent for detection of the first embodiment can optionally further includes various reagents for performing the hybrid formation method, for example, a substrate compound for use in the detection of a label, a hybridization buffer, instructions, equipment, and/or so forth.

Moreover, an agent for detection for performing the detection with high accuracy includes the agent for detection further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the agent for detection further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The second embodiment of the agent for detection according to the present invention includes an agent for detection for performing the second embodiment of the detection method according to the present invention, and specifically, includes an agent for detecting expression of a 187A5 gene, comprising at least the primer according to the present invention or the primer set according to the present invention. The agent for detection detects the expression of the 187A5 gene by the nucleic acid amplification method. Therefore, the agent for detection of the second embodiment can optionally further include various reagents for performing the nucleic acid amplification method, for example, a buffer, an internal standard indicating that the amplification reaction can normally progress, instructions, equipment, and/or so forth.

Moreover, an agent for detection for performing the detection with high accuracy includes the agent for detection further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the agent for detection further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

The third embodiment of the agent for detection according to the present invention includes an agent for detection for performing the third embodiment of the detection method according to the present invention, and specifically, includes a agent for detecting a 187A5 protein, comprising at least the antibody according to the present invention. This antibody may be labeled. The agent for detection detects the expression of the 187A5 protein by detecting the antigen-antibody reaction. Therefore, the agent for detection of the third embodiment can optionally further include various reagents for performing the antigen-antibody reaction, for example, a secondary antibody for use in an ELISA method or the like, a coloring reagent, a buffer, instructions, equipment, and/or so forth.

Moreover, an agent for detection for performing the detection with high accuracy includes the agent for detection further comprising a probe, a primer, a primer set or an antibody which can detect expression of a dopaminergic neuron proliferative progenitor cell marker gene other than the 187A5 gene, or a protein thereof, expression of a postmitotic dopaminergic neuron precursor cell marker gene, or a protein thereof, expression of a dopaminergic neuron progenitor cell marker gene other than the 187A5 gene, or a protein thereof, or expression of a mature dopaminergic neuron cell marker gene, or a protein thereof. The probe, the primer, the primer set or the antibody may be labeled. By any of the hybrid formation method, the nucleic acid amplification method and the antigen-antibody reaction method, the agent for detection further detects the expression of the dopaminergic neuron proliferative progenitor cell marker gene other than the 187A5 gene, or the protein thereof, the expression of the postmitotic dopaminergic neuron precursor cell marker gene, or the protein thereof, the expression of the dopaminergic neuron progenitor cell marker gene other than the 187A5 gene, or the protein thereof, or the expression of the mature dopaminergic neuron cell marker gene, or the protein thereof.

Furthermore, an agent for detection for performing the detection with high accuracy includes the agents for detection of the first to third embodiment according to the present invention, further comprising a vector comprising a gene construct in which a promoter of the 187A5 gene is operably linked to a marker gene.

[Screening Method]

The detection method according to the present invention can be applied to screening for an effective substance for inducing differentiation into a dopaminergic neuron progenitor cell. Specifically, whether or not the addition of a candidate substance has induced the differentiation into a dopaminergic neuron progenitor cell, and preferably a dopaminergic neuron proliferative progenitor cell is determined by using expression of a 187A5 gene, or a protein thereof as an index, and thereby, the effective substance for inducing differentiation into a dopaminergic neuron progenitor cell can be screened for.

Therefore, the present invention provides a method for screening for an effective substance for inducing differentiation into a dopaminergic neuron progenitor cell, comprising the following steps of:
(i) contacting a cell that can differentiate into a dopaminergic neuron progenitor cell, with a substance to be tested; and
(ii) detecting expression of a 187A5 gene, or a protein thereof in the cell that has been contacted with the substance to be tested.

The cell that can differentiate into a dopaminergic neuron progenitor cell in step (i) is preferably a cell that can differentiate into a dopaminergic neuron proliferative progenitor cell, and can be preferably collected from an embryonic mesencephalon or from culture cells containing neuron progenitor cells induced to differentiate from ES cells.

"Contacting with a substance to be tested" in step (i) can be performed, for example, by adding the substance to be tested to culture cells containing the cell that can differentiate into a dopaminergic neuron progenitor cell, and preferably a dopaminergic neuron proliferative progenitor cell.

The "substance to be tested" includes a synthesized low-molecular compound, a protein, a synthesized peptide, a purified or partially purified polypeptide, an antibody, a bacterium-releasing material (including bacterial metabolites) and a nucleic acid (such as antisense, ribozyme and RNAi), and is preferably a compound or a salt thereof, or a solvate thereof (for example, a hydrate), but is not limited thereto. The "substance to be tested" may be a novel substance or a known substance.

In step (ii), according to the detection method according to the present invention, the expression of the 187A5 gene, or the protein thereof can be detected.

Specifically, steps (a-1) and (b-1) are performed for the detection by using the hybridization method. Steps (a-2) and (b-2) are performed for the detection by using the nucleic acid amplification method. Steps (c-1) and (d-1) are performed for the detection by using the antigen-antibody reaction method. Thus, the expression of the 187A5 gene, or the protein thereof can be detected.

In step (ii), when the expression of the 187A5 gene, or the protein thereof is detected in the cell sample to be tested by contacting the substance to be tested, the substance can be determined as the effective substance for inducing differentiation into a dopaminergic neuron progenitor cell, and preferably a dopaminergic neuron proliferative progenitor cell.

The substance specified by the screening method according to the present invention can be used as the effective substance for inducing differentiation into a dopaminergic neuron progenitor cell, and preferably a dopaminergic neuron proliferative progenitor cell.

The present invention provides the method for screening for an effective substance for inducing differentiation into a dopaminergic neuron progenitor cell, further comprising the following step of:
(iii-1) detecting expression of a dopaminergic neuron proliferative progenitor cell marker gene other than the 187A5 gene, or a protein thereof in the cell that has been contacted with the substance to be tested.

When the expression of the 187A5 gene, or the protein thereof is detected in step (ii), and the expression of the dopaminergic neuron proliferative progenitor cell marker gene other than the 187A5 gene, or the protein thereof is detected in step (iii-1), the substance can be determined as the effective substance for inducing differentiation into a dopaminergic neuron progenitor cell, and preferably a dopaminergic neuron proliferative progenitor cell, with high accuracy.

Step (iii-1) may be performed after step (i) and may be performed before or after step (ii).

The present invention provides the method for screening for an effective substance for inducing differentiation into a dopaminergic neuron progenitor cell, further comprising the following step of:
(iii-2) detecting expression of a postmitotic dopaminergic neuron precursor cell marker gene, or a protein thereof in the cell that has been contacted with the substance to be tested.

When the expression of the 187A5 gene, or the protein thereof is detected in step (ii), but the postmitotic dopaminergic neuron precursor cell marker gene or the protein thereof is not detected in step (iii-2), the substance can be determined as the effective substance for inducing differentiation into a dopaminergic neuron progenitor cell, and preferably a dopaminergic neuron proliferative progenitor cell, with high accuracy.

Step (iii-2) may be performed after step (i) and may be performed before or after step (ii).

"The dopaminergic neuron proliferative progenitor cell marker gene other than the 187A5 gene or the protein thereof" is a "dopaminergic neuron proliferative progenitor cell marker gene other than the 187A5 gene" or a "dopaminergic neuron proliferative progenitor cell marker protein other than the 187A5 protein".

"The dopaminergic neuron proliferative progenitor cell marker gene other than the 187A5 gene" includes a dopaminergic neuron proliferative progenitor cell marker gene other than the 187A5 gene which is expressed in the mesencephalon most ventral ventricular zone (VZ region), and includes an Lrp4 gene, a Nato3 gene, an Msx1 gene, an Msx2 gene and a Mash1 gene.

The detection of the dopaminergic neuron proliferative progenitor cell marker gene other than the 187A5 gene is not particularly limited as long as using a method by which the expression of the known gene can be detected, and, for example, includes the hybridization method and the nucleic acid amplification method.

"The dopaminergic neuron proliferative progenitor cell marker protein other than the 187A5 protein" includes a dopaminergic neuron proliferative progenitor cell marker protein other than the 187A5 protein which is expressed in the mesencephalon most ventral ventricular zone (VZ region), and, preferably, includes a protein detected only in dopaminergic neuron proliferative progenitor cells.

Such a protein includes proteins of an Lrp4 gene, a Nato3 gene, an Msx1 gene, an Msx2 gene and a Mash1 gene.

The detection of the dopaminergic neuron proliferative progenitor cell marker protein other than the 187A5 protein is not particularly limited as long as using a method by which the expression of the known protein can be detected, and, for example, includes the antigen-antibody reaction method.

"The postmitotic dopaminergic neuron precursor cell marker gene or the protein thereof" includes a gene expressed in the mesencephalon most ventral mantle layer (ML region) or a protein thereof, and includes a Nurr1 gene, an En1 gene, an En2 gene, a Ptx3 gene and a TH gene. Moreover, the marker gene or the protein thereof includes a gene expressed in the mesencephalon most ventral ventricular zone (VZ region) or a protein thereof, and includes a 65B13 gene.

The detection of the postmitotic dopaminergic neuron precursor cell marker gene or the protein thereof is not particularly limited as long as using a method by which the expression of the known gene or the protein thereof can be detected, and, for example, includes the hybridization method, the nucleic acid amplification method and the antigen-antibody reaction method.

The present invention provides the method for screening for an effective substance for inducing differentiation into a dopaminergic neuron progenitor cell, further comprising the following step of:

(iii-3) transforming the cell that has been contacted with the substance to be tested, with a vector comprising a gene construct in which a promoter of the 187A5 gene is operably linked to a marker gene, and detecting expression of the marker gene in the cell.

When the expression of the 187A5 gene, or the protein thereof is detected in step (ii), and the expression of the marker gene is detected in step (iii-3), the substance can be determined as the effective substance for inducing differentiation into a dopaminergic neuron progenitor cell, and preferably a dopaminergic neuron proliferative progenitor cell, with high accuracy.

Step (iii-3) may be performed after step (i) and may be performed before or after step (ii). Furthermore, step (iii-3) may be performed after step (iii-1) or (iii-2).

[Production Method]

The detection method according to the present invention can detect or select dopaminergic neuron progenitor cells. The dopaminergic neuron progenitor cells can be used in the treatment of the Parkinson's disease. Therefore, the dopaminergic neuron progenitor cells for use in the treatment of the Parkinson's disease can be produced from dopaminergic neuron progenitor cells detected or selected by using expression of a 187A5 gene, or a protein as an index.

The dopaminergic neuron progenitor cells used herein are preferably dopaminergic neuron proliferative progenitor cells.

The present invention provides a method for producing a dopaminergic neuron progenitor cell, comprising the following steps of:

(i) obtaining cells that can contain a dopaminergic neuron progenitor cell;

(ii) detecting or selecting the dopaminergic neuron progenitor cell by using the detection method according to the present invention; and (iii) culturing the cell obtained in step (ii).

The present invention provides a therapeutic agent for the Parkinson's disease, comprising dopaminergic neuron progenitor cells, and preferably dopaminergic neuron proliferative progenitor cells detected or selected by the detection method according to the present invention.

The present invention provides use of dopaminergic neuron progenitor cells, and preferably dopaminergic neuron proliferative progenitor cells detected or selected by the detection method according to the present invention, for the production of a drug for use in the treatment of the Parkinson's disease.

The present invention provides a method for treating the Parkinson's disease, comprising transplanting dopaminergic neuron progenitor cells, and preferably dopaminergic neuron proliferative progenitor cells detected or selected by the detection method according to the present invention, into the brain of a mammal including a human.

In the present specification, the "detection" also includes "discrimination". Moreover, the "detection" includes not only the case that cells as an object are discriminated as being cells of a particular kind but also the case that cells as an object are discriminated as not being cells of a particular kind.

EXAMPLES

Example 1

Isolation and Sequence Analysis of Dopaminergic Neuron Progenitor Cell-Selective Gene An Lrp4 gene has been identified as a cell surface marker for separating dopaminergic neuron proliferative progenitor cells (WO 2004/065599). By using an anti-Lrp4 antibody, it becomes possible to separate dopaminergic neuron proliferative progenitor cells derived from ES cells. Thus, hereinafter, the isolation and sequence analysis of a gene selective for dopaminergic neuron proliferative progenitor cells will be described.

(1) Isolation of Lrp4-Positive Cell

Figure 2:
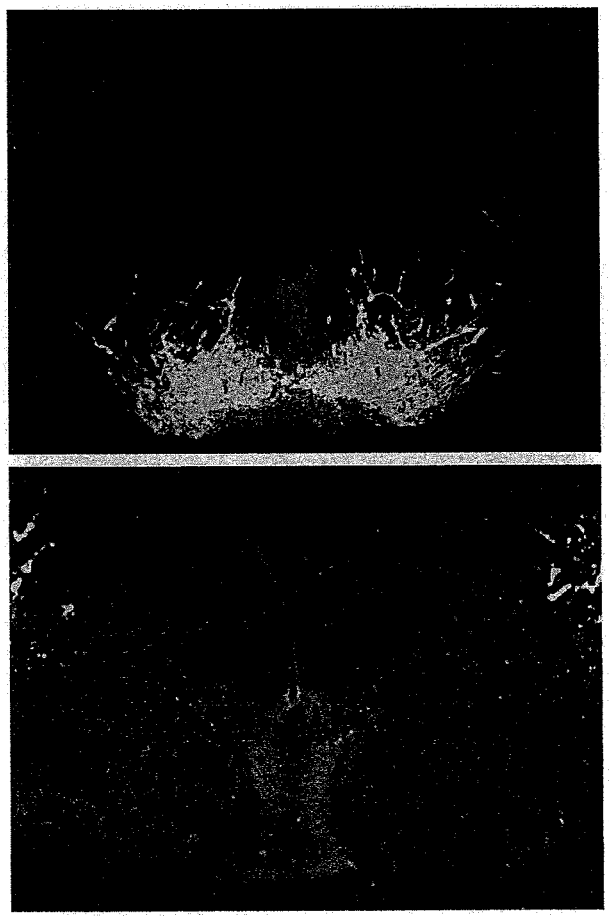
FIG. 2 shows the results of analyzing, by an immunostaining method, protein expressions of Lrp4 and TH in the mesencephalon and metencephalon of a 14.5-day rat embryo.

First, the mesencephalon and metencephalon ventral regions of a 13.5-day rat embryo were dispersed by using the accumax (MS Techno Systems), and then, without being subjected to fixation and permeabilization treatments, the cells were stained for 30 minutes at 4° C. by using an anti-Lrp4 monoclonal antibody (obtained from hybridomas (Deposition No. FERM BP-10315 and No. FERM BP-10316), diluted to 1/10, 1% fetal bovine serum (JRH), 5% fetal rat serum (JRH), 1 mM EDTA (Invitrogen)/PBS (Sigma)). Then, by using an FACS buffer (PBS+1% fetal bovine serum (JRH)+1 mM EDTA), rinsing was performed for 3 minutes at 4° C. three times, and the cells were stained for 20 minutes at 4° C. by using a PE-labeled anti-hamster IgG antibody (Becton Dickinson, 8 μg/ml, 1% fetal bovine serum, 5% fetal rat serum, 1 mM EDTA/PBS). Then, rinsing was performed in the same manner. After the staining, Lrp4-positive cells were separated by a cell sorter (FACS vantage SE, Becton Dickinson) (FIG. 2). The total RNA was prepared from the cells immediately after the separation by using the RNeasy mini kit (Qiagen), and double-strand cDNA was synthesized by using the cDNA synthesis kit (TAKARA). Next, the synthesized cDNA was digested with the restriction enzyme RsaI (TAKARA), and then, ad2 was added thereto. The cDNA was amplified by PCR using ad2S as a primer.

The amplification was carried out under the conditions that incubation was performed for 5 minutes at 72° C., then, reactions for 30 seconds at 94° C., for 30 seconds at 65° C. and for 2 minutes at 72° C. were performed at 20 cycles, and finally, incubation was performed for 2 minutes at 72° C.

ad2S: CAGCTCCACAACCTACATCATTCCGT (SEQ ID NO: 29)

ad2A: ACGGAATGATGT (SEQ ID NO: 30)

PCR was performed by using a reaction solution with the following composition.

| | |
|---|---|
| 10 × ExTaq | 5 μl |
| 2.5 mM dNTP | 4 μl |
| ExTaq | 0.25 μl |
| 100 μM primer | 0.5 μl |
| cDNA | 2 μl |
| Distilled water | 38.25 μl |

Next, by using the cDNAs corresponding to the amplified cDNA of 4 ng, 0.4 ng and 0.04 ng as templates, PCR was performed in the following reaction system.

| | |
|---|---|
| 10 × ExTaq | 1 μl |
| 2.5 mM dNTP | 0.8 μl |
| ExTaq | 0.05 μl |
| 100 μM primer | 0.1 μl for each |
| cDNA | 1 μl |
| Distilled water | 6.95 μl |

After Incubation for 2 minutes at 94° C., the amplification reactions were performed for 30 seconds at 94° C., for 30 seconds at 65° C. and for 2 minutes at 72° C., and finally, incubation was performed for 2 minutes at 72° C. The amplifications of PCR were performed at 26 cycles.

The following primers were used in the PCR.

```
Lrp4:
TAGTCTACCACTGCTCGACTGTAACG      (SEQ ID NO: 31)

CAGAGTGAACCCAGTGGACATATCTG      (SEQ ID NO: 32)

Lmx1a:
TGGTTCAGGTGTGGTTCCAGAACCAG      (SEQ ID NO: 33)

GAGTTGTAGACGCTCTGTTCAATGGC      (SEQ ID NO: 34)
```

Figure 3:
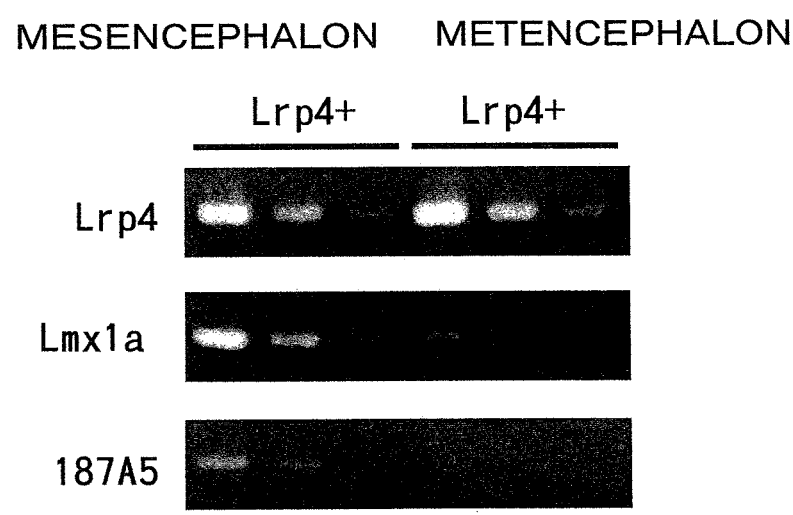
FIG. 3 shows the results of analyzing, by a RT-PCR method, mRNA expressions of 187A5, Lmx1a and Lrp4 in mesencephalon and metencephalon Lrp4-positive cells.

As a result, the Lrp4 gene is expressed at the approximately equal level in any of the mesencephalon and metencephalon Lrp4-positive cells. However, it was confirmed that an Lmx1a gene (WO 2005/052190), which is a marker gene of dopaminergic neurons and dopaminergic neuron progenitor cells, is strongly expressed only in the mesencephalon Lrp4-positive cells (FIG. 3). Therefore, it is thought that the mesencephalon Lrp4-positive cells contain the dopaminergic neuron proliferative progenitor cells, but the metencephalon Lrp4-positive cells do not contain the dopaminergic neuron proliferative progenitor cells.

Thus, next, by using this sample, a gene specific for the Lrp4-positive cells in the mesencephalon was searched by a subtraction (N-RDA) method (described in WO 2004/065599). As a result, one (187A5) of the isolated cDNA fragments was a fragment encoding a functionally unknown gene. Next, expression of this gene was confirmed by the above-described RT-PCR method using the following primers.

```
187A5:
ACCAGGAAGGACAATGCCATTCGTCC      (SEQ ID NO: 35)

CCTTCTTCACCTTGGCTCTTAGGATG      (SEQ ID NO: 36)
```

As a result, it was confirmed that the 187A5 gene is specifically expressed in the Lrp4-positive cells in the mesencephalon in the same manner as the Lmx1a gene (FIG. 3).

(2) Sequence Analysis

As a result of database search, rat and mouse cDNA sequences that are thought to be the full length of this gene were obtained (for example, Sequence Number: Mouse 187A5 AK028289, Mouse 187A5 AK157823 (frame shift), Mouse 187A5 AK028541, Mouse 187A5 XM_485684 (alternative), Mouse 187A5 AK163356 (frame shift), Rat 187A5 XM_344107 (predicted)). A partial sequence (SEQ ID NO: 1) that is thought to be a human homologous gene was also obtained, but the full length could not be obtained. Thus, homology search was performed with respect to the human genomic sequence, and a human cDNA sequence was predicted. However, for the neighborhood of the 5' end, a region having high homology could not be found. Therefore, sequence determination was performed by using a 5' RACE method.

From 1 μg of human embryonic brain mRNA (Clontech), cDNA was amplified by using the 5' RACE core kit (TAKARA), and self-ligation was performed. By using the following primers, the cDNA 5' end was amplified. The obtained fragments were cloned into pCRII (Invitrogen), and sequence determination was performed.

```
RT Reaction:
CATCCCAGTCTC                    (SEQ ID NO: 37)

Primary PCR:
TGGAGAAGGTTGTGCCTCTGGACTTG      (SEQ ID NO: 38)

CTGGTTGGCTTCCTTGAGGAAGAAGG      (SEQ ID NO: 39)

Secondary PCR:
TCCTGCGGGACAAAGTCTACCTGAGC      (SEQ ID NO: 40)

CTGAGGATGTGGTAGCTCACAGGTAG      (SEQ ID NO: 41)
```

The PCR reaction was performed with the following composition.

| | |
|---|---|
| 10 × ExTaq | 5 μl |
| 2.5 mM dNTP | 4 μl |
| ExTaq | 0.25 μl |
| 100 μM primer | 0.5 μl for each |
| Template | 1 μl |
| DMSO | 1.5 μl |
| Distilled water | 37.25 μl |

After incubation for 2 minutes at 94° C., the amplification reactions were performed for 30 seconds at 94° C., for 30 seconds at 65° C. and for 2 minutes at 72° C., and finally, incubation was performed for 2 minutes at 72° C. The amplifications of PCR were performed at 35 cycles for primary PCR, and secondary PCR was performed by using the primary PCR products diluted 10-fold as templates and performing amplifications at 20 cycles.

Next, in order to confirm that the predicted sequence is correct, each of three divided regions thereof was amplified by RT-PCR. The PCR products were cloned into pCRII (Invitrogen), and sequence determination was performed.

From 0.5 μg of human embryonic brain mRNA (Clontech), cDNA was amplified by using the RNA PCR kit (TAKARA). By using the cDNA as a template, PCR was performed.

The neighborhood of the 5' end was amplified by using the following primers.

```
Human 187A5 F4:
                                (SEQ ID NO: 42)
GAGGTCGACGCCACCATGCGCTCCGAGGGTGCGGCCCCC Human 187a5 R1:
                                (SEQ ID NO: 43)
GGGTCCATAGCTGGCATTGAGCACTG
```

The PCR reaction was performed with the following composition.

| | |
|---|---|
| 10 × LATaq | 5 μl |
| MgCl$_2$ | 5 μl |
| 2.5 mM dNTP | 8 μl |
| LATaq | 0.5 μl |
| 100 μM primer | 0.5 μl for each |
| cDNA | 1 μl |
| DMSO | 1.5 μl |
| Distilled water | 28 μl |

After incubation for 2 minutes at 94° C., the amplification reactions for 30 seconds at 94° C., for 30 seconds at 65° C. and for 3.5 minutes at 72° C. were performed at 35 cycles, and finally, incubation was performed for 2 minutes at 72° C.

The remaining regions were amplified by using the following primers F12 and R5 as well as F 13 and R4 in combination.

Human 187A5 F12:
(SEQ ID NO: 44)
CTACCTGTGAGCTACCACATCCTCAG

Human 187A5 R5:
(SEQ ID NO: 45)
TTCTCTGCCAGGATGGAGTCAGACAG

Human 187A5 F13:
(SEQ ID NO: 46)
ACTGGCAGTTCGACATCACTCACCTG

Human 187A5 R4:
(SEQ ID NO: 47)
GAGGAATTCCAGTACAAGGAAGGCATCTGGGCAGG

As a result of sequence determination, a protein encoding this human gene exhibited a high homology to the mouse 187A5 protein over the whole region and had 77% amino acid identity and 87% amino acid homology. Therefore, this gene is thought to be a human 187A5 homologous gene (SEQ ID NO: 1).

Example 2

Expression Analysis by In Situ Hybridization of 187A5 Gene

In order to investigate the expression pattern of the 187A5 gene in detail in the cells of dopaminergic neuron lineage, expression analysis of mRNAs of 187A5 and Lrp4 was performed by in situ hybridization according to the following protocol.

First, a DIG-probe was produced by the following method.

From a 12.5-day mouse (obtained from SLC) embryo, the mesencephalon metencephalon region was cut out. The total RNA was prepared by using the RNeasy mini kit (Qiagen), and double-strand cDNA was synthesized by using the cDNA synthesis kit (TAKARA). Next, by using the synthesized cDNA as a template, cDNAs of 187A5 and Lrp4 were amplified in the following reaction system.

| | |
|---|---|
| 10 × ExTaq | 5 µl |
| 2.5 mM dNTP | 4 µl |
| ExTaq | 0.25 µl |
| 100 µM primer | 0.5 µl for each |
| cDNA | 1 µl |
| DMSO | 1.5 µl |
| Distilled water | 37.25 µl |

The amplification was carried out under the conditions that incubation was performed for 5 minutes at 94° C., then reactions for 30 seconds at 94° C., for 30 seconds at 65° C. and for 2 minutes at 72° C. were performed at 35 cycles, and finally, incubation was performed for 2 minutes at 72° C.

The following primers were used in the PCR.

187A5:
AGCTGAGCCACCTTCTCAGTCCAGAC (SEQ ID NO: 48)

CCACGTCCAGGTCTTGACAAACCCAC (SEQ ID NO: 49)

Lrp4:
GACAGTGAACCTTTGGTCACTGATGG (SEQ ID NO: 50)

GCCTTCCTGTCCTGGGATCAGCTTGG (SEQ ID NO: 51)

The amplified cDNA fragments were cloned into pCRII (Invitrogen) and used as templates, and thereby, DIG-probes were synthesized in the following reaction system (all of the reagents were purchased from Roche).

| | |
|---|---|
| RNA Polymerase Buffer | 2 µl |
| NTP Labeling Mix | 2 µl |
| RNase Inhibitor | 1 µl |
| RNA polymerase (T7 or SP6) | 2 µl |
| Template DNA | 1 µg |
| Distilled water Total | 20 µl |

After 2 hours at 37° C., DNaseI (Roche) treatment was performed for 15 minutes at 37° C., and the DIG-RNA probe was collected by ethanol precipitation.

Next, a 12.5-day mouse embryo was excised and fixed for 2 hours at 4° C. by using 4% PFA (WAKO)/PBS. Then, the solution was replaced at 4° C. overnight by 20% sucrose (WAKO)/PBS, and then, the embryo was embedded with OCT (Sakura Seiki Co., Ltd.). Sections of 12 µm thickness were prepared, dried on slide glasses, and then fixed again for 30 minutes at room temperature by using 4% PFA. After rinsing with PBS, hybridization (1 µg/ml DIG-RNA probe, 50% formamide (Nacalai Tesque, Inc.), 5×SSC, 1% SDS, 50 µg/ml yeast RNA (Sigma), 50 µg/ml heparin) was performed for 40 hours at 68° C. Then, rinsing (50% formamide, 5×SSC, 1% SDS) was performed at 68° C., and further rinsing (50% formamide, 5×SSC) was performed at 68° C. After rinsing with 1×TBST at room temperature, blocking (blocking agent: Roche) was performed. An alkaline phosphatase-labeled anti-DIG antibody (DAKO) was reacted therewith at 4° C. overnight, and after rinsing (1×TBST, 2 mM levamisole), NBT/BCIP (DAKO) was used as the substrate for coloring.

Figure 4:
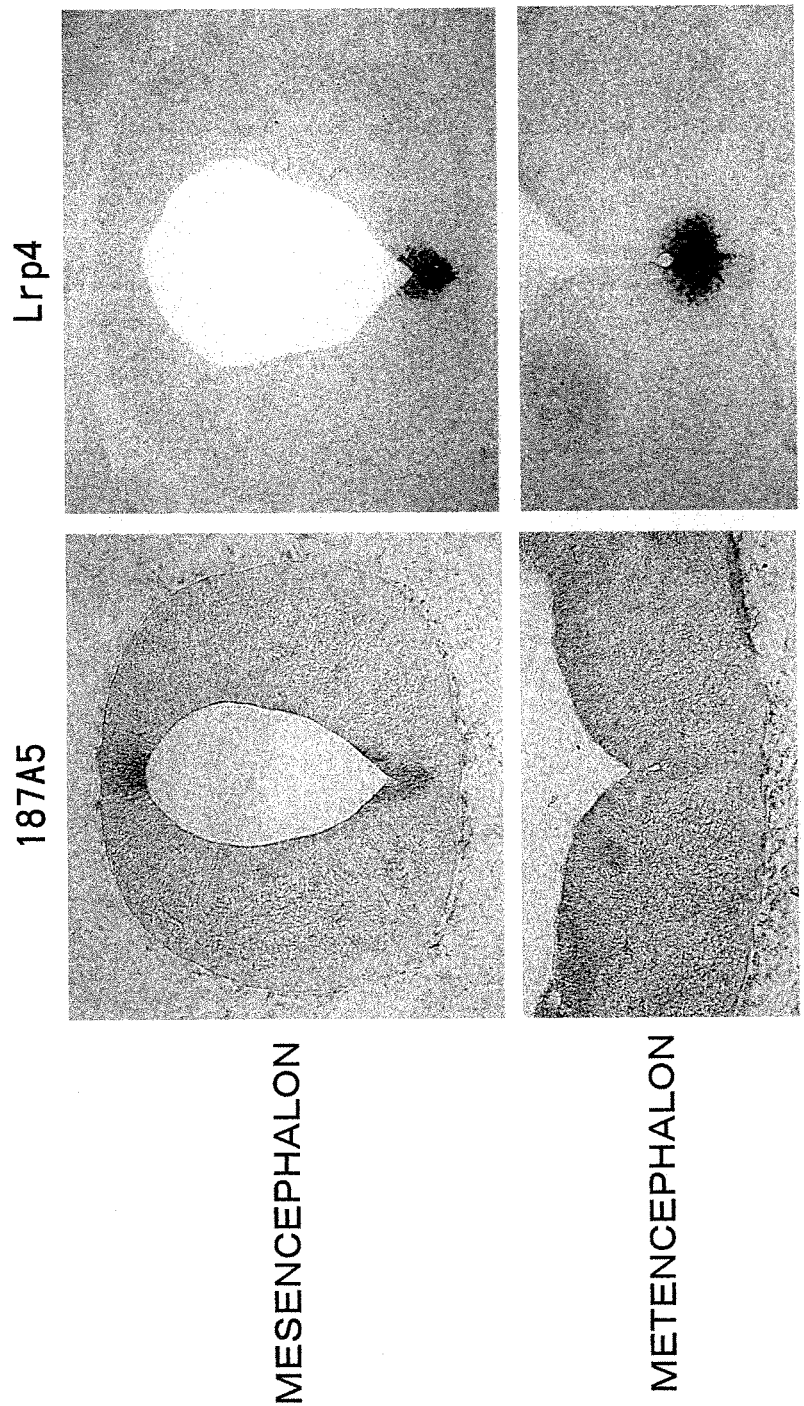
FIG. 4 shows the results of analyzing, by in situ hybridization, mRNA expressions of 187A5 and Lrp4 in the mesencephalon and metencephalon of a 12.5-day mouse embryo.

As a result, in the 12.5-day mouse embryo which is in the period of generating dopaminergic neurons, it became revealed that mRNA of 187A5 is selectively expressed in the mesencephalon most ventral ventricular zone (ventricular zone: VZ) in which the Lrp4-positive dopaminergic neuron progenitor cells exist and the mesencephalon most dorsal roof plate region (FIG. 4). On the other hand, the expression was not recognized in the metencephalon ventral region. Therefore, it was confirmed that mRNA of 187A5 is not expressed in the metencephalon floor plate cells positive for Lrp4.

From the above-described results, it became revealed that mRNA of 187A5 is selectively expressed in the dopaminergic neuron proliferative progenitor cells. Cells simultaneously expressing both of the Lrp4 and 187A5 genes are limited to the dopaminergic neuron proliferative progenitor cells that exist in the mesencephalon most ventral ventricular zone. Therefore, it is thought that the dopaminergic neuron proliferative progenitor cells can be discriminated with higher accuracy by using these markers in combination.

Example 3

Expression of 187A5 Gene in Dopaminergic Neurons Induced to Differentiate from ES Cells Whether or not the 187A5 gene is expressed when ES cells are induced to differentiate into dopaminergic neurons in vitro was studied.

First, according to the SDIA method (Kawasaki et al. Neuron. 2000 October; 28 (1): 31-40), ES cells (mouse-derived CCE strain provided from Mr. Nishikawa in Riken CDB, Kawasaki et al. Neuron. 2000 28 (1): 31-40.) were induced to differentiate into dopaminergic neurons. Lrp4-positive and Lrp4-negative cells were separated from the cells in the sixth day after the induction (Example 5 of WO 2004/065599), and the total RNA was prepared from the cells immediately after the separation. By using this total RNA as a template, cDNA was synthesized and amplified.

Moreover, according to the 5-stage method (Lee et al. (2000) Nat. Biotech. 18: 675-679, mouse dopaminergic neuron differentiation kit (R & D Systems)), ES cells (CCE) were induced to differentiate into dopaminergic neurons. Lrp4-positive and Lrp4-negative cells were separated from the cells in the seventh day of stage 4 (Example 8 of WO 2004/065599), and the total RNA was prepared from the cells immediately after the separation. By using this total RNA as a template, cDNA was synthesized and amplified.

Next, by using the cDNAs corresponding to the amplified cDNA of 4 ng, 0.4 ng and 0.04 ng as templates, PCR was performed in the following reaction system.

| | |
|---|---|
| 10 × ExTaq | 1 µl |
| 2.5 mM dNTP | 0.8 µl |
| ExTaq | 0.05 µl |
| 100 µM primer | 0.1 µl for each |
| cDNA | 1 µl |
| DMSO | 0.3 µl |
| Distilled water | 6.65 µl |

After incubation for 2 minutes at 94° C., the amplification reactions were performed for 30 seconds at 94° C., for 30 seconds at 65° C. and for 2 minutes at 72° C., and finally, incubation was performed for 2 minutes at 72° C. The amplifications of PCR were performed at 26 cycles.

The following primers were used in the PCR.

```
Lmx1a:
TGGTTCAGGTGTGGTTCCAGAACCAG    (SEQ ID NO: 33)

TCTGAGGTTGCCAGGAAGCAGTCTCC    (SEQ ID NO: 52)
```

In addition, for Lrp4 and 187A5, the primers of Example 1 were used.

Figure 5:
FIG. 5 shows the results of analyzing, by a RT-PCR method, mRNA expressions of 187A5, Lmx1a and Lrp4 in dopaminergic neuron proliferative progenitor cells induced to differentiate from ES cells by an SDIA method.
Figure 6:
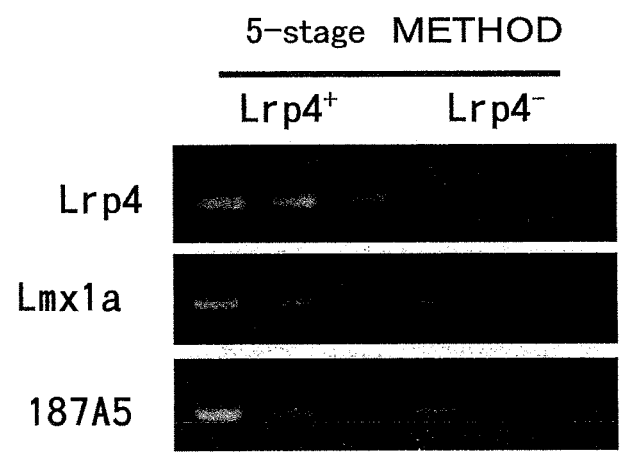
FIG. 6 shows the results of analyzing, by a RT-PCR method, mRNA expressions of 187A5, Lmx1a and Lrp4 in dopaminergic neuron progenitor cells induced to differentiate from ES cells by a 5-stage method.

As a result, it was confirmed that the 187A5 gene is expressed in the differentiation induction by any of the methods, and strongly expressed, particularly, in the Lrp4-positive cells (FIGS. 5 and 6). Therefore, it became revealed that mRNA of 187A5 is expressed in the dopaminergic neuron progenitor cells not only in the cells derived from the mouse and rat embryonic mesencephalons but also in the cells induced to differentiate by any of the SDIA method and the 5-stage method. Specifically, it became revealed that the 187A5 gene serves as a useful marker for discriminating not only the dopaminergic neuron progenitor cells derived from the embryonic mesencephalon but also the dopaminergic neuron progenitor cells induced to differentiate from ES cells in vitro.

Example 4

Expression of 187A5 Protein on Cell Surface

In the 187A5 protein, a sequence that is thought to be a transmembrane region exists at one site. If the 187A5 protein is expressed on the cell surface, 187A5-positive live cells can be separated by flow cytometry using an antibody capable of binding to the 187A5 protein and are expected to be useful in preparation of a transplant material for the Parkinson's disease or the like. Therefore, the intracellular localization of the 187A5 protein was studied.

(1) Analysis of Signal Sequence

In the case of a type I transmembrane protein, a signal sequence generally exists in the neighborhood of the N-terminal and is cleaved off immediately after the signal sequence, and thereby, the protein can be expressed on the membrane. As a result of computer search (PSORT II, http://psort.ims.u-tokyo.ac.jp/form2.html), a sequence that is predicted to be a signal sequence was not found in the mouse 187A5 gene. On the other hand, a signal sequence-like sequence existed in the neighborhood of the N-terminal of the human 187A5 gene. Therefore, whether a functional signal sequence exists in the 187A5 gene was studied.

A construct in which a region encoding the amino acids from the N-terminal to amino acid 45 in mouse cDNA was linked to signal sequence-deficient secreted alkaline phosphatase cDNA was prepared and transfected into 293E cells. A culture supernatant in the fourth day of culture was collected, and alkaline phosphatase activity was measured by using the Aurora kit (ICN) (FIG. 7).

As a result, when signal sequence-deficient secreted alkaline phosphatase (control) is expressed, this protein is not secreted. Therefore, alkaline phosphatase activity is not recognized in the supernatant. By contrast, in the case of the fusion protein in which the N-terminal sequence was linked, strong activity was recognized in the supernatant. Therefore, it became revealed that the fusion protein is efficiently secreted by the N-terminal sequence of 187A5 (FIG. 8). Therefore, it became revealed that a functional signal sequence exists in the neighborhood of the N-terminal of 187A5. This indicates that the 187A5 protein is a type I single transmembrane molecule.

(2) Expression of 187A5 on Cell Surface (Biotinylation Method)

In order to confirm whether or not the 187A5 protein is expressed on the cell surface, whether the 187A5 protein is biotinylated when only proteins on the cell surface are biotin-labeled was studied.

A construct in which an HA tag was added to the C-terminal of 187A5 was transfected into NS20Y cells. After 2 days, the cells were rinsed with cold PBS twice, and then, 5 ml of 0.5 mg/ml EZ-link Sulfo-NHS-SS-Biotin (PIERCE) (dissolved in PBS+1 mM $CaCl_2$, 0.5 mM $MgCl_2$) was added thereto. The reaction was performed for 30 minutes at room temperature. After rinsing with cold PBS twice, the cells were collected, then suspended in 600 µl of a dissolution buffer (1% SDS, 10 mM Tris-Cl, 100 mM NaCl, 1 mM EDTA), and subjected to ultrasonication. After centrifugation for 3 minutes at 14000 rpm, the supernatant was collected. 20 µl of streptavidin beads (PIERCE) was added thereto, and after rotation for 1 hour at room temperature, rinsing was performed with a dissolution buffer twice. To the beads, 75 µl of SDS-PAGE sample buffer was added, and after 3 minutes at 100° C., the bound proteins were collected by centrifugation. The 187A5 protein was detected by western blotting using an anti-HA antibody (Roche).

Figure 9:
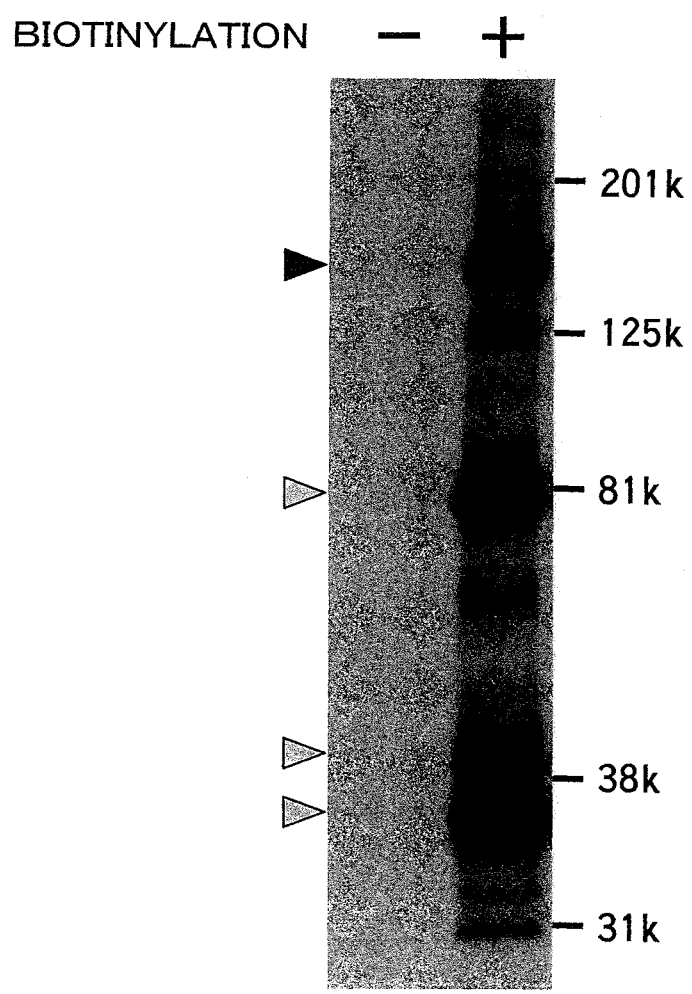
FIG. 9 shows the results of analyzing expression of a 187A5 protein on the cell surface by a biotinylation method of cell surface proteins.

As a result, it became revealed that the 187A5 protein is biotinylated with high efficiency (FIG. 9). Therefore, it is thought that the 187A5 protein is expressed on the cell surface.

(3) Expression of 187A5 on Cell Surface (FACS Analysis)

Whether the 187A5 protein can be detected by a FACS method was studied. A construct in which cDNA encoding the C-terminal side from the predicted cleavage site (amino acid 39) of 187A5 was linked immediately after a signal sequence of Preprotrypsin and a sequence encoding a FLAG tag was prepared. By expressing this construct, 187A5 in which the FLAG tag is added to the N-terminal can be expressed after the cleavage of the signal sequence. This construct was stably introduced into B300.19 cells through retrovirus vectors. The parent cells and transformants were rinsed with a FACS buffer (PBS+1% fetal bovine serum (JRH)+1 mM EDTA). Then, reaction with 10 µg/ml anti-FLAG antibody (SIGMA) was performed for 30 minutes on ice, and rinsing was performed with a FACS buffer. Sequentially, reaction with a PE-labeled anti-mouse IgG antibody (Jackson) (diluted to 1/200) was performed for 30 minutes on ice, and rinsing was performed with a FACS buffer. After staining, analysis was performed by flow cytometry (FACS calibur, Becton Dickinson).

Figure 10:
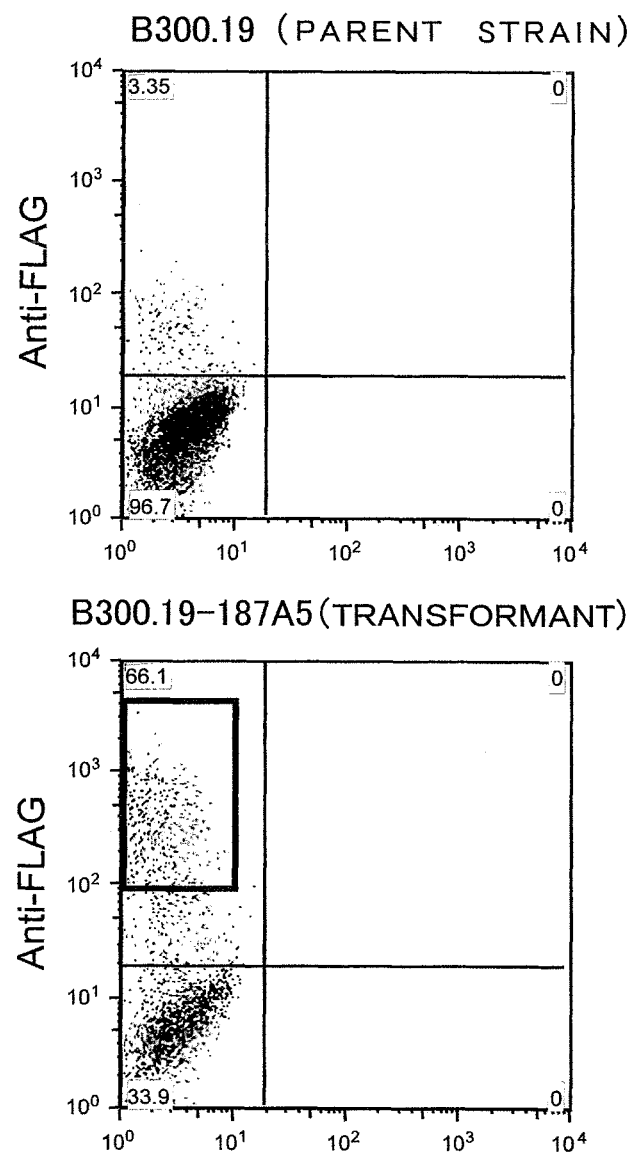
FIG. 10 shows the results of investigating expression of a 187A5 protein on the cell surface by FACS analysis. In the drawing, a boxed area represents 187A5-expressing cells.

As a result, unlike the parent strains, a population that strongly reacts with the FLAG antibody was detected in the stable transformants (FIG. 10). Therefore, it became revealed that 187A5 is expressed on the cell surface in a direction wherein the N-terminal side thereof can be located in the extracellular space, and can be detected by FACS using an antibody. Specifically, it is thought that 187A5 is useful as a marker for separating dopaminergic neuron progenitor cells as live cells.

Example 5

Expression Analysis of 187A5 Protein

By using a gene sequence encoding the extracellular region in the 187A5 gene, an anti-187A5 antibody was produced according to the following protocol, and expression analysis was performed by immunohistologic staining.

First, a gene sequence encoding the extracellular region (amino acids 1 to 919 of SEQ ID NO: 15) in the mouse 187A5 gene was gene-transfected into 293E cells, and the extracellular region of the 187A5 protein was expressed and collected. A rat was immunized with the collected protein, and then, lymphocytic cells were extracted and cell-fused with myeloma cells. From the fused cell population, a clone capable of reacting with 187A5 was selected. An anti-187A5 monoclonal antibody was purified from a culture supernatant of this clone. Next, an 11.5-day mouse embryo was fixed for 2 hours at 4° C. by using 4% PFA/PBS (−). Then, the solution was replaced at 4° C. overnight by 20% sucrose/PBS (−), and then, the embryo was embedded with OCT. Sections of 12 µm thickness were prepared, mounted on slide glasses, then dried for 30 minutes at room temperature, and moistened again with PBS (−). Then, blocking (25% Blockace (Dainippon Sumitomo Pharma Co., Ltd.)) was performed for 30 minutes at room temperature. The prepared anti-187A5 monoclonal antibody (culture supernatant diluted 2-fold, 2.5% Blockace/PBS) was reacted therewith for 2.5 hours at room temperature, and then, rinsing was performed for 10 minutes at room temperature four times by using 0.01% Triton X-100/PBS (−). A Cy3-labeled anti-rat IgG antibody (Jackson, 10 µg/ml, 2.5% Blockace/PBS) was reacted therewith for 1 hour at room temperature, and rinsing was performed in the same manner. Then, rinsing with PBS (−) was performed for 5 minutes at room temperature, and sealing was performed.

Figure 11:
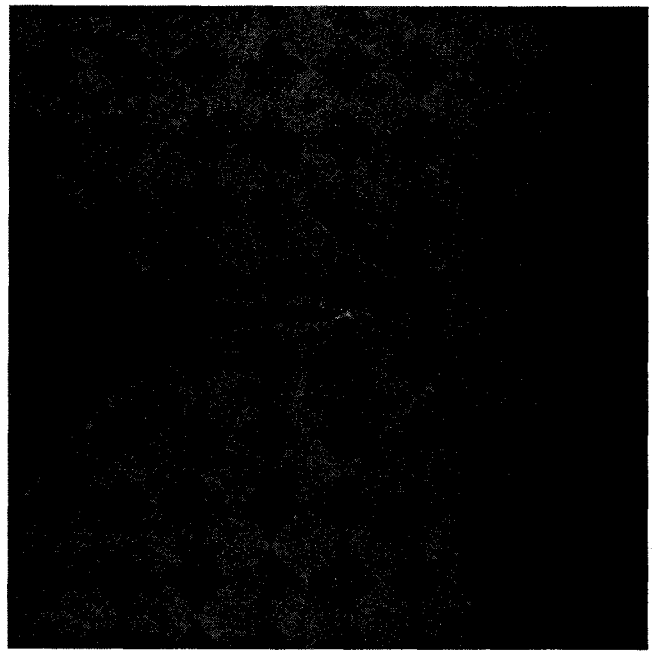
FIG. 11 shows the results of analyzing, by an immunostaining method, expression of a 187A5 protein in the mesencephalon and metencephalon ventral regions of an 11.5-day mouse embryo.
Figure 11:
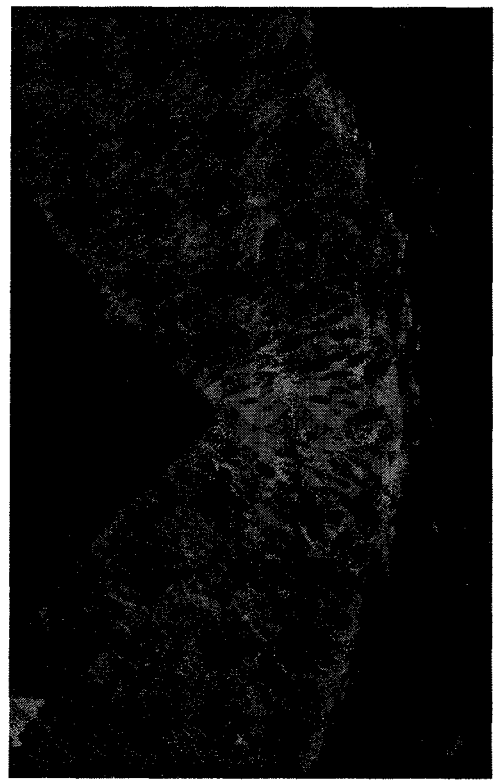

As a result of expression analysis by immunohistologic staining using the prepared anti-187A5 monoclonal antibody, as with the results of Example 2, the existence of the 187A5 protein was recognized in the mesencephalon ventral region of E11.5 which is in the period of generating dopaminergic neurons, and was not recognized in the metencephalon ventral region in which dopaminergic neurons are not generated (FIG. 11).

From these results, it was confirmed that the 187A5 protein exists in dopaminergic neuron progenitor cells.

Example 6

Detection of Cell in which 187A5 Protein Exists

By using the anti-187A5 monoclonal antibody prepared in Example 5, cells in which the 187A5 protein exists were detected by flow cytometry.

First, the mesencephalon and metencephalon ventral regions of a mouse E12.5 embryo were dispersed by using the cell dissociation buffer (Invitrogen), and then, without being subjected to fixation and permeabilization treatments, the cells were stained for 20 minutes at 4° C. by using the anti-187A5 monoclonal antibody (purified antibody diluted to 1/10, 1% fetal bovine serum, 1 mM EDTA/PBS) and an anti-Lrp4 antibody (culture supernatant diluted to 1/2, 1% fetal bovine serum, 1 mM EDTA/PBS). Then, by using 1% fetal bovine serum and 1 mM EDTA/PBS−, rinsing was performed for 3 minutes at 4° C. three times. The cells were stained for 20 minutes at 4° C. by using a biotin-labeled anti-Armenian hamster IgG antibody (Jackson, 10 µg/ml, 1% fetal bovine serum, 1 mM EDTA/PBS), and rinsing was performed in the same manner. Then, the cells were stained for 20 minutes at 4° C. by using APC-labeled streptavidin (Pharmingen, 8 µg/ml, 1% fetal bovine serum, 1 mM EDTA/PBS) and a PE-labeled anti-rat IgG antibody (Jackson, 20 µg/ml, 1% fetal bovine serum, 1 mM EDTA/PBS), and rinsing was performed in the same manner. After the staining, detection was performed by using a flow cytometer.

Figure 12:
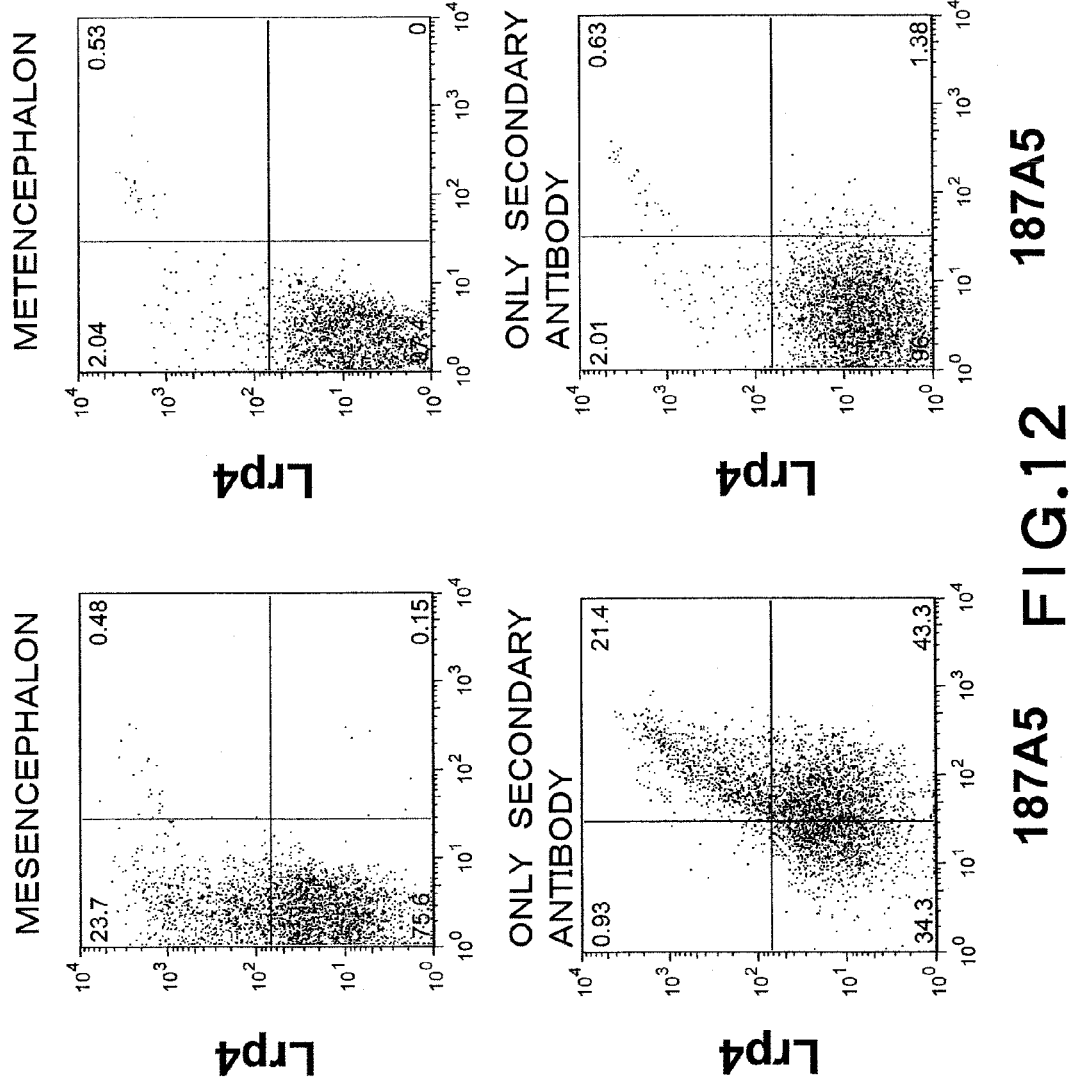
FIG. 12 shows the results of investigating, by FACS analysis, expressions of 187A5 and Lrp4 proteins in the mesencephalon and metencephalon ventral regions of a 12.5-day mouse embryo.

As a result of flow cytometry by using the prepared anti-187A5 monoclonal antibody, a cell population in which the 187A5 protein exists was detected (FIG. 12). Here, the cells in which the 187A5 protein exists can be detected without being subjected to fixation and permeabilization treatments. Therefore, it was suggested that the cells in which the 187A5 protein exists can be separated as live cells by using a flow cytometer equipped with a cell sorter. Moreover, it was confirmed that the 187A5 protein exists in all of the mesencephalon Lrp4-positive cells, namely, the dopaminergic neuron progenitor cells. On the other hand, it was confirmed that the 187A5 protein does not exist in the metencephalon Lrp4-positive cells which do not contain dopaminergic neuron progenitor cells (FIG. 12).

From these results, it was shown that the 187A5 antibody is useful for separating dopaminergic neuron progenitor cells.

Example 7

Expression of 187A5 Protein in Dopaminergic Neurons Induced to Differentiate from ES Cells The group of the cells containing the dopaminergic neuron progenitor cells induced to differentiate from ES cells in vitro by the SDIA method was dispersed by using the cell dissociation buffer (Invitrogen), and then, without being subjected to fixation and permeabilization treatments, the cells were stained for 20 minutes at 4° C. by using the anti-187A5 monoclonal antibody (purified antibody diluted to 1/10, 10% knockout serum replacement, 1% fetal bovine serum, 1 mM EDTA/SDIA differentiation medium) prepared in Example 5 and an anti-Lrp4 antibody (culture supernatant diluted to 1/2, 10% knockout serum replacement, 1% fetal bovine serum, 1 mM EDTA/SDIA differentiation medium). Then, by using 10% knockout serum replacement, 1% fetal bovine serum and 1 mM EDTA/SDIA differentiation medium, rinsing was performed for 3 minutes at 4° C. three times. The cells were stained for 20 minutes at 4° C. by using a biotin-labeled anti-Armenian hamster IgG antibody (Jackson, 10 µg/ml, 10% knockout serum replacement, 1% fetal bovine serum, 1 mM EDTA/SDIA differentiation medium), and rinsing was performed in the same manner. Then, the cells were stained for 20 minutes at 4° C. by using APC-labeled streptavidin (Pharmingen, 8 µg/ml, 10% knockout serum replacement, 1% fetal bovine serum, 1 mM EDTA/SDIA differentiation medium) and a PE-labeled anti-rat IgG antibody (Jackson, 20 µg/ml, 10% knockout serum replacement, 1% fetal bovine serum, 1 mM EDTA/SDIA differentiation medium), and rinsing was performed in the same manner. After the staining, 187A5- and Lrp4-expressing cells were detected by using a flow cytometer.

Figure 13:
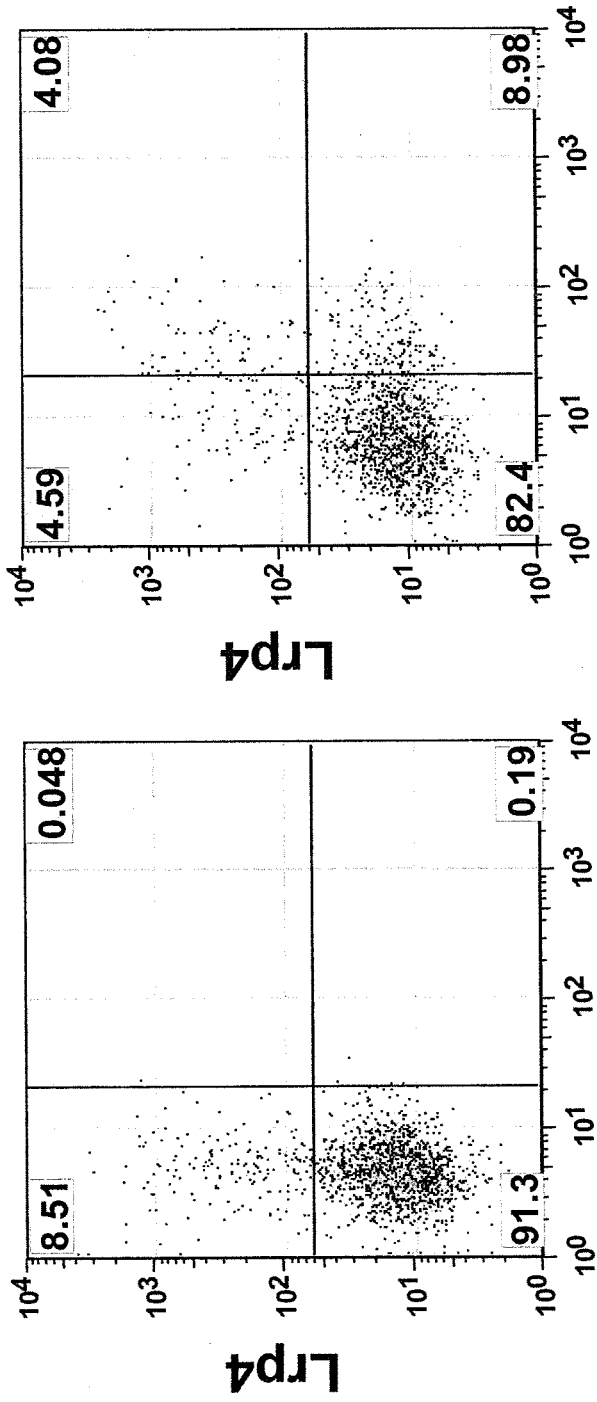
FIG. 13 shows the results of investigating, by FACS analysis, expressions of 187A5 and Lrp4 proteins in dopaminergic neuron proliferative progenitor cells induced to differentiate from ES cells by an SDIA method.

As a result of flow cytometry, a cell population in which the 187A5 and Lrp4 proteins exist was detected in the same manner as the mouse embryonic mesencephalon (FIG. 13).

From these results, it was shown that the 187A5 antibody is also useful for separating dopaminergic neuron progenitor cells derived from ES cells.

Example 8

Separation of Lrp4-Expressing Cell by Using Antibody

In order to confirm that the separated 187A5/Lrp4-copositive cells differentiate into dopaminergic neurons, the following experiment was performed by using Nurr1, a postmitotic dopaminergic neuron precursor cell marker.

The cells separated after being induced to differentiate from ES cells in vitro by the SDIA method were inoculated onto a slide glass coated with poly-L-ornithine (Sigma, 0.002% in PBS), laminin (Invitrogen, 2.5 µg/ml in PBS) and fibronectin (Sigma, 5 µg/ml in PBS), and cultured for 6 days at 37° C. in N2 (Invitrogen, 1×), B27 (Invitrogen, 1×), ascorbic acid (Sigma, 200 uM) BDNF (Invitrogen, 20 ng/ml) and 10% knockout serum replacement (Invitrogen)/SDIA differentiation medium. The cultured cells were fixed for 20 minutes at 4° C. by using 2% PFA/PBS, and rinsing with PBS was performed for 10 minutes at 4° C. twice. Then, permeabilization treatment with 0.3% Triton X-100/PBS was performed for 30 minutes at room temperature, and blocking was performed for 20 minutes at room temperature with 10% normal donkey serum/Blockace. Sequentially, reaction with an anti-Nurr1 antibody (in house culture supernatant diluted to 1/1000, 10% normal donkey serum, 2.5% Blockace, 0.1% Triton X-100/PBS) and an anti-HuC/D antibody (Molecular Probe, 1/50, 4 µg/ml, 10% normal donkey serum, 2.5% Blockace, 0.1% Triton X-100/PBS) was performed for 1 hour at room temperature, and sequentially, the reaction was performed overnight at 4° C. On the next day, by using 0.1% Triton X-100/PBS, rinsing was performed for 10 minutes at room temperature four times. Then, reaction with an FITC-labeled anti-mouse IgG antibody and a Cy3-labeled anti-rat IgG antibody (all Jackson, 3 µg/ml, 10% normal donkey serum, 2.5% Blockace, 0.1% Triton X-100/PBS) was performed for 1 hour at room temperature. Then, rinsing was performed in the same manner, and rinsing with PBS was performed for 5 minutes at room temperature. After sealing, the cells were observed.

Figure 14:
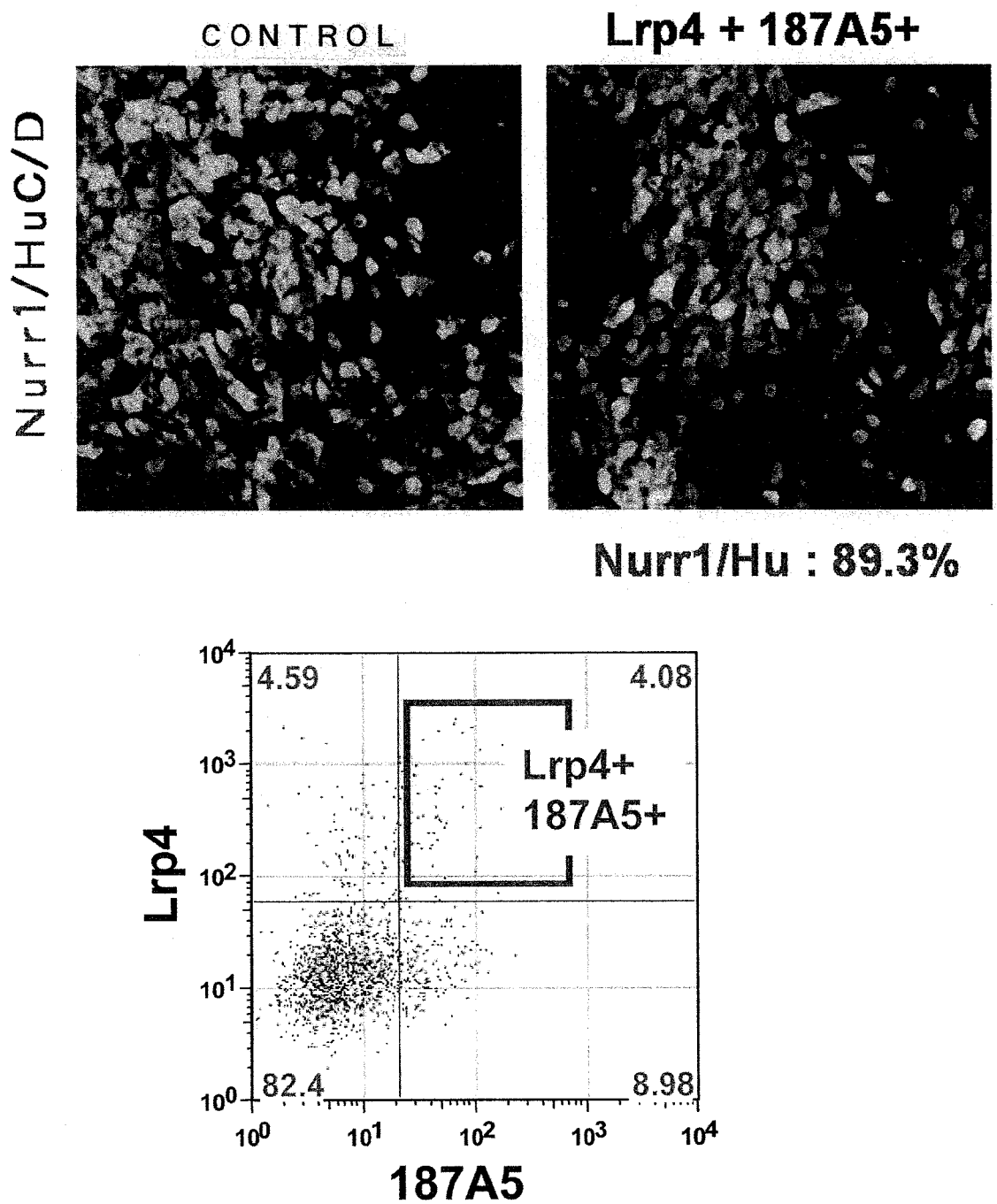
FIG. 14 shows the results of separating 187A5/Lrp4-copositive cells induced to differentiate from ES cells by an SDIA method, and culturing.

As a result of culturing the cells separated by flow cytometry for 6 days in vitro, evidently many Nurr1-positive dopaminergic neurons were induced, compared to unseparated cells as controls (FIG. 14).

From these results, it became revealed that the 187A5/Lrp4-copositive cells were certainly progenitor cells of dopaminergic neuron lineage and can be matured in vitro.

What is claimed is:

1. A method for detecting or selecting a dopaminergic neuron progenitor cell, comprising the step of detecting expression of a polynucleotide selected from the following (i), (ii), (iii) and (iv):
   (i) a polynucleotide comprising the nucleotide sequence of SEQ ID NO: 1;
   (ii) a polynucleotide encoding a protein which consists of an amino acid sequence encoded by a nucleotide sequence of SEQ ID NO: 1 in which one or more nucleotides are inserted, substituted and/or deleted, and/or one or more nucleotides are added to one or both of ends;
   (iii) a polynucleotide which hybridizes under rinsing conditions of 0.2 or 2×SSC, 0.1% SDS, and a temperature of 20° C. to 68° C. to a polynucleotide consisting of the complementary sequence of nucleotide sequence of SEQ ID NO: 1; and
   (iv) a polynucleotide which has 70% or more identity with a polynucleotide consisting of the nucleotide sequence of SEQ ID NO: 1;
   or the step of detecting a protein selected from the following (v), (vi), (vii) and (viii):
   (v) a protein comprising the amino acid sequence of SEQ ID NO: 2;
   (vi) a protein which consists of an amino acid sequence of SEQ ID NO: 2 in which one or more amino acids are inserted, substituted and/or deleted, and/or one or more amino acids are added to one or both of ends;
   (vii) a protein which is encoded by a polynucleotide which hybridizes under rinsing conditions of 0.2 or 2×SSC, 0.1% SDS, and a temperature of 20° C. to 68° C. to a polynucleotide consisting of a complementary sequence of a nucleotide sequence of a polynucleotide encoding the amino acid sequence of SEQ ID NO: 2; and
   (viii) a protein which consists of an amino acid sequence having 70% or more identity with the amino acid sequence of SEQ ID NO: 2.

2. The method according to claim 1, wherein the dopaminergic neuron progenitor cell is a dopaminergic neuron proliferative progenitor cell.

3. The method according to claim 1, wherein the step of detecting the protein further comprises the following steps of:
   (a) contacting a cell sample to be tested, with an antibody which binds to a protein selected from the (v), (vi), (vii) and (viii) of claim 1; and
   (b) detecting the presence or absence of reactivity.

4. The method according to claim 1, wherein the step of detecting the protein comprises the following steps of:
   (a) contacting the protein derived from a cell sample to be tested, with an antibody which binds to a protein selected from the (v), (vi), (vii) and (viii) of claim 1; and
   (b) detecting an antigen-antibody complex.

* * * * *

SEQUENCE LISTING

```
<160> NUMBER OF SEQ ID NOS: 52

<210> SEQ ID NO 1
<211> LENGTH: 3402
<212> TYPE: DNA
<213> ORGANISM: Homo sapiens
<220> FEATURE:
<221> NAME/KEY: CDS
<222> LOCATION: (31)..(3357)
<223> OTHER INFORMATION:

<400> SEQUENCE: 1
ggcgggctgc gtgagcggcc gggacgcagg atg cgc tcc gag ggt gcg gcc ccc        54
                                 Met Arg Ser Glu Gly Ala Ala Pro
                                  1               5 ggg ccg gcg gcg ccg ctg tgc ggg gcg ctg agc ctg ctg ctg ggc gcg       102
Gly Pro Ala Ala Pro Leu Cys Gly Ala Leu Ser Leu Leu Leu Gly Ala
         10                  15                  20 ctg ctg ggc aaa gtg ata gag ggt cac ggg gtc aca gac aac ata cag       150
Leu Leu Gly Lys Val Ile Glu Gly His Gly Val Thr Asp Asn Ile Gln
 25                  30                  35                  40 aga ttc tcc tca ctg cca cct tac cta cct gtg agc tac cac atc ctc       198
Arg Phe Ser Ser Leu Pro Pro Tyr Leu Pro Val Ser Tyr His Ile Leu
                 45                  50                  55
```

| | | |
|---|---|---|
| aga gca gag acc tcc ttc ttc ctc aag gaa gcc aac cag gac ctg ctg<br>Arg Ala Glu Thr Ser Phe Phe Leu Lys Glu Ala Asn Gln Asp Leu Leu<br>             60                      65                70 | | 246 |
| cgg aac tcc agc ctg cag gcg agg gtg gag tcc ttc ttt acc tac aaa<br>Arg Asn Ser Ser Leu Gln Ala Arg Val Glu Ser Phe Phe Thr Tyr Lys<br>    75                   80                   85 | | 294 |
| acc agg cag ccc cca gtg ctc aat gcc agc tat gga ccc ttt tct gtg<br>Thr Arg Gln Pro Pro Val Leu Asn Ala Ser Tyr Gly Pro Phe Ser Val<br> 90                   95                  100 | | 342 |
| gag aag gtt gtg cct ctg gac ttg atg ttg act tca aac ttt tta ggt<br>Glu Lys Val Val Pro Leu Asp Leu Met Leu Thr Ser Asn Phe Leu Gly<br>105                  110                115             120 | | 390 |
| cca acc aat aag ttt agt ttt gat tgg aaa cta aaa gcc cac atc ctg<br>Pro Thr Asn Lys Phe Ser Phe Asp Trp Lys Leu Lys Ala His Ile Leu<br>                    125                130             135 | | 438 |
| cgg gac aaa gtc tac ctg agc cgg ccc aaa gtg cag gtt ctt ttc cac<br>Arg Asp Lys Val Tyr Leu Ser Arg Pro Lys Val Gln Val Leu Phe His<br>             140                   145             150 | | 486 |
| atc atg ggc aga gac tgg gat gac cgc ggc gcc ggg gag aag ctg cca<br>Ile Met Gly Arg Asp Trp Asp Asp Arg Gly Ala Gly Glu Lys Leu Pro<br>        155                  160             165 | | 534 |
| tgc ctg agg gtc ttt gct ttc cga gaa acc aga gag gtg cgg ggc agc<br>Cys Leu Arg Val Phe Ala Phe Arg Glu Thr Arg Glu Val Arg Gly Ser<br>170                  175                180 | | 582 |
| tgc cgg ctg aag ggg gac ctg ggg ctg tgt gtg gct gag ctg gag ctc<br>Cys Arg Leu Lys Gly Asp Leu Gly Leu Cys Val Ala Glu Leu Glu Leu<br>185                  190              195             200 | | 630 |
| ctg tcc agc tgg ttc agt gcc ccg acg gtg ggt gcc ggg agg aag aag<br>Leu Ser Ser Trp Phe Ser Ala Pro Thr Val Gly Ala Gly Arg Lys Lys<br>             205                   210             215 | | 678 |
| tcc atg gac cag ccg gag ggg acc cct gtg gag ctc tac tac acc gtg<br>Ser Met Asp Gln Pro Glu Gly Thr Pro Val Glu Leu Tyr Tyr Thr Val<br>        220                  225             230 | | 726 |
| cac cca gga aac gag cga ggg gac tgt gcc ggg ggt gac ttc agg aag<br>His Pro Gly Asn Glu Arg Gly Asp Cys Ala Gly Gly Asp Phe Arg Lys<br>             235                  240            245 | | 774 |
| ggc aac gcc atc cgt cca gga aag gat ggg ctg gag gaa acc acg tcc<br>Gly Asn Ala Ile Arg Pro Gly Lys Asp Gly Leu Glu Glu Thr Thr Ser<br>      250                  255             260 | | 822 |
| cac ctg cag agg atc ggc acc gtc ggc ctt tac cgg gcc cag gac agc<br>His Leu Gln Arg Ile Gly Thr Val Gly Leu Tyr Arg Ala Gln Asp Ser<br>265                  270              275             280 | | 870 |
| gcc cag ctc agc gag ctc cgt ttg gat ggt aac gtg gtc atc tgg ctg<br>Ala Gln Leu Ser Glu Leu Arg Leu Asp Gly Asn Val Val Ile Trp Leu<br>             285                  290             295 | | 918 |
| cct tcc agg cca gtc aag cag gga gag gtg gtc acg gcc tat gtc acc<br>Pro Ser Arg Pro Val Lys Gln Gly Glu Val Val Thr Ala Tyr Val Thr<br>        300                  305             310 | | 966 |
| atc tcg agc aat tcc tct gtg gac ctc ttc atc ttg aga gcc aag gtg<br>Ile Ser Ser Asn Ser Ser Val Asp Leu Phe Ile Leu Arg Ala Lys Val<br>             315                  320            325 | | 1014 |
| aag aag ggg gtg aac atc ctg agt gct cag acc cgt gag ccc cgg cag<br>Lys Lys Gly Val Asn Ile Leu Ser Ala Gln Thr Arg Glu Pro Arg Gln<br>330                  335              340 | | 1062 |
| tgg ggc gtc aag cag gag gtg ggc agc ggc gga aag cac gtg acg gcc<br>Trp Gly Val Lys Gln Glu Val Gly Ser Gly Gly Lys His Val Thr Ala<br>345                  350              355             360 | | 1110 |
| acc gtg gcc tgc cag cgc ctg ggg ccc agc cca cgc aac agg agc agc<br>Thr Val Ala Cys Gln Arg Leu Gly Pro Ser Pro Arg Asn Arg Ser Ser<br>             365                  370             375 | | 1158 |

```
                                            -continued agt tta ttc aat gag gtt gtg cag atg aac ttt gaa ata gcc agt ttc      1206
Ser Leu Phe Asn Glu Val Val Gln Met Asn Phe Glu Ile Ala Ser Phe
        380                 385                 390 agc agc ctt tca ggg act cag ccc atc acg tgg cag gtg gag tac cca      1254
Ser Ser Leu Ser Gly Thr Gln Pro Ile Thr Trp Gln Val Glu Tyr Pro
    395                 400                 405 cgg aag ggg acc aca gac atc gcc gtg tcc gag atc ttt gtc agc cag      1302
Arg Lys Gly Thr Thr Asp Ile Ala Val Ser Glu Ile Phe Val Ser Gln
410                 415                 420 aag gac ctg gtg ggc atc gtt ccc ttg gct atg gac act gaa att ctg      1350
Lys Asp Leu Val Gly Ile Val Pro Leu Ala Met Asp Thr Glu Ile Leu
425                 430                 435                 440 aac acc gcc gta ctc aca gga aag aca gtt gcc atg cct atc aag gtg      1398
Asn Thr Ala Val Leu Thr Gly Lys Thr Val Ala Met Pro Ile Lys Val
            445                 450                 455 gtc tct gtg gag gag aac agt gcc gtg atg gac atc tca gag tcg gtg      1446
Val Ser Val Glu Glu Asn Ser Ala Val Met Asp Ile Ser Glu Ser Val
        460                 465                 470 gag tgc aag tcc aca gac gag gac gtt atc aaa gtg tct gag cgc tgt      1494
Glu Cys Lys Ser Thr Asp Glu Asp Val Ile Lys Val Ser Glu Arg Cys
    475                 480                 485 gac tac atc ttt gtc aat ggc aaa gag atc aaa gga aag atg gat gcg      1542
Asp Tyr Ile Phe Val Asn Gly Lys Glu Ile Lys Gly Lys Met Asp Ala
490                 495                 500 gtg gtg aac ttc aca tac cag tac ctg agc gcc ccc ctg tgt gtc acc      1590
Val Val Asn Phe Thr Tyr Gln Tyr Leu Ser Ala Pro Leu Cys Val Thr
505                 510                 515                 520 gtg tgg gtg ccc cgg ctg ccc ctg cag atc gag gtc tct gac acg gag      1638
Val Trp Val Pro Arg Leu Pro Leu Gln Ile Glu Val Ser Asp Thr Glu
            525                 530                 535 ctc agc cag ata aag ggc tgg agg gtc ccc att gtg acc aat aag agg      1686
Leu Ser Gln Ile Lys Gly Trp Arg Val Pro Ile Val Thr Asn Lys Arg
        540                 545                 550 ccc act cgt gag agc gag gat gag gac gag gag cgg cgg ggc cgg          1734
Pro Thr Arg Glu Ser Glu Asp Glu Asp Glu Glu Arg Arg Gly Arg
    555                 560                 565 ggc tgc gca ctg caa tac cag cac gcc acc gtg cgg gtc ctc acc cag      1782
Gly Cys Ala Leu Gln Tyr Gln His Ala Thr Val Arg Val Leu Thr Gln
570                 575                 580 ttt gtg tct gag ggc gcc ggt cca tgg ggc cag ccg aac tac ctg ctt      1830
Phe Val Ser Glu Gly Ala Gly Pro Trp Gly Gln Pro Asn Tyr Leu Leu
585                 590                 595                 600 agt cct aac tgg cag ttc gac atc act cac ctg gtg gca gac ttc atg      1878
Ser Pro Asn Trp Gln Phe Asp Ile Thr His Leu Val Ala Asp Phe Met
            605                 610                 615 aag ctg gag gaa cct cac gtg gcc acc ctc cag gac agc cgg gtc ctg      1926
Lys Leu Glu Glu Pro His Val Ala Thr Leu Gln Asp Ser Arg Val Leu
        620                 625                 630 gtt ggg cga gag gtt ggg atg acg acc atc cag gtg ttg tct cca ctg      1974
Val Gly Arg Glu Val Gly Met Thr Thr Ile Gln Val Leu Ser Pro Leu
    635                 640                 645 tct gac tcc atc ctg gca gag aag acg ata acc gtg cta gat gac aaa      2022
Ser Asp Ser Ile Leu Ala Glu Lys Thr Ile Thr Val Leu Asp Asp Lys
650                 655                 660 gtg tcg gtg aca gac ttg gcc atc cag ctc gtg gct ggg ctg tct gtc      2070
Val Ser Val Thr Asp Leu Ala Ile Gln Leu Val Ala Gly Leu Ser Val
665                 670                 675                 680 gcc ctt tac ccc aac gca gaa aac agc aag gcc gta aca gct gtg gtc      2118
Ala Leu Tyr Pro Asn Ala Glu Asn Ser Lys Ala Val Thr Ala Val Val
            685                 690                 695
```

```
aca gct gag gag gtg ctg cgg acc ccc aaa cag gag gct gta ttc agc      2166
Thr Ala Glu Glu Val Leu Arg Thr Pro Lys Gln Glu Ala Val Phe Ser
        700                 705                 710 acg tgg ctg cag ttc agt gat ggc tct gtg acg ccc ctg gac atc tac      2214
Thr Trp Leu Gln Phe Ser Asp Gly Ser Val Thr Pro Leu Asp Ile Tyr
        715                 720                 725 gac acc aag gac ttc tcc ctg gca gcc acc tcc cag gac gag gct gtc      2262
Asp Thr Lys Asp Phe Ser Leu Ala Ala Thr Ser Gln Asp Glu Ala Val
730                 735                 740 gtg tca gtc ccc cag ccc cgc tct ccc agg tgg ccc gtt gtg gtg gcc      2310
Val Ser Val Pro Gln Pro Arg Ser Pro Arg Trp Pro Val Val Val Ala
745                 750                 755                 760 gaa ggg gaa ggc cag ggc cca ctg atc cga gtg gac atg acg atc gcc      2358
Glu Gly Glu Gly Gln Gly Pro Leu Ile Arg Val Asp Met Thr Ile Ala
                765                 770                 775 gag gcc tgc cag aaa tct aaa cgc aag agc atc ctg gct gtg ggc gtc      2406
Glu Ala Cys Gln Lys Ser Lys Arg Lys Ser Ile Leu Ala Val Gly Val
            780                 785                 790 ggc aac gtc agg gtc aag ttc gga cag aac gat gct gac tcc agc ccc      2454
Gly Asn Val Arg Val Lys Phe Gly Gln Asn Asp Ala Asp Ser Ser Pro
        795                 800                 805 ggc agg gac tat gag gaa gat gag atc aag aac cac gcc agc gac cgc      2502
Gly Arg Asp Tyr Glu Glu Asp Glu Ile Lys Asn His Ala Ser Asp Arg
    810                 815                 820 cgg cag aag ggc cag cac cat gag cgc aca ggc cag gat ggg cac ctc      2550
Arg Gln Lys Gly Gln His His Glu Arg Thr Gly Gln Asp Gly His Leu
825                 830                 835                 840 tat ggc agc tct ccc gtg gag cgt gag gaa ggg gct ctc cga aga gcc      2598
Tyr Gly Ser Ser Pro Val Glu Arg Glu Glu Gly Ala Leu Arg Arg Ala
                845                 850                 855 act acc acg gcc agg tcc ctg ctg gac aac aaa gtg gtg aag aac agt      2646
Thr Thr Thr Ala Arg Ser Leu Leu Asp Asn Lys Val Val Lys Asn Ser
            860                 865                 870 cgg gca gac ggg ggc agg ctg gca gga gag ggg cag ctg cag aac atc      2694
Arg Ala Asp Gly Gly Arg Leu Ala Gly Glu Gly Gln Leu Gln Asn Ile
        875                 880                 885 ccc att gac ttc acc aac ttc cct gcc cac gtg gac ctc ccc aag gcc      2742
Pro Ile Asp Phe Thr Asn Phe Pro Ala His Val Asp Leu Pro Lys Ala
    890                 895                 900 ggg agt ggg ctg gag gaa aac gac ctg gtg cag act ccg cgg ggc ctg      2790
Gly Ser Gly Leu Glu Glu Asn Asp Leu Val Gln Thr Pro Arg Gly Leu
905                 910                 915                 920 agt gat ctg gag ata ggg atg tac gcc ctc ctg ggg gtg ttc tgc ctg      2838
Ser Asp Leu Glu Ile Gly Met Tyr Ala Leu Leu Gly Val Phe Cys Leu
                925                 930                 935 gcc atc ctc gtc ttc ctg atc aac tgc gcc acc ttt gcc ctg aag tac      2886
Ala Ile Leu Val Phe Leu Ile Asn Cys Ala Thr Phe Ala Leu Lys Tyr
            940                 945                 950 agg cac aag caa gtg ccc ctg gaa ggt cag gcc tcc atg acc cac tct      2934
Arg His Lys Gln Val Pro Leu Glu Gly Gln Ala Ser Met Thr His Ser
        955                 960                 965 cac gac tgg gtg tgg ctt ggc aat gag gcc gaa ctc ctg gag agc atg      2982
His Asp Trp Val Trp Leu Gly Asn Glu Ala Glu Leu Leu Glu Ser Met
    970                 975                 980 ggg gat gca ccg ccg ccc cag gac gag cac acc acc atc ata gac cgc      3030
Gly Asp Ala Pro Pro Pro Gln Asp Glu His Thr Thr Ile Ile Asp Arg
985                 990                 995                 1000 gga ccg ggg gcc tgc  gag gag agc aac cat  ctc ctg ctc aat ggt        3075
Gly Pro Gly Ala Cys  Glu Glu Ser Asn His  Leu Leu Leu Asn Gly
                1005                1010                1015
```

-continued

```
ggc tcc cac aag cac gtg cag agc cag att cac agg tca gcc gac      3120
Gly Ser His Lys His Val Gln Ser Gln Ile His Arg Ser Ala Asp
            1020                1025                1030 tcc ggg ggg cgg cag ggc aga gaa cag aag cag gac ccc ctg cac      3165
Ser Gly Gly Arg Gln Gly Arg Glu Gln Lys Gln Asp Pro Leu His
    1035                1040                1045 tcg ccc acc tcc aag agg aag aag gtg aaa ttt acc acc ttt acc      3210
Ser Pro Thr Ser Lys Arg Lys Lys Val Lys Phe Thr Thr Phe Thr
1050                1055                1060 acc atc ccc ccg gac gac agc tgc ccc acg gtg aac tcc atc gtc      3255
Thr Ile Pro Pro Asp Asp Ser Cys Pro Thr Val Asn Ser Ile Val
                1065                1070                1075 agc agc aat gat gag gac atc aaa tgg gtg tgt caa gac gtg gct      3300
Ser Ser Asn Asp Glu Asp Ile Lys Trp Val Cys Gln Asp Val Ala
            1080                1085                1090 gtg ggt gcc ccc aag gaa ctt aga aac tat ctg gag aaa ctc aaa      3345
Val Gly Ala Pro Lys Glu Leu Arg Asn Tyr Leu Glu Lys Leu Lys
        1095                1100                1105 gat aag gct tag gcccctctag ccaaagggcc ctgcccagat gccttccttg tactg   3402
Asp Lys Ala <210> SEQ ID NO 2
<211> LENGTH: 1108
<212> TYPE: PRT
<213> ORGANISM: Homo sapiens

<400> SEQUENCE: 2

Met Arg Ser Glu Gly Ala Ala Pro Gly Pro Ala Ala Pro Leu Cys Gly
1               5                   10                  15

Ala Leu Ser Leu Leu Leu Gly Ala Leu Leu Gly Lys Val Ile Glu Gly
            20                  25                  30

His Gly Val Thr Asp Asn Ile Gln Arg Phe Ser Ser Leu Pro Pro Tyr
        35                  40                  45

Leu Pro Val Ser Tyr His Ile Leu Arg Ala Glu Thr Ser Phe Phe Leu
    50                  55                  60

Lys Glu Ala Asn Gln Asp Leu Leu Arg Asn Ser Ser Leu Gln Ala Arg
65                  70                  75                  80

Val Glu Ser Phe Phe Thr Tyr Lys Thr Arg Gln Pro Pro Val Leu Asn
                85                  90                  95

Ala Ser Tyr Gly Pro Phe Ser Val Glu Lys Val Val Pro Leu Asp Leu
            100                 105                 110

Met Leu Thr Ser Asn Phe Leu Gly Pro Thr Asn Lys Phe Ser Phe Asp
        115                 120                 125

Trp Lys Leu Lys Ala His Ile Leu Arg Asp Lys Val Tyr Leu Ser Arg
    130                 135                 140

Pro Lys Val Gln Val Leu Phe His Ile Met Gly Arg Asp Trp Asp Asp
145                 150                 155                 160

Arg Gly Ala Gly Glu Lys Leu Pro Cys Leu Arg Val Phe Ala Phe Arg
                165                 170                 175

Glu Thr Arg Glu Val Arg Gly Ser Cys Arg Leu Lys Gly Asp Leu Gly
            180                 185                 190

Leu Cys Val Ala Glu Leu Glu Leu Leu Ser Ser Trp Phe Ser Ala Pro
        195                 200                 205

Thr Val Gly Ala Gly Arg Lys Lys Ser Met Asp Gln Pro Glu Gly Thr
    210                 215                 220

Pro Val Glu Leu Tyr Tyr Thr Val His Pro Gly Asn Glu Arg Gly Asp
225                 230                 235                 240
```

```
Cys Ala Gly Gly Asp Phe Arg Lys Gly Asn Ala Ile Arg Pro Gly Lys
                245                 250                 255

Asp Gly Leu Glu Glu Thr Thr Ser His Leu Gln Arg Ile Gly Thr Val
            260                 265                 270

Gly Leu Tyr Arg Ala Gln Asp Ser Ala Gln Leu Ser Glu Leu Arg Leu
        275                 280                 285

Asp Gly Asn Val Val Ile Trp Leu Pro Ser Arg Pro Val Lys Gln Gly
    290                 295                 300

Glu Val Val Thr Ala Tyr Val Thr Ile Ser Ser Asn Ser Ser Val Asp
305                 310                 315                 320

Leu Phe Ile Leu Arg Ala Lys Val Lys Lys Gly Val Asn Ile Leu Ser
                325                 330                 335

Ala Gln Thr Arg Glu Pro Arg Gln Trp Gly Val Lys Gln Glu Val Gly
            340                 345                 350

Ser Gly Gly Lys His Val Thr Ala Thr Val Ala Cys Gln Arg Leu Gly
        355                 360                 365

Pro Ser Pro Arg Asn Arg Ser Ser Leu Phe Asn Glu Val Val Gln
    370                 375                 380

Met Asn Phe Glu Ile Ala Ser Phe Ser Ser Leu Ser Gly Thr Gln Pro
385                 390                 395                 400

Ile Thr Trp Gln Val Glu Tyr Pro Arg Lys Gly Thr Thr Asp Ile Ala
                405                 410                 415

Val Ser Glu Ile Phe Val Ser Gln Lys Asp Leu Val Gly Ile Val Pro
            420                 425                 430

Leu Ala Met Asp Thr Glu Ile Leu Asn Thr Ala Val Leu Thr Gly Lys
        435                 440                 445

Thr Val Ala Met Pro Ile Lys Val Val Ser Val Glu Glu Asn Ser Ala
    450                 455                 460

Val Met Asp Ile Ser Glu Ser Val Glu Cys Lys Ser Thr Asp Glu Asp
465                 470                 475                 480

Val Ile Lys Val Ser Glu Arg Cys Asp Tyr Ile Phe Val Asn Gly Lys
                485                 490                 495

Glu Ile Lys Gly Lys Met Asp Ala Val Val Asn Phe Thr Tyr Gln Tyr
            500                 505                 510

Leu Ser Ala Pro Leu Cys Val Thr Val Trp Val Pro Arg Leu Pro Leu
        515                 520                 525

Gln Ile Glu Val Ser Asp Thr Glu Leu Ser Gln Ile Lys Gly Trp Arg
    530                 535                 540

Val Pro Ile Val Thr Asn Lys Arg Pro Thr Arg Glu Ser Glu Asp Glu
545                 550                 555                 560

Asp Glu Glu Glu Arg Arg Gly Arg Gly Cys Ala Leu Gln Tyr Gln His
                565                 570                 575

Ala Thr Val Arg Val Leu Thr Gln Phe Val Ser Glu Gly Ala Gly Pro
            580                 585                 590

Trp Gly Gln Pro Asn Tyr Leu Leu Ser Pro Asn Trp Gln Phe Asp Ile
        595                 600                 605

Thr His Leu Val Ala Asp Phe Met Lys Leu Glu Pro His Val Ala
    610                 615                 620

Thr Leu Gln Asp Ser Arg Val Leu Val Gly Arg Glu Val Gly Met Thr
625                 630                 635                 640

Thr Ile Gln Val Leu Ser Pro Leu Ser Asp Ser Ile Leu Ala Glu Lys
                645                 650                 655

Thr Ile Thr Val Leu Asp Asp Lys Val Ser Val Thr Asp Leu Ala Ile
            660                 665                 670
```

```
Gln Leu Val Ala Gly Leu Ser Val Ala Leu Tyr Pro Asn Ala Glu Asn
            675                 680                 685

Ser Lys Ala Val Thr Ala Val Thr Ala Glu Glu Val Leu Arg Thr
690                 695                 700

Pro Lys Gln Glu Ala Val Phe Ser Thr Trp Leu Gln Phe Ser Asp Gly
705                 710                 715                 720

Ser Val Thr Pro Leu Asp Ile Tyr Asp Thr Lys Asp Phe Ser Leu Ala
            725                 730                 735

Ala Thr Ser Gln Asp Glu Ala Val Val Ser Val Pro Gln Pro Arg Ser
            740                 745                 750

Pro Arg Trp Pro Val Val Ala Glu Gly Glu Gly Gln Gly Pro Leu
            755                 760                 765

Ile Arg Val Asp Met Thr Ile Ala Glu Ala Cys Gln Lys Ser Lys Arg
770                 775                 780

Lys Ser Ile Leu Ala Val Gly Val Gly Asn Val Arg Val Lys Phe Gly
785                 790                 795                 800

Gln Asn Asp Ala Asp Ser Ser Pro Gly Arg Asp Tyr Glu Glu Asp Glu
            805                 810                 815

Ile Lys Asn His Ala Ser Asp Arg Arg Gln Lys Gly Gln His His Glu
            820                 825                 830

Arg Thr Gly Gln Asp Gly His Leu Tyr Gly Ser Ser Pro Val Glu Arg
            835                 840                 845

Glu Glu Gly Ala Leu Arg Arg Ala Thr Thr Thr Ala Arg Ser Leu Leu
            850                 855                 860

Asp Asn Lys Val Val Lys Asn Ser Arg Ala Asp Gly Gly Arg Leu Ala
865                 870                 875                 880

Gly Glu Gly Gln Leu Gln Asn Ile Pro Ile Asp Phe Thr Asn Phe Pro
            885                 890                 895

Ala His Val Asp Leu Pro Lys Ala Gly Ser Gly Leu Glu Glu Asn Asp
            900                 905                 910

Leu Val Gln Thr Pro Arg Gly Leu Ser Asp Leu Glu Ile Gly Met Tyr
            915                 920                 925

Ala Leu Leu Gly Val Phe Cys Leu Ala Ile Leu Val Phe Leu Ile Asn
            930                 935                 940

Cys Ala Thr Phe Ala Leu Lys Tyr Arg His Lys Gln Val Pro Leu Glu
945                 950                 955                 960

Gly Gln Ala Ser Met Thr His Ser His Asp Trp Val Trp Leu Gly Asn
            965                 970                 975

Glu Ala Glu Leu Leu Glu Ser Met Gly Asp Ala Pro Pro Gln Asp
            980                 985                 990

Glu His Thr Thr Ile Ile Asp Arg Gly Pro Gly Ala Cys Glu Glu Ser
            995                 1000                1005

Asn His Leu Leu Leu Asn Gly Gly Ser His Lys His Val Gln Ser
            1010                1015                1020

Gln Ile His Arg Ser Ala Asp Ser Gly Gly Arg Gln Gly Arg Glu
            1025                1030                1035

Gln Lys Gln Asp Pro Leu His Ser Pro Thr Ser Lys Arg Lys Lys
            1040                1045                1050

Val Lys Phe Thr Thr Phe Thr Thr Ile Pro Pro Asp Asp Ser Cys
            1055                1060                1065

Pro Thr Val Asn Ser Ile Val Ser Ser Asn Asp Glu Asp Ile Lys
            1070                1075                1080

Trp Val Cys Gln Asp Val Ala Val Gly Ala Pro Lys Glu Leu Arg
```

```
                1085                1090                1095
Asn Tyr Leu Glu Lys Leu Lys Asp Lys Ala
    1100                1105

<210> SEQ ID NO 3
<211> LENGTH: 5961
<212> TYPE: DNA
<213> ORGANISM: Homo sapiens
<220> FEATURE:
<221> NAME/KEY: CDS
<222> LOCATION: (1)..(4347)
<223> OTHER INFORMATION:

<400> SEQUENCE: 3 atg tct ctg ggc ctt atc tcc ata ttt cag aaa cca agt tca ggg tca      48
Met Ser Leu Gly Leu Ile Ser Ile Phe Gln Lys Pro Ser Ser Gly Ser
1               5                   10                  15 gtc aca ggg aag tca cct gaa ccg gac agc aag gtc tgt gac tgc ctt      96
Val Thr Gly Lys Ser Pro Glu Pro Asp Ser Lys Val Cys Asp Cys Leu
                20                  25                  30 atc cac agg cag atc ccg ctc gcc ctg ccc tgg cat cac cac cac tgg     144
Ile His Arg Gln Ile Pro Leu Ala Leu Pro Trp His His His His Trp
            35                  40                  45 gca gct ttg cct ctc act aga tat gaa aaa agt gga aaa gca aaa cag     192
Ala Ala Leu Pro Leu Thr Arg Tyr Glu Lys Ser Gly Lys Ala Lys Gln
        50                  55                  60 aaa cta aag gtg aca act ctg cag agc tgg gca cgt tgg aaa ggc caa     240
Lys Leu Lys Val Thr Thr Leu Gln Ser Trp Ala Arg Trp Lys Gly Gln
65                  70                  75                  80 gcc tta acc ctg tct ctc tct ctc tcc cat ctt cat ccc cac aga gcc     288
Ala Leu Thr Leu Ser Leu Ser Leu Ser His Leu His Pro His Arg Ala
                85                  90                  95 aag gtg aag aag ggg gtg aac atc ctg agt gct cag acc cgt gag ccc     336
Lys Val Lys Lys Gly Val Asn Ile Leu Ser Ala Gln Thr Arg Glu Pro
                100                 105                 110 cgg cag tgg ggc gtc aag cag gag gtg ggc agc ggc gga aag cac gtg     384
Arg Gln Trp Gly Val Lys Gln Glu Val Gly Ser Gly Gly Lys His Val
            115                 120                 125 acg gcc acc gtg gcc tgc cag cgc ctg ggg ccc agc cca cgc aac aga     432
Thr Ala Thr Val Ala Cys Gln Arg Leu Gly Pro Ser Pro Arg Asn Arg
        130                 135                 140 acc cac tcc tct gtc ctt cct tta atg tgt aat gag aaa aag aaa atc     480
Thr His Ser Ser Val Leu Pro Leu Met Cys Asn Glu Lys Lys Lys Ile
145                 150                 155                 160 tgg tgt ccc aaa cag ttc aca aac tca aat gcc aac cgt cac cat cat     528
Trp Cys Pro Lys Gln Phe Thr Asn Ser Asn Ala Asn Arg His His His
                165                 170                 175 tac ccc aag aag gat ttt agt gca tct ggc gga gga agc atc ttc cgc     576
Tyr Pro Lys Lys Asp Phe Ser Ala Ser Gly Gly Gly Ser Ile Phe Arg
                180                 185                 190 ctc ccc ctt cat ctc ctt tcc tcg gtc tgc atc ttt ttt caa aac cag     624
Leu Pro Leu His Leu Leu Ser Ser Val Cys Ile Phe Phe Gln Asn Gln
            195                 200                 205 gtg tcc ggc tcc ggg ggt gtc tgt gcc cag gac tgg tta cgg gcc atg     672
Val Ser Gly Ser Gly Gly Val Cys Ala Gln Asp Trp Leu Arg Ala Met
        210                 215                 220 tgg gag act ttc act tta acc tca aaa ctt cta aaa gaa tct aaa aag     720
Trp Glu Thr Phe Thr Leu Thr Ser Lys Leu Leu Lys Glu Ser Lys Lys
225                 230                 235                 240 gaa aca ctt tct gtc cac gtg att caa cct tac tca agg gat gca cgt     768
Glu Thr Leu Ser Val His Val Ile Gln Pro Tyr Ser Arg Asp Ala Arg
                245                 250                 255
```

|  |  |
|---|---|
| tgc ctt ttg gaa acc ttt cct ggg ata ctt cat cag tcc cct aga ggg<br>Cys Leu Leu Glu Thr Phe Pro Gly Ile Leu His Gln Ser Pro Arg Gly<br>260                       265                  270 | 816 |
| gct gtc act gac act tgt aca gag ttt gca gca aaa cag ctg tct ggg<br>Ala Val Thr Asp Thr Cys Thr Glu Phe Ala Ala Lys Gln Leu Ser Gly<br>           275                  280                  285 | 864 |
| aac tcg act gtg cct ctt ttg gag gga ctt aga aag aag gcc agc tgt<br>Asn Ser Thr Val Pro Leu Leu Glu Gly Leu Arg Lys Lys Ala Ser Cys<br>290                       295                  300 | 912 |
| ttc aaa gac tca gct gcc cct cat ttt cac cac acg agc cct cct aaa<br>Phe Lys Asp Ser Ala Ala Pro His Phe His His Thr Ser Pro Pro Lys<br>305                       310                 315           320 | 960 |
| cag agc aca tcg cac aga cgc tcc tgt att tcc agc aga tgc tat aaa<br>Gln Ser Thr Ser His Arg Arg Ser Cys Ile Ser Ser Arg Cys Tyr Lys<br>                  325                  330                335 | 1008 |
| cac gca tct gag ctc cgg ttc tta tgg cta agc agc tgc tgc atc ccc<br>His Ala Ser Glu Leu Arg Phe Leu Trp Leu Ser Ser Cys Cys Ile Pro<br>                340                  345                350 | 1056 |
| aag ctc ctt aat tca aga gcc agc atc gtg ctt cag gga ctc tct gct<br>Lys Leu Leu Asn Ser Arg Ala Ser Ile Val Leu Gln Gly Leu Ser Ala<br>355                       360                 365 | 1104 |
| gca ggg gag aaa agt aaa tca ggc agg aat tcc agt tca acc atg atg<br>Ala Gly Glu Lys Ser Lys Ser Gly Arg Asn Ser Ser Ser Thr Met Met<br>370                       375                  380 | 1152 |
| ttt tct gat tct tac atc aac cct gag ata tgg gta cga tgg gtc cca<br>Phe Ser Asp Ser Tyr Ile Asn Pro Glu Ile Trp Val Arg Trp Val Pro<br>385                       390                 395           400 | 1200 |
| tat tcc aga aaa caa tgt gac atg aag aca gag ccc aca cta gag cgg<br>Tyr Ser Arg Lys Gln Cys Asp Met Lys Thr Glu Pro Thr Leu Glu Arg<br>                  405                  410                415 | 1248 |
| ctt gtg gag aga gta gta aaa cct gac agg ctc ctt agc acc aga gag<br>Leu Val Glu Arg Val Val Lys Pro Asp Arg Leu Leu Ser Thr Arg Glu<br>                420                  425                430 | 1296 |
| gag tgg aaa ggt gaa aga aag aaa att caa ggg ctg aaa aat atc tac<br>Glu Trp Lys Gly Glu Arg Lys Lys Ile Gln Gly Leu Lys Asn Ile Tyr<br>            435                  440                445 | 1344 |
| acc tcc cca ccc ccg cac ccc cca cac act cac act gtg gtc aca ttg<br>Thr Ser Pro Pro Pro His Pro Pro His Thr His Thr Val Val Thr Leu<br>450                       455                 460 | 1392 |
| aga aaa gat gca aga cgc att ctg aca ctt aga ttg cga tgt gga gac<br>Arg Lys Asp Ala Arg Arg Ile Leu Thr Leu Arg Leu Arg Cys Gly Asp<br>465                       470                 475           480 | 1440 |
| act cac aca gcc aat cca tgg agc tca ggc ttt gac ctg gat atg cct<br>Thr His Thr Ala Asn Pro Trp Ser Ser Gly Phe Asp Leu Asp Met Pro<br>                  485                  490                495 | 1488 |
| gat tcc tgc atg gga att gga gtt gag ttg gtc tgg gtt ccg gtc ctg<br>Asp Ser Cys Met Gly Ile Gly Val Glu Leu Val Trp Val Pro Val Leu<br>                500                  505                510 | 1536 |
| ctc cag cag ctc tgt gca ctg ggg cag gtc ctg att ctg cag gag gcc<br>Leu Gln Gln Leu Cys Ala Leu Gly Gln Val Leu Ile Leu Gln Glu Ala<br>            515                  520                525 | 1584 |
| ggt gcc tac ttt acg aac agc tac ggc ctc agt gcc tgt gat ttg aaa<br>Gly Ala Tyr Phe Thr Asn Ser Tyr Gly Leu Ser Ala Cys Asp Leu Lys<br>530                       535                 540 | 1632 |
| aat gcc cct agc tgt ccg tcc cgg ctg ctg aag gga acg agc ttc ggt<br>Asn Ala Pro Ser Cys Pro Ser Arg Leu Leu Lys Gly Thr Ser Phe Gly<br>545                       550                 555           560 | 1680 |
| ggt gac tgc atc cct cac atc cga gga ggg tcc tgg tac aga ggc agc<br>Gly Asp Cys Ile Pro His Ile Arg Gly Gly Ser Trp Tyr Arg Gly Ser<br>                  565                  570                575 | 1728 |

| | | | | | | | | | | | | | | | |
|---|---|---|---|---|---|---|---|---|---|---|---|---|---|---|---|
| agg | gct | tca | ctg | atc | ccg | ttt | tct | gtc | cat | cac | act | ggg | ctg | ccc | ctt | 1776 |
| Arg | Ala | Ser | Leu | Ile | Pro | Phe | Ser | Val | His | His | Thr | Gly | Leu | Pro | Leu |
| | | | 580 | | | | 585 | | | | | 590 | | | |
| tcg | cag | gtc | ctg | gta | cag | agg | tgg | cac | ggc | ttg | act | gat | ccc | gtg | ttc | 1824 |
| Ser | Gln | Val | Leu | Val | Gln | Arg | Trp | His | Gly | Leu | Thr | Asp | Pro | Val | Phe |
| | | 595 | | | | | 600 | | | | | 605 | | | |
| tct | cca | tca | cac | tgg | gct | gcc | cct | ttc | gca | ggt | cct | gtg | ggc | tgc | ccc | 1872 |
| Ser | Pro | Ser | His | Trp | Ala | Ala | Pro | Phe | Ala | Gly | Pro | Val | Gly | Cys | Pro |
| | | 610 | | | | | 615 | | | | | 620 | | | |
| ttt | cgc | agg | tct | tgg | tac | aga | ggt | ggc | agg | gct | tca | ctg | atc | cca | tgt | 1920 |
| Phe | Arg | Arg | Ser | Trp | Tyr | Arg | Gly | Gly | Arg | Ala | Ser | Leu | Ile | Pro | Cys |
| 625 | | | | | 630 | | | | | 635 | | | | | 640 |
| tct | ctc | cgt | cac | act | ggg | ctg | ccc | ctt | ttg | cag | gtc | ctg | gta | cag | agg | 1968 |
| Ser | Leu | Arg | His | Thr | Gly | Leu | Pro | Leu | Leu | Gln | Val | Leu | Val | Gln | Arg |
| | | | | 645 | | | | | 650 | | | | | 655 | |
| cgg | cag | ggc | ttc | act | gat | ccc | tgt | tct | gtc | cat | cgc | act | ggg | ctg | ccc | 2016 |
| Arg | Gln | Gly | Phe | Thr | Asp | Pro | Cys | Ser | Val | His | Arg | Thr | Gly | Leu | Pro |
| | | | 660 | | | | | 665 | | | | | 670 | | |
| ctt | ttg | cag | gtc | ctg | gta | cag | agg | cac | cag | ggc | ttc | act | gat | ccc | atg | 2064 |
| Leu | Leu | Gln | Val | Leu | Val | Gln | Arg | His | Gln | Gly | Phe | Thr | Asp | Pro | Met |
| | | 675 | | | | | 680 | | | | | 685 | | | |
| tcc | tct | cca | tca | cac | tgg | gct | gcc | cct | ttc | gca | ggt | cct | gat | cct | cgc | 2112 |
| Ser | Ser | Pro | Ser | His | Trp | Ala | Ala | Pro | Phe | Ala | Gly | Pro | Asp | Pro | Arg |
| | | 690 | | | | | 695 | | | | | 700 | | | |
| cta | aga | cag | ctg | gtg | gtc | aag | aac | cac | ctg | agc | agc | agt | tta | ttc | aat | 2160 |
| Leu | Arg | Gln | Leu | Val | Val | Lys | Asn | His | Leu | Ser | Ser | Ser | Leu | Phe | Asn |
| 705 | | | | | 710 | | | | | 715 | | | | | 720 |
| gag | gtt | gtg | cag | atg | aac | ttt | gaa | ata | gcc | agt | ttc | agc | agc | ctt | tca | 2208 |
| Glu | Val | Val | Gln | Met | Asn | Phe | Glu | Ile | Ala | Ser | Phe | Ser | Ser | Leu | Ser |
| | | | | 725 | | | | | 730 | | | | | 735 | |
| ggg | act | cag | ccc | atc | acg | tgg | cag | gtg | gag | tac | cca | cgg | aag | ggg | acc | 2256 |
| Gly | Thr | Gln | Pro | Ile | Thr | Trp | Gln | Val | Glu | Tyr | Pro | Arg | Lys | Gly | Thr |
| | | | 740 | | | | | 745 | | | | | 750 | | |
| aca | gac | atc | gcc | gtg | tcc | gag | atc | ttt | gtc | agc | cag | aag | gac | ctg | gtg | 2304 |
| Thr | Asp | Ile | Ala | Val | Ser | Glu | Ile | Phe | Val | Ser | Gln | Lys | Asp | Leu | Val |
| | | 755 | | | | | 760 | | | | | 765 | | | |
| ggc | atc | gtt | ccc | ttg | gct | atg | gac | act | gaa | att | ctg | aac | acc | gcc | gta | 2352 |
| Gly | Ile | Val | Pro | Leu | Ala | Met | Asp | Thr | Glu | Ile | Leu | Asn | Thr | Ala | Val |
| | | 770 | | | | | 775 | | | | | 780 | | | |
| ctc | aca | gga | aag | aca | gtt | gcc | atg | cct | atc | aag | gtg | gtc | tct | gtg | gag | 2400 |
| Leu | Thr | Gly | Lys | Thr | Val | Ala | Met | Pro | Ile | Lys | Val | Val | Ser | Val | Glu |
| 785 | | | | | 790 | | | | | 795 | | | | | 800 |
| gag | aac | agt | gcc | gtg | atg | gac | atc | tca | gag | tcg | gtg | gag | tgc | aag | tcc | 2448 |
| Glu | Asn | Ser | Ala | Val | Met | Asp | Ile | Ser | Glu | Ser | Val | Glu | Cys | Lys | Ser |
| | | | | 805 | | | | | 810 | | | | | 815 | |
| aca | gac | gag | gac | gtt | atc | aaa | gtg | tct | gag | cgc | tgt | gac | tac | atc | ttt | 2496 |
| Thr | Asp | Glu | Asp | Val | Ile | Lys | Val | Ser | Glu | Arg | Cys | Asp | Tyr | Ile | Phe |
| | | | 820 | | | | | 825 | | | | | 830 | | |
| gtc | aat | ggc | aaa | gag | atc | aaa | gga | aag | atg | gat | gcg | gtg | gtg | aac | ttc | 2544 |
| Val | Asn | Gly | Lys | Glu | Ile | Lys | Gly | Lys | Met | Asp | Ala | Val | Val | Asn | Phe |
| | | 835 | | | | | 840 | | | | | 845 | | | |
| aca | tac | cag | tac | ctg | agc | gcc | ccc | ctg | tgt | gtc | acc | gtg | tgg | gtg | ccc | 2592 |
| Thr | Tyr | Gln | Tyr | Leu | Ser | Ala | Pro | Leu | Cys | Val | Thr | Val | Trp | Val | Pro |
| | | 850 | | | | | 855 | | | | | 860 | | | |
| cgg | ctg | ccc | ctg | cag | atc | gag | gtc | tct | gac | acg | gag | ctc | agc | cag | ata | 2640 |
| Arg | Leu | Pro | Leu | Gln | Ile | Glu | Val | Ser | Asp | Thr | Glu | Leu | Ser | Gln | Ile |
| 865 | | | | | 870 | | | | | 875 | | | | | 880 |
| aag | ggc | tgg | agg | gtc | ccc | att | gtg | acc | aat | aag | agg | ccc | act | cgt | gag | 2688 |
| Lys | Gly | Trp | Arg | Val | Pro | Ile | Val | Thr | Asn | Lys | Arg | Pro | Thr | Arg | Glu |
| | | | | 885 | | | | | 890 | | | | | 895 | |

-continued

| | | |
|---|---|---|
| agc gag gat gag gac gag gag gag cgg cgg ggc cgg ggc tgc gca ctg<br>Ser Glu Asp Glu Asp Glu Glu Glu Arg Arg Gly Arg Gly Cys Ala Leu<br>        900                      905                  910 | 2736 |
| caa tac cag cac gcc acc gtg cgg gtc ctc acc cag ttt gtg tct gag<br>Gln Tyr Gln His Ala Thr Val Arg Val Leu Thr Gln Phe Val Ser Glu<br>        915                      920                  925 | 2784 |
| ggc gcc ggt cca tgg ggc cag ccg aac tac ctg ctt agt cct aac tgg<br>Gly Ala Gly Pro Trp Gly Gln Pro Asn Tyr Leu Leu Ser Pro Asn Trp<br>930                      935                  940 | 2832 |
| cag ttc gac atc act cac ctg gtg gca gac ttc atg aag ctg gag gaa<br>Gln Phe Asp Ile Thr His Leu Val Ala Asp Phe Met Lys Leu Glu Glu<br>945                      950                  955                  960 | 2880 |
| cct cac gtg gcc acc ctc cag gac agc cgg gtc ctg gtt ggg cga gag<br>Pro His Val Ala Thr Leu Gln Asp Ser Arg Val Leu Val Gly Arg Glu<br>        965                      970                  975 | 2928 |
| gtt ggg atg acg acc atc cag gtg ttg tct cca ctg tct gac tcc atc<br>Val Gly Met Thr Thr Ile Gln Val Leu Ser Pro Leu Ser Asp Ser Ile<br>              980                  985                  990 | 2976 |
| ctg gca gag aag aca ata acc gtg cta gat gac aaa gta tcg gtg aca<br>Leu Ala Glu Lys Thr Ile Thr Val Leu Asp Asp Lys Val Ser Val Thr<br>995                      1000                1005 | 3024 |
| gac ttg gcc atc cag ctc gtg gct ggg ctg tct gtc gcc ctt tac<br>Asp Leu Ala Ile Gln Leu Val Ala Gly Leu Ser Val Ala Leu Tyr<br>1010                1015                1020 | 3069 |
| ccc aac gca gaa aac agc aag gcc gta aca gct gtg gtc aca gct<br>Pro Asn Ala Glu Asn Ser Lys Ala Val Thr Ala Val Val Thr Ala<br>1025                1030                1035 | 3114 |
| gag gag gtg ctg cgg acc ccc aaa cag gag gct gta ttc agc acg<br>Glu Glu Val Leu Arg Thr Pro Lys Gln Glu Ala Val Phe Ser Thr<br>1040                1045                1050 | 3159 |
| tgg ctg cag ttc agt gat ggc tct gtg acg ccc ctg gac atc tac<br>Trp Leu Gln Phe Ser Asp Gly Ser Val Thr Pro Leu Asp Ile Tyr<br>1055                1060                1065 | 3204 |
| gac acc aag gac ttc tcc ctg gca gcc acc tcc cag gac gag gct<br>Asp Thr Lys Asp Phe Ser Leu Ala Ala Thr Ser Gln Asp Glu Ala<br>1070                1075                1080 | 3249 |
| gtc gtg tca gtc ccc cag ccc cgc tct ccc agg tgg ccc gtt gtg<br>Val Val Ser Val Pro Gln Pro Arg Ser Pro Arg Trp Pro Val Val<br>1085                1090                1095 | 3294 |
| gtg gcc gaa ggg gaa ggc cag ggc cca ctg atc cga gtg gac atg<br>Val Ala Glu Gly Glu Gly Gln Gly Pro Leu Ile Arg Val Asp Met<br>1100                1105                1110 | 3339 |
| acg atc gcc gag gcc tgc cag aaa tct aaa cgc aag agc atc ctg<br>Thr Ile Ala Glu Ala Cys Gln Lys Ser Lys Arg Lys Ser Ile Leu<br>1115                1120                1125 | 3384 |
| gct gtg ggc gtc ggc aac gtc agg gtc aag ttc gga cag aac gat<br>Ala Val Gly Val Gly Asn Val Arg Val Lys Phe Gly Gln Asn Asp<br>1130                1135                1140 | 3429 |
| gct gac tcc agc ccc ggc ggg gac tat gag gaa gat gag atc aag<br>Ala Asp Ser Ser Pro Gly Gly Asp Tyr Glu Glu Asp Glu Ile Lys<br>1145                1150                1155 | 3474 |
| aac cac gcc agc gac cgc cgg cag aag ggc cag cac cat gag cgc<br>Asn His Ala Ser Asp Arg Arg Gln Lys Gly Gln His His Glu Arg<br>1160                1165                1170 | 3519 |
| aca ggc caa gat ggg cac ctc tat ggc agc tct ccc gtg gag cgt<br>Thr Gly Gln Asp Gly His Leu Tyr Gly Ser Ser Pro Val Glu Arg<br>1175                1180                1185 | 3564 |
| gag gaa ggg gct ctc cga aga gcc act acc acg gcc agg tcc ctg<br>Glu Glu Gly Ala Leu Arg Arg Ala Thr Thr Thr Ala Arg Ser Leu<br>1190                1195                1200 | 3609 |

| | | |
|---|---|---|
| ctg gac aac aaa gtg gtg aag aac agt cgg gca gac ggg ggc agg<br>Leu Asp Asn Lys Val Val Lys Asn Ser Arg Ala Asp Gly Gly Arg<br>1205                         1210                          1215 | | 3654 |
| ctg gca gga gag ggg cag ctg cag aac atc ccc att gac ttc acc<br>Leu Ala Gly Glu Gly Gln Leu Gln Asn Ile Pro Ile Asp Phe Thr<br>1220                         1225                          1230 | | 3699 |
| aac ttc cct gcc cac gtg gac ctc ccc aag gcc ggg agt ggg ctg<br>Asn Phe Pro Ala His Val Asp Leu Pro Lys Ala Gly Ser Gly Leu<br>1235                         1240                          1245 | | 3744 |
| gag gaa aac gac ctg gtg cag act ccg cgg ggc ctg agt gat ctg<br>Glu Glu Asn Asp Leu Val Gln Thr Pro Arg Gly Leu Ser Asp Leu<br>1250                         1255                          1260 | | 3789 |
| gag ata ggg atg tac gcc ctc ctg ggg gtg ttc tgc ctg gcc atc<br>Glu Ile Gly Met Tyr Ala Leu Leu Gly Val Phe Cys Leu Ala Ile<br>1265                         1270                          1275 | | 3834 |
| ctc gtc ttc ctg atc aac tgc gcc acc ttt gcc ctg aag tac agg<br>Leu Val Phe Leu Ile Asn Cys Ala Thr Phe Ala Leu Lys Tyr Arg<br>1280                         1285                          1290 | | 3879 |
| cac aag caa gtg ccc ctg gaa ggt cag gcc tcc atg acc cac tct<br>His Lys Gln Val Pro Leu Glu Gly Gln Ala Ser Met Thr His Ser<br>1295                         1300                          1305 | | 3924 |
| cac gac tgg gtg tgg ctt ggc aat gag gcc gaa ctc ctg gag agc<br>His Asp Trp Val Trp Leu Gly Asn Glu Ala Glu Leu Leu Glu Ser<br>1310                         1315                          1320 | | 3969 |
| atg ggg gat gcg ccg ccg ccc cag gac gag cac acc acc atc ata<br>Met Gly Asp Ala Pro Pro Pro Gln Asp Glu His Thr Thr Ile Ile<br>1325                         1330                          1335 | | 4014 |
| gac cgc gga ccg ggg gcc tgc gag gag agc aac cat ctc ctg ctc<br>Asp Arg Gly Pro Gly Ala Cys Glu Glu Ser Asn His Leu Leu Leu<br>1340                         1345                          1350 | | 4059 |
| aat ggt ggc tcc cac aag cac gtg cag agc cag att cac agg tca<br>Asn Gly Gly Ser His Lys His Val Gln Ser Gln Ile His Arg Ser<br>1355                         1360                          1365 | | 4104 |
| gcc gac tcc ggg ggg cgg cag ggc aga gaa cag aag cag gac ccc<br>Ala Asp Ser Gly Gly Arg Gln Gly Arg Glu Gln Lys Gln Asp Pro<br>1370                         1375                          1380 | | 4149 |
| ctg cac tcg ccc acc tcc aag agg aag aag gtg aaa ttt acc acc<br>Leu His Ser Pro Thr Ser Lys Arg Lys Lys Val Lys Phe Thr Thr<br>1385                         1390                          1395 | | 4194 |
| ttt acc acc atc ccc ccg gac gac agc tgc ccc acg gtg aac tcc<br>Phe Thr Thr Ile Pro Pro Asp Asp Ser Cys Pro Thr Val Asn Ser<br>1400                         1405                          1410 | | 4239 |
| atc gtc agc agc aat gat gag gac atc aaa tgg gtg tgt caa gac<br>Ile Val Ser Ser Asn Asp Glu Asp Ile Lys Trp Val Cys Gln Asp<br>1415                         1420                          1425 | | 4284 |
| gtg gct gtg ggt gcc ccc aag gaa ctt aga aac tat ctg gag aaa<br>Val Ala Val Gly Ala Pro Lys Glu Leu Arg Asn Tyr Leu Glu Lys<br>1430                         1435                          1440 | | 4329 |
| ctc aaa gat aag gct tag gcccctctag ccaaagggcc ctgcccagat<br>Leu Lys Asp Lys Ala<br>1445 | | 4377 |
| gccttccttg tactggaaac tggcccaagt ggggcagaag gcgttgtcag tggggttaag | | 4437 |
| aagggacggt cccagggtcc atgctagacc agttggaaag ttttgaagtc aggaaaagac | | 4497 |
| gttttttgtat caagggattt ttagcagtta atggtggtgg attttttaaag gtcagggaa | | 4557 |
| taaagtctgg ggcatgggga gtgcagacca agttactgaa ctgcacaggc aaaattagga | | 4617 |
| aggttatttt atgagtcaaa acatactaca gacaagctac caaaaattat tgttaaaaa | | 4677 |
| atgcaacaag acaaataaaa agagaaataa tcatctgttt atatttctaa taaggagca | | 4737 |

```
aaatataaaa ataggacctg ctaagagaca ttttccattc taattcacga ttcactttc      4797 caaggacagc cttcaactgt caccacacag ctggggggga gtcatttctt aacaagggat      4857
gcctcttggg atagaactag ggagttttaa atctttactt gatcatcttt tattttcttt      4917 tccactttt cctttttct ctctctctgt gtcctagact tccattgcat ttatatttaa       4977 tgtttattc tgagaatcaa gcagtatatt tttcctaaat gaaacataaa ttatattcct      5037
attcattaga taggttccta ggaacaatgc caattaatcc attgtttaag tagtaacttg     5097 aatgttttc tatatccctc cagctttgtt gatagtggcg ggttttgtac aattggaggg      5157
agccctcaga gccttctggg ggaggagagg aactgtcctt aatccatcac cactaccata     5217
gggcaaagcc agcaggtgtg gccctgtgag gggctgtaca gacgggatgt ggccaggaga     5277
acagagcccc acctggacca cctgacccct cgggattcca ccctgtcat cgtgggatg       5337 ttcctatatg ggagaaagtt gggttaaatc aaaaaagagg ccacgcccag gtgtaatcag     5397
agccaacctg gtgggcttgg tctatcacaa gacataactg atgctgaaca tgaacaaaga     5457
taaaaactgt ttggagggtt tttgagttgt ttttcttatg ttgttgggtg gggtatacca     5517
gcataaactc taaagataaa atctatgtta gattgtcaat caactgtgtt tttgaacagc     5577
ataattgtgt agcagcacat tgcaaaaatg cattcatcca aagcgacaca tgtggcaacg     5637
tagaccacgc cagtgaaata agccccttcg tgatcacctg actccagttc tccgtgtgct     5697
ccattggctg cggctgcagg aggaagatgc ctgacagccc tcatgctctc cgcagggggg     5757
cgctcacaaa gatgccaggg gtgttattg tgtttatttt tttaattact aaaatcagta      5817
gctaagaaag ggtccttgaa gcctcctaac ctgggttgga cctttgaaaa atatatttgt     5877
agcacatatt atagatggaa agaagaagat atttatttat acctgtgatg ccaattgtca     5937
ttaaaaggct tttcatggct tgac                                            5961

<210> SEQ ID NO 4
<211> LENGTH: 1448
<212> TYPE: PRT
<213> ORGANISM: Homo sapiens

<400> SEQUENCE: 4

Met Ser Leu Gly Leu Ile Ser Ile Phe Gln Lys Pro Ser Ser Gly Ser
1               5                   10                  15

Val Thr Gly Lys Ser Pro Glu Pro Asp Ser Lys Val Cys Asp Cys Leu
            20                  25                  30

Ile His Arg Gln Ile Pro Leu Ala Leu Pro Trp His His His Trp
        35                  40                  45

Ala Ala Leu Pro Leu Thr Arg Tyr Glu Lys Ser Gly Lys Ala Lys Gln
    50                  55                  60

Lys Leu Lys Val Thr Thr Leu Gln Ser Trp Ala Arg Trp Lys Gly Gln
65                  70                  75                  80

Ala Leu Thr Leu Ser Leu Ser Leu Ser His Leu His Pro His Arg Ala
                85                  90                  95

Lys Val Lys Lys Gly Val Asn Ile Leu Ser Ala Gln Thr Arg Glu Pro
            100                 105                 110

Arg Gln Trp Gly Val Lys Gln Glu Val Gly Ser Gly Lys His Val
        115                 120                 125

Thr Ala Thr Val Ala Cys Gln Arg Leu Gly Pro Ser Pro Arg Asn Arg
    130                 135                 140

Thr His Ser Ser Val Leu Pro Leu Met Cys Asn Glu Lys Lys Lys Ile
145                 150                 155                 160
```

```
Trp Cys Pro Lys Gln Phe Thr Asn Ser Asn Ala Asn Arg His His His
            165                 170                 175
Tyr Pro Lys Lys Asp Phe Ser Ala Ser Gly Gly Gly Ser Ile Phe Arg
            180                 185                 190
Leu Pro Leu His Leu Leu Ser Val Cys Ile Phe Phe Gln Asn Gln
        195                 200                 205
Val Ser Gly Ser Gly Gly Val Cys Ala Gln Asp Trp Leu Arg Ala Met
    210                 215                 220
Trp Glu Thr Phe Thr Leu Thr Ser Lys Leu Leu Lys Glu Ser Lys Lys
225                 230                 235                 240
Glu Thr Leu Ser Val His Val Ile Gln Pro Tyr Ser Arg Asp Ala Arg
                245                 250                 255
Cys Leu Leu Glu Thr Phe Pro Gly Ile Leu His Gln Ser Pro Arg Gly
            260                 265                 270
Ala Val Thr Asp Thr Cys Thr Glu Phe Ala Ala Lys Gln Leu Ser Gly
        275                 280                 285
Asn Ser Thr Val Pro Leu Leu Glu Gly Leu Arg Lys Lys Ala Ser Cys
    290                 295                 300
Phe Lys Asp Ser Ala Ala Pro His Phe His His Thr Ser Pro Pro Lys
305                 310                 315                 320
Gln Ser Thr Ser His Arg Arg Ser Cys Ile Ser Ser Arg Cys Tyr Lys
                325                 330                 335
His Ala Ser Glu Leu Arg Phe Leu Trp Leu Ser Ser Cys Cys Ile Pro
            340                 345                 350
Lys Leu Leu Asn Ser Arg Ala Ser Ile Val Leu Gln Gly Leu Ser Ala
        355                 360                 365
Ala Gly Glu Lys Ser Lys Ser Gly Arg Asn Ser Ser Thr Met Met
    370                 375                 380
Phe Ser Asp Ser Tyr Ile Asn Pro Glu Ile Trp Val Arg Trp Val Pro
385                 390                 395                 400
Tyr Ser Arg Lys Gln Cys Asp Met Lys Thr Glu Pro Thr Leu Glu Arg
                405                 410                 415
Leu Val Glu Arg Val Val Lys Pro Asp Arg Leu Leu Ser Thr Arg Glu
            420                 425                 430
Glu Trp Lys Gly Glu Arg Lys Lys Ile Gln Gly Leu Lys Asn Ile Tyr
        435                 440                 445
Thr Ser Pro Pro His Pro Pro His Thr His Thr Val Val Thr Leu
    450                 455                 460
Arg Lys Asp Ala Arg Arg Ile Leu Thr Leu Arg Leu Arg Cys Gly Asp
465                 470                 475                 480
Thr His Thr Ala Asn Pro Trp Ser Ser Gly Phe Asp Leu Asp Met Pro
                485                 490                 495
Asp Ser Cys Met Gly Ile Gly Val Glu Leu Val Trp Val Pro Val Leu
            500                 505                 510
Leu Gln Gln Leu Cys Ala Leu Gly Gln Val Leu Ile Leu Gln Glu Ala
        515                 520                 525
Gly Ala Tyr Phe Thr Asn Ser Tyr Gly Leu Ser Ala Cys Asp Leu Lys
    530                 535                 540
Asn Ala Pro Ser Cys Pro Ser Arg Leu Leu Lys Gly Thr Ser Phe Gly
545                 550                 555                 560
Gly Asp Cys Ile Pro His Ile Arg Gly Gly Ser Trp Tyr Arg Gly Ser
                565                 570                 575
Arg Ala Ser Leu Ile Pro Phe Ser Val His His Thr Gly Leu Pro Leu
```

-continued

```
              580                 585                 590
Ser Gln Val Leu Val Gln Arg Trp His Gly Leu Thr Asp Pro Val Phe
            595                 600                 605

Ser Pro Ser His Trp Ala Ala Pro Phe Ala Gly Pro Val Gly Cys Pro
            610                 615                 620

Phe Arg Arg Ser Trp Tyr Arg Gly Gly Arg Ala Ser Leu Ile Pro Cys
625                 630                 635                 640

Ser Leu Arg His Thr Gly Leu Pro Leu Leu Gln Val Leu Val Gln Arg
                645                 650                 655

Arg Gln Gly Phe Thr Asp Pro Cys Ser Val His Arg Thr Gly Leu Pro
            660                 665                 670

Leu Leu Gln Val Leu Val Gln Arg His Gln Gly Phe Thr Asp Pro Met
            675                 680                 685

Ser Ser Pro Ser His Trp Ala Ala Pro Phe Ala Gly Pro Asp Pro Arg
            690                 695                 700

Leu Arg Gln Leu Val Val Lys Asn His Leu Ser Ser Ser Leu Phe Asn
705                 710                 715                 720

Glu Val Val Gln Met Asn Phe Glu Ile Ala Ser Phe Ser Ser Leu Ser
                725                 730                 735

Gly Thr Gln Pro Ile Thr Trp Gln Val Glu Tyr Pro Arg Lys Gly Thr
            740                 745                 750

Thr Asp Ile Ala Val Ser Glu Ile Phe Val Ser Gln Lys Asp Leu Val
            755                 760                 765

Gly Ile Val Pro Leu Ala Met Asp Thr Glu Ile Leu Asn Thr Ala Val
            770                 775                 780

Leu Thr Gly Lys Thr Val Ala Met Pro Ile Lys Val Val Ser Val Glu
785                 790                 795                 800

Glu Asn Ser Ala Val Met Asp Ile Ser Glu Ser Val Glu Cys Lys Ser
                805                 810                 815

Thr Asp Glu Asp Val Ile Lys Val Ser Glu Arg Cys Asp Tyr Ile Phe
            820                 825                 830

Val Asn Gly Lys Glu Ile Lys Gly Lys Met Asp Ala Val Val Asn Phe
            835                 840                 845

Thr Tyr Gln Tyr Leu Ser Ala Pro Leu Cys Val Thr Val Trp Val Pro
850                 855                 860

Arg Leu Pro Leu Gln Ile Glu Val Ser Asp Thr Glu Leu Ser Gln Ile
865                 870                 875                 880

Lys Gly Trp Arg Val Pro Ile Val Thr Asn Lys Arg Pro Thr Arg Glu
                885                 890                 895

Ser Glu Asp Glu Asp Glu Glu Arg Arg Gly Arg Gly Cys Ala Leu
            900                 905                 910

Gln Tyr Gln His Ala Thr Val Arg Val Leu Thr Gln Phe Val Ser Glu
            915                 920                 925

Gly Ala Gly Pro Trp Gly Gln Pro Asn Tyr Leu Leu Ser Pro Asn Trp
            930                 935                 940

Gln Phe Asp Ile Thr His Leu Val Ala Asp Phe Met Lys Leu Glu Glu
945                 950                 955                 960

Pro His Val Ala Thr Leu Gln Asp Ser Arg Val Leu Val Gly Arg Glu
                965                 970                 975

Val Gly Met Thr Thr Ile Gln Val Leu Ser Pro Leu Ser Asp Ser Ile
            980                 985                 990

Leu Ala Glu Lys Thr Ile Thr Val   Leu Asp Asp Lys Val   Ser Val Thr
            995                 1000                1005
```

```
Asp Leu Ala Ile Gln Leu Val Ala Gly Leu Ser Val Ala Leu Tyr
    1010                1015                1020

Pro Asn Ala Glu Asn Ser Lys Ala Val Thr Ala Val Val Thr Ala
    1025                1030                1035

Glu Glu Val Leu Arg Thr Pro Lys Gln Glu Ala Val Phe Ser Thr
    1040                1045                1050

Trp Leu Gln Phe Ser Asp Gly Ser Val Thr Pro Leu Asp Ile Tyr
    1055                1060                1065

Asp Thr Lys Asp Phe Ser Leu Ala Ala Thr Ser Gln Asp Glu Ala
    1070                1075                1080

Val Val Ser Val Pro Gln Pro Arg Ser Pro Arg Trp Pro Val Val
    1085                1090                1095

Val Ala Glu Gly Glu Gly Gln Gly Pro Leu Ile Arg Val Asp Met
    1100                1105                1110

Thr Ile Ala Glu Ala Cys Gln Lys Ser Lys Arg Lys Ser Ile Leu
    1115                1120                1125

Ala Val Gly Val Gly Asn Val Arg Val Lys Phe Gly Gln Asn Asp
    1130                1135                1140

Ala Asp Ser Ser Pro Gly Gly Asp Tyr Glu Glu Asp Glu Ile Lys
    1145                1150                1155

Asn His Ala Ser Asp Arg Arg Gln Lys Gly Gln His His Glu Arg
    1160                1165                1170

Thr Gly Gln Asp Gly His Leu Tyr Gly Ser Ser Pro Val Glu Arg
    1175                1180                1185

Glu Glu Gly Ala Leu Arg Arg Ala Thr Thr Thr Ala Arg Ser Leu
    1190                1195                1200

Leu Asp Asn Lys Val Val Lys Asn Ser Arg Ala Asp Gly Gly Arg
    1205                1210                1215

Leu Ala Gly Glu Gly Gln Leu Gln Asn Ile Pro Ile Asp Phe Thr
    1220                1225                1230

Asn Phe Pro Ala His Val Asp Leu Pro Lys Ala Gly Ser Gly Leu
    1235                1240                1245

Glu Glu Asn Asp Leu Val Gln Thr Pro Arg Gly Leu Ser Asp Leu
    1250                1255                1260

Glu Ile Gly Met Tyr Ala Leu Leu Gly Val Phe Cys Leu Ala Ile
    1265                1270                1275

Leu Val Phe Leu Ile Asn Cys Ala Thr Phe Ala Leu Lys Tyr Arg
    1280                1285                1290

His Lys Gln Val Pro Leu Glu Gly Gln Ala Ser Met Thr His Ser
    1295                1300                1305

His Asp Trp Val Trp Leu Gly Asn Glu Ala Glu Leu Leu Glu Ser
    1310                1315                1320

Met Gly Asp Ala Pro Pro Pro Gln Asp Glu His Thr Thr Ile Ile
    1325                1330                1335

Asp Arg Gly Pro Gly Ala Cys Glu Glu Ser Asn His Leu Leu Leu
    1340                1345                1350

Asn Gly Gly Ser His Lys His Val Gln Ser Gln Ile His Arg Ser
    1355                1360                1365

Ala Asp Ser Gly Gly Arg Gln Gly Arg Glu Gln Lys Gln Asp Pro
    1370                1375                1380

Leu His Ser Pro Thr Ser Lys Arg Lys Lys Val Lys Phe Thr Thr
    1385                1390                1395

Phe Thr Thr Ile Pro Pro Asp Asp Ser Cys Pro Thr Val Asn Ser
    1400                1405                1410
```

```
Ile Val Ser Ser Asn Asp Glu Asp Ile Lys Trp Val Cys Gln Asp
    1415            1420                1425

Val Ala Val Gly Ala Pro Lys Glu Leu Arg Asn Tyr Leu Glu Lys
1430            1435                1440

Leu Lys Asp Lys Ala
    1445

<210> SEQ ID NO 5
<211> LENGTH: 3810
<212> TYPE: DNA
<213> ORGANISM: Homo sapiens
<220> FEATURE:
<221> NAME/KEY: CDS
<222> LOCATION: (1)..(2196)
<223> OTHER INFORMATION:

<400> SEQUENCE: 5 tta ttc aat gag gtt gtg cag atg aac ttt gaa ata gcc agt ttc agc      48
Leu Phe Asn Glu Val Val Gln Met Asn Phe Glu Ile Ala Ser Phe Ser
1               5                   10                  15 agc ctt tca ggg act cag ccc atc acg tgg cag gtg gag tac cca cgg      96
Ser Leu Ser Gly Thr Gln Pro Ile Thr Trp Gln Val Glu Tyr Pro Arg
            20                  25                  30 aag ggg acc aca gac atc gcc ttg tcc gag atc ttt gtc agc cag aag     144
Lys Gly Thr Thr Asp Ile Ala Leu Ser Glu Ile Phe Val Ser Gln Lys
        35                  40                  45 gac ctg gtg ggc atc gtt ccc ttg gct atg gac act gaa att ctg aac     192
Asp Leu Val Gly Ile Val Pro Leu Ala Met Asp Thr Glu Ile Leu Asn
    50                  55                  60 acc gcc gta ctc aca gga aag aca gtt gcc atg cct atc aag gtg gtc     240
Thr Ala Val Leu Thr Gly Lys Thr Val Ala Met Pro Ile Lys Val Val
65                  70                  75                  80 tct gtg gag gag aac agt gcc gtg atg gac atc tca gag tcg gtg gag     288
Ser Val Glu Glu Asn Ser Ala Val Met Asp Ile Ser Glu Ser Val Glu
                85                  90                  95 tgc aag tcc aca gac gag gac gtt atc aaa gtg tct gag cgc tgt gac     336
Cys Lys Ser Thr Asp Glu Asp Val Ile Lys Val Ser Glu Arg Cys Asp
            100                 105                 110 tac atc ttt gtc aat ggc aaa gag atc aaa gga aag atg gat gcg gtg     384
Tyr Ile Phe Val Asn Gly Lys Glu Ile Lys Gly Lys Met Asp Ala Val
        115                 120                 125 gtg aac ttc aca tac cag tac ctg agc gcc ccc ctg tgt gtc acc gtg     432
Val Asn Phe Thr Tyr Gln Tyr Leu Ser Ala Pro Leu Cys Val Thr Val
    130                 135                 140 tgg gtg ccc cgg ctg ccc ctg cag atc gag gtc tct gac acg gag ctc     480
Trp Val Pro Arg Leu Pro Leu Gln Ile Glu Val Ser Asp Thr Glu Leu
145                 150                 155                 160 agc cag ata aag ggc tgg agg gtc ccc att gtg acc aat aag agg ccc     528
Ser Gln Ile Lys Gly Trp Arg Val Pro Ile Val Thr Asn Lys Arg Pro
                165                 170                 175 act cgt gag agc gag gat gag gac gag gag gag cgg cgg ggc cgg ggc     576
Thr Arg Glu Ser Glu Asp Glu Asp Glu Glu Glu Arg Arg Gly Arg Gly
            180                 185                 190 tgc gca ctg caa tac cag cac gcc acc gtg cgg gtc ctc acc cag ttt     624
Cys Ala Leu Gln Tyr Gln His Ala Thr Val Arg Val Leu Thr Gln Phe
        195                 200                 205 gtg tct gag ggc gcc ggt cca tgg ggc cag ccg aac tac ctg ctt agt     672
Val Ser Glu Gly Ala Gly Pro Trp Gly Gln Pro Asn Tyr Leu Leu Ser
    210                 215                 220 cct aac tgg cag ttc gac atc act cac ctg gtg gca gac ttc atg aag     720
Pro Asn Trp Gln Phe Asp Ile Thr His Leu Val Ala Asp Phe Met Lys
```

-continued

```
                225                 230                 235                 240
ctg gag gaa cct cac gtg gcc acc ctc cag gac agc cgg gtc ctg gtt          768
Leu Glu Glu Pro His Val Ala Thr Leu Gln Asp Ser Arg Val Leu Val
                245                 250                 255 ggg cga gag gtt ggg atg acg acc atc cag gtg ttg tct cca ctg tct          816
Gly Arg Glu Val Gly Met Thr Thr Ile Gln Val Leu Ser Pro Leu Ser
            260                 265                 270 gac tcc atc ctg gca gag aag acg ata acc gtg cta gat gac aaa gtg          864
Asp Ser Ile Leu Ala Glu Lys Thr Ile Thr Val Leu Asp Asp Lys Val
        275                 280                 285 tcg gtg aca gac ttg gcc atc cag ctc gtg gct ggg ctg tct gtc gcc          912
Ser Val Thr Asp Leu Ala Ile Gln Leu Val Ala Gly Leu Ser Val Ala
    290                 295                 300 ctt tac ccc aac gca gaa aac agc aag gcc gta aca gct gtg gtc aca          960
Leu Tyr Pro Asn Ala Glu Asn Ser Lys Ala Val Thr Ala Val Val Thr
305                 310                 315                 320 gct gag gag gtg ctg cgg acc ccc aaa cag gag gct gta ttc agc acg         1008
Ala Glu Glu Val Leu Arg Thr Pro Lys Gln Glu Ala Val Phe Ser Thr
                325                 330                 335 tgg ctg cag ttc agt gat ggc tct gtg acg ccc ctg gac atc tac gac         1056
Trp Leu Gln Phe Ser Asp Gly Ser Val Thr Pro Leu Asp Ile Tyr Asp
            340                 345                 350 acc aag gac ttc tcc ctg gca gcc atc tcc cag gac ggg gct gtc gtg         1104
Thr Lys Asp Phe Ser Leu Ala Ala Ile Ser Gln Asp Gly Ala Val Val
        355                 360                 365 tca gtc ccc cag ccc cgc tct ccc agg tgg ccc gtt gtg gtg gcc gaa         1152
Ser Val Pro Gln Pro Arg Ser Pro Arg Trp Pro Val Val Val Ala Glu
    370                 375                 380 ggg gaa ggc cag ggc cca ctg atc cga gtg gac atg acg atc gcc gag         1200
Gly Glu Gly Gln Gly Pro Leu Ile Arg Val Asp Met Thr Ile Ala Glu
385                 390                 395                 400 gcc tgc cag aaa tct aaa cgc aag agc atc ctg gct gtg ggc gtc ggc         1248
Ala Cys Gln Lys Ser Lys Arg Lys Ser Ile Leu Ala Val Gly Val Gly
                405                 410                 415 aac gtc agg gtc aag ttc gga cag aac gat gct gac tcc agc ccc ggc         1296
Asn Val Arg Val Lys Phe Gly Gln Asn Asp Ala Asp Ser Ser Pro Gly
            420                 425                 430 agg gac tat gag gaa gat gag atc aag aac cac gcc agc gac cgc cgg         1344
Arg Asp Tyr Glu Glu Asp Glu Ile Lys Asn His Ala Ser Asp Arg Arg
        435                 440                 445 cag aag ggc cag cac cat gag cgc aca ggc cag gat ggg cac ctc tat         1392
Gln Lys Gly Gln His His Glu Arg Thr Gly Gln Asp Gly His Leu Tyr
    450                 455                 460 ggc agc tct ccc gtg gag cgt gag gaa ggg gct ctc cga aga gcc act         1440
Gly Ser Ser Pro Val Glu Arg Glu Glu Gly Ala Leu Arg Arg Ala Thr
465                 470                 475                 480 acc acg gcc agg tcc ctg ctg gac aac aaa gtg gtg aag aac agt cgg         1488
Thr Thr Ala Arg Ser Leu Leu Asp Asn Lys Val Val Lys Asn Ser Arg
                485                 490                 495 gca gac ggg ggc agg ctg gca gga gag ggg cag ctg cag aac atc ccc         1536
Ala Asp Gly Gly Arg Leu Ala Gly Glu Gly Gln Leu Gln Asn Ile Pro
            500                 505                 510 att gac ttc acc aac ttc cct gcc cac gtg gac ctc ccc aag gcc ggg         1584
Ile Asp Phe Thr Asn Phe Pro Ala His Val Asp Leu Pro Lys Ala Gly
        515                 520                 525 agt ggg ctg gag gaa aac gac ctg gtg cag act ccg cgg ggc ctg agt         1632
Ser Gly Leu Glu Glu Asn Asp Leu Val Gln Thr Pro Arg Gly Leu Ser
    530                 535                 540 gat ctg gag ata ggg atg tac gcc ctc ctg ggg gtg ttc tgc ctg gcc         1680
Asp Leu Glu Ile Gly Met Tyr Ala Leu Leu Gly Val Phe Cys Leu Ala
```

```
                545                 550                 555                 560
atc ctc gtc ttc ctg atc aac tgc gcc acc ttt gcc ctg aag tac agg         1728
Ile Leu Val Phe Leu Ile Asn Cys Ala Thr Phe Ala Leu Lys Tyr Arg
                565                 570                 575 cac aag caa gtg ccc ctg gaa ggt cag gcc tcc atg acc cac tct cac         1776
His Lys Gln Val Pro Leu Glu Gly Gln Ala Ser Met Thr His Ser His
                580                 585                 590 gac tgg gtg tgg ctt ggc aat gag gcc gaa ctc ctg gag agc atg ggg         1824
Asp Trp Val Trp Leu Gly Asn Glu Ala Glu Leu Leu Glu Ser Met Gly
                595                 600                 605 gat gca ccg ccg ccc cag gac gag cac acc acc atc ata gac cgc gga         1872
Asp Ala Pro Pro Pro Gln Asp Glu His Thr Thr Ile Ile Asp Arg Gly
                610                 615                 620 ccg ggg gcc tgc gag gag agc aac cat ctc ctg ctc aat ggt ggc tcc         1920
Pro Gly Ala Cys Glu Glu Ser Asn His Leu Leu Leu Asn Gly Gly Ser
625                 630                 635                 640 cac aag cac gtg cag agc cag att cac agg tca gcc gac tcc ggg ggg         1968
His Lys His Val Gln Ser Gln Ile His Arg Ser Ala Asp Ser Gly Gly
                645                 650                 655 cgg cag ggc aga gaa cag aag cag gac ccc ctg cac tcg ccc acc tcc         2016
Arg Gln Gly Arg Glu Gln Lys Gln Asp Pro Leu His Ser Pro Thr Ser
                660                 665                 670 aag agg aag aag gtg aaa ttt acc acc ttt acc acc atc ccc ccg gac         2064
Lys Arg Lys Lys Val Lys Phe Thr Thr Phe Thr Thr Ile Pro Pro Asp
                675                 680                 685 gac agc tgc ccc acg gtg aac tcc atc gtc agc agc aat gat gag gac         2112
Asp Ser Cys Pro Thr Val Asn Ser Ile Val Ser Ser Asn Asp Glu Asp
                690                 695                 700 atc aaa tgg gtg tgt caa gac gtg gct gtg ggt gcc ccc aag gaa ctt         2160
Ile Lys Trp Val Cys Gln Asp Val Ala Val Gly Ala Pro Lys Glu Leu
705                 710                 715                 720 aga aac tat ctg gag aaa ctc aaa gat aag gct tag gcccctctag              2206
Arg Asn Tyr Leu Glu Lys Leu Lys Asp Lys Ala
                725                 730 ccaaagggcc ctgcccagat gccttccttg tactggaaac tggcccaagt ggggcagaag       2266
gcgttgtcag tggggttaag aagggacggt cccagggtcc atgctagacc agttggaaag       2326
ttttgaagtc aggaaaagac gttttttgtat caagggattt ttagcagtta atggtggtgg      2386
atttttaaag gtcaggggaa taaagtctgg ggcatgggga gtgcagacca agttactgaa       2446
ctgcacaggc aaaattagga aggttatttt atgagtcaaa acatactaca gacaagctac       2506 caaaattat ttgttaaaaa atgcaacaag acaaataaaa agagaaataa tcatctgttt        2566
atatttctaa taaaggagca aaatataaaa ataggacctg ctaagagaca ttttccattc       2626
taattcacga ttcactttc caaggacagc cttcaactgt caccacacag ctgggggga         2686 gtcatttctt aacaagggat gcctcttggg atagaactag ggagttttaa atctttactt      2746
gatcatcttt tattttcttt tccacttttt ccttttctct ctctctctgt gtcctagact       2806
tccattgcat ttatatttaa tgtttatttc tgagaatcaa gcagtatatt tttcctaaat       2866
gaaacataaa ttatattcct attcattaga taggttccta ggaacaatgc caattaatcc      2926
attgtttaag tagtaacttg aatgtttttc tatatccctc cagctttgtt gatagtggcg      2986
ggttttgtac aattggaggg agccctcaga gccttctggg ggaggagagg aactgtcctt     3046
aatccatcac cactaccata gggcaaagcc agcaggtgtg gccctgtgag gggctgtaca     3106
gacgggatgt ggccaggaga acagagcccc acctggacca cctgacccct cgggattcca      3166
cccctgtcat cgtggggatg ttcctatata ggagaaagtt gggttaaatc aaaaaagagg      3226
```

-continued

```
ccacgcccag gtgtaatcag agccaacctg gtgggctggg tctatcacaa gacataactg    3286
atgctgaaca tgaacaaaga taaaaactgt ttggagggtt tttgagttgt ttttcttatg    3346
ttgttgggtg gggtatacca gcataaactc taaagataaa atctatgtta gattgtcaat    3406
caactgtgtt tttgaacagc ataattgtgt agcagcacat tgcaaaaatg cattcatcca    3466
aagcgacaca tgtggcaacg tagaccacgc cagtgaaata agccccttcg tgatcacctg    3526
actccagttc tccgtgtgct ccattggctg cggctgcagg aggaagatgc ctgacagccc    3586
tcatgctctc cgcagggggg cgctcacaaa gatgccaggg gtgtttattg tgtttatttt    3646
tttaattact aaaatcagta gctaagaaag ggtccttgaa gcctcctaac ctgggttgga    3706
cctttgaaaa atatatttgt agcacatatt atagatggaa agaagaagat atttatttat    3766
acctgtgatg ccaattgtca ttaaaaggct tttcatggct tgac                     3810
```

<210> SEQ ID NO 6
<211> LENGTH: 731
<212> TYPE: PRT
<213> ORGANISM: Homo sapiens

<400> SEQUENCE: 6

```
Leu Phe Asn Glu Val Val Gln Met Asn Phe Glu Ile Ala Ser Phe Ser
1               5                   10                  15

Ser Leu Ser Gly Thr Gln Pro Ile Thr Trp Gln Val Glu Tyr Pro Arg
            20                  25                  30

Lys Gly Thr Thr Asp Ile Ala Leu Ser Glu Ile Phe Val Ser Gln Lys
        35                  40                  45

Asp Leu Val Gly Ile Val Pro Leu Ala Met Asp Thr Glu Ile Leu Asn
    50                  55                  60

Thr Ala Val Leu Thr Gly Lys Thr Val Ala Met Pro Ile Lys Val Val
65                  70                  75                  80

Ser Val Glu Glu Asn Ser Ala Val Met Asp Ile Ser Glu Ser Val Glu
                85                  90                  95

Cys Lys Ser Thr Asp Glu Asp Val Ile Lys Val Ser Glu Arg Cys Asp
            100                 105                 110

Tyr Ile Phe Val Asn Gly Lys Glu Ile Lys Gly Lys Met Asp Ala Val
        115                 120                 125

Val Asn Phe Thr Tyr Gln Tyr Leu Ser Ala Pro Leu Cys Val Thr Val
    130                 135                 140

Trp Val Pro Arg Leu Pro Leu Gln Ile Glu Val Ser Asp Thr Glu Leu
145                 150                 155                 160

Ser Gln Ile Lys Gly Trp Arg Val Pro Ile Val Thr Asn Lys Arg Pro
                165                 170                 175

Thr Arg Glu Ser Glu Asp Glu Asp Glu Glu Arg Arg Gly Arg Gly
            180                 185                 190

Cys Ala Leu Gln Tyr Gln His Ala Thr Val Arg Val Leu Thr Gln Phe
        195                 200                 205

Val Ser Glu Gly Ala Gly Pro Trp Gly Gln Pro Asn Tyr Leu Leu Ser
    210                 215                 220

Pro Asn Trp Gln Phe Asp Ile Thr His Leu Val Ala Asp Phe Met Lys
225                 230                 235                 240

Leu Glu Glu Pro His Val Ala Thr Leu Gln Asp Ser Arg Val Leu Val
                245                 250                 255

Gly Arg Glu Val Gly Met Thr Thr Ile Gln Val Leu Ser Pro Leu Ser
            260                 265                 270

Asp Ser Ile Leu Ala Glu Lys Thr Ile Thr Val Leu Asp Asp Lys Val
```

```
                275                 280                 285
Ser Val Thr Asp Leu Ala Ile Gln Leu Val Ala Gly Leu Ser Val Ala
290                 295                 300
Leu Tyr Pro Asn Ala Glu Asn Ser Lys Ala Val Thr Ala Val Val Thr
305                 310                 315                 320
Ala Glu Glu Val Leu Arg Thr Pro Lys Gln Glu Ala Val Phe Ser Thr
                325                 330                 335
Trp Leu Gln Phe Ser Asp Gly Ser Val Thr Pro Leu Asp Ile Tyr Asp
                340                 345                 350
Thr Lys Asp Phe Ser Leu Ala Ala Ile Ser Gln Asp Gly Ala Val Val
                355                 360                 365
Ser Val Pro Gln Pro Arg Ser Pro Arg Trp Pro Val Val Ala Glu
370                 375                 380
Gly Glu Gly Gln Gly Pro Leu Ile Arg Val Asp Met Thr Ile Ala Glu
385                 390                 395                 400
Ala Cys Gln Lys Ser Lys Arg Lys Ser Ile Leu Ala Val Gly Val Gly
                405                 410                 415
Asn Val Arg Val Lys Phe Gly Gln Asn Asp Ala Asp Ser Ser Pro Gly
                420                 425                 430
Arg Asp Tyr Glu Glu Asp Glu Ile Lys Asn His Ala Ser Asp Arg Arg
                435                 440                 445
Gln Lys Gly Gln His His Glu Arg Thr Gly Gln Asp Gly His Leu Tyr
                450                 455                 460
Gly Ser Ser Pro Val Glu Arg Glu Gly Ala Leu Arg Arg Ala Thr
465                 470                 475                 480
Thr Thr Ala Arg Ser Leu Leu Asp Asn Lys Val Val Lys Asn Ser Arg
                485                 490                 495
Ala Asp Gly Gly Arg Leu Ala Gly Glu Gly Gln Leu Gln Asn Ile Pro
                500                 505                 510
Ile Asp Phe Thr Asn Phe Pro Ala His Val Asp Leu Pro Lys Ala Gly
                515                 520                 525
Ser Gly Leu Glu Glu Asn Asp Leu Val Gln Thr Pro Arg Gly Leu Ser
530                 535                 540
Asp Leu Glu Ile Gly Met Tyr Ala Leu Leu Gly Val Phe Cys Leu Ala
545                 550                 555                 560
Ile Leu Val Phe Leu Ile Asn Cys Ala Thr Phe Ala Leu Lys Tyr Arg
                565                 570                 575
His Lys Gln Val Pro Leu Glu Gly Gln Ala Ser Met Thr His Ser His
                580                 585                 590
Asp Trp Val Trp Leu Gly Asn Glu Ala Glu Leu Leu Glu Ser Met Gly
                595                 600                 605
Asp Ala Pro Pro Gln Asp Glu His Thr Thr Ile Ile Asp Arg Gly
610                 615                 620
Pro Gly Ala Cys Glu Glu Ser Asn His Leu Leu Leu Asn Gly Gly Ser
625                 630                 635                 640
His Lys His Val Gln Ser Gln Ile His Arg Ser Ala Asp Ser Gly Gly
                645                 650                 655
Arg Gln Gly Arg Glu Gln Lys Gln Asp Pro Leu His Ser Pro Thr Ser
                660                 665                 670
Lys Arg Lys Lys Val Lys Phe Thr Thr Phe Thr Thr Ile Pro Pro Asp
                675                 680                 685
Asp Ser Cys Pro Thr Val Asn Ser Ile Val Ser Ser Asn Asp Glu Asp
                690                 695                 700
```

```
Ile Lys Trp Val Cys Gln Asp Val Ala Val Gly Ala Pro Lys Glu Leu
705                 710                 715                 720

Arg Asn Tyr Leu Glu Lys Leu Lys Asp Lys Ala
                725                 730

<210> SEQ ID NO 7
<211> LENGTH: 3804
<212> TYPE: DNA
<213> ORGANISM: Homo sapiens
<220> FEATURE:
<221> NAME/KEY: CDS
<222> LOCATION: (3)..(2174)
<223> OTHER INFORMATION:

<400> SEQUENCE: 7 tg aac ttt gaa ata gcc agt ttc agc agc ctt tca ggg act cag ccc         47
   Asn Phe Glu Ile Ala Ser Phe Ser Ser Leu Ser Gly Thr Gln Pro
    1               5                  10                  15 atc acg tgg cag gtg gag tac cca cgg aag ggg acc aca gac atc gcc        95
Ile Thr Trp Gln Val Glu Tyr Pro Arg Lys Gly Thr Thr Asp Ile Ala
                 20                  25                  30 gtg tcc gag atc ttt gtc agc cag aag gac ctg gtg ggc atc gtt ccc       143
Val Ser Glu Ile Phe Val Ser Gln Lys Asp Leu Val Gly Ile Val Pro
             35                  40                  45 ttg gct atg gac act gaa att ctg aac acc gcc gta ctc aca gga aag       191
Leu Ala Met Asp Thr Glu Ile Leu Asn Thr Ala Val Leu Thr Gly Lys
         50                  55                  60 aca gtt gcc atg cct atc aag gtg gtc tct gtg gag gag aac agt gcc       239
Thr Val Ala Met Pro Ile Lys Val Val Ser Val Glu Glu Asn Ser Ala
 65                  70                  75 gtg atg gac atc tca gag tcg gtg gag tgc aag tcc aca gac gag gac       287
Val Met Asp Ile Ser Glu Ser Val Glu Cys Lys Ser Thr Asp Glu Asp
 80                  85                  90                  95 gtt atc aaa gtg tct gag cgc tgt gac tac atc ttt gtc aat ggc aaa       335
Val Ile Lys Val Ser Glu Arg Cys Asp Tyr Ile Phe Val Asn Gly Lys
            100                 105                 110 gag atc aaa gga aag atg gat gcg gtg gtg aac ttc aca tac cag tac       383
Glu Ile Lys Gly Lys Met Asp Ala Val Val Asn Phe Thr Tyr Gln Tyr
            115                 120                 125 ctg agc gcc ccc ctg tgt gtc acc gtg tgg gtg ccc cgg ctg ccc ctg       431
Leu Ser Ala Pro Leu Cys Val Thr Val Trp Val Pro Arg Leu Pro Leu
        130                 135                 140 cag atc gag gtc tct gac acg gag ctc agc cag ata aag ggc tgg agg       479
Gln Ile Glu Val Ser Asp Thr Glu Leu Ser Gln Ile Lys Gly Trp Arg
        145                 150                 155 gtc ccc att gtg acc aat aag agg ccc act cgt gag agc gag gat gag       527
Val Pro Ile Val Thr Asn Lys Arg Pro Thr Arg Glu Ser Glu Asp Glu
160                 165                 170                 175 gac gag gag gag cgg cgg ggc cgg ggc tgc gca ctg caa tac cag cac       575
Asp Glu Glu Glu Arg Arg Gly Arg Gly Cys Ala Leu Gln Tyr Gln His
                180                 185                 190 gcc acc gtg cgg gtc ctc acc cag ttt gtg tct gag ggc gcc ggt cca       623
Ala Thr Val Arg Val Leu Thr Gln Phe Val Ser Glu Gly Ala Gly Pro
            195                 200                 205 tgg ggc cag ccg aac tac ctg ctt agt cct aac tgg cag ttc gac atc       671
Trp Gly Gln Pro Asn Tyr Leu Leu Ser Pro Asn Trp Gln Phe Asp Ile
            210                 215                 220 act cac ctg gtg gca gac ttc atg aag ctg gag gaa cct cac gtg gcc       719
Thr His Leu Val Ala Asp Phe Met Lys Leu Glu Glu Pro His Val Ala
        225                 230                 235 acc ctc cag gac agc cgg gtc ctg gtt ggg cga gag gtt ggg atg acg       767
Thr Leu Gln Asp Ser Arg Val Leu Val Gly Arg Glu Val Gly Met Thr
```

```
                240                 245                 250                 255
acc atc cag gtg ttg tct cca ctg tct gac tcc atc ctg gca gag aag      815
Thr Ile Gln Val Leu Ser Pro Leu Ser Asp Ser Ile Leu Ala Glu Lys
            260                 265                 270 acg ata acc gtg cta gat gac aaa gtg tcg gtg aca gac ttg gcc atc      863
Thr Ile Thr Val Leu Asp Asp Lys Val Ser Val Thr Asp Leu Ala Ile
                275                 280                 285 cag ctc gtg gct ggg ctg tct gtc gcc ctt tac ccc aac gca gaa aac      911
Gln Leu Val Ala Gly Leu Ser Val Ala Leu Tyr Pro Asn Ala Glu Asn
            290                 295                 300 agc aag gcc gta aca gct gtg gtc aca gct gag gag gtg ctg cgg acc      959
Ser Lys Ala Val Thr Ala Val Val Thr Ala Glu Glu Val Leu Arg Thr
        305                 310                 315 ccc aaa cag gag gct gta ttc agc acg tgg ctg cag ttc agt gat ggc     1007
Pro Lys Gln Glu Ala Val Phe Ser Thr Trp Leu Gln Phe Ser Asp Gly
320                 325                 330                 335 tct gtg acg ccc ctg gac atc tac gac acc aag gac ttc tcc ctg gca     1055
Ser Val Thr Pro Leu Asp Ile Tyr Asp Thr Lys Asp Phe Ser Leu Ala
            340                 345                 350 gcc acc tcc cag gac gag gct gtc gtg tca gtc ccc cag ccc cgc tct     1103
Ala Thr Ser Gln Asp Glu Ala Val Val Ser Val Pro Gln Pro Arg Ser
                355                 360                 365 ccc agg tgg ccc gtt gtg gtg gcc gaa ggg gaa ggc cag ggc cca ctg     1151
Pro Arg Trp Pro Val Val Val Ala Glu Gly Glu Gly Gln Gly Pro Leu
            370                 375                 380 atc cga gtg gac atg acg atc gcc gag gcc tgc cag aaa tct aaa cgc     1199
Ile Arg Val Asp Met Thr Ile Ala Glu Ala Cys Gln Lys Ser Lys Arg
        385                 390                 395 aag agc atc ctg gct gtg ggc gtc ggc aac gtc agg gtc aag ttc gga     1247
Lys Ser Ile Leu Ala Val Gly Val Gly Asn Val Arg Val Lys Phe Gly
400                 405                 410                 415 cag aac gat gct gac tcc agc ccc ggc agg gac tat gag gaa gat gag     1295
Gln Asn Asp Ala Asp Ser Ser Pro Gly Arg Asp Tyr Glu Glu Asp Glu
            420                 425                 430 atc aag aac cac gcc agc gac cgc cgg cag aag ggc cag cac cat gag     1343
Ile Lys Asn His Ala Ser Asp Arg Arg Gln Lys Gly Gln His His Glu
                435                 440                 445 cgc aca ggc cag gat ggg cac ctc tat ggc agc tct ccc gtg gag cgt     1391
Arg Thr Gly Gln Asp Gly His Leu Tyr Gly Ser Ser Pro Val Glu Arg
            450                 455                 460 gag gaa ggg gct ctc cga aga gcc act acc acg gcc agg tcc ctg ctg     1439
Glu Glu Gly Ala Leu Arg Arg Ala Thr Thr Thr Ala Arg Ser Leu Leu
        465                 470                 475 gac aac aaa gtg gtg aag aac agt cgg gca gac ggg ggc agg ctg gca     1487
Asp Asn Lys Val Val Lys Asn Ser Arg Ala Asp Gly Gly Arg Leu Ala
480                 485                 490                 495 gga gag ggg cag ctg cag aac atc ccc att gac ttc acc aac ttc cct     1535
Gly Glu Gly Gln Leu Gln Asn Ile Pro Ile Asp Phe Thr Asn Phe Pro
            500                 505                 510 gcc cac gtg gac ctc ccc aag gcc ggg agt ggg ctg gag gaa aac gac     1583
Ala His Val Asp Leu Pro Lys Ala Gly Ser Gly Leu Glu Glu Asn Asp
                515                 520                 525 ctg gtg cag act ccg cgg ggc ctg agt gat ctg gag ata ggg atg tac     1631
Leu Val Gln Thr Pro Arg Gly Leu Ser Asp Leu Glu Ile Gly Met Tyr
            530                 535                 540 gcc ctc ctg ggg gtg ttc tgc ctg gcc atc ctc gtc ttc ctg atc aac     1679
Ala Leu Leu Gly Val Phe Cys Leu Ala Ile Leu Val Phe Leu Ile Asn
        545                 550                 555 tgc gcc acc ttt gcc ctg aag tac agg cac aag caa gtg ccc ctg gaa     1727
Cys Ala Thr Phe Ala Leu Lys Tyr Arg His Lys Gln Val Pro Leu Glu
```

```
                560              565              570              575
ggt cag gcc tcc atg acc cac tct cac gac tgg gtg tgg ctt ggc aat       1775
Gly Gln Ala Ser Met Thr His Ser His Asp Trp Val Trp Leu Gly Asn
                580                  585                  590 gag gcc gaa ctc ctg gag agc atg ggg gat gca ccg ccg ccc cag gac       1823
Glu Ala Glu Leu Leu Glu Ser Met Gly Asp Ala Pro Pro Pro Gln Asp
                595                  600                  605 gag cac acc acc atc ata gac cgc gga ccg ggg gcc tgc gag gag agc       1871
Glu His Thr Thr Ile Ile Asp Arg Gly Pro Gly Ala Cys Glu Glu Ser
        610                  615                  620 aac cat ctc ctg ctc aat ggt ggc tcc cac aag cac gtg cag agc cag       1919
Asn His Leu Leu Leu Asn Gly Gly Ser His Lys His Val Gln Ser Gln
    625                  630                  635 att cac agg tca gcc gac tcc ggg ggg cgg cag ggc aga gaa cag aag       1967
Ile His Arg Ser Ala Asp Ser Gly Gly Arg Gln Gly Arg Glu Gln Lys
640                  645                  650                  655 cag gac ccc ctg cac tcg ccc acc tcc aag agg aag aag gtg aaa ttt       2015
Gln Asp Pro Leu His Ser Pro Thr Ser Lys Arg Lys Lys Val Lys Phe
                660                  665                  670 acc acc ttt acc acc atc ccc ccg gac gac agc tgc ccc acg gtg aac       2063
Thr Thr Phe Thr Thr Ile Pro Pro Asp Asp Ser Cys Pro Thr Val Asn
                675                  680                  685 tcc atc gtc agc agc aat gat gag gac atc aaa tgg gtg tgt caa gac       2111
Ser Ile Val Ser Ser Asn Asp Glu Asp Ile Lys Trp Val Cys Gln Asp
            690                  695                  700 gtg gct gtg ggt gcc ccc aag gaa ctt aga aac tat ctg gag aaa ctc       2159
Val Ala Val Gly Ala Pro Lys Glu Leu Arg Asn Tyr Leu Glu Lys Leu
            705                  710                  715 aaa gat aag gct tag gcccctctag ccaagggcc ctgcccagat gccttccttg        2214
Lys Asp Lys Ala
720 tactggaaac tggcccaagt ggggcagaag gcgttgtcag tggggttaag aagggacggt    2274
cccagggtcc atgctagacc agttggaaag ttttgaagtc aggaaaagac gttttgtat    2334
caagggattt ttagcagtta atggtggtgg atttttaaag gtcaggggaa taaagtctgg    2394
ggcatgggga gtgcagacca agttactgaa ctgcacaggc aaaattagga aggttatttt    2454
atgagtcaaa acatactaca gacaagctac caaaaattat ttgttaaaaa atgcaacaag    2514
acaaataaaa agagaaataa tcatctgttt atatttctaa taaggagca aaatataaaa     2574
ataggacctg ctaagagaca ttttccattc taattcacga ttcactttc caaggacagc     2634
cttcaactgt caccacacag ctgggggga gtcatttctt aacaagggat gcctcttggg     2694
atagaactag ggagttttaa atctttactt gatcatcttt tattttcttt tccacttttt    2754
cctttctct ctctctctgt gtcctagact tccattgcat ttatatttaa tgtttatttc     2814
tgagaatcaa gcagtatatt tttcctaaat gaaacataaa ttatattcct attcattaga    2874
taggttccta ggaacaatgc caattaatcc attgtttaag tagtaacttg aatgttttc     2934
tatatccctc cagctttgtt gatagtggcg ggttttgtac aattggaggg agccctcaga    2994
gccttctggg ggaggagagg aactgtcctt aatccatcac cactaccata gggcaaagcc    3054
agcaggtgtg gccctgtgag gggctgtaca gacgggatgt ggccaggaga acagagcccc    3114
acctggacca cctgacccct cgggattcca ccctgtcat cgtggggatg ttcctatata     3174
ggagaaagtt gggttaaatc aaaaaagagg ccacgcccag gtgtaatcag agccaacctg    3234
gtgggctggg tctatcacaa gacataactg atgctgaaca tgaacaaaga taaaaactgt    3294
ttggagggtt tttgagttgt ttttcttatg ttgttgggtg gggtatacca gcataaactc    3354
```

```
taaagataaa atctatgtta gattgtcaat caactgtgtt tttgaacagc ataattgtgt    3414
agcagcacat tgcaaaaatg cattcatcca aagcgacaca tgtggcaacg tagaccacgc    3474
cagtgaaata agccccttcg tgatcacctg actccagttc tccgtgtgct ccattggctg    3534
cggctgcagg aggaagatgc ctgacagccc tcatgctctc cgcagggggg cgctcacaaa    3594
gatgccaggg gtgtttattg tgtttatttt tttaattact aaaatcagta gctaagaaag    3654
ggtccttgaa gcctcctaac ctgggttgga cctttgaaaa atatatttgt agcacatatt    3714
atagatggaa agaagaagat atttatttat acctgtgatg ccaattgtca ttaaaaggct    3774
tttcatggct taaaaaaaaa aaaaaaaaaa                                     3804

<210> SEQ ID NO 8
<211> LENGTH: 723
<212> TYPE: PRT
<213> ORGANISM: Homo sapiens

<400> SEQUENCE: 8

Asn Phe Glu Ile Ala Ser Phe Ser Ser Leu Ser Gly Thr Gln Pro Ile
1               5                   10                  15

Thr Trp Gln Val Glu Tyr Pro Arg Lys Gly Thr Thr Asp Ile Ala Val
            20                  25                  30

Ser Glu Ile Phe Val Ser Gln Lys Asp Leu Val Gly Ile Val Pro Leu
        35                  40                  45

Ala Met Asp Thr Glu Ile Leu Asn Thr Ala Val Leu Thr Gly Lys Thr
    50                  55                  60

Val Ala Met Pro Ile Lys Val Val Ser Val Glu Asn Ser Ala Val
65                  70                  75                  80

Met Asp Ile Ser Glu Ser Val Glu Cys Lys Ser Thr Asp Glu Asp Val
                85                  90                  95

Ile Lys Val Ser Glu Arg Cys Asp Tyr Ile Phe Val Asn Gly Lys Glu
            100                 105                 110

Ile Lys Gly Lys Met Asp Ala Val Val Asn Phe Thr Tyr Gln Tyr Leu
        115                 120                 125

Ser Ala Pro Leu Cys Val Thr Val Trp Val Pro Arg Leu Pro Leu Gln
    130                 135                 140

Ile Glu Val Ser Asp Thr Glu Leu Ser Gln Ile Lys Gly Trp Arg Val
145                 150                 155                 160

Pro Ile Val Thr Asn Lys Arg Pro Thr Arg Glu Ser Glu Asp Glu Asp
                165                 170                 175

Glu Glu Glu Arg Arg Gly Arg Gly Cys Ala Leu Gln Tyr Gln His Ala
            180                 185                 190

Thr Val Arg Val Leu Thr Gln Phe Val Ser Gly Ala Gly Pro Trp
        195                 200                 205

Gly Gln Pro Asn Tyr Leu Leu Ser Pro Asn Trp Gln Phe Asp Ile Thr
    210                 215                 220

His Leu Val Ala Asp Phe Met Lys Leu Glu Glu Pro His Val Ala Thr
225                 230                 235                 240

Leu Gln Asp Ser Arg Val Leu Val Gly Arg Glu Val Gly Met Thr Thr
                245                 250                 255

Ile Gln Val Leu Ser Pro Leu Ser Asp Ser Ile Leu Ala Glu Lys Thr
            260                 265                 270

Ile Thr Val Leu Asp Asp Lys Val Ser Val Thr Asp Leu Ala Ile Gln
        275                 280                 285

Leu Val Ala Gly Leu Ser Val Ala Leu Tyr Pro Asn Ala Glu Asn Ser
    290                 295                 300
```

```
Lys Ala Val Thr Ala Val Val Thr Ala Glu Glu Val Leu Arg Thr Pro
305                 310                 315                 320

Lys Gln Glu Ala Val Phe Ser Thr Trp Leu Gln Phe Ser Asp Gly Ser
            325                 330                 335

Val Thr Pro Leu Asp Ile Tyr Asp Thr Lys Asp Phe Ser Leu Ala Ala
            340                 345                 350

Thr Ser Gln Asp Glu Ala Val Val Ser Val Pro Gln Pro Arg Ser Pro
        355                 360                 365

Arg Trp Pro Val Val Val Ala Glu Gly Glu Gly Gln Gly Pro Leu Ile
        370                 375                 380

Arg Val Asp Met Thr Ile Ala Glu Ala Cys Gln Lys Ser Lys Arg Lys
385                 390                 395                 400

Ser Ile Leu Ala Val Gly Val Gly Asn Val Arg Val Lys Phe Gly Gln
                405                 410                 415

Asn Asp Ala Asp Ser Ser Pro Gly Arg Asp Tyr Glu Glu Asp Glu Ile
            420                 425                 430

Lys Asn His Ala Ser Asp Arg Arg Gln Lys Gly Gln His His Glu Arg
        435                 440                 445

Thr Gly Gln Asp Gly His Leu Tyr Gly Ser Ser Pro Val Glu Arg Glu
    450                 455                 460

Glu Gly Ala Leu Arg Arg Ala Thr Thr Thr Ala Arg Ser Leu Leu Asp
465                 470                 475                 480

Asn Lys Val Val Lys Asn Ser Arg Ala Asp Gly Gly Arg Leu Ala Gly
                485                 490                 495

Glu Gly Gln Leu Gln Asn Ile Pro Ile Asp Phe Thr Asn Phe Pro Ala
            500                 505                 510

His Val Asp Leu Pro Lys Ala Gly Ser Gly Leu Glu Glu Asn Asp Leu
        515                 520                 525

Val Gln Thr Pro Arg Gly Leu Ser Asp Leu Glu Ile Gly Met Tyr Ala
    530                 535                 540

Leu Leu Gly Val Phe Cys Leu Ala Ile Leu Val Phe Leu Ile Asn Cys
545                 550                 555                 560

Ala Thr Phe Ala Leu Lys Tyr Arg His Lys Gln Val Pro Leu Glu Gly
                565                 570                 575

Gln Ala Ser Met Thr His Ser His Asp Trp Val Trp Leu Gly Asn Glu
            580                 585                 590

Ala Glu Leu Leu Glu Ser Met Gly Asp Ala Pro Pro Gln Asp Glu
        595                 600                 605

His Thr Thr Ile Ile Asp Arg Gly Pro Gly Ala Cys Glu Glu Ser Asn
    610                 615                 620

His Leu Leu Leu Asn Gly Gly Ser His Lys His Val Gln Ser Gln Ile
625                 630                 635                 640

His Arg Ser Ala Asp Ser Gly Gly Arg Gln Gly Arg Glu Gln Lys Gln
                645                 650                 655

Asp Pro Leu His Ser Pro Thr Ser Lys Arg Lys Lys Val Lys Phe Thr
            660                 665                 670

Thr Phe Thr Thr Ile Pro Pro Asp Asp Ser Cys Pro Thr Val Asn Ser
        675                 680                 685

Ile Val Ser Ser Asn Asp Glu Asp Ile Lys Trp Val Cys Gln Asp Val
    690                 695                 700

Ala Val Gly Ala Pro Lys Glu Leu Arg Asn Tyr Leu Glu Lys Leu Lys
705                 710                 715                 720

Asp Lys Ala
```

-continued

```
<210> SEQ ID NO 9
<211> LENGTH: 3558
<212> TYPE: DNA
<213> ORGANISM: Homo sapiens
<220> FEATURE:
<221> NAME/KEY: CDS
<222> LOCATION: (2)..(1801)
<223> OTHER INFORMATION:

<400> SEQUENCE: 9 a tac cag tac ctg agc gcc ccc ctg tgt gtc acc gtg tgg gtc ccc cgg          49
  Tyr Gln Tyr Leu Ser Ala Pro Leu Cys Val Thr Val Trp Val Pro Arg
  1               5                  10                  15 ctg ccc ctg cag atc gag gtc tct gac acg gag ctc agc cag ata aag            97
Leu Pro Leu Gln Ile Glu Val Ser Asp Thr Glu Leu Ser Gln Ile Lys
            20                  25                  30 ggc tgg agg gtc ccc att gtg acc aat aag agg ccc act cgt gag agc           145
Gly Trp Arg Val Pro Ile Val Thr Asn Lys Arg Pro Thr Arg Glu Ser
        35                  40                  45 gag gat gag gac gag gag gag cgg cgg ggc cgg ggc tgc gca ctg caa           193
Glu Asp Glu Asp Glu Glu Glu Arg Arg Gly Arg Gly Cys Ala Leu Gln
    50                  55                  60 tac cag cac gcc acc gtg cgg gtc ctc acc cag ttt gtg tct gag ggc           241
Tyr Gln His Ala Thr Val Arg Val Leu Thr Gln Phe Val Ser Glu Gly
65                  70                  75                  80 gcc ggt cca tgg ggc cag ccg aac tac ctg ctt agt cct aac tgg cag           289
Ala Gly Pro Trp Gly Gln Pro Asn Tyr Leu Leu Ser Pro Asn Trp Gln
                85                  90                  95 ttc gac atc act cac ctg gtg gca gac ttc atg aag ctg gag gaa cct           337
Phe Asp Ile Thr His Leu Val Ala Asp Phe Met Lys Leu Glu Glu Pro
            100                 105                 110 cac gtg gcc acc ctc cag gac agc cgg gtc ctg gtt ggg cga gag gtt           385
His Val Ala Thr Leu Gln Asp Ser Arg Val Leu Val Gly Arg Glu Val
        115                 120                 125 ggg atg acg acc atc cag gtg ttg tct cca ctg tct gac tcc atc ctg           433
Gly Met Thr Thr Ile Gln Val Leu Ser Pro Leu Ser Asp Ser Ile Leu
    130                 135                 140 gca gag aag acg ata acc gtg cta gat gac aaa gtg tcg gtg aca gac           481
Ala Glu Lys Thr Ile Thr Val Leu Asp Asp Lys Val Ser Val Thr Asp
145                 150                 155                 160 ttg gcc atc cag ctc gtg gct ggg ctg tct gtc gcc ctt tac ccc aac           529
Leu Ala Ile Gln Leu Val Ala Gly Leu Ser Val Ala Leu Tyr Pro Asn
                165                 170                 175 gca gaa aac agc aag gcc gta aca gct gtg gtc aca gct gag gag gtg           577
Ala Glu Asn Ser Lys Ala Val Thr Ala Val Val Thr Ala Glu Glu Val
            180                 185                 190 ctg cgg acc ccc aaa cag gag gct gta ttc agc acg tgg ctg cag ttc           625
Leu Arg Thr Pro Lys Gln Glu Ala Val Phe Ser Thr Trp Leu Gln Phe
        195                 200                 205 agt gat ggc tct gtg acg ccc ctg gac atc tac gac acc aag gac ttc           673
Ser Asp Gly Ser Val Thr Pro Leu Asp Ile Tyr Asp Thr Lys Asp Phe
    210                 215                 220 tcc ctg gca gcc acc tcc cag gac gag gct gtc gtg tca gtc ccc cag           721
Ser Leu Ala Ala Thr Ser Gln Asp Glu Ala Val Val Ser Val Pro Gln
225                 230                 235                 240 ccc agc tct ccc agg tgg ccc gtt gtg gtg gcc gaa ggg gaa ggc cag           769
Pro Ser Ser Pro Arg Trp Pro Val Val Val Ala Glu Gly Glu Gly Gln
                245                 250                 255 ggc cca ctg atc cga gtg gac atg acg atc gcc gag gcc tgc cag aaa           817
Gly Pro Leu Ile Arg Val Asp Met Thr Ile Ala Glu Ala Cys Gln Lys
            260                 265                 270
```

| | | |
|---|---|---|
| tct aaa cgc aag agc atc ctg gct gtg ggc gtc ggc aac gtc agg gtc<br>Ser Lys Arg Lys Ser Ile Leu Ala Val Gly Val Gly Asn Val Arg Val<br>275 280 285 | | 865 |
| aag ttc gga cag aac gat gct gac tcc agc ccc ggc ggg gac tat gag<br>Lys Phe Gly Gln Asn Asp Ala Asp Ser Ser Pro Gly Gly Asp Tyr Glu<br>290 295 300 | | 913 |
| gaa gat gag atc aag aac cac gcc agc gac cgc cgg cag aag ggc cag<br>Glu Asp Glu Ile Lys Asn His Ala Ser Asp Arg Arg Gln Lys Gly Gln<br>305 310 315 320 | | 961 |
| cac cat gag cgc aca ggc cag gat ggg cac ctc tat ggc agc tct ccc<br>His His Glu Arg Thr Gly Gln Asp Gly His Leu Tyr Gly Ser Ser Pro<br>325 330 335 | | 1009 |
| gtg gag cgt gag gaa ggg gct ctc cga aga gcc act acc acg gcc agg<br>Val Glu Arg Glu Glu Gly Ala Leu Arg Arg Ala Thr Thr Thr Ala Arg<br>340 345 350 | | 1057 |
| tcc ctg ctg gac aac aaa gtg gtg aag aac agt cgg gca gac ggg ggc<br>Ser Leu Leu Asp Asn Lys Val Val Lys Asn Ser Arg Ala Asp Gly Gly<br>355 360 365 | | 1105 |
| agg ctg gca gga gag ggg cag ctg cag aac atc ccc att gac ttc acc<br>Arg Leu Ala Gly Glu Gly Gln Leu Gln Asn Ile Pro Ile Asp Phe Thr<br>370 375 380 | | 1153 |
| aac ttc cct gcc cac gtg gac ctc ccc aag gcc ggg agt ggg ctg gag<br>Asn Phe Pro Ala His Val Asp Leu Pro Lys Ala Gly Ser Gly Leu Glu<br>385 390 395 400 | | 1201 |
| gaa aac gac ctg gtg cag act ccg cgg ggc ctg agt gat ctg gag ata<br>Glu Asn Asp Leu Val Gln Thr Pro Arg Gly Leu Ser Asp Leu Glu Ile<br>405 410 415 | | 1249 |
| ggg atg tac gcc ctc ctg ggg gtg ttc tgc ctg gcc atc ctc gtc ttc<br>Gly Met Tyr Ala Leu Leu Gly Val Phe Cys Leu Ala Ile Leu Val Phe<br>420 425 430 | | 1297 |
| ctg atc aac tgc gcc acc ttt gcc ctg aag tac agg cac aag caa gtg<br>Leu Ile Asn Cys Ala Thr Phe Ala Leu Lys Tyr Arg His Lys Gln Val<br>435 440 445 | | 1345 |
| ccc ctg gaa ggt cag gcc tcc atg acc cac tct cac gac tgg gtg tgg<br>Pro Leu Glu Gly Gln Ala Ser Met Thr His Ser His Asp Trp Val Trp<br>450 455 460 | | 1393 |
| ctt ggc aat gag gcc gaa ctc ctg gag agc atg ggg gat gcg ccg ccg<br>Leu Gly Asn Glu Ala Glu Leu Leu Glu Ser Met Gly Asp Ala Pro Pro<br>465 470 475 480 | | 1441 |
| ccc cag gac gag cac acc acc atc ata gac cgc gga ccg ggg gcc tgc<br>Pro Gln Asp Glu His Thr Thr Ile Ile Asp Arg Gly Pro Gly Ala Cys<br>485 490 495 | | 1489 |
| gag gag agc aac cat ctc ctg ctc aat ggt ggc tcc cac aag cac gtg<br>Glu Glu Ser Asn His Leu Leu Leu Asn Gly Gly Ser His Lys His Val<br>500 505 510 | | 1537 |
| cag agc cag att cac agg tca gcc gac tcc ggg ggg cgg cag ggc aga<br>Gln Ser Gln Ile His Arg Ser Ala Asp Ser Gly Gly Arg Gln Gly Arg<br>515 520 525 | | 1585 |
| gaa cag aag cag gac ccc ctg cac tcg ccc acc tcc aag agg aag aag<br>Glu Gln Lys Gln Asp Pro Leu His Ser Pro Thr Ser Lys Arg Lys Lys<br>530 535 540 | | 1633 |
| gtg aaa ttt acc acc ttt acc acc atc ccc ccg gac gac agc tgc ccc<br>Val Lys Phe Thr Thr Phe Thr Thr Ile Pro Pro Asp Asp Ser Cys Pro<br>545 550 555 560 | | 1681 |
| acg gtg aac tcc atc gtc agc agc aat gat gag gac atc aaa tgg gtg<br>Thr Val Asn Ser Ile Val Ser Ser Asn Asp Glu Asp Ile Lys Trp Val<br>565 570 575 | | 1729 |
| tgt caa gac gtg gct gtg ggt gcc ccc aag gaa ctt aga aac tat ctg<br>Cys Gln Asp Val Ala Val Gly Ala Pro Lys Glu Leu Arg Asn Tyr Leu<br>580 585 590 | | 1777 |

```
gag aaa ctc aaa gat aag gct tag gccctctag ccaaagggcc ctgcccagat      1831
Glu Lys Leu Lys Asp Lys Ala
        595 gccttccttg tactggaaac tggcccaagt ggggcagaag gcgttgtcag tggggttaag    1891 aagggacggt cccagggtcc atgctagacc agttggaaag ttttgaagtc aggaaaagac    1951 gttttgtat  caaggattt  ttagcagtta atggtggtgg attttaaag  gtcaggggaa    2011 taaagtctgg ggcatgggga gtgcagacca agttactgaa ctgcacaggc aaaattagga    2071 aggttatttt atgagtcaaa acatactaca gacaagctac caaaaattat ttgttaaaaa    2131 atgcaacaag acaaataaaa agagaaataa tcatctgttt atatttctaa taaggagca    2191 aaatataaaa ataggacctg ctaagagaca ttttccattc taattcacga ttcacttttc    2251 caaggacagc cttcaactgt caccacacag ctgggggga  gtcatttctt aacaagggat    2311 gcctcttggg atagaactag ggagttttaa atctttactt gatcatcttt tattttcttt    2371 tccactttt  cctttttct  ctctctctgt gtcctagact tccattgcat ttatatttaa    2431 tgtttatttc tgagaatcaa gcagtatatt tttcctaaat gaaacataaa ttatattcct    2491 attcattaga taggttccta ggaacaatgc caattaatcc attgtttaag tagtaacttg    2551 aatgttttc  tatatccctc cagctttgtt gatagtggcg ggttttgtac aattggaggg    2611 agccctcaga gccttctggg ggaggagagg aactgtcctt aatccatcac cactaccata    2671 gggcaaagcc agcaggtgtg gccctgtgag gggctgtaca gatgggatgt ggccaggaga    2731 acagagcccc acctggacca cctgacccct cgggattcca cccctgtcat cgtggggatg    2791 ttcctatatg ggagaaagtt gggttaaatc aaaaagagg  ccacgcccag gtgtaatcag    2851 agccaacctg gtgggctggg tctatcacaa gacataactg atgctgaaca tgaacaaaga    2911 taaaaactgt ttggagggtt tttgagttgt ttttcttatg ttgttgggtg gggtatacca    2971 gcataaactc taaagataaa atctatgtta gattgtcaat caactgtgtt tttgaacagc    3031 ataattgtgt agcagcacat tgcaaaaatg cattcatcca aagcgacaca tgtggcaacg    3091 tagaccacgc cagtgaaata agccccttcg tgatcacctg actccagttc tccgtgtgct    3151 ccattggctg cggctgcagg aggaagatgc ctgacagccc tcatgctctc cgcaggggg    3211 cgctcacaaa gatgccaggg gtgtttattg tgtttatttt tttaattact aaaatcagta    3271 gctaagaaag ggtccttgaa gcctcctaac ctgggttgga cctttgaaaa atatatttgt    3331 agcacatatt atagatggaa agaagaagat atttatttat acctgtgatg ccaattgtca    3391 ttaaaaggct tttcatggct tgacaaaaaa aaaaaaaaa  aaaaaaaaa  aaaaaaaaa     3451 aaaaaaaaa  aaaaaaaaa  aaaaaaaaa  aaaaaaaaa  aaaaaaaaa  aaaaaaaaa     3511 aaaaaaaaa  aaaaaaaaa  aaaaaaaaa  aaaaaaaaa  aaaaaaa                  3558
```

<210> SEQ ID NO 10
<211> LENGTH: 599
<212> TYPE: PRT
<213> ORGANISM: Homo sapiens

<400> SEQUENCE: 10

```
Tyr Gln Tyr Leu Ser Ala Pro Leu Cys Val Thr Val Trp Val Pro Arg
1               5                   10                  15

Leu Pro Leu Gln Ile Glu Val Ser Asp Thr Glu Leu Ser Gln Ile Lys
            20                  25                  30

Gly Trp Arg Val Pro Ile Val Thr Asn Lys Arg Pro Thr Arg Glu Ser
        35                  40                  45
```

-continued

```
Glu Asp Glu Asp Glu Glu Arg Arg Gly Arg Gly Cys Ala Leu Gln
 50                  55                  60

Tyr Gln His Ala Thr Val Arg Val Leu Thr Gln Phe Val Ser Glu Gly
 65                  70                  75                  80

Ala Gly Pro Trp Gly Gln Pro Asn Tyr Leu Leu Ser Pro Asn Trp Gln
                 85                  90                  95

Phe Asp Ile Thr His Leu Val Ala Asp Phe Met Lys Leu Glu Glu Pro
            100                 105                 110

His Val Ala Thr Leu Gln Asp Ser Arg Val Leu Val Gly Arg Glu Val
        115                 120                 125

Gly Met Thr Thr Ile Gln Val Leu Ser Pro Leu Ser Asp Ser Ile Leu
    130                 135                 140

Ala Glu Lys Thr Ile Thr Val Leu Asp Asp Lys Val Ser Val Thr Asp
145                 150                 155                 160

Leu Ala Ile Gln Leu Val Ala Gly Leu Ser Val Ala Leu Tyr Pro Asn
                165                 170                 175

Ala Glu Asn Ser Lys Ala Val Thr Ala Val Val Thr Ala Glu Glu Val
            180                 185                 190

Leu Arg Thr Pro Lys Gln Glu Ala Val Phe Ser Thr Trp Leu Gln Phe
        195                 200                 205

Ser Asp Gly Ser Val Thr Pro Leu Asp Ile Tyr Asp Thr Lys Asp Phe
210                 215                 220

Ser Leu Ala Ala Thr Ser Gln Asp Glu Ala Val Val Ser Val Pro Gln
225                 230                 235                 240

Pro Ser Ser Pro Arg Trp Pro Val Val Ala Glu Gly Glu Gly Gln
                245                 250                 255

Gly Pro Leu Ile Arg Val Asp Met Thr Ile Ala Glu Ala Cys Gln Lys
            260                 265                 270

Ser Lys Arg Lys Ser Ile Leu Ala Val Gly Val Gly Asn Val Arg Val
        275                 280                 285

Lys Phe Gly Gln Asn Asp Ala Asp Ser Ser Pro Gly Gly Asp Tyr Glu
    290                 295                 300

Glu Asp Glu Ile Lys Asn His Ala Ser Asp Arg Arg Gln Lys Gly Gln
305                 310                 315                 320

His His Glu Arg Thr Gly Gln Asp Gly His Leu Tyr Gly Ser Ser Pro
                325                 330                 335

Val Glu Arg Glu Glu Gly Ala Leu Arg Arg Ala Thr Thr Thr Ala Arg
            340                 345                 350

Ser Leu Leu Asp Asn Lys Val Val Lys Asn Ser Arg Ala Asp Gly Gly
        355                 360                 365

Arg Leu Ala Gly Glu Gly Gln Leu Gln Asn Ile Pro Ile Asp Phe Thr
370                 375                 380

Asn Phe Pro Ala His Val Asp Leu Pro Lys Ala Gly Ser Gly Leu Glu
385                 390                 395                 400

Glu Asn Asp Leu Val Gln Thr Pro Arg Gly Leu Ser Asp Leu Glu Ile
                405                 410                 415

Gly Met Tyr Ala Leu Leu Gly Val Phe Cys Leu Ala Ile Leu Val Phe
            420                 425                 430

Leu Ile Asn Cys Ala Thr Phe Ala Leu Lys Tyr Arg His Lys Gln Val
        435                 440                 445

Pro Leu Glu Gly Gln Ala Ser Met Thr His Ser His Asp Trp Val Trp
    450                 455                 460

Leu Gly Asn Glu Ala Glu Leu Leu Glu Ser Met Gly Asp Ala Pro Pro
465                 470                 475                 480
```

```
Pro Gln Asp Glu His Thr Thr Ile Ile Asp Arg Gly Pro Gly Ala Cys
                485                 490                 495
Glu Glu Ser Asn His Leu Leu Leu Asn Gly Gly Ser His Lys His Val
            500                 505                 510
Gln Ser Gln Ile His Arg Ser Ala Asp Ser Gly Gly Arg Gln Gly Arg
        515                 520                 525
Glu Gln Lys Gln Asp Pro Leu His Ser Pro Thr Ser Lys Arg Lys Lys
    530                 535                 540
Val Lys Phe Thr Thr Phe Thr Thr Ile Pro Pro Asp Asp Ser Cys Pro
545                 550                 555                 560
Thr Val Asn Ser Ile Val Ser Ser Asn Asp Glu Asp Ile Lys Trp Val
                565                 570                 575
Cys Gln Asp Val Ala Val Gly Ala Pro Lys Glu Leu Arg Asn Tyr Leu
            580                 585                 590
Glu Lys Leu Lys Asp Lys Ala
        595

<210> SEQ ID NO 11
<211> LENGTH: 3820
<212> TYPE: DNA
<213> ORGANISM: Mus musculus
<220> FEATURE:
<221> NAME/KEY: CDS
<222> LOCATION: (1)..(3432)
<223> OTHER INFORMATION:

<400> SEQUENCE: 11
```

| | | | | | | | | | | | | | | | | |
|---|---|---|---|---|---|---|---|---|---|---|---|---|---|---|---|---|
| gaa | ccc | gag | aaa | agt | tgt | ccg | gac | ccg | ttc | agg | agc | agc | cgc | cgg | agc | 48 |
| Glu | Pro | Glu | Lys | Ser | Cys | Pro | Asp | Pro | Phe | Arg | Ser | Ser | Arg | Arg | Ser | |
| 1 | | | | 5 | | | | | 10 | | | | | 15 | | |
| cgg | agc | gct | gcc | ggg | ggc | ggc | ccc | ggg | cat | ggg | gca | acc | ggc | gcg | gtc | 96 |
| Arg | Ser | Ala | Ala | Gly | Gly | Gly | Pro | Gly | His | Gly | Ala | Thr | Gly | Ala | Val | |
| | | | 20 | | | | | 25 | | | | | 30 | | | |
| ccg | ggg | ctg | gcg | atg | gat | ggc | gtg | aca | gcg | gcc | acg | atg | cgc | tcc | gag | 144 |
| Pro | Gly | Leu | Ala | Met | Asp | Gly | Val | Thr | Ala | Ala | Thr | Met | Arg | Ser | Glu | |
| | | 35 | | | | | 40 | | | | | 45 | | | | |
| ggc | gcg | gcc | ccg | agg | cgg | gcg | gcg | cgg | tac | ggg | gcg | ctg | agc | ctg | gtc | 192 |
| Gly | Ala | Ala | Pro | Arg | Arg | Ala | Ala | Arg | Tyr | Gly | Ala | Leu | Ser | Leu | Val | |
| | 50 | | | | | 55 | | | | | 60 | | | | | |
| cta | gcc | acg | cta | ctg | ggc | caa | gtg | acc | gaa | agc | cga | ggg | gtc | atg | gat | 240 |
| Leu | Ala | Thr | Leu | Leu | Gly | Gln | Val | Thr | Glu | Ser | Arg | Gly | Val | Met | Asp | |
| 65 | | | | | 70 | | | | | 75 | | | | | 80 | |
| aat | ata | cag | aga | ttc | tct | tca | ttg | ccg | ccg | tac | ctg | ccc | gtg | agc | ttc | 288 |
| Asn | Ile | Gln | Arg | Phe | Ser | Ser | Leu | Pro | Pro | Tyr | Leu | Pro | Val | Ser | Phe | |
| | | | | 85 | | | | | 90 | | | | | 95 | | |
| cac | gtc | ctc | aga | gcc | gag | act | gca | ttc | ttc | cta | aag | gag | gcc | aac | ccc | 336 |
| His | Val | Leu | Arg | Ala | Glu | Thr | Ala | Phe | Phe | Leu | Lys | Glu | Ala | Asn | Pro | |
| | | | 100 | | | | | 105 | | | | | 110 | | | |
| gac | ccg | ctg | cgg | aat | gcc | agc | ctg | cag | tcc | agg | gtg | gag | tct | ttc | ttc | 384 |
| Asp | Pro | Leu | Arg | Asn | Ala | Ser | Leu | Gln | Ser | Arg | Val | Glu | Ser | Phe | Phe | |
| | | 115 | | | | | 120 | | | | | 125 | | | | |
| atc | tac | aag | gcc | cag | cag | ccc | ccg | gta | tta | aac | gtc | agc | tat | ggg | cct | 432 |
| Ile | Tyr | Lys | Ala | Gln | Gln | Pro | Pro | Val | Leu | Asn | Val | Ser | Tyr | Gly | Pro | |
| | 130 | | | | | 135 | | | | | 140 | | | | | |
| tac | tct | gca | gaa | aag | gtc | atc | cct | ctg | gac | ttg | atg | ttg | aac | ccc | aac | 480 |
| Tyr | Ser | Ala | Glu | Lys | Val | Ile | Pro | Leu | Asp | Leu | Met | Leu | Asn | Pro | Asn | |
| 145 | | | | | 150 | | | | | 155 | | | | | 160 | |
| ttt | tta | ggc | cca | acc | agt | aag | ttt | ccc | ttt | gac | tgg | agg | ctg | aag | gcc | 528 |
| Phe | Leu | Gly | Pro | Thr | Ser | Lys | Phe | Pro | Phe | Asp | Trp | Arg | Leu | Lys | Ala | |
| | | | | 165 | | | | | 170 | | | | | 175 | | |

-continued

| | |
|---|---|
| tac atc ctt caa gag aaa gtc tac ctg agc cat ccc aaa gta cag gtg<br>Tyr Ile Leu Gln Glu Lys Val Tyr Leu Ser His Pro Lys Val Gln Val<br>         180                      185                      190 | 576 |
| ctc ttc cac atc gtg ggc cga gac tgg gat gac cac agg gac gag aaa<br>Leu Phe His Ile Val Gly Arg Asp Trp Asp Asp His Arg Asp Glu Lys<br>       195                      200                      205 | 624 |
| ctg ccc tgc ctg cgg gtc ttt gcg ttc aga gac agc cgg gag gtt cga<br>Leu Pro Cys Leu Arg Val Phe Ala Phe Arg Asp Ser Arg Glu Val Arg<br>210                      215                      220 | 672 |
| ggc agc tgt cgt ctg ggt ggg ccc ctg gga ctg tgc gtg gcc cag ctg<br>Gly Ser Cys Arg Leu Gly Gly Pro Leu Gly Leu Cys Val Ala Gln Leu<br>225                      230                      235                      240 | 720 |
| gag atg ctg cct ggc tgg ttc agt ccc ccg gcg gtt tat tct ggg cgc<br>Glu Met Leu Pro Gly Trp Phe Ser Pro Pro Ala Val Val Ser Gly Arg<br>                      245                      250                      255 | 768 |
| agg agg cca gca gag cgg cca gag ggg agt ccg gtg gaa ctg tat tat<br>Arg Arg Pro Ala Glu Arg Pro Glu Gly Ser Pro Val Glu Leu Tyr Tyr<br>       260                      265                      270 | 816 |
| gct gta cag cca ggg gac gag cgt ggt gac tgc act gga ggt gac acc<br>Ala Val Gln Pro Gly Asp Glu Arg Gly Asp Cys Thr Gly Gly Asp Thr<br>275                      280                      285 | 864 |
| agg aag gac aat gct att cgt cca gga aag gat gga cag gag ggc agg<br>Arg Lys Asp Asn Ala Ile Arg Pro Gly Lys Asp Gly Gln Glu Gly Arg<br>       290                      295                      300 | 912 |
| aca tcc cac cta cag aag att ggc acc att agc ctt tac cgc gcc cag<br>Thr Ser His Leu Gln Lys Ile Gly Thr Ile Ser Leu Tyr Arg Ala Gln<br>305                      310                      315                      320 | 960 |
| gac agc aac cag ctc agc gaa ctg cgc ctg gat ggc aat gtg gtc atc<br>Asp Ser Asn Gln Leu Ser Glu Leu Arg Leu Asp Gly Asn Val Val Ile<br>                      325                      330                      335 | 1008 |
| tgg ctg ccc tcc cag ccc gtc aag cag gga gac ata gtc acc gca tct<br>Trp Leu Pro Ser Gln Pro Val Lys Gln Gly Asp Ile Val Thr Ala Ser<br>                      340                      345                      350 | 1056 |
| gtc acc atc gcc aat aac tct act gtg gac cat ttc atc cta aga gcc<br>Val Thr Ile Ala Asn Asn Ser Thr Val Asp His Phe Ile Leu Arg Ala<br>                355                      360                      365 | 1104 |
| aag gtg aag aag ggg gtg aac atc ctg acc gtg cag acc agc gag cct<br>Lys Val Lys Lys Gly Val Asn Ile Leu Thr Val Gln Thr Ser Glu Pro<br>370                      375                      380 | 1152 |
| cgg cag tgg gat gtg agg caa gag gtg ggc aat gga ggg aag cac acc<br>Arg Gln Trp Asp Val Arg Gln Glu Val Gly Asn Gly Gly Lys His Thr<br>385                      390                      395                      400 | 1200 |
| acc acc tcg gtg gcc tgc cag cgc ctg ggc cct ggg gca cga aat agg<br>Thr Thr Ser Val Ala Cys Gln Arg Leu Gly Pro Gly Ala Arg Asn Arg<br>                      405                      410                      415 | 1248 |
| agc agc aat tta ttc agc gag gtc atg cag atg aat ttt gaa atc gcc<br>Ser Ser Asn Leu Phe Ser Glu Val Met Gln Met Asn Phe Glu Ile Ala<br>                      420                      425                      430 | 1296 |
| agc ttc agc agc ctc tcg ggg aca cag cct atc aca tgg cag gtg gag<br>Ser Phe Ser Ser Leu Ser Gly Thr Gln Pro Ile Thr Trp Gln Val Glu<br>                435                      440                      445 | 1344 |
| tac ccg agg aag ggg gcc acg gac att gct gtg tcg gag atc ttc atc<br>Tyr Pro Arg Lys Gly Ala Thr Asp Ile Ala Val Ser Glu Ile Phe Ile<br>450                      455                      460 | 1392 |
| agc cag aag gac cta gtt gcc atc gtc ccc ctt gct atg gac act gaa<br>Ser Gln Lys Asp Leu Val Ala Ile Val Pro Leu Ala Met Asp Thr Glu<br>465                      470                      475                      480 | 1440 |
| ctc ctg aac aca gcc atc ctc aca ggg aag acg gtg gcc atg cct gtc<br>Leu Leu Asn Thr Ala Ile Leu Thr Gly Lys Thr Val Ala Met Pro Val<br>                485                      490                      495 | 1488 |

-continued

| | | |
|---|---|---|
| agg gtg gtg tcg gtg gaa gag aat agc acc ctg agg gac atc tcg gag<br>Arg Val Val Ser Val Glu Glu Asn Ser Thr Leu Arg Asp Ile Ser Glu<br>500 505 510 | 1536 | |
| ttg gtg gag tgc aag gcc aca gac gag aat gtc atc aag gtc tcg gac<br>Leu Val Glu Cys Lys Ala Thr Asp Glu Asn Val Ile Lys Val Ser Asp<br>515 520 525 | 1584 | |
| cac tgt gac tat gtc ttt gtc aat ggt aaa gag atc aag ggc aag atg<br>His Cys Asp Tyr Val Phe Val Asn Gly Lys Glu Ile Lys Gly Lys Met<br>530 535 540 | 1632 | |
| gac tct gtg gtg aac ttc acc tac cag cac ctg agc gca ccg ctg cat<br>Asp Ser Val Val Asn Phe Thr Tyr Gln His Leu Ser Ala Pro Leu His<br>545 550 555 560 | 1680 | |
| gtc act gtg tgg gtg cca cgg ctt ccc ctg cag atc gag gtc tct gac<br>Val Thr Val Trp Val Pro Arg Leu Pro Leu Gln Ile Glu Val Ser Asp<br>565 570 575 | 1728 | |
| aca gaa ctc agc cag gtt aag ggc tgg aga gtc ccc atc gtg gcc agc<br>Thr Glu Leu Ser Gln Val Lys Gly Trp Arg Val Pro Ile Val Ala Ser<br>580 585 590 | 1776 | |
| aag agg ccc act cgg gac agt gag gag gaa gaa gag gaa gaa cag aaa<br>Lys Arg Pro Thr Arg Asp Ser Glu Glu Glu Glu Glu Glu Gln Lys<br>595 600 605 | 1824 | |
| ggc cgg ggt tgt acc ctg cag ttc cag cat gcc aca gtg cgc gtc ctc<br>Gly Arg Gly Cys Thr Leu Gln Phe Gln His Ala Thr Val Arg Val Leu<br>610 615 620 | 1872 | |
| acc caa ttt gta tca gag ggt gct ggg ccc tgg ggc cag ctg agc cac<br>Thr Gln Phe Val Ser Glu Gly Ala Gly Pro Trp Gly Gln Leu Ser His<br>625 630 635 640 | 1920 | |
| ctt ctc agt cca gac tgg cag ttt gac atc acc cac ctg gtg gct gac<br>Leu Leu Ser Pro Asp Trp Gln Phe Asp Ile Thr His Leu Val Ala Asp<br>645 650 655 | 1968 | |
| ttt atg aag ctg gag tcc cca cac ata gcc acc ctg cag gac agc agg<br>Phe Met Lys Leu Glu Ser Pro His Ile Ala Thr Leu Gln Asp Ser Arg<br>660 665 670 | 2016 | |
| gtc ttg gtt ggg cgg gaa gtc gga atg acc acc atc cag gtg ttg tct<br>Val Leu Val Gly Arg Glu Val Gly Met Thr Thr Ile Gln Val Leu Ser<br>675 680 685 | 2064 | |
| ccc ctg tcc gac tcc atc ttg gcc gag aag aca gta act gtg ctg gat<br>Pro Leu Ser Asp Ser Ile Leu Ala Glu Lys Thr Val Thr Val Leu Asp<br>690 695 700 | 2112 | |
| gac aaa gta tct gtg aca gac tta gct gtc cag gtg gtg gct ggg ctg<br>Asp Lys Val Ser Val Thr Asp Leu Ala Val Gln Val Val Ala Gly Leu<br>705 710 715 720 | 2160 | |
| tct gtc acc cta cac ccc atc tca gag aac aac aag gcc acc tca gct<br>Ser Val Thr Leu His Pro Ile Ser Glu Asn Asn Lys Ala Thr Ser Ala<br>725 730 735 | 2208 | |
| gtg gcc atg gca gaa gag ctg cta cgt gcc cca aaa aag gaa gct ata<br>Val Ala Met Ala Glu Glu Leu Leu Arg Ala Pro Lys Lys Glu Ala Ile<br>740 745 750 | 2256 | |
| atc agc aca tgg ctc cag ttc agt gat ggc tca gtg aca ccc ctg gat<br>Ile Ser Thr Trp Leu Gln Phe Ser Asp Gly Ser Val Thr Pro Leu Asp<br>755 760 765 | 2304 | |
| atc tac gac tcc aag gac ttc tcc ttg act gcc atc tct ttg gac gag<br>Ile Tyr Asp Ser Lys Asp Phe Ser Leu Thr Ala Ile Ser Leu Asp Glu<br>770 775 780 | 2352 | |
| gct gtc gtg tcc atc ccc caa ccc ctc tcg cct tgg tgg ccc acc gtg<br>Ala Val Val Ser Ile Pro Gln Pro Leu Ser Pro Trp Trp Pro Thr Val<br>785 790 795 800 | 2400 | |
| gta gct gaa gga gaa ggc cag ggc cca ctg ctc cgg gtc gat atg tcc<br>Val Ala Glu Gly Glu Gly Gln Gly Pro Leu Leu Arg Val Asp Met Ser<br>805 810 815 | 2448 | |

```
att gcc gaa gcc tgt cag aaa tcc aag cgc aag agt gtg ctg gct gtt      2496
Ile Ala Glu Ala Cys Gln Lys Ser Lys Arg Lys Ser Val Leu Ala Val
            820                 825                 830 ggc att ggc cac gtg ggg gtc aag ttt gga tgg gat gac gct gac tcc      2544
Gly Ile Gly His Val Gly Val Lys Phe Gly Trp Asp Asp Ala Asp Ser
835                 840                 845 agc cag act gga gaa aag gat gag gag gag atc aag aac cat gcc agt      2592
Ser Gln Thr Gly Glu Lys Asp Glu Glu Glu Ile Lys Asn His Ala Ser
        850                 855                 860 gac cgt cgg cag aag att cag gac ctg gaa cgc cca ggc cag gat gaa      2640
Asp Arg Arg Gln Lys Ile Gln Asp Leu Glu Arg Pro Gly Gln Asp Glu
865                 870                 875                 880 cta tac cat ggc aac ttt cct ggg gat cgt gaa gaa gga gcg ctg agt      2688
Leu Tyr His Gly Asn Phe Pro Gly Asp Arg Glu Glu Gly Ala Leu Ser
                885                 890                 895 gct acc acc act acc aag tcc ctg ctg gat aac aac gtg ggg aag agt      2736
Ala Thr Thr Thr Thr Lys Ser Leu Leu Asp Asn Asn Val Gly Lys Ser
            900                 905                 910 ggc agg cgg gac ggg gct agg cta cac agc ata ccc att gac ttc acc      2784
Gly Arg Arg Asp Gly Ala Arg Leu His Ser Ile Pro Ile Asp Phe Thr
        915                 920                 925 aat ttc ccg gcc cat gtg gac ctc ccc aag gcc aag acc agg ggc aca      2832
Asn Phe Pro Ala His Val Asp Leu Pro Lys Ala Lys Thr Arg Gly Thr
930                 935                 940 ctg gag gag aat ggt ctc atg cag aca gcc cat ggc ctg agt gac cta      2880
Leu Glu Glu Asn Gly Leu Met Gln Thr Ala His Gly Leu Ser Asp Leu
945                 950                 955                 960 gag att ggg atg tat gcc ctc cta ggt gtc ttc tgc ctg gcc atc ctt      2928
Glu Ile Gly Met Tyr Ala Leu Leu Gly Val Phe Cys Leu Ala Ile Leu
                965                 970                 975 gtc ttt ctc att aac tgc gcc acc ttt gcc ttc aag tac agg cac aaa      2976
Val Phe Leu Ile Asn Cys Ala Thr Phe Ala Phe Lys Tyr Arg His Lys
            980                 985                 990 cag gtg cct ctg gaa ggc cag gca tcc atg acc cac tct cat gac tgg     3024
Gln Val Pro Leu Glu Gly Gln Ala Ser Met Thr His Ser His Asp Trp
        995                 1000                1005 gtc tgg ctg ggc aat gag gcg gag ctc ttg gag aac att ggg gac        3069
Val Trp Leu Gly Asn Glu Ala Glu Leu Leu Glu Asn Ile Gly Asp
    1010                1015                1020 ctg tcc cca ccc cag gat gag cac acg acc atc ata gac cga ggg        3114
Leu Ser Pro Pro Gln Asp Glu His Thr Thr Ile Ile Asp Arg Gly
    1025                1030                1035 ctg ggg ggc tgt gag gag aac aac cac tta ctt ctc aac ggt ggc        3159
Leu Gly Gly Cys Glu Glu Asn Asn His Leu Leu Leu Asn Gly Gly
    1040                1045                1050 tcc caa aag ccc acg cag agc cag gtt cac agg ccg cca ggc tcc        3204
Ser Gln Lys Pro Thr Gln Ser Gln Val His Arg Pro Pro Gly Ser
    1055                1060                1065 ggg gga cgg cag acc agg gag ccc agg cag gag cct gca aac tca        3249
Gly Gly Arg Gln Thr Arg Glu Pro Arg Gln Glu Pro Ala Asn Ser
    1070                1075                1080 ccc acc tcc aag atg aag aag gtc aag ttt gcc aca ttc acc atc        3294
Pro Thr Ser Lys Met Lys Lys Val Lys Phe Ala Thr Phe Thr Ile
    1085                1090                1095 cca cct gag gaa agc tgc ccc acg gtg aac tcc atc ctc agt ggg        3339
Pro Pro Glu Glu Ser Cys Pro Thr Val Asn Ser Ile Leu Ser Gly
    1100                1105                1110 gaa gat gat atc aag tgg gtt tgt caa gac ctg gac gtg ggc gca        3384
Glu Asp Asp Ile Lys Trp Val Cys Gln Asp Leu Asp Val Gly Ala
    1115                1120                1125
```

-continued

```
ccc aag gaa ctc aga acc tac ctg gag aaa ttc caa gac agt gtg      3429
Pro Lys Glu Leu Arg Thr Tyr Leu Glu Lys Phe Gln Asp Ser Val
    1130                1135                1140 tag cgctctggcc tcctcgccaa cttgggacag tagcctcctt cccgacctcc       3482
ctcagcagag tagctgaacg gaaggagctc tcagtggact gagtgaggaa atctggggcc 3542 cacagaatac caggtagcag gttagaagct gggaagggat gttttttatac taaagcagtt 3602 ttttttgttt tttgttttttt gttttttgtt tttttagca gcaaaggatg gtaggtttcc  3662
agaagtttga gtctctgact cagcagcgag gcagagtgga tccgaaagag aactgctcag  3722
acatgagaga gttatttat gaatcaaacg acactgcaga caagctacca aaaatatttg   3782
ttaaaaaaaa tatataaaaa gacgaataaa aaaacac                          3820
```

<210> SEQ ID NO 12
<211> LENGTH: 1143
<212> TYPE: PRT
<213> ORGANISM: Mus musculus

<400> SEQUENCE: 12

```
Glu Pro Glu Lys Ser Cys Pro Asp Pro Phe Arg Ser Ser Arg Arg Ser
1               5                   10                  15

Arg Ser Ala Ala Gly Gly Gly Pro Gly His Gly Ala Thr Gly Ala Val
            20                  25                  30

Pro Gly Leu Ala Met Asp Gly Val Thr Ala Ala Thr Met Arg Ser Glu
        35                  40                  45

Gly Ala Ala Pro Arg Arg Ala Ala Arg Tyr Gly Ala Leu Ser Leu Val
    50                  55                  60

Leu Ala Thr Leu Leu Gly Gln Val Thr Glu Ser Arg Gly Val Met Asp
65                  70                  75                  80

Asn Ile Gln Arg Phe Ser Ser Leu Pro Pro Tyr Leu Pro Val Ser Phe
                85                  90                  95

His Val Leu Arg Ala Glu Thr Ala Phe Phe Leu Lys Glu Ala Asn Pro
            100                 105                 110

Asp Pro Leu Arg Asn Ala Ser Leu Gln Ser Arg Val Glu Ser Phe Phe
        115                 120                 125

Ile Tyr Lys Ala Gln Gln Pro Pro Val Leu Asn Val Ser Tyr Gly Pro
    130                 135                 140

Tyr Ser Ala Glu Lys Val Ile Pro Leu Asp Leu Met Leu Asn Pro Asn
145                 150                 155                 160

Phe Leu Gly Pro Thr Ser Lys Phe Pro Phe Asp Trp Arg Leu Lys Ala
                165                 170                 175

Tyr Ile Leu Gln Glu Lys Val Tyr Leu Ser His Pro Lys Val Gln Val
            180                 185                 190

Leu Phe His Ile Val Gly Arg Asp Trp Asp Asp His Arg Asp Glu Lys
        195                 200                 205

Leu Pro Cys Leu Arg Val Phe Ala Phe Arg Asp Ser Arg Glu Val Arg
    210                 215                 220

Gly Ser Cys Arg Leu Gly Gly Pro Leu Gly Leu Cys Val Ala Gln Leu
225                 230                 235                 240

Glu Met Leu Pro Gly Trp Phe Ser Pro Ala Val Val Ser Gly Arg
                245                 250                 255

Arg Arg Pro Ala Glu Arg Pro Glu Gly Ser Pro Val Glu Leu Tyr Tyr
            260                 265                 270

Ala Val Gln Pro Gly Asp Glu Arg Gly Asp Cys Thr Gly Gly Asp Thr
        275                 280                 285
```

```
Arg Lys Asp Asn Ala Ile Arg Pro Gly Lys Asp Gly Gln Glu Gly Arg
    290                 295                 300
Thr Ser His Leu Gln Lys Ile Gly Thr Ile Ser Leu Tyr Arg Ala Gln
305                 310                 315                 320
Asp Ser Asn Gln Leu Ser Glu Leu Arg Leu Asp Gly Asn Val Val Ile
                325                 330                 335
Trp Leu Pro Ser Gln Pro Val Lys Gln Gly Asp Ile Val Thr Ala Ser
                340                 345                 350
Val Thr Ile Ala Asn Asn Ser Thr Val Asp His Phe Ile Leu Arg Ala
            355                 360                 365
Lys Val Lys Lys Gly Val Asn Ile Leu Thr Val Gln Thr Ser Glu Pro
            370                 375                 380
Arg Gln Trp Asp Val Arg Gln Glu Val Gly Asn Gly Lys His Thr
385                 390                 395                 400
Thr Thr Ser Val Ala Cys Gln Arg Leu Gly Pro Gly Ala Arg Asn Arg
                405                 410                 415
Ser Ser Asn Leu Phe Ser Glu Val Met Gln Met Asn Phe Glu Ile Ala
                420                 425                 430
Ser Phe Ser Ser Leu Ser Gly Thr Gln Pro Ile Thr Trp Gln Val Glu
            435                 440                 445
Tyr Pro Arg Lys Gly Ala Thr Asp Ile Ala Val Ser Glu Ile Phe Ile
            450                 455                 460
Ser Gln Lys Asp Leu Val Ala Ile Val Pro Leu Ala Met Asp Thr Glu
465                 470                 475                 480
Leu Leu Asn Thr Ala Ile Leu Thr Gly Lys Thr Val Ala Met Pro Val
                485                 490                 495
Arg Val Val Ser Val Glu Glu Asn Ser Thr Leu Arg Asp Ile Ser Glu
                500                 505                 510
Leu Val Glu Cys Lys Ala Thr Asp Glu Asn Val Ile Lys Val Ser Asp
            515                 520                 525
His Cys Asp Tyr Val Phe Val Asn Gly Lys Glu Ile Lys Gly Lys Met
            530                 535                 540
Asp Ser Val Val Asn Phe Thr Tyr Gln His Leu Ser Ala Pro Leu His
545                 550                 555                 560
Val Thr Val Trp Val Pro Arg Leu Pro Leu Gln Ile Glu Val Ser Asp
                565                 570                 575
Thr Glu Leu Ser Gln Val Lys Gly Trp Arg Val Pro Ile Val Ala Ser
                580                 585                 590
Lys Arg Pro Thr Arg Asp Ser Glu Glu Glu Glu Glu Glu Glu Gln Lys
            595                 600                 605
Gly Arg Gly Cys Thr Leu Gln Phe Gln His Ala Thr Val Arg Val Leu
            610                 615                 620
Thr Gln Phe Val Ser Glu Gly Ala Gly Pro Trp Gly Gln Leu Ser His
625                 630                 635                 640
Leu Leu Ser Pro Asp Trp Gln Phe Asp Ile Thr His Leu Val Ala Asp
                645                 650                 655
Phe Met Lys Leu Glu Ser Pro His Ile Ala Thr Leu Gln Asp Ser Arg
                660                 665                 670
Val Leu Val Gly Arg Glu Val Gly Met Thr Thr Ile Gln Val Leu Ser
            675                 680                 685
Pro Leu Ser Asp Ser Ile Leu Ala Glu Lys Thr Val Thr Val Leu Asp
            690                 695                 700
Asp Lys Val Ser Val Thr Asp Leu Ala Val Gln Val Val Ala Gly Leu
```

```
                        705                 710                 715                 720
Ser Val Thr Leu His Pro Ile Ser Glu Asn Asn Lys Ala Thr Ser Ala
                    725                 730                 735

Val Ala Met Ala Glu Glu Leu Leu Arg Ala Pro Lys Lys Glu Ala Ile
                    740                 745                 750

Ile Ser Thr Trp Leu Gln Phe Ser Asp Gly Ser Val Thr Pro Leu Asp
                    755                 760                 765

Ile Tyr Asp Ser Lys Asp Phe Ser Leu Thr Ala Ile Ser Leu Asp Glu
                    770                 775                 780

Ala Val Val Ser Ile Pro Gln Pro Leu Ser Pro Trp Trp Pro Thr Val
785                 790                 795                 800

Val Ala Glu Gly Glu Gly Gln Gly Pro Leu Leu Arg Val Asp Met Ser
                    805                 810                 815

Ile Ala Glu Ala Cys Gln Lys Ser Lys Arg Lys Ser Val Leu Ala Val
                    820                 825                 830

Gly Ile Gly His Val Gly Val Lys Phe Gly Trp Asp Asp Ala Asp Ser
                    835                 840                 845

Ser Gln Thr Gly Glu Lys Asp Glu Glu Ile Lys Asn His Ala Ser
    850                 855                 860

Asp Arg Arg Gln Lys Ile Gln Asp Leu Glu Arg Pro Gly Gln Asp Glu
865                 870                 875                 880

Leu Tyr His Gly Asn Phe Pro Gly Asp Arg Glu Glu Ala Leu Ser
                    885                 890                 895

Ala Thr Thr Thr Thr Lys Ser Leu Leu Asp Asn Asn Val Gly Lys Ser
                    900                 905                 910

Gly Arg Arg Asp Gly Ala Arg Leu His Ser Ile Pro Ile Asp Phe Thr
                    915                 920                 925

Asn Phe Pro Ala His Val Asp Leu Pro Lys Ala Lys Thr Arg Gly Thr
                    930                 935                 940

Leu Glu Glu Asn Gly Leu Met Gln Thr Ala His Gly Leu Ser Asp Leu
945                 950                 955                 960

Glu Ile Gly Met Tyr Ala Leu Leu Gly Val Phe Cys Leu Ala Ile Leu
                    965                 970                 975

Val Phe Leu Ile Asn Cys Ala Thr Phe Ala Phe Lys Tyr Arg His Lys
                    980                 985                 990

Gln Val Pro Leu Glu Gly Gln Ala  Ser Met Thr His Ser  His Asp Trp
                    995                 1000                1005

Val Trp Leu Gly Asn Glu Ala  Glu Leu Leu Glu Asn  Ile Gly Asp
    1010                1015                1020

Leu Ser Pro Pro Gln Asp Glu  His Thr Thr Ile Ile  Asp Arg Gly
    1025                1030                1035

Leu Gly Gly Cys Glu Glu Asn  Asn His Leu Leu Leu  Asn Gly Gly
    1040                1045                1050

Ser Gln Lys Pro Thr Gln Ser  Gln Val His Arg Pro  Pro Gly Ser
    1055                1060                1065

Gly Gly Arg Gln Thr Arg Glu  Pro Arg Gln Glu Pro  Ala Asn Ser
    1070                1075                1080

Pro Thr Ser Lys Met Lys Lys  Val Lys Phe Ala Thr  Phe Thr Ile
    1085                1090                1095

Pro Pro Glu Glu Ser Cys Pro  Thr Val Asn Ser Ile  Leu Ser Gly
    1100                1105                1110

Glu Asp Asp Ile Lys Trp Val  Cys Gln Asp Leu Asp  Val Gly Ala
    1115                1120                1125
```

| Pro | Lys | Glu | Leu | Arg | Thr | Tyr | Leu | Glu | Lys | Phe | Gln | Asp | Ser | Val |
|---|---|---|---|---|---|---|---|---|---|---|---|---|---|---|
| | 1130 | | | | 1135 | | | | | 1140 | | | | |

<210> SEQ ID NO 13
<211> LENGTH: 5114
<212> TYPE: DNA
<213> ORGANISM: Mus musculus

<400> SEQUENCE: 13

```
gggacccgtt caggagcagc cgccggagcc ggagcgctgc cggggcggc cccgggcatg    60
gggcaaccgg cgcggtcccg ggctggcga tggatggcgt gacagcggcc acgatgcgct   120
ccgagggcgc ggccccgagg cgggcggcgc ggtacggggc gctgagcctg gtcctagcca   180
cgctactggg ccaagtgacc gaaagccgag gggtcatgga taatatacag agattctctt   240
cattgccgcc gtacctgccc gtgagcttcc acgtcctcag agccgagact gcattcttcc   300
taaaggaggc caaccccgac ccgctgcgga atgccagcct gcagtccagg gtggagtctt   360
tcttcatcta caaggcccag cagccccgg tattaaacgt cagctatggg ccttactctg   420
cagaaaaggt catccctctg gacttgatgt tgaaccccaa cttttaggc ccaaccagta   480
agtttccctt tgactggagg ctgaaggcct acatccttca agagaaagtc tacctgagcc   540
atcccaaagt acaggtgctc ttccacatcg tgggccgaga ctgggatgac cacagggacg   600
agaaactgcc ctgcctgcgg gtctttgcgt tcagagacag ccgggaggtt cgaggcagct   660
gtcgtctggg tgggccctg ggactgtgcg tgcccagct ggagatgctg cctggctggt   720
tcagtccccc agcggttgta tctgggcgca ggaggccagc agagcggcca gaggggagtc   780
cggtggaact gtattatgct gtacagccag ggacgagcg tggtgactgc actggaggtg   840
acaccaggaa ggacaatgct attcgtccag gaaaggatgg acaggagggc aggacatccc   900
acctacagaa gattggcacc attagccttt accgcgccca ggacagcacc cagcctcagc   960
gaactgcgcc tggatggcaa tgtggtcatc tgctgccct cccagcccgt caagcaggga  1020
gacatagtca ccgcatctgt caccatcgcc aataactcta ctgtggacca tttcatccta  1080
agagccaagg tgaagaaggg ggtgaacatc ctgaccgtgc agaccagcga gcctcggcag  1140
tgggatgtga ggcaagaggt gggcaatgga gggaagcaca ccaccacctc ggtggcctgc  1200
cagcgcctgg gccctggggc acgaaatagg agcagcaatt tattcagcga ggtcatgcag  1260
atgaattttg aaatcgccag cttcagcagc ctctcgggga cacagcctat cacatggcag  1320
gtggagtacc cgaggaaggg ggccacggac attgctgtgt cggagatctt catcagccag  1380
aaggacctag ttgccatcgt cccccttgct atggacactg aactcctgaa cacagccatc  1440
ctcacaggga gacggtggc catgcctgtc agggtggtgt cggtggaaga gaatagcacc  1500
ctgagggaca tctcggagtt ggtggagtgc aaggccacag acgagaatgt catcaaggtc  1560
tcggaccact gtgactatgt ctttgtcaat ggtaaagaga tcaagggcaa gatggactct  1620
gtggtgaact tcacctacca gcacctgagc gcaccgctgc atgtcactgt gtgggtgcca  1680
cggcttcccc tgcagatcga ggtctctgac acagaactca gccaggttaa gggctggaga  1740
gtccccatcg tggccagcaa gaggcccact cgggacagtg aggaggaaga agaggaagaa  1800
cagaaaggcc ggggttgtac cctgcagttc cagcatgcca cagtgcgcgt cctcacccaa  1860
tttgtatcag agggtgctgg gccctggggc agctgagcc accttctcag tccagactgg  1920
cagtttgaca tcacccacct ggtggctgac tttatgaagc tggagtcccc acacatagcc  1980
accctgcagg acagcagggt cttggttggg cgggaagtcg gaatgaccac catccaggtg  2040
ttgtctcccc tgtccgactc catcttggcc gagaagacag taactgtgct ggatgacaaa  2100
```

```
gtatctgtga cagacttagc tgtccaggtg gtggctgggc tgtctgtcac cctacacccc    2160
atctcagaga acaacaaggc cacctcagct gtggccatgg cagaagagct gctacgtgcc    2220
ccaaaaaagg aagctataat cagcacatgg ctccagttca gtgatggctc agtgacaccc    2280
ctggatatct acgactccaa ggacttctcc ttgactgcca tctctttgga cgaggctgtc    2340
gtgtccatcc cccaacccct ctcgccttgg tggcccaccg tggtagctga aggagaaggc    2400
cagggcccac tgctccgggt cgatatgtcc attgccgaag cctgtcagaa atccaagcgc    2460
aagagtgtgc tggctgttgg cattggccac gtgggggtca agtttggatg ggatgacgct    2520
gactccagcc agactggaga aaaggatgag gaggagatca agaaccatgc cagtgaccgt    2580
cggcagaaga ttcaggacct ggaacgccca ggccaggatg aactatacca tggcaacttt    2640
cctggggatc gtgaagaagg agcgctgagt gctaccacca ctaccaagtc cctgctggat    2700
aacaacgtgg ggaagagtgg caggcgggac ggggctaggc tacacagcat acccattgac    2760
ttcaccaatt tcccggccca tgtggacctc cccaaggcca agaccagggg cacactggag    2820
gagaatggtc tcatgcagac agcccatggc ctgagtgacc tagagattgg gatgtatgcc    2880
ctcctaggtg tcttctgcct ggccatcctt gtctttctca ttaactgcgc cacctttgcc    2940
ttcaagtaca ggcacaaaca ggtgcctctg gaaggccagg catccatgac ccactctcat    3000
gactgggtct ggctgggcaa tgaggcggag ctcttggaga acattgggga cctgtcccca    3060
ccccaggatg agcacacgac catcatagac cgagggctgg ggggctgtga ggagaacaac    3120
cacttacttc tcaacggtgg ctcccaaaag cccacgcaga gccaggttca caggccgcca    3180
ggctccgggg gacggcagac cagggagccc aggcaggagc ctgcaaactc acccacctcc    3240
aagatgaaga aggtcaagtt tgccacattc accatcccac tgaggaaagc tgccccacg    3300 gtgaactcca tcctcagtgg ggaagatgat atcaagtggg tttgtcaaga cctggacgtg    3360
ggcgcaccca aggaactcag aacctacctg gagaaattcc aagacagtgt gtagcgctct    3420
ggcctcctcg ccaacttggg acagtagcct ccttcccgac ctccctcagc agagtagctg    3480
aacggaagga gctctcagtg gactgagtga ggaaatctgg ggcccacaga ataccaggta    3540
gcaggttaga agctgggaag ggatgttttt atactaaagc agttttttt gttttttgtt    3600 ttttgttttt tgttttttt agcagcaaag gatggtaggt ttccagaagt ttgagtctct    3660
gactcagcag cgaggcagag tggatccgaa agagaactgc tcagacatga gagagttatt    3720
ttatgaatca aacgacactg cagacaagct accaaaaata tttgttaaaa aaatatata    3780 aaaagacgaa taaaaaaaac acacaaatga ctgtcggttt atatttctaa taaggaaca    3840 aaatgtaaga atagggcttg ctaaaagaag gcctacattt taattcagtc tttatgcttc    3900
tgaggacagt ccaggtctgt tagccttctg cccaaggaga ggcacatctg aacaatggtc    3960
acctcttagg aagaatgaga attttacatt ggattccatt atctctgttt gcttccatgt    4020
ttctttctaa ggtcctaagc ctccatttga ttcaatgtca tgtttatttc tgaggaccaa    4080
gtggtacatt ttcctaaatg aaatgtaaat tatatttcta ttcattagat agcttttcc    4140 ccctctttt aagaagatca tcaacgaatc cagtctttac gttgtaacat taacctgtct    4200
ttatattata catctcttgc tttgttaata ttttctggct tgtttgtaat tcttttgtt    4260 tttttgtttt gttttgtttt aacaatatag caagtgtgca gttccccaca tggggagagt    4320 gcacccaca atctgtcatc agccgggtca ggccaatgag tggaataatg ttcacagcta    4380
tctgaatagg gtatggccaa gagaacagag tgcagcctgt gacacctggc cactccctat    4440
ggagacagag actcagtggg tgtctccggc agtttgggca tagggatgcc tctatgtgaa    4500
```

```
gagctgtgag tgaaatccat aaactcgagg tgtgcagagt caggcagatg ggccatgtct    4560
accacaagat acagccgacc ctgtactgaa caaacagaaa agacatgtgg gggaggggca    4620
ggctggagtt atctgatttt attactgggc aaggcgaacc agcatgaact caaaatgatt    4680 ttttaaaaa aagaaatct atgttagatt gtcaatcaaa ctgcggcttt gaagagtatg      4740
gctgtgttaa cagcacaatg cagtatcata tccactcaaa acagagtgtt tacgcaaaaa    4800
gcaggaggga tcaaatgaac taggatgtcc ggagcctggc gctctccatc catcagctga    4860
gggagaggat gttgggcact gtgaccctca gcagagcagc attcacagag agaccagggg    4920
acggccattg tttgggtttt tttgttttt ttctattact aaaatcagta gctgagaaaa     4980
ggtctcagaa gcctagtggc cttggttgga cctttgacac atatatttgt agcatttaca    5040
atagattaaa aaaaaaaag ctatttattt ataccctgtgg tggcagttgt cattaaaacg    5100
cttgccatgc ttcc                                                     5114

<210> SEQ ID NO 14
<211> LENGTH: 4226
<212> TYPE: DNA
<213> ORGANISM: Mus musculus
<220> FEATURE:
<221> NAME/KEY: CDS
<222> LOCATION: (91)..(3414)
<223> OTHER INFORMATION:

<400> SEQUENCE: 14
agggacccgt tcaggagcag ccgccggagc cggagcgctg ccgggggcgg ccccgggcat         60
ggggcaaccg gcgcggtccc ggggctggcg atg gat ggc gtg aca gcg gcc acg        114
                                   Met Asp Gly Val Thr Ala Ala Thr
                                     1               5 atg cgc tcc gag ggc gcg gcc ccg agg cgg gcg gcg cgg tac ggg gcg          162
Met Arg Ser Glu Gly Ala Ala Pro Arg Arg Ala Ala Arg Tyr Gly Ala
         10                  15                  20 ctg agc ctg gtc cta gcc acg cta ctg ggc caa gtg acc gaa agc cga          210
Leu Ser Leu Val Leu Ala Thr Leu Leu Gly Gln Val Thr Glu Ser Arg
 25                  30                  35                  40 ggg gtc atg gat aat ata cag aga ttc tct tca ttg ccg ccg tac ctg          258
Gly Val Met Asp Asn Ile Gln Arg Phe Ser Ser Leu Pro Pro Tyr Leu
                 45                  50                  55 ccc gtg agc ttc cac gtc ctc aga gcc gag act gca ttc ttc cta aag         306
Pro Val Ser Phe His Val Leu Arg Ala Glu Thr Ala Phe Phe Leu Lys
             60                  65                  70 gag gcc aac ccc gac ccg ctg cgg aat gcc agc ctg cag tcc agg gtg         354
Glu Ala Asn Pro Asp Pro Leu Arg Asn Ala Ser Leu Gln Ser Arg Val
         75                  80                  85 gag tct ttc ttc atc tac aag gcc cag cag ccc ccg gta tta aac gtc        402
Glu Ser Phe Phe Ile Tyr Lys Ala Gln Gln Pro Pro Val Leu Asn Val
 90                  95                 100 agc tat ggg cct tac tct gca gaa aag gtc atc cct ctg gac ttg atg        450
Ser Tyr Gly Pro Tyr Ser Ala Glu Lys Val Ile Pro Leu Asp Leu Met
105                 110                 115                 120 ttg aac ccc aac ttt tta ggc cca acc agt aag ttt ccc ttt gac tgg        498
Leu Asn Pro Asn Phe Leu Gly Pro Thr Ser Lys Phe Pro Phe Asp Trp
                125                 130                 135 agg ctg aag gcc tac atc ctt caa gag aaa gtc tac ctg agc cat ccc        546
Arg Leu Lys Ala Tyr Ile Leu Gln Glu Lys Val Tyr Leu Ser His Pro
            140                 145                 150 aaa gta cag gtg ctc ttc cac atc gtg ggc cga gac tgg gat gac cac        594
Lys Val Gln Val Leu Phe His Ile Val Gly Arg Asp Trp Asp Asp His
        155                 160                 165
```

```
agg gac gag aaa ctg ccc tgc ctg cgg gtc ttt gcg ttc aga gac agc        642
Arg Asp Glu Lys Leu Pro Cys Leu Arg Val Phe Ala Phe Arg Asp Ser
        170             175             180 cgg gag gtt cga ggc agc tgt cgt ctg ggt ggg ccc ctg gga ctg tgc        690
Arg Glu Val Arg Gly Ser Cys Arg Leu Gly Gly Pro Leu Gly Leu Cys
185             190             195             200 gtg gcc cag ctg gag atg ctg cct ggc tgg ttc agt ccc cca gcg gtt        738
Val Ala Gln Leu Glu Met Leu Pro Gly Trp Phe Ser Pro Pro Ala Val
                205             210             215 gta tct ggg cgc agg agg cca gca gag cgg cca gag ggg agt ccg gtg        786
Val Ser Gly Arg Arg Arg Pro Ala Glu Arg Pro Glu Gly Ser Pro Val
        220             225             230 gaa ctg tat tat gct gta cag cca ggg gac gag cgt ggt gac tgc act        834
Glu Leu Tyr Tyr Ala Val Gln Pro Gly Asp Glu Arg Gly Asp Cys Thr
            235             240             245 gga ggt gac acc agg aag gac aat gct att cgt cca gga aag gat gga        882
Gly Gly Asp Thr Arg Lys Asp Asn Ala Ile Arg Pro Gly Lys Asp Gly
250             255             260 cag gag ggc agg aca tcc cac cta cag aag att ggc acc att agc ctt        930
Gln Glu Gly Arg Thr Ser His Leu Gln Lys Ile Gly Thr Ile Ser Leu
265             270             275             280 tac cgc gcc cag gac agc acc cag ctc agc gaa ctg cgc ctg gat ggc        978
Tyr Arg Ala Gln Asp Ser Thr Gln Leu Ser Glu Leu Arg Leu Asp Gly
                285             290             295 aat gtg gtc atc tgg ctg ccc tcc cag ccc gtc aag cag gga gac ata       1026
Asn Val Val Ile Trp Leu Pro Ser Gln Pro Val Lys Gln Gly Asp Ile
        300             305             310 gtc acc gca tct gtc acc atc gcc aat aac tct act gtg gac cat ttc       1074
Val Thr Ala Ser Val Thr Ile Ala Asn Asn Ser Thr Val Asp His Phe
            315             320             325 atc cta aga gcc aag gtg aag aag ggg gtg aac atc ctg acc gtg cag       1122
Ile Leu Arg Ala Lys Val Lys Lys Gly Val Asn Ile Leu Thr Val Gln
330             335             340 acc agc gag cct cgg cag tgg gat gtg agg caa gag gtg ggc aat gga       1170
Thr Ser Glu Pro Arg Gln Trp Asp Val Arg Gln Glu Val Gly Asn Gly
345             350             355             360 ggg aag cac acc acc acc tcg gtg gcc tgc cag cgc ctg ggc cct ggg       1218
Gly Lys His Thr Thr Thr Ser Val Ala Cys Gln Arg Leu Gly Pro Gly
                365             370             375 gca cga aat agg agc agc aat tta ttc agc gag gtc atg cag atg aat       1266
Ala Arg Asn Arg Ser Ser Asn Leu Phe Ser Glu Val Met Gln Met Asn
        380             385             390 ttt gaa atc gcc agc ttc agc aga ctc tcg ggg aca cag cct atc aca       1314
Phe Glu Ile Ala Ser Phe Ser Arg Leu Ser Gly Thr Gln Pro Ile Thr
            395             400             405 tgg cag gtg gag tac ccg agg aag ggg gcc acg gac att gct gtg tcg       1362
Trp Gln Val Glu Tyr Pro Arg Lys Gly Ala Thr Asp Ile Ala Val Ser
410             415             420 gag atc ttc atc agc cag aag gac cta gtt gcc atc gtc ccc ctt gct       1410
Glu Ile Phe Ile Ser Gln Lys Asp Leu Val Ala Ile Val Pro Leu Ala
425             430             435             440 atg gac act gaa ctc ctg aac aca gcc atc ctc aca ggg aag acg gtg       1458
Met Asp Thr Glu Leu Leu Asn Thr Ala Ile Leu Thr Gly Lys Thr Val
                445             450             455 gcc atg cct gtc agg gtg gtg tcg gtg gaa gag aat agc acc ctg agg       1506
Ala Met Pro Val Arg Val Val Ser Val Glu Glu Asn Ser Thr Leu Arg
        460             465             470 gac atc tcg gag ttg gtg gag tgc aag gcc aca gac gag aat gtc atc       1554
Asp Ile Ser Glu Leu Val Glu Cys Lys Ala Thr Asp Glu Asn Val Ile
            475             480             485
```

```
aag gtc tcg gac cac tgt gac tat gtc ttt gtc aat ggt aaa gag atc    1602
Lys Val Ser Asp His Cys Asp Tyr Val Phe Val Asn Gly Lys Glu Ile
490                 495                 500 aag ggc aag atg gac tct gtg gtg aac ttc acc tac cag cac ctg agc    1650
Lys Gly Lys Met Asp Ser Val Val Asn Phe Thr Tyr Gln His Leu Ser
505                 510                 515                 520 gca ccg ctg cat gtc act gtg tgg gtg cca cgg ctt ccc ctg cag atc    1698
Ala Pro Leu His Val Thr Val Trp Val Pro Arg Leu Pro Leu Gln Ile
                525                 530                 535 gag gtc tct gac aca gaa ctc agc cag gtt aag ggc tgg aga gtc ccc    1746
Glu Val Ser Asp Thr Glu Leu Ser Gln Val Lys Gly Trp Arg Val Pro
        540                 545                 550 atc gtg gcc agc aag agg ccc act cgg gac agt gag gag gaa gag        1794
Ile Val Ala Ser Lys Arg Pro Thr Arg Asp Ser Glu Glu Glu Glu
555                 560                 565 gaa gaa cag aaa ggc cgg ggt tgt acc ctg cag ttc cag cat gcc aca    1842
Glu Glu Gln Lys Gly Arg Gly Cys Thr Leu Gln Phe Gln His Ala Thr
570                 575                 580 gtg cgc gtc ctc acc caa ttt gta tca gag ggt gct ggg ccc tgg ggc    1890
Val Arg Val Leu Thr Gln Phe Val Ser Glu Gly Ala Gly Pro Trp Gly
585                 590                 595                 600 cag ctg agc cac ctt ctc agt cca gac tgg cag ttt gac atc acc cac    1938
Gln Leu Ser His Leu Leu Ser Pro Asp Trp Gln Phe Asp Ile Thr His
                605                 610                 615 ctg gtg gct gac ttt atg aag ctg gag tcc cca cac ata gcc acc ctg    1986
Leu Val Ala Asp Phe Met Lys Leu Glu Ser Pro His Ile Ala Thr Leu
        620                 625                 630 cag gac agc agg gtc ttg gtt ggg cgg gaa gtc gga atg acc acc atc    2034
Gln Asp Ser Arg Val Leu Val Gly Arg Glu Val Gly Met Thr Thr Ile
635                 640                 645 cag gtg ttg tct ccc ctg tcc gac tca atc ttg gcc gag aag aca gta    2082
Gln Val Leu Ser Pro Leu Ser Asp Ser Ile Leu Ala Glu Lys Thr Val
650                 655                 660 act gtg ctg gat gac aaa gta tct gtg aca gac tta gct gtc cag gtg    2130
Thr Val Leu Asp Asp Lys Val Ser Val Thr Asp Leu Ala Val Gln Val
665                 670                 675                 680 gtg gct ggg ctg tct gtc acc cta cac ccc atc tca gag aac aac aag    2178
Val Ala Gly Leu Ser Val Thr Leu His Pro Ile Ser Glu Asn Asn Lys
                685                 690                 695 gcc acc tca gct gtg gcc atg gca gaa gag ctg cta cgt gcc cca aaa    2226
Ala Thr Ser Ala Val Ala Met Ala Glu Glu Leu Leu Arg Ala Pro Lys
        700                 705                 710 aag gaa gct ata atc agc aca tgg ctc cag ttc agt gat ggc tca gtg    2274
Lys Glu Ala Ile Ile Ser Thr Trp Leu Gln Phe Ser Asp Gly Ser Val
715                 720                 725 aca ccc ctg gat atc tac gac tcc aag gac ttc tcc ttg act gcc atc    2322
Thr Pro Leu Asp Ile Tyr Asp Ser Lys Asp Phe Ser Leu Thr Ala Ile
730                 735                 740 tct ttg gac gag gct gtc gtg tcc atc ccc caa ccc ctc tcg cct tgg    2370
Ser Leu Asp Glu Ala Val Val Ser Ile Pro Gln Pro Leu Ser Pro Trp
745                 750                 755                 760 tgg ccc acc gtg gta gct gaa gga gaa ggc cag ggc cca ctg ctc cgg    2418
Trp Pro Thr Val Val Ala Glu Gly Glu Gly Gln Gly Pro Leu Leu Arg
                765                 770                 775 gtc gat atg tcc att gcc gaa gcc tgt cag aaa tcc aag cgc aag agt    2466
Val Asp Met Ser Ile Ala Glu Ala Cys Gln Lys Ser Lys Arg Lys Ser
        780                 785                 790 gtg ctg gct gtt ggc att ggc cac gtg ggg gtc aag ttt gga tgg gat    2514
Val Leu Ala Val Gly Ile Gly His Val Gly Val Lys Phe Gly Trp Asp
795                 800                 805
```

```
gac gct gac tcc agc cag act gga gaa aag gat gag gag atc aag         2562
Asp Ala Asp Ser Ser Gln Thr Gly Glu Lys Asp Glu Glu Ile Lys
    810                 815                 820 aac cat gcc agt gac cgt cgg cag aag att cag gac ctg gaa cgc cca     2610
Asn His Ala Ser Asp Arg Arg Gln Lys Ile Gln Asp Leu Glu Arg Pro
825                 830                 835                 840 ggc cag gat gaa cta tac cat ggc aac ttt cct ggg gat cgt gaa gaa     2658
Gly Gln Asp Glu Leu Tyr His Gly Asn Phe Pro Gly Asp Arg Glu Glu
                845                 850                 855 gga gcg ctg agt gct acc acc act acc aag tcc ctg ctg gat aac aac     2706
Gly Ala Leu Ser Ala Thr Thr Thr Thr Lys Ser Leu Leu Asp Asn Asn
            860                 865                 870 gtg ggg aag agt ggc agg cgg gac ggg gct agg cta cac agc ata ccc     2754
Val Gly Lys Ser Gly Arg Arg Asp Gly Ala Arg Leu His Ser Ile Pro
        875                 880                 885 att gac ttc acc aat ttc ccg gcc cat gtg gac ctc ccc aag gcc aag     2802
Ile Asp Phe Thr Asn Phe Pro Ala His Val Asp Leu Pro Lys Ala Lys
    890                 895                 900 acc agg ggc aca ctg gag gag aat ggt ctc atg cag aca gcc cat ggc     2850
Thr Arg Gly Thr Leu Glu Glu Asn Gly Leu Met Gln Thr Ala His Gly
905                 910                 915                 920 ctg agt gac cta gag att ggg atg tat gcc ctc cta ggt gtc ttc tgc     2898
Leu Ser Asp Leu Glu Ile Gly Met Tyr Ala Leu Leu Gly Val Phe Cys
                925                 930                 935 ctg gcc atc ctt gtc ttt ctc att aac tgc gcc acc ttt gcc ttc aag     2946
Leu Ala Ile Leu Val Phe Leu Ile Asn Cys Ala Thr Phe Ala Phe Lys
            940                 945                 950 tac agg cac aaa cag gtg cct ctg gaa ggc cag gca tcc atg acc cac     2994
Tyr Arg His Lys Gln Val Pro Leu Glu Gly Gln Ala Ser Met Thr His
        955                 960                 965 tct cat gac tgg gtc tgg ctg ggc aat gag gcg gag ctc ttg gag aac     3042
Ser His Asp Trp Val Trp Leu Gly Asn Glu Ala Glu Leu Leu Glu Asn
    970                 975                 980 att ggg gac ctg tcc cca ccc cag gat gag cac acg acc atc ata gac     3090
Ile Gly Asp Leu Ser Pro Pro Gln Asp Glu His Thr Thr Ile Ile Asp
985                 990                 995                 1000 cga ggg ctg ggg ggc  tgt gag gag aac aac  cac tta ctt ctc aac       3135
Arg Gly Leu Gly Gly Cys Glu Glu Asn Asn  His Leu Leu Leu Asn
                1005                1010                1015 ggt ggc tcc caa aag ccc acg cag agc cag gtt cac agg ccg cca         3180
Gly Gly Ser Gln Lys Pro Thr Gln Ser Gln Val His Arg Pro Pro
            1020                1025                1030 ggc tcc ggg gga cgg cag acc agg gag ccc agg cag gag cct gca         3225
Gly Ser Gly Gly Arg Gln Thr Arg Glu Pro Arg Gln Glu Pro Ala
            1035                1040                1045 aac tca ccc acc tcc aag atg aag aag gtc aag ttt gcc aca ttc         3270
Asn Ser Pro Thr Ser Lys Met Lys Lys Val Lys Phe Ala Thr Phe
            1050                1055                1060 acc atc cca cct gag gaa agc tgc ccc acg gtg aac tcc atc ctc         3315
Thr Ile Pro Pro Glu Glu Ser Cys Pro Thr Val Asn Ser Ile Leu
            1065                1070                1075 agt ggg gaa gat gat atc aag tgg gtt tgt caa gac ctg gac gtg         3360
Ser Gly Glu Asp Asp Ile Lys Trp Val Cys Gln Asp Leu Asp Val
            1080                1085                1090 ggc gca ccc aag gaa ctc aga acc tac ctg gag aaa ttc caa gac         3405
Gly Ala Pro Lys Glu Leu Arg Thr Tyr Leu Glu Lys Phe Gln Asp
            1095                1100                1105 agt gtg tag cgctctggcc tcctcgccaa cttgggacag tagcctcctt             3454
Ser Val
```

```
cccgacctcc ctcagcagag tagctgaacg gaaggagctc tcagtggact gagtgaggaa      3514
atctggggcc cacagaatac caggtagcag gttagaagct gggaagggat gtttttatac      3574
taaagcagtt ttttttgttt tttgttttttt gtttttttgtt tttttttagca gcaaaggatg   3634
gtaggtttcc agaagtttga gtctctgact cagcagcgag gcagagtgga tccgaaagag      3694
aactgctcag acatgagaga gttattttat gaatcaaacg acactgcaga caagctacca      3754
aaaatatttg ttaaaaaaaa tatataaaaa gacgaataaa aaaacacac aaatgactgt       3814
cggtttatat ttctaataaa ggaacaaaat gtaaaaatag ggcttgctaa agaaggcct       3874
acattttaat tcagtcttta tgcttctgag gacagtccag gtctgttagc cttctgccca      3934
aggagaggca catctgaaca atggtcacct cttaggaaga atgagaattt tacattggat      3994
tccattatct ctgtttgctt ccatgtttct ttctaaggtc ctaagcctcc atttgattca      4054
atgtcatgtt tatttctgag gaccaagtgg tacattttcc taaatgaaat gtaaattata     4114
tttctattca ttagatagct ttttccccct ctttttaaga agatcatcaa cgaatccagt      4174
ctttacgttg taacattaac ctgtctttat attatacatc tcttgctttg tt             4226
```

<210> SEQ ID NO 15
<211> LENGTH: 1107
<212> TYPE: PRT
<213> ORGANISM: Mus musculus

<400> SEQUENCE: 15

Met Asp Gly Val Thr Ala Ala Thr Met Arg Ser Glu Gly Ala Ala Pro
1               5                   10                  15

Arg Arg Ala Ala Arg Tyr Gly Ala Leu Ser Leu Val Leu Ala Thr Leu
            20                  25                  30

Leu Gly Gln Val Thr Glu Ser Arg Gly Val Met Asp Asn Ile Gln Arg
        35                  40                  45

Phe Ser Ser Leu Pro Pro Tyr Leu Pro Val Ser Phe His Val Leu Arg
    50                  55                  60

Ala Glu Thr Ala Phe Phe Leu Lys Glu Ala Asn Pro Asp Pro Leu Arg
65                  70                  75                  80

Asn Ala Ser Leu Gln Ser Arg Val Glu Ser Phe Phe Ile Tyr Lys Ala
                85                  90                  95

Gln Gln Pro Pro Val Leu Asn Val Ser Tyr Gly Pro Tyr Ser Ala Glu
            100                 105                 110

Lys Val Ile Pro Leu Asp Leu Met Leu Asn Pro Asn Phe Leu Gly Pro
        115                 120                 125

Thr Ser Lys Phe Pro Phe Asp Trp Arg Leu Lys Ala Tyr Ile Leu Gln
    130                 135                 140

Glu Lys Val Tyr Leu Ser His Pro Lys Val Gln Val Leu Phe His Ile
145                 150                 155                 160

Val Gly Arg Asp Trp Asp His Arg Asp Glu Lys Leu Pro Cys Leu
                165                 170                 175

Arg Val Phe Ala Phe Arg Asp Ser Arg Glu Val Arg Gly Ser Cys Arg
            180                 185                 190

Leu Gly Gly Pro Leu Gly Leu Cys Val Ala Gln Leu Glu Met Leu Pro
        195                 200                 205

Gly Trp Phe Ser Pro Pro Ala Val Val Ser Gly Arg Arg Pro Ala
    210                 215                 220

Glu Arg Pro Glu Gly Ser Pro Val Glu Leu Tyr Tyr Ala Val Gln Pro
225                 230                 235                 240

Gly Asp Glu Arg Gly Asp Cys Thr Gly Gly Asp Thr Arg Lys Asp Asn

-continued

```
                245                 250                 255
Ala Ile Arg Pro Gly Lys Asp Gly Gln Glu Gly Arg Thr Ser His Leu
                260                 265                 270

Gln Lys Ile Gly Thr Ile Ser Leu Tyr Arg Ala Gln Asp Ser Thr Gln
                275                 280                 285

Leu Ser Glu Leu Arg Leu Asp Gly Asn Val Val Ile Trp Leu Pro Ser
                290                 295                 300

Gln Pro Val Lys Gln Gly Asp Ile Val Thr Ala Ser Val Thr Ile Ala
305                 310                 315                 320

Asn Asn Ser Thr Val Asp His Phe Ile Leu Arg Ala Lys Val Lys Lys
                325                 330                 335

Gly Val Asn Ile Leu Thr Val Gln Thr Ser Glu Pro Arg Gln Trp Asp
                340                 345                 350

Val Arg Gln Glu Val Gly Asn Gly Lys His Thr Thr Thr Ser Val
                355                 360                 365

Ala Cys Gln Arg Leu Gly Pro Gly Ala Arg Asn Arg Ser Ser Asn Leu
                370                 375                 380

Phe Ser Glu Val Met Gln Met Asn Phe Glu Ile Ala Ser Phe Ser Arg
385                 390                 395                 400

Leu Ser Gly Thr Gln Pro Ile Thr Trp Gln Val Glu Tyr Pro Arg Lys
                405                 410                 415

Gly Ala Thr Asp Ile Ala Val Ser Glu Ile Phe Ile Ser Gln Lys Asp
                420                 425                 430

Leu Val Ala Ile Val Pro Leu Ala Met Asp Thr Glu Leu Leu Asn Thr
                435                 440                 445

Ala Ile Leu Thr Gly Lys Thr Val Ala Met Pro Val Arg Val Val Ser
                450                 455                 460

Val Glu Glu Asn Ser Thr Leu Arg Asp Ile Ser Glu Leu Val Glu Cys
465                 470                 475                 480

Lys Ala Thr Asp Glu Asn Val Ile Lys Val Ser Asp His Cys Asp Tyr
                485                 490                 495

Val Phe Val Asn Gly Lys Glu Ile Lys Gly Lys Met Asp Ser Val Val
                500                 505                 510

Asn Phe Thr Tyr Gln His Leu Ser Ala Pro Leu His Val Thr Val Trp
                515                 520                 525

Val Pro Arg Leu Pro Leu Gln Ile Glu Val Ser Asp Thr Glu Leu Ser
                530                 535                 540

Gln Val Lys Gly Trp Arg Val Pro Ile Val Ala Ser Lys Arg Pro Thr
545                 550                 555                 560

Arg Asp Ser Glu Glu Glu Glu Glu Glu Lys Gly Arg Gly Cys
                565                 570                 575

Thr Leu Gln Phe Gln His Ala Thr Val Arg Val Leu Thr Gln Phe Val
                580                 585                 590

Ser Glu Gly Ala Gly Pro Trp Gly Gln Leu Ser His Leu Leu Ser Pro
                595                 600                 605

Asp Trp Gln Phe Asp Ile Thr His Leu Val Ala Asp Phe Met Lys Leu
                610                 615                 620

Glu Ser Pro His Ile Ala Thr Leu Gln Asp Ser Arg Val Leu Val Gly
625                 630                 635                 640

Arg Glu Val Gly Met Thr Thr Ile Gln Val Leu Ser Pro Leu Ser Asp
                645                 650                 655

Ser Ile Leu Ala Glu Lys Thr Val Thr Val Leu Asp Asp Lys Val Ser
                660                 665                 670
```

```
Val Thr Asp Leu Ala Val Gln Val Ala Gly Leu Ser Val Thr Leu
        675                 680                 685

His Pro Ile Ser Glu Asn Asn Lys Ala Thr Ser Ala Val Ala Met Ala
    690                 695                 700

Glu Glu Leu Leu Arg Ala Pro Lys Lys Glu Ala Ile Ile Ser Thr Trp
705                 710                 715                 720

Leu Gln Phe Ser Asp Gly Ser Val Thr Pro Leu Asp Ile Tyr Asp Ser
                725                 730                 735

Lys Asp Phe Ser Leu Thr Ala Ile Ser Leu Asp Glu Ala Val Val Ser
                740                 745                 750

Ile Pro Gln Pro Leu Ser Pro Trp Trp Pro Thr Val Val Ala Glu Gly
        755                 760                 765

Glu Gly Gln Gly Pro Leu Leu Arg Val Asp Met Ser Ile Ala Glu Ala
770                 775                 780

Cys Gln Lys Ser Lys Arg Lys Ser Val Leu Ala Val Gly Ile Gly His
785                 790                 795                 800

Val Gly Val Lys Phe Gly Trp Asp Asp Ala Asp Ser Ser Gln Thr Gly
                805                 810                 815

Glu Lys Asp Glu Glu Glu Ile Lys Asn His Ala Ser Arg Arg Gln
                820                 825                 830

Lys Ile Gln Asp Leu Glu Arg Pro Gly Gln Asp Glu Leu Tyr His Gly
                835                 840                 845

Asn Phe Pro Gly Asp Arg Glu Glu Gly Ala Leu Ser Ala Thr Thr Thr
    850                 855                 860

Thr Lys Ser Leu Leu Asp Asn Asn Val Gly Lys Ser Gly Arg Arg Asp
865                 870                 875                 880

Gly Ala Arg Leu His Ser Ile Pro Ile Asp Phe Thr Asn Phe Pro Ala
                885                 890                 895

His Val Asp Leu Pro Lys Ala Lys Thr Arg Gly Thr Leu Glu Glu Asn
                900                 905                 910

Gly Leu Met Gln Thr Ala His Gly Leu Ser Asp Leu Glu Ile Gly Met
        915                 920                 925

Tyr Ala Leu Leu Gly Val Phe Cys Leu Ala Ile Leu Val Phe Leu Ile
    930                 935                 940

Asn Cys Ala Thr Phe Ala Phe Lys Tyr Arg His Lys Gln Val Pro Leu
945                 950                 955                 960

Glu Gly Gln Ala Ser Met Thr His Ser His Asp Trp Val Trp Leu Gly
                965                 970                 975

Asn Glu Ala Glu Leu Leu Glu Asn Ile Gly Asp Leu Ser Pro Pro Gln
                980                 985                 990

Asp Glu His Thr Thr Ile Ile Asp Arg Gly Leu Gly Gly Cys Glu Glu
        995                 1000                1005

Asn Asn His Leu Leu Leu Asn Gly Gly Ser Gln Lys Pro Thr Gln
    1010                1015                1020

Ser Gln Val His Arg Pro Pro Gly Ser Gly Gly Arg Gln Thr Arg
    1025                1030                1035

Glu Pro Arg Gln Glu Pro Ala Asn Ser Pro Thr Ser Lys Met Lys
    1040                1045                1050

Lys Val Lys Phe Ala Thr Phe Thr Ile Pro Pro Glu Glu Ser Cys
    1055                1060                1065

Pro Thr Val Asn Ser Ile Leu Ser Gly Glu Asp Asp Ile Lys Trp
    1070                1075                1080

Val Cys Gln Asp Leu Asp Val Gly Ala Pro Lys Glu Leu Arg Thr
    1085                1090                1095
```

```
Tyr Leu Glu Lys Phe Gln Asp Ser Val
    1100            1105

<210> SEQ ID NO 16
<211> LENGTH: 3582
<212> TYPE: DNA
<213> ORGANISM: Mus musculus
<220> FEATURE:
<221> NAME/KEY: CDS
<222> LOCATION: (152)..(2311)
<223> OTHER INFORMATION:

<400> SEQUENCE: 16
gaacatcctg accgtgcaga ccagcgagcc tcggcagtgg gatgtgaggc aagaggtggg      60
caatggaggg aagcacacca ccacctcggt ggcctgccag cgcctgggcc ctggggcacg     120
aaataggagc agcaatttat tcagcgaggt c atg cag atg aat ttt gaa atc       172
                                  Met Gln Met Asn Phe Glu Ile
                                    1               5 gcc agc ttc agc agc ctc tcg ggg aca cag cct atc aca tgg cag gtg       220
Ala Ser Phe Ser Ser Leu Ser Gly Thr Gln Pro Ile Thr Trp Gln Val
            10                  15                  20 gag tac ccg agg aag ggg gcc acg gac att gct gtg tcg gag atc ttc       268
Glu Tyr Pro Arg Lys Gly Ala Thr Asp Ile Ala Val Ser Glu Ile Phe
 25                  30                  35 atc agc cag aag gac cta gtt gcc atc gtc ccc ctt gct atg gac act       316
Ile Ser Gln Lys Asp Leu Val Ala Ile Val Pro Leu Ala Met Asp Thr
 40                  45                  50                  55 gaa ctc ctg aac aca gcc atc ctc aca ggg aag acg gtg gcc atg cct       364
Glu Leu Leu Asn Thr Ala Ile Leu Thr Gly Lys Thr Val Ala Met Pro
                60                  65                  70 gtc agg gtg gtg tcg gtg gaa gag aat agc acc ctg agg gac atc tcg       412
Val Arg Val Val Ser Val Glu Glu Asn Ser Thr Leu Arg Asp Ile Ser
             75                  80                  85 gag ttg gtg gag tgc aag gcc aca gac gag aat gtc atc aag gtc tcg       460
Glu Leu Val Glu Cys Lys Ala Thr Asp Glu Asn Val Ile Lys Val Ser
         90                  95                 100 gac cac tgt gac tat gtc ttt gtc aat ggt aaa gag atc aag ggc aag       508
Asp His Cys Asp Tyr Val Phe Val Asn Gly Lys Glu Ile Lys Gly Lys
    105                 110                 115 atg gac tct gtg gtg aac ttc acc tac cag cac ctg agc gca ccg ctg       556
Met Asp Ser Val Val Asn Phe Thr Tyr Gln His Leu Ser Ala Pro Leu
120                 125                 130                 135 cat gtc act gtg tgg gtg cca cgg ctt ccc ctg cag atc gag gtc tct       604
His Val Thr Val Trp Val Pro Arg Leu Pro Leu Gln Ile Glu Val Ser
                140                 145                 150 gac aca gaa ctc agc cag gtt aag ggc tgg aga gtc ccc atc gtg gcc       652
Asp Thr Glu Leu Ser Gln Val Lys Gly Trp Arg Val Pro Ile Val Ala
            155                 160                 165 agc aag agg ccc act cgg gac agt gag gag gaa gaa gag gaa gaa cag       700
Ser Lys Arg Pro Thr Arg Asp Ser Glu Glu Glu Glu Glu Glu Glu Gln
        170                 175                 180 aaa ggc cgg ggt tgt acc ctg cag ttc cag cat gcc aca gtg cgc gtc       748
Lys Gly Arg Gly Cys Thr Leu Gln Phe Gln His Ala Thr Val Arg Val
    185                 190                 195 ctc acc caa ttt gta tca gag ggt gct ggg ccc tgg ggc cag ctg agc       796
Leu Thr Gln Phe Val Ser Glu Gly Ala Gly Pro Trp Gly Gln Leu Ser
200                 205                 210                 215 cac ctt ctc agt cca gac tgg cag ttt gac atc acc cac ctg gtg gct       844
His Leu Leu Ser Pro Asp Trp Gln Phe Asp Ile Thr His Leu Val Ala
                220                 225                 230
```

```
gac ttt atg aag ctg gag tcc cca cac ata gcc acc ctg cag gac agc      892
Asp Phe Met Lys Leu Glu Ser Pro His Ile Ala Thr Leu Gln Asp Ser
        235                 240                 245 agg gtc ttg gtt ggg cgg gaa gtc gga atg acc acc atc cag gtg ttg      940
Arg Val Leu Val Gly Arg Glu Val Gly Met Thr Thr Ile Gln Val Leu
        250                 255                 260 tct ccc ctg tcc gac tcc atc ttg gcc gag aag aca gta act gtg ctg      988
Ser Pro Leu Ser Asp Ser Ile Leu Ala Glu Lys Thr Val Thr Val Leu
        265                 270                 275 gat gac aaa gta tct gtg aca gac tta gct gtc cag gtg gtg gct ggg     1036
Asp Asp Lys Val Ser Val Thr Asp Leu Ala Val Gln Val Val Ala Gly
280                 285                 290                 295 ctg tct gtc acc cta cac ccc atc tca gag aac aac aag gcc acc tca     1084
Leu Ser Val Thr Leu His Pro Ile Ser Glu Asn Asn Lys Ala Thr Ser
                300                 305                 310 gct gtg gcc atg gca gaa gag ctg cta cgt gcc cca aaa aag gaa gct     1132
Ala Val Ala Met Ala Glu Glu Leu Leu Arg Ala Pro Lys Lys Glu Ala
        315                 320                 325 ata atc agc aca tgg ctc cag ttc agt gat ggc tca gtg aca ccc ctg     1180
Ile Ile Ser Thr Trp Leu Gln Phe Ser Asp Gly Ser Val Thr Pro Leu
        330                 335                 340 gat atc tac gac tcc aag gac ttc tcc ttg act gcc atc tct ttg gac     1228
Asp Ile Tyr Asp Ser Lys Asp Phe Ser Leu Thr Ala Ile Ser Leu Asp
        345                 350                 355 gag gct gtc gtg tcc atc ccc caa ccc ctc tcg cct tgg tgg ccc acc     1276
Glu Ala Val Val Ser Ile Pro Gln Pro Leu Ser Pro Trp Trp Pro Thr
360                 365                 370                 375 gtg gta gct gaa gga gaa ggc cag ggc cca ctc ctc cgg gtc gat atg     1324
Val Val Ala Glu Gly Glu Gly Gln Gly Pro Leu Leu Arg Val Asp Met
                380                 385                 390 tcc att gcc gaa gcc tgt cag aaa tcc aag cgc aag agt gtg ctg gct     1372
Ser Ile Ala Glu Ala Cys Gln Lys Ser Lys Arg Lys Ser Val Leu Ala
        395                 400                 405 gtt ggc att ggc cac gtg ggg gtc aag ttt gga tgg gat gac gct gac     1420
Val Gly Ile Gly His Val Gly Val Lys Phe Gly Trp Asp Asp Ala Asp
        410                 415                 420 tcc agc cag act gga gaa aag gat gag gag gag atc aag aac cat gcc     1468
Ser Ser Gln Thr Gly Glu Lys Asp Glu Glu Glu Ile Lys Asn His Ala
425                 430                 435 agt gac cgt cgg cag aag att cag gac ctg gaa cgc cca ggc cag gat     1516
Ser Asp Arg Arg Gln Lys Ile Gln Asp Leu Glu Arg Pro Gly Gln Asp
440                 445                 450                 455 gaa cta tac cat ggc aac ttt cct ggg gat cgt gaa gaa gga gcg ctg     1564
Glu Leu Tyr His Gly Asn Phe Pro Gly Asp Arg Glu Glu Gly Ala Leu
        460                 465                 470 agt gct acc acc act acc aag tcc ctg ctg gat aac aac gtg ggg aag     1612
Ser Ala Thr Thr Thr Thr Lys Ser Leu Leu Asp Asn Asn Val Gly Lys
        475                 480                 485 agt ggc agg cgg gac ggg gct agg cta cac agc ata ccc att gac ttc     1660
Ser Gly Arg Arg Asp Gly Ala Arg Leu His Ser Ile Pro Ile Asp Phe
        490                 495                 500 acc aat ttc ccg gcc cat gtg gac ctc ccc aag gcc aag acc agg ggc     1708
Thr Asn Phe Pro Ala His Val Asp Leu Pro Lys Ala Lys Thr Arg Gly
        505                 510                 515 aca ctg gag gag aat ggt ctc atg cag aca gcc cat ggc ctg agt gac     1756
Thr Leu Glu Glu Asn Gly Leu Met Gln Thr Ala His Gly Leu Ser Asp
520                 525                 530                 535 cta gag att ggg atg tat gcc ctc cta ggt gtc ttc tgc ctg gcc atc     1804
Leu Glu Ile Gly Met Tyr Ala Leu Leu Gly Val Phe Cys Leu Ala Ile
                540                 545                 550
```

```
ctt gtc ttt ctc att aac tgc gcc acc ttt gcc ttc aag tac agg cac    1852
Leu Val Phe Leu Ile Asn Cys Ala Thr Phe Ala Phe Lys Tyr Arg His
            555                 560                 565 aaa cag gtg cct ctg gaa ggc cag gca tcc atg acc cac tct cat gac    1900
Lys Gln Val Pro Leu Glu Gly Gln Ala Ser Met Thr His Ser His Asp
        570                 575                 580 tgg gtc tgg ctg ggc aat gag gcg gag ctc ttg gag aac att ggg gac    1948
Trp Val Trp Leu Gly Asn Glu Ala Glu Leu Leu Glu Asn Ile Gly Asp
    585                 590                 595 ctg tcc cca ccc cag gat gag cac acg acc atc ata gac cga ggg ctg    1996
Leu Ser Pro Pro Gln Asp Glu His Thr Thr Ile Ile Asp Arg Gly Leu
600                 605                 610                 615 ggg ggc tgt gag gag aac aac cac tta ctt ctc aac ggt ggc tcc caa    2044
Gly Gly Cys Glu Glu Asn Asn His Leu Leu Leu Asn Gly Gly Ser Gln
                620                 625                 630 aag ccc acg cag agc cag gtt cac agg ccg cca ggc tcc ggg gga cgg    2092
Lys Pro Thr Gln Ser Gln Val His Arg Pro Pro Gly Ser Gly Gly Arg
            635                 640                 645 cag acc agg gag ccc agg cag gag cct gca aac tca ccc acc tcc aag    2140
Gln Thr Arg Glu Pro Arg Gln Glu Pro Ala Asn Ser Pro Thr Ser Lys
        650                 655                 660 atg aag aag gtc aag ttt gcc aca ttc acc atc cca cct gag gaa agc    2188
Met Lys Lys Val Lys Phe Ala Thr Phe Thr Ile Pro Pro Glu Glu Ser
    665                 670                 675 tgc ccc acg gtg aac tcc atc ctc agt ggg gaa gat gat atc aag tgg    2236
Cys Pro Thr Val Asn Ser Ile Leu Ser Gly Glu Asp Asp Ile Lys Trp
680                 685                 690                 695 gtt tgt caa gac ctg gac gtg ggc gca ccc aag gaa ctc aga acc tac    2284
Val Cys Gln Asp Leu Asp Val Gly Ala Pro Lys Glu Leu Arg Thr Tyr
                700                 705                 710 ctg gag aaa ttc caa gac agt gtg tag cgctctggcc tcctcgccaa          2331
Leu Glu Lys Phe Gln Asp Ser Val
            715 cttgggacag tagcctcctt cccgacctcc ctcagcagag tagctgaacg gaaggagctc   2391 tcagtggact gagtgaggaa atctggggcc cacagaatac caggtagcag gttagaagct   2451 gggaagggat gttttatac taaagcagtt ttttttgttt tttgttttt gttttttgtt    2511 ttttttagca gcaaaggatg gtaggtttcc agaagtttga gtctctgact cagcagcgag   2571 gcagagtgga tccgaaagag aactgctcag acatgagaga gttatttat gaatcaaacg    2631 acactgcaga caagctacca aaaatatttg ttaaaaaaaa tatataaaaa gacgaataaa   2691 aaaaacacac aaatgactgt cggtttatat ttctaataaa ggaacaaaat gtaaaaatag   2751 ggcttgctaa aagaaggcct acattttaat tcagtcttta tgcttctgag gacagtccag   2811 gtctgttagc cttctgccca aggagaggca catctgaaca atggtcacct cttaggaaga   2871 atgagaattt tacattggat tccattatct ctgtttgctt ccatgtttct ttctaaggtc   2931 ctaagcctcc atttgattca atgtcatgtt tatttctgag gaccaagtgg tacattttcc   2991 taaatgaaat gtaaattata tttctattca ttagatagct ttttcccct cttttttaaga   3051 agatcatcaa cgaatccagt ctttacgttg taacattaac ctgtctttat attatacatc   3111 tcttgctttg ttaatatttt ctggcttgtt tgtaattctt tttgttttt tgttttgttt   3171 tgttttaaca atatagcaag tgtgcagttc cccacatggg gagagtgcac cccacaatct   3231 gtcatcagcc gggtcaggcc aatgagtgga ataatgttca cagctatctg aatagggtat   3291 ggccaagaga acagagtgca gcctgtgaca cctggccact ccctatggag acagagactc   3351 agtgggtgtc tccggcagtt tgggcatagg gatgcctcta tgtgaagagc tgtgagtgaa   3411
```

```
atccataaac tcgaggtgtg cagagtcagg cagatgggcc atgtctacca caagatacag    3471
ccgaccctgt actgaacaaa cagaaaagac atgtggggga ggggcaggct ggagttatct    3531
gattttatta ctgggcaagg cgaaccagca tgaactcaaa atgatttttt t             3582
```

<210> SEQ ID NO 17
<211> LENGTH: 719
<212> TYPE: PRT
<213> ORGANISM: Mus musculus

<400> SEQUENCE: 17

```
Met Gln Met Asn Phe Glu Ile Ala Ser Phe Ser Ser Leu Ser Gly Thr
1               5                   10                  15

Gln Pro Ile Thr Trp Gln Val Glu Tyr Pro Arg Lys Gly Ala Thr Asp
            20                  25                  30

Ile Ala Val Ser Glu Ile Phe Ile Ser Gln Lys Asp Leu Val Ala Ile
        35                  40                  45

Val Pro Leu Ala Met Asp Thr Glu Leu Leu Asn Thr Ala Ile Leu Thr
    50                  55                  60

Gly Lys Thr Val Ala Met Pro Val Arg Val Ser Val Glu Glu Asn
65                  70                  75                  80

Ser Thr Leu Arg Asp Ile Ser Glu Leu Val Glu Cys Lys Ala Thr Asp
                85                  90                  95

Glu Asn Val Ile Lys Val Ser Asp His Cys Asp Tyr Val Phe Val Asn
            100                 105                 110

Gly Lys Glu Ile Lys Gly Lys Met Asp Ser Val Val Asn Phe Thr Tyr
        115                 120                 125

Gln His Leu Ser Ala Pro Leu His Val Thr Val Trp Val Pro Arg Leu
    130                 135                 140

Pro Leu Gln Ile Glu Val Ser Asp Thr Glu Leu Ser Gln Val Lys Gly
145                 150                 155                 160

Trp Arg Val Pro Ile Val Ala Ser Lys Arg Pro Thr Arg Asp Ser Glu
                165                 170                 175

Glu Glu Glu Glu Glu Glu Gln Lys Gly Arg Gly Cys Thr Leu Gln Phe
            180                 185                 190

Gln His Ala Thr Val Arg Val Leu Thr Gln Phe Val Ser Glu Gly Ala
        195                 200                 205

Gly Pro Trp Gly Gln Leu Ser His Leu Leu Ser Pro Asp Trp Gln Phe
    210                 215                 220

Asp Ile Thr His Leu Val Ala Asp Phe Met Lys Leu Glu Ser Pro His
225                 230                 235                 240

Ile Ala Thr Leu Gln Asp Ser Arg Val Leu Val Gly Arg Glu Val Gly
                245                 250                 255

Met Thr Thr Ile Gln Val Leu Ser Pro Leu Ser Asp Ser Ile Leu Ala
            260                 265                 270

Glu Lys Thr Val Thr Val Leu Asp Asp Lys Val Ser Val Thr Asp Leu
        275                 280                 285

Ala Val Gln Val Val Ala Gly Leu Ser Val Thr Leu His Pro Ile Ser
    290                 295                 300

Glu Asn Asn Lys Ala Thr Ser Ala Val Ala Met Ala Glu Glu Leu Leu
305                 310                 315                 320

Arg Ala Pro Lys Lys Glu Ala Ile Ile Ser Thr Trp Leu Gln Phe Ser
                325                 330                 335

Asp Gly Ser Val Thr Pro Leu Ser Ile Tyr Asp Ser Lys Asp Phe Ser
            340                 345                 350
```

| Leu | Thr | Ala | Ile | Ser | Leu | Asp | Glu | Ala | Val | Val | Ser | Ile | Pro | Gln | Pro |
|---|---|---|---|---|---|---|---|---|---|---|---|---|---|---|---|
| | | 355 | | | | 360 | | | | 365 | | | | | |

| Leu | Ser | Pro | Trp | Trp | Pro | Thr | Val | Val | Ala | Glu | Gly | Glu | Gly | Gln | Gly |
|---|---|---|---|---|---|---|---|---|---|---|---|---|---|---|---|
| | 370 | | | | | 375 | | | | | 380 | | | | |

| Pro | Leu | Leu | Arg | Val | Asp | Met | Ser | Ile | Ala | Glu | Ala | Cys | Gln | Lys | Ser |
|---|---|---|---|---|---|---|---|---|---|---|---|---|---|---|---|
| 385 | | | | | 390 | | | | | 395 | | | | | 400 |

| Lys | Arg | Lys | Ser | Val | Leu | Ala | Val | Gly | Ile | Gly | His | Val | Gly | Val | Lys |
|---|---|---|---|---|---|---|---|---|---|---|---|---|---|---|---|
| | | | | 405 | | | | | 410 | | | | | 415 | |

| Phe | Gly | Trp | Asp | Asp | Ala | Asp | Ser | Ser | Gln | Thr | Gly | Glu | Lys | Asp | Glu |
|---|---|---|---|---|---|---|---|---|---|---|---|---|---|---|---|
| | | | 420 | | | | | 425 | | | | 430 | | | |

| Glu | Glu | Ile | Lys | Asn | His | Ala | Ser | Asp | Arg | Arg | Gln | Lys | Ile | Gln | Asp |
|---|---|---|---|---|---|---|---|---|---|---|---|---|---|---|---|
| | | | 435 | | | | 440 | | | | | 445 | | | |

| Leu | Glu | Arg | Pro | Gly | Gln | Asp | Glu | Leu | Tyr | His | Gly | Asn | Phe | Pro | Gly |
|---|---|---|---|---|---|---|---|---|---|---|---|---|---|---|---|
| | 450 | | | | | 455 | | | | | 460 | | | | |

| Asp | Arg | Glu | Glu | Gly | Ala | Leu | Ser | Ala | Thr | Thr | Thr | Lys | Ser | Leu |
|---|---|---|---|---|---|---|---|---|---|---|---|---|---|---|
| 465 | | | | | 470 | | | | | 475 | | | | 480 |

| Leu | Asp | Asn | Asn | Val | Gly | Lys | Ser | Gly | Arg | Arg | Asp | Gly | Ala | Arg | Leu |
|---|---|---|---|---|---|---|---|---|---|---|---|---|---|---|---|
| | | | | 485 | | | | | 490 | | | | | 495 | |

| His | Ser | Ile | Pro | Ile | Asp | Phe | Thr | Asn | Phe | Pro | Ala | His | Val | Asp | Leu |
|---|---|---|---|---|---|---|---|---|---|---|---|---|---|---|---|
| | | | 500 | | | | | 505 | | | | | 510 | | |

| Pro | Lys | Ala | Lys | Thr | Arg | Gly | Thr | Leu | Glu | Glu | Asn | Gly | Leu | Met | Gln |
|---|---|---|---|---|---|---|---|---|---|---|---|---|---|---|---|
| | 515 | | | | | 520 | | | | | 525 | | | | |

| Thr | Ala | His | Gly | Leu | Ser | Asp | Leu | Glu | Ile | Gly | Met | Tyr | Ala | Leu | Leu |
|---|---|---|---|---|---|---|---|---|---|---|---|---|---|---|---|
| 530 | | | | | 535 | | | | | 540 | | | | | |

| Gly | Val | Phe | Cys | Leu | Ala | Ile | Leu | Val | Phe | Leu | Ile | Asn | Cys | Ala | Thr |
|---|---|---|---|---|---|---|---|---|---|---|---|---|---|---|---|
| 545 | | | | | 550 | | | | | 555 | | | | | 560 |

| Phe | Ala | Phe | Lys | Tyr | Arg | His | Lys | Gln | Val | Pro | Leu | Glu | Gly | Gln | Ala |
|---|---|---|---|---|---|---|---|---|---|---|---|---|---|---|---|
| | | | | 565 | | | | | 570 | | | | | 575 | |

| Ser | Met | Thr | His | Ser | His | Asp | Trp | Val | Trp | Leu | Gly | Asn | Glu | Ala | Glu |
|---|---|---|---|---|---|---|---|---|---|---|---|---|---|---|---|
| | | | 580 | | | | | 585 | | | | | 590 | | |

| Leu | Leu | Glu | Asn | Ile | Gly | Asp | Leu | Ser | Pro | Pro | Gln | Asp | Glu | His | Thr |
|---|---|---|---|---|---|---|---|---|---|---|---|---|---|---|---|
| | | | 595 | | | | | 600 | | | | | 605 | | |

| Thr | Ile | Ile | Asp | Arg | Gly | Leu | Gly | Gly | Cys | Glu | Glu | Asn | Asn | His | Leu |
|---|---|---|---|---|---|---|---|---|---|---|---|---|---|---|---|
| 610 | | | | | 615 | | | | | 620 | | | | | |

| Leu | Leu | Asn | Gly | Gly | Ser | Gln | Lys | Pro | Thr | Gln | Ser | Gln | Val | His | Arg |
|---|---|---|---|---|---|---|---|---|---|---|---|---|---|---|---|
| 625 | | | | | 630 | | | | | 635 | | | | | 640 |

| Pro | Pro | Gly | Ser | Gly | Gly | Arg | Gln | Thr | Arg | Glu | Pro | Arg | Gln | Glu | Pro |
|---|---|---|---|---|---|---|---|---|---|---|---|---|---|---|---|
| | | | | 645 | | | | | 650 | | | | | 655 | |

| Ala | Asn | Ser | Pro | Thr | Ser | Lys | Met | Lys | Lys | Val | Lys | Phe | Ala | Thr | Phe |
|---|---|---|---|---|---|---|---|---|---|---|---|---|---|---|---|
| | | | 660 | | | | | 665 | | | | | 670 | | |

| Thr | Ile | Pro | Pro | Glu | Glu | Ser | Cys | Pro | Thr | Val | Asn | Ser | Ile | Leu | Ser |
|---|---|---|---|---|---|---|---|---|---|---|---|---|---|---|---|
| | | 675 | | | | | 680 | | | | | 685 | | | |

| Gly | Glu | Asp | Asp | Ile | Lys | Trp | Val | Cys | Gln | Asp | Leu | Asp | Val | Gly | Ala |
|---|---|---|---|---|---|---|---|---|---|---|---|---|---|---|---|
| | 690 | | | | | 695 | | | | | 700 | | | | |

| Pro | Lys | Glu | Leu | Arg | Thr | Tyr | Leu | Glu | Lys | Phe | Gln | Asp | Ser | Val |
|---|---|---|---|---|---|---|---|---|---|---|---|---|---|---|
| 705 | | | | | 710 | | | | | 715 | | | | |

<210> SEQ ID NO 18
<211> LENGTH: 5639
<212> TYPE: DNA
<213> ORGANISM: Mus musculus
<220> FEATURE:
<221> NAME/KEY: CDS
<222> LOCATION: (79)..(3936)
<223> OTHER INFORMATION:

<400> SEQUENCE: 18

```
aggagcagcc gccggagccg gagcgctgcc gggggcggcc ccgggcatgg ggcaaccggc      60
gcggtcccgg ggctggcg atg gat ggc gtg aca gcg gcc acg atg cgc tcc      111
                    Met Asp Gly Val Thr Ala Ala Thr Met Arg Ser
                    1             5                  10 gag ggc gcg gcc ccg agg cgg gcg gcg cgg tac ggg gcg ctg agc ctg      159
Glu Gly Ala Ala Pro Arg Arg Ala Ala Arg Tyr Gly Ala Leu Ser Leu
             15                  20                  25 gtc cta gcc acg cta ctg ggc caa gtg acc gaa agc cga ggg gtc atg      207
Val Leu Ala Thr Leu Leu Gly Gln Val Thr Glu Ser Arg Gly Val Met
         30                  35                  40 gat aat ata cag aga ttc tct tca ttg ccg ccg tac ctg ccc gtg agc      255
Asp Asn Ile Gln Arg Phe Ser Ser Leu Pro Pro Tyr Leu Pro Val Ser
     45                  50                  55 ttc cac gtc ctc aga gcc gag act gca ttc ttc cta aag gag gcc aac      303
Phe His Val Leu Arg Ala Glu Thr Ala Phe Phe Leu Lys Glu Ala Asn
60                  65                  70                  75 ccc gac ccg ctg cgg aat gcc agc ctg cag tcc agg gtg gag tct ttc      351
Pro Asp Pro Leu Arg Asn Ala Ser Leu Gln Ser Arg Val Glu Ser Phe
                 80                  85                  90 ttc atc tac aag gcc cag cag ccc cgg gta tta aac gtc agc tat ggg      399
Phe Ile Tyr Lys Ala Gln Gln Pro Pro Val Leu Asn Val Ser Tyr Gly
             95                 100                 105 cct tac tct gca gaa aag gtc atc cct ctg gac ttg atg ttg aac ccc      447
Pro Tyr Ser Ala Glu Lys Val Ile Pro Leu Asp Leu Met Leu Asn Pro
        110                 115                 120 aac ttt tta ggc cca acc agt aag ttt ccc ttt gac tgg agg ctg aag      495
Asn Phe Leu Gly Pro Thr Ser Lys Phe Pro Phe Asp Trp Arg Leu Lys
    125                 130                 135 gcc tac atc ctt caa gag aaa gtc tac ctg agc cat ccc aaa gta cag      543
Ala Tyr Ile Leu Gln Glu Lys Val Tyr Leu Ser His Pro Lys Val Gln
140                 145                 150                 155 gtg ctc ttc cac atc gtg ggc cga gac tgg gat gac cac agg gac gag      591
Val Leu Phe His Ile Val Gly Arg Asp Trp Asp Asp His Arg Asp Glu
                160                 165                 170 aaa ctg ccc tgc ctg cgg gtc ttt gcg ttc aga gac agc cgg gag gtt      639
Lys Leu Pro Cys Leu Arg Val Phe Ala Phe Arg Asp Ser Arg Glu Val
            175                 180                 185 cga ggc agc tgt cgt ctg ggt ggg ccc ctg gga ctg tgc gtg gcc cag      687
Arg Gly Ser Cys Arg Leu Gly Gly Pro Leu Gly Leu Cys Val Ala Gln
        190                 195                 200 ctg gag atg ctg cct ggc tgg ttc agt ccc cca gcg gtt gta tct ggg      735
Leu Glu Met Leu Pro Gly Trp Phe Ser Pro Pro Ala Val Val Ser Gly
    205                 210                 215 cgc agg agg cca gca gag cgg cca gag ggg agt ccg gtg gaa ctg tat      783
Arg Arg Arg Pro Ala Glu Arg Pro Glu Gly Ser Pro Val Glu Leu Tyr
220                 225                 230                 235 tat gct gta cag cca ggg gac gag cgt ggt gac tgc act gga ggt gac      831
Tyr Ala Val Gln Pro Gly Asp Glu Arg Gly Asp Cys Thr Gly Gly Asp
                240                 245                 250 acc agg aag gac aat gct att cgt cca gga aag gat gga cag gag ggc      879
Thr Arg Lys Asp Asn Ala Ile Arg Pro Gly Lys Asp Gly Gln Glu Gly
            255                 260                 265 agg aca tcc cac cta cag aag att ggc acc att agc ctt tac cgc gcc      927
Arg Thr Ser His Leu Gln Lys Ile Gly Thr Ile Ser Leu Tyr Arg Ala
        270                 275                 280 cag gac agc acc cag ctc agc gaa ctg cgc ctg gat ggc aat gtg gtc      975
Gln Asp Ser Thr Gln Leu Ser Glu Leu Arg Leu Asp Gly Asn Val Val
    285                 290                 295 atc tgg ctg ccc tcc cag ccc gtc aag cag gga gac ata gtc acc gca      1023
```

```
                                    -continued
Ile Trp Leu Pro Ser Gln Pro Val Lys Gln Gly Asp Ile Val Thr Ala
300                 305                 310                 315 tct gtc acc atc gcc aat aac tct act gtg gac cat ttc atc cta aga       1071
Ser Val Thr Ile Ala Asn Asn Ser Thr Val Asp His Phe Ile Leu Arg
                320                 325                 330 gcc aag gtg aag aag ggg gtg aac atc ctg acc gtg cag acc agc gag       1119
Ala Lys Val Lys Lys Gly Val Asn Ile Leu Thr Val Gln Thr Ser Glu
                335                 340                 345 cct cgg cag tgg gat gtg agg caa gag gtg ggc aat gga ggg aag cac       1167
Pro Arg Gln Trp Asp Val Arg Gln Glu Val Gly Asn Gly Gly Lys His
            350                 355                 360 acc acc acc tcg gtg gcc tgc cag cgc ctg ggc cct ggg gca cga aat       1215
Thr Thr Thr Ser Val Ala Cys Gln Arg Leu Gly Pro Gly Ala Arg Asn
        365                 370                 375 agg agc agc aat tta ttc agc gag gtc atg cag atg aat ttt gaa atc       1263
Arg Ser Ser Asn Leu Phe Ser Glu Val Met Gln Met Asn Phe Glu Ile
380                 385                 390                 395 gcc agc ttc agc agc ctc tcg ggg aca cag cct atc aca tgg cag gtg       1311
Ala Ser Phe Ser Ser Leu Ser Gly Thr Gln Pro Ile Thr Trp Gln Val
                400                 405                 410 gag tac ccg agg aag ggg gcc acg gac att gct gtg tcg gag atc ttc       1359
Glu Tyr Pro Arg Lys Gly Ala Thr Asp Ile Ala Val Ser Glu Ile Phe
                415                 420                 425 atc agc cag aag gac cta gtt gcc atc gtc ccc ctt gct atg aac gat       1407
Ile Ser Gln Lys Asp Leu Val Ala Ile Val Pro Leu Ala Met Asn Asp
                430                 435                 440 aag aca ttc aaa tgc ttt gaa aag caa aac cat tat aaa gac ata aga       1455
Lys Thr Phe Lys Cys Phe Glu Lys Gln Asn His Tyr Lys Asp Ile Arg
            445                 450                 455 tat tat tcc ggt cca ttg tca aca ctt tta cct cta gtg aat tcc gat       1503
Tyr Tyr Ser Gly Pro Leu Ser Thr Leu Leu Pro Leu Val Asn Ser Asp
460                 465                 470                 475 tgg ctt cat gcc atc atc aca gac aat gat gcc atc tcc aca gga cct       1551
Trp Leu His Ala Ile Ile Thr Asp Asn Asp Ala Ile Ser Thr Gly Pro
                480                 485                 490 gta gcc agg acc tgg aat tat tgc tgt gtg gct gtg agg cgc gca gag       1599
Val Ala Arg Thr Trp Asn Tyr Cys Cys Val Ala Val Arg Arg Ala Glu
                495                 500                 505 gtg tta gca tgt gtc ctc ggg gaa gga gag aaa ttt gct cag cta cct       1647
Val Leu Ala Cys Val Leu Gly Glu Gly Glu Lys Phe Ala Gln Leu Pro
            510                 515                 520 tcg gag agc agc agt aac tcc ctg gaa agg atg ggc cct atc tgg tat       1695
Ser Glu Ser Ser Ser Asn Ser Leu Glu Arg Met Gly Pro Ile Trp Tyr
525                 530                 535 cga ctg aca tct ggg gtc atc tta gac aac ctg cag gaa ccg cag ggg       1743
Arg Leu Thr Ser Gly Val Ile Leu Asp Asn Leu Gln Glu Pro Gln Gly
540                 545                 550                 555 tct gaa act cat cca ctc ctg cat cca gcg agg acc ttt gtc cct cta       1791
Ser Glu Thr His Pro Leu Leu His Pro Ala Arg Thr Phe Val Pro Leu
                560                 565                 570 gag ata tcg gaa atg cct ctg ggg aca aaa ctg tcc ctg gtc agg atc       1839
Glu Ile Ser Glu Met Pro Leu Gly Thr Lys Leu Ser Leu Val Arg Ile
            575                 580                 585 ttc tgc att aaa aat ctg gct gct gtg atg aag gaa tgt aca gac agc       1887
Phe Cys Ile Lys Asn Leu Ala Ala Val Met Lys Glu Cys Thr Asp Ser
        590                 595                 600 tac aga aga gtc ttc tgc agc aag aag agg gga tgc aaa ggc cct gtg       1935
Tyr Arg Arg Val Phe Cys Ser Lys Lys Arg Gly Cys Lys Gly Pro Val
605                 610                 615 gtc ctc atg gac agt gac cta atg ctg atc caa ttt tcc acc aag cat       1983
```

```
Val Leu Met Asp Ser Asp Leu Met Leu Ile Gln Phe Ser Thr Lys His
620             625             630             635 tcg gct cac gtg cac agc cca ccg aca gag atg aaa aga ttc cga gaa      2031
Ser Ala His Val His Ser Pro Pro Thr Glu Met Lys Arg Phe Arg Glu
            640             645             650 aca cag cca atg ggc tgg aaa gat tcc tgc agg aat cag ttc ctt ttt      2079
Thr Gln Pro Met Gly Trp Lys Asp Ser Cys Arg Asn Gln Phe Leu Phe
                655             660             665 gtc tcg gac cac tgt gac tat gtc ttt gtc aat ggt aaa gag atc aag      2127
Val Ser Asp His Cys Asp Tyr Val Phe Val Asn Gly Lys Glu Ile Lys
            670             675             680 ggc aag atg gac tct gtg gtg aac ttc acc tac cag cac ctg agc gca      2175
Gly Lys Met Asp Ser Val Val Asn Phe Thr Tyr Gln His Leu Ser Ala
        685             690             695 ccg ctg cat gtc act gtg tgg gtg cca cgg ctt ccc ctg cag atc gag      2223
Pro Leu His Val Thr Val Trp Val Pro Arg Leu Pro Leu Gln Ile Glu
700             705             710             715 gtc tct gac aca gaa ctc agc cag gtt aag ggc tgg aga gtc ccc atc      2271
Val Ser Asp Thr Glu Leu Ser Gln Val Lys Gly Trp Arg Val Pro Ile
            720             725             730 gtg gcc agc aag agg ccc act cgg gac agt gag gag gaa gaa gag gaa      2319
Val Ala Ser Lys Arg Pro Thr Arg Asp Ser Glu Glu Glu Glu Glu Glu
        735             740             745 gaa cag aaa ggc cgg ggt tgt acc ctg cag ttc cag cat gcc aca gtg      2367
Glu Gln Lys Gly Arg Gly Cys Thr Leu Gln Phe Gln His Ala Thr Val
    750             755             760 cgc gtc ctc acc caa ttt gta tca gag ggt gct ggg ccc tgg ggc cag      2415
Arg Val Leu Thr Gln Phe Val Ser Glu Gly Ala Gly Pro Trp Gly Gln
765             770             775 ctg agc cac ctt ctc agt cca gac tgg cag ttt gac atc acc cac ctg      2463
Leu Ser His Leu Leu Ser Pro Asp Trp Gln Phe Asp Ile Thr His Leu
780             785             790             795 gtg gct gac ttt atg aag ctg gag tcc cca cac ata gcc acc ctg cag      2511
Val Ala Asp Phe Met Lys Leu Glu Ser Pro His Ile Ala Thr Leu Gln
            800             805             810 gac agc agg gtc ttg gtt ggg cgg gaa gtc gga atg acc acc atc cag      2559
Asp Ser Arg Val Leu Val Gly Arg Glu Val Gly Met Thr Thr Ile Gln
        815             820             825 gtg ttg tct ccc ctg tcc gac tcc atc ttg gcc gag aag aca gta act      2607
Val Leu Ser Pro Leu Ser Asp Ser Ile Leu Ala Glu Lys Thr Val Thr
830             835             840 gtg ctg gat gac aaa gta tct gtg aca gac tta gct gtc cag gtg gtg      2655
Val Leu Asp Asp Lys Val Ser Val Thr Asp Leu Ala Val Gln Val Val
845             850             855 gct ggg ctg tct gtc acc cta cac ccc atc tca gag aac aac aag gcc      2703
Ala Gly Leu Ser Val Thr Leu His Pro Ile Ser Glu Asn Asn Lys Ala
860             865             870             875 acc tca gct gtg gcc atg gca gaa gag ctg cta cgt gcc cca aaa aag      2751
Thr Ser Ala Val Ala Met Ala Glu Glu Leu Leu Arg Ala Pro Lys Lys
            880             885             890 gaa gct ata atc agc aca tgg ctc cag ttc agt gat ggc tca gtg aca      2799
Glu Ala Ile Ile Ser Thr Trp Leu Gln Phe Ser Asp Gly Ser Val Thr
        895             900             905 ccc ctg gat atc tac gac tcc aag gac ttc tcc ttg act gcc atc tct      2847
Pro Leu Asp Ile Tyr Asp Ser Lys Asp Phe Ser Leu Thr Ala Ile Ser
    910             915             920 ttg gac gag gct gtc gtg tcc atc ccc caa ccc ctc tcg cct tgg tgg      2895
Leu Asp Glu Ala Val Val Ser Ile Pro Gln Pro Leu Ser Pro Trp Trp
925             930             935 ccc acc gtg gta gct gaa gga gaa ggc cag ggc cca ctg ctc cgg gtc      2943
```

```
                  Pro Thr Val Val Ala Glu Gly Glu Gly Gln Gly Pro Leu Leu Arg Val
                  940                 945                 950                 955 gat atg tcc att gcc gaa gcc tgt cag aaa tcc aag cgc aag agt gtg        2991
Asp Met Ser Ile Ala Glu Ala Cys Gln Lys Ser Lys Arg Lys Ser Val
            960                 965                 970 ctg gct gtt ggc att ggc cac gtg ggg gtc aag ttt gga tgg gat gac        3039
Leu Ala Val Gly Ile Gly His Val Gly Val Lys Phe Gly Trp Asp Asp
                975                 980                 985 gct gac tcc agc cag act gga gaa aag gat gag gag gag atc aag aac        3087
Ala Asp Ser Ser Gln Thr Gly Glu Lys Asp Glu Glu Glu Ile Lys Asn
            990                 995                 1000 cat gcc agt gac cgt cgg cag aag att cag gac ctg gaa cgc cca            3132
His Ala Ser Asp Arg Arg Gln Lys Ile Gln Asp Leu Glu Arg Pro
        1005                1010                1015 ggc cag gat gaa cta tac cat ggc aac ttt cct ggg gat cgt gaa            3177
Gly Gln Asp Glu Leu Tyr His Gly Asn Phe Pro Gly Asp Arg Glu
    1020                1025                1030 gaa gga gcg ctg agt gct acc acc act acc aag tcc ctg ctg gat            3222
Glu Gly Ala Leu Ser Ala Thr Thr Thr Thr Lys Ser Leu Leu Asp
    1035                1040                1045 aac aac gtg ggg aag agt ggc agg cgg gac ggg gct agg cta cac            3267
Asn Asn Val Gly Lys Ser Gly Arg Arg Asp Gly Ala Arg Leu His
    1050                1055                1060 agc ata ccc att gac ttc acc aat ttc ccg gcc cat gtg gac ctc            3312
Ser Ile Pro Ile Asp Phe Thr Asn Phe Pro Ala His Val Asp Leu
    1065                1070                1075 ccc aag gcc aag acc agg ggc aca ctg gag gag aat ggt ctc atg            3357
Pro Lys Ala Lys Thr Arg Gly Thr Leu Glu Glu Asn Gly Leu Met
    1080                1085                1090 cag aca gcc cat ggc ctg agt gac cta gag att ggg atg tat gcc            3402
Gln Thr Ala His Gly Leu Ser Asp Leu Glu Ile Gly Met Tyr Ala
    1095                1100                1105 ctc cta ggt gtc ttc tgc ctg gcc atc ctt gtc ttt ctc att aac            3447
Leu Leu Gly Val Phe Cys Leu Ala Ile Leu Val Phe Leu Ile Asn
    1110                1115                1120 tgc gcc acc ttt gcc ttc aag tac agg cac aaa cag gtg cct ctg            3492
Cys Ala Thr Phe Ala Phe Lys Tyr Arg His Lys Gln Val Pro Leu
    1125                1130                1135 gaa ggc cag gca tcc atg acc cac tct cat gac tgg gtc tgg ctg            3537
Glu Gly Gln Ala Ser Met Thr His Ser His Asp Trp Val Trp Leu
    1140                1145                1150 ggc aat gag gcg gag ctc ttg gag aac att ggg gac ctg tcc cca            3582
Gly Asn Glu Ala Glu Leu Leu Glu Asn Ile Gly Asp Leu Ser Pro
    1155                1160                1165 ccc cag gat gag cac acg acc atc ata gac cga ggg ctg ggg ggc            3627
Pro Gln Asp Glu His Thr Thr Ile Ile Asp Arg Gly Leu Gly Gly
    1170                1175                1180 tgt gag gag aac aac cac tta ctt ctc aac ggt ggc tcc caa aag            3672
Cys Glu Glu Asn Asn His Leu Leu Leu Asn Gly Gly Ser Gln Lys
    1185                1190                1195 ccc acg cag agc cag gtt cac agg ccg cca ggc tcc ggg gga cgg            3717
Pro Thr Gln Ser Gln Val His Arg Pro Pro Gly Ser Gly Gly Arg
    1200                1205                1210 cag acc agg gag ccc agg cag gag cct gca aac tca ccc acc tcc            3762
Gln Thr Arg Glu Pro Arg Gln Glu Pro Ala Asn Ser Pro Thr Ser
    1215                1220                1225 aag atg aag aag gtc aag ttt gcc aca ttc acc atc cca cct gag            3807
Lys Met Lys Lys Val Lys Phe Ala Thr Phe Thr Ile Pro Pro Glu
    1230                1235                1240 gaa agc tgc ccc acg gtg aac tcc atc ctc agt ggg gaa gat gat            3852
```

| | | | | | | | | | | | | | | | |
|---|---|---|---|---|---|---|---|---|---|---|---|---|---|---|---|
|Glu|Ser|Cys|Pro|Thr|Val|Asn|Ser|Ile|Leu|Ser|Gly|Glu|Asp|Asp| |
| |1245| | | |1250| | | | |1255| | | | | |

```
atc aag tgg gtt tgt caa gac ctg gac gtg ggc gca ccc aag gaa      3897
Ile Lys Trp Val Cys Gln Asp Leu Asp Val Gly Ala Pro Lys Glu
    1260                1265                1270 ctc aga acc tac ctg gag aaa ttc caa gac agt gtg tag cgctctggcc   3946
Leu Arg Thr Tyr Leu Glu Lys Phe Gln Asp Ser Val
    1275                1280            1285 tcctcgccaa cttgggacag tagcctcctt cccgacctcc ctcagcagag tagctgaacg 4006 gaaggagctc tcagtggact gagtgaggaa atctggggcc cacagaatac caggtagcag 4066 gttagaagct gggaagggat gtttttatac taaagcagtt ttttttgttt tttgtttttt 4126 gtttttgtt tttttagca gcaaaggatg gtaggtttcc agaagtttga gtctctgact   4186
cagcagcgag gcagagtgga tccgaaagag aactgctcag acatgagaga gttatttat  4246 gaatcaaacg acactgcaga caagctacca aaaatatttg ttaaaaaaa tatataaaaa  4306 gacgaataaa aaaacacac aaatgactgt cggtttatat ttctaataaa ggaacaaaat  4366
gtaaaaatag ggcttgctaa agaaggcct acatttttaat tcagtcttta tgcttctgag 4426 gacagtccag gtctgttagc cttctgccca aggagaggca catctgaaca atggtcacct 4486 cttaggaaga atgagaattt tacattggat tccattatct ctgtttgctt ccatgtttct 4546 ttctaaggtc ctaagcctcc atttgattca atgtcatgtt tatttctgag gaccaagtgg 4606 tacatttcc taaatgaaat gtaaattata tttctattca ttagatagct ttttcccct   4666 ctttttaaga agatcatcaa cgaatccagt ctttacgttg taacattaac ctgtctttat 4726 attatacatc tcttgctttg ttaatatttt ctggcttgtt tgtaattctt tttgttttt  4786 tgttttgttt tgtttttaaca atatagcaag tgtgcagttc cccacatggg gagagtgcac 4846 cccacaatct gtcatcagcc gggtcaggcc aatgagtgga ataatgttca cagctatctg 4906 aatagggtat ggccaagaga acagagtgca gcctgtgaca cctggccact ccctatggag 4966 acagagactc agtgggtgtc tccggcagtt tgggcatagg gatgcctcta tgtgaagagc 5026 tgtgagtgaa atccataaac tcgaggtgtg cagagtcagg cagatgggcc atgtctacca 5086 caagatacag ccgaccctgt actgaacaaa cagaaaagac atgtggggga ggggcaggct 5146 ggagttatct gatttattta ctgggcaagg cgaaccagca tgaactcaaa atgatttttt 5206 taaaaaaaag aaatctatgt tagattgtca atcaaactgc ggctttgaag agtatggctg 5266 tgttaacagc acaatgcagt atcatatcca ctcaaaacag agtgtttacg caaaaagcag 5326 gagggatcaa atgaactagg atgtccggag cctggcgctc tccatccatc agctgaggga 5386 gaggatgttg ggcactgtga ccctcagcag agcagcattc acagagagac caggggacgg 5446 ccattgtttg ggttttttg tttttttct attactaaaa tcagtagctg agaaaaggtc   5506
tcagaagcct agtggccttg gttggaccttt tgacacatat atttgtagca tttacaatag 5566 attaaaaaa aaaaagctat ttatttatac ctgtggtggc agttgtcatt aaaacgcttg   5626
ccatgcttcc aaa                                                   5639
```

<210> SEQ ID NO 19
<211> LENGTH: 1285
<212> TYPE: PRT
<213> ORGANISM: Mus musculus

<400> SEQUENCE: 19

| | | | | | | | | | | | | | | | |
|---|---|---|---|---|---|---|---|---|---|---|---|---|---|---|---|
|Met|Asp|Gly|Val|Thr|Ala|Ala|Thr|Met|Arg|Ser|Glu|Gly|Ala|Ala|Pro|
|1| | | |5| | | | |10| | | | |15| |

-continued

```
Arg Arg Ala Ala Arg Tyr Gly Ala Leu Ser Leu Val Leu Ala Thr Leu
            20                  25                  30

Leu Gly Gln Val Thr Glu Ser Arg Gly Val Met Asp Asn Ile Gln Arg
        35                  40                  45

Phe Ser Ser Leu Pro Pro Tyr Leu Pro Val Ser Phe His Val Leu Arg
 50                  55                  60

Ala Glu Thr Ala Phe Phe Leu Lys Glu Ala Asn Pro Asp Pro Leu Arg
 65                  70                  75                  80

Asn Ala Ser Leu Gln Ser Arg Val Glu Ser Phe Ile Tyr Lys Ala
                85                  90                  95

Gln Gln Pro Pro Val Leu Asn Val Ser Tyr Gly Pro Tyr Ser Ala Glu
            100                 105                 110

Lys Val Ile Pro Leu Asp Leu Met Leu Asn Pro Asn Phe Leu Gly Pro
            115                 120                 125

Thr Ser Lys Phe Pro Phe Asp Trp Arg Leu Lys Ala Tyr Ile Leu Gln
        130                 135                 140

Glu Lys Val Tyr Leu Ser His Pro Lys Val Gln Val Leu Phe His Ile
145                 150                 155                 160

Val Gly Arg Asp Trp Asp His Arg Asp Glu Lys Leu Pro Cys Leu
            165                 170                 175

Arg Val Phe Ala Phe Arg Asp Ser Arg Glu Val Arg Gly Ser Cys Arg
            180                 185                 190

Leu Gly Gly Pro Leu Gly Leu Cys Val Ala Gln Leu Glu Met Leu Pro
        195                 200                 205

Gly Trp Phe Ser Pro Pro Ala Val Val Ser Gly Arg Arg Arg Pro Ala
210                 215                 220

Glu Arg Pro Glu Gly Ser Pro Val Glu Leu Tyr Tyr Ala Val Gln Pro
225                 230                 235                 240

Gly Asp Glu Arg Gly Asp Cys Thr Gly Asp Thr Arg Lys Asp Asn
            245                 250                 255

Ala Ile Arg Pro Gly Lys Asp Gly Gln Glu Gly Arg Thr Ser His Leu
        260                 265                 270

Gln Lys Ile Gly Thr Ile Ser Leu Tyr Arg Ala Gln Asp Ser Thr Gln
        275                 280                 285

Leu Ser Glu Leu Arg Leu Asp Gly Asn Val Val Ile Trp Leu Pro Ser
290                 295                 300

Gln Pro Val Lys Gln Gly Asp Ile Val Thr Ala Ser Val Thr Ile Ala
305                 310                 315                 320

Asn Asn Ser Thr Val Asp His Phe Ile Leu Arg Ala Lys Val Lys Lys
            325                 330                 335

Gly Val Asn Ile Leu Thr Val Thr Ser Glu Pro Arg Gln Trp Asp
        340                 345                 350

Val Arg Gln Glu Val Gly Asn Gly Lys His Thr Thr Thr Ser Val
            355                 360                 365

Ala Cys Gln Arg Leu Gly Pro Gly Ala Arg Asn Arg Ser Asn Leu
            370                 375                 380

Phe Ser Glu Val Met Gln Met Asn Phe Glu Ile Ala Ser Phe Ser Ser
385                 390                 395                 400

Leu Ser Gly Thr Gln Pro Ile Thr Trp Gln Val Glu Tyr Pro Arg Lys
            405                 410                 415

Gly Ala Thr Asp Ile Ala Val Ser Glu Ile Phe Ile Ser Gln Lys Asp
            420                 425                 430

Leu Val Ala Ile Val Pro Leu Ala Met Asn Asp Lys Thr Phe Lys Cys
        435                 440                 445
```

```
Phe Glu Lys Gln Asn His Tyr Lys Asp Ile Arg Tyr Tyr Ser Gly Pro
    450                 455                 460

Leu Ser Thr Leu Leu Pro Leu Val Asn Ser Asp Trp Leu His Ala Ile
465                 470                 475                 480

Ile Thr Asp Asn Asp Ala Ile Ser Thr Gly Pro Val Ala Arg Thr Trp
            485                 490                 495

Asn Tyr Cys Cys Val Ala Val Arg Arg Ala Glu Val Leu Ala Cys Val
            500                 505                 510

Leu Gly Glu Gly Glu Lys Phe Ala Gln Leu Pro Ser Glu Ser Ser Ser
            515                 520             525

Asn Ser Leu Glu Arg Met Gly Pro Ile Trp Tyr Arg Leu Thr Ser Gly
530                 535                 540

Val Ile Leu Asp Asn Leu Gln Glu Pro Gln Gly Ser Gly Thr His Pro
545                 550                 555                 560

Leu Leu His Pro Ala Arg Thr Phe Val Pro Leu Glu Ile Ser Glu Met
                565                 570                 575

Pro Leu Gly Thr Lys Leu Ser Leu Val Arg Ile Phe Cys Ile Lys Asn
                580                 585                 590

Leu Ala Ala Val Met Lys Glu Cys Thr Asp Ser Tyr Arg Arg Val Phe
                595                 600                 605

Cys Ser Lys Lys Arg Gly Cys Lys Gly Pro Val Val Leu Met Asp Ser
610                 615                 620

Asp Leu Met Leu Ile Gln Phe Ser Thr Lys His Ser Ala His Val His
625                 630                 635                 640

Ser Pro Pro Thr Glu Met Lys Arg Phe Arg Glu Thr Gln Pro Met Gly
                645                 650                 655

Trp Lys Asp Ser Cys Arg Asn Gln Phe Leu Phe Val Ser Asp His Cys
                660                 665                 670

Asp Tyr Val Phe Val Asn Gly Lys Glu Ile Lys Gly Lys Met Asp Ser
            675                 680                 685

Val Val Asn Phe Thr Tyr Gln His Leu Ser Ala Pro Leu His Val Thr
            690                 695                 700

Val Trp Val Pro Arg Leu Pro Leu Gln Ile Glu Val Ser Asp Thr Glu
705                 710                 715                 720

Leu Ser Gln Val Lys Gly Trp Arg Val Pro Ile Val Ala Ser Lys Arg
                725                 730                 735

Pro Thr Arg Asp Ser Glu Glu Glu Glu Glu Gln Lys Gly Arg
                740                 745                 750

Gly Cys Thr Leu Gln Phe Gln His Ala Thr Val Arg Val Leu Thr Gln
        755                 760                 765

Phe Val Ser Glu Gly Ala Gly Pro Trp Gly Gln Leu Ser His Leu Leu
    770                 775                 780

Ser Pro Asp Trp Gln Phe Asp Ile Thr His Leu Val Ala Asp Phe Met
785                 790                 795                 800

Lys Leu Glu Ser Pro His Ile Ala Thr Leu Gln Asp Ser Arg Val Leu
                805                 810                 815

Val Gly Arg Glu Val Gly Met Thr Thr Ile Gln Val Leu Ser Pro Leu
            820                 825                 830

Ser Asp Ser Ile Leu Ala Glu Lys Thr Val Thr Val Leu Asp Asp Lys
            835                 840                 845

Val Ser Val Thr Asp Leu Ala Val Gln Val Val Ala Gly Leu Ser Val
850                 855                 860

Thr Leu His Pro Ile Ser Glu Asn Asn Lys Ala Thr Ser Ala Val Ala
```

```
                865                 870                 875                 880
Met Ala Glu Glu Leu Leu Arg Ala Pro Lys Lys Glu Ala Ile Ile Ser
                    885                 890                 895
Thr Trp Leu Gln Phe Ser Asp Gly Ser Val Thr Pro Leu Asp Ile Tyr
                    900                 905                 910
Asp Ser Lys Asp Phe Ser Leu Thr Ala Ile Ser Leu Asp Glu Ala Val
                    915                 920                 925
Val Ser Ile Pro Gln Pro Leu Ser Pro Trp Trp Pro Thr Val Val Ala
                    930                 935                 940
Glu Gly Glu Gly Gln Gly Pro Leu Leu Arg Val Asp Met Ser Ile Ala
945                 950                 955                 960
Glu Ala Cys Gln Lys Ser Lys Arg Lys Ser Val Leu Ala Val Gly Ile
                    965                 970                 975
Gly His Val Gly Val Lys Phe Gly Trp Asp Asp Ala Asp Ser Ser Gln
                    980                 985                 990
Thr Gly Glu Lys Asp Glu Glu Glu Ile Lys Asn His Ala Ser Asp Arg
                    995                 1000                1005
Arg Gln Lys Ile Gln Asp Leu Glu Arg Pro Gly Gln Asp Glu Leu
1010                1015                1020
Tyr His Gly Asn Phe Pro Gly Asp Arg Glu Glu Gly Ala Leu Ser
1025                1030                1035
Ala Thr Thr Thr Thr Lys Ser Leu Leu Asp Asn Asn Val Gly Lys
1040                1045                1050
Ser Gly Arg Arg Asp Gly Ala Arg Leu His Ser Ile Pro Ile Asp
1055                1060                1065
Phe Thr Asn Phe Pro Ala His Val Asp Leu Pro Lys Ala Lys Thr
1070                1075                1080
Arg Gly Thr Leu Glu Glu Asn Gly Leu Met Gln Thr Ala His Gly
1085                1090                1095
Leu Ser Asp Leu Glu Ile Gly Met Tyr Ala Leu Leu Gly Val Phe
1100                1105                1110
Cys Leu Ala Ile Leu Val Phe Leu Ile Asn Cys Ala Thr Phe Ala
1115                1120                1125
Phe Lys Tyr Arg His Lys Gln Val Pro Leu Glu Gly Gln Ala Ser
1130                1135                1140
Met Thr His Ser His Asp Trp Val Trp Leu Gly Asn Glu Ala Glu
1145                1150                1155
Leu Leu Glu Asn Ile Gly Asp Leu Ser Pro Pro Gln Asp Glu His
1160                1165                1170
Thr Thr Ile Ile Asp Arg Gly Leu Gly Gly Cys Glu Glu Asn Asn
1175                1180                1185
His Leu Leu Leu Asn Gly Gly Ser Gln Lys Pro Thr Gln Ser Gln
1190                1195                1200
Val His Arg Pro Pro Gly Ser Gly Gly Arg Gln Thr Arg Glu Pro
1205                1210                1215
Arg Gln Glu Pro Ala Asn Ser Pro Thr Ser Lys Met Lys Lys Val
1220                1225                1230
Lys Phe Ala Thr Phe Thr Ile Pro Pro Glu Glu Ser Cys Pro Thr
1235                1240                1245
Val Asn Ser Ile Leu Ser Gly Glu Asp Asp Ile Lys Trp Val Cys
1250                1255                1260
Gln Asp Leu Asp Val Gly Ala Pro Lys Glu Leu Arg Thr Tyr Leu
1265                1270                1275
```

Glu Lys Phe Gln Asp Ser Val
    1280            1285

<210> SEQ ID NO 20
<211> LENGTH: 2683
<212> TYPE: DNA
<213> ORGANISM: Mus musculus

<400> SEQUENCE: 20

| | | | | | |
|---|---|---|---|---|---|
| tgagctcttg | ctcttgctcc | tgctccttcg | cctgcttgct | gcgtgagact | gagtaactgc | 60 |
| tagatccttg | gacttccatt | cacagctgcg | actgaacaat | tgttgggaat | tgggctgccg | 120 |
| actgtctcgg | accactgtga | ctatgtcttt | gtcaatggta | aagagatcaa | gggcaagatg | 180 |
| gactctgtgg | tgaacttcac | ctaccagcac | ctgagcgcac | cgctgcatgt | cactgtgtgg | 240 |
| gtgccacggc | ttcccctgca | gatcgaggtc | tctgacacag | aactcagcca | ggttaagggc | 300 |
| tggagagtcc | ccatcgtggc | cagcaagagg | cccactcggg | acagtgagga | ggaagaagag | 360 |
| gaagaacaga | aaggccgggg | ttgtaccctg | cagttccagc | atgccacagt | gcgcgtcctc | 420 |
| acccaatttg | tatcagaggg | tgctgggccc | tggggccagc | tgagccacct | tctcagtcca | 480 |
| gactggcagt | ttgacatcac | ccacctggtg | ggctgacttt | atgaagctgg | agtccccaca | 540 |
| catagccacc | ctgcaggaca | gcagggtctt | ggttgggcgg | aagtcggaa | tgaccaccat | 600 |
| ccaggtgttg | tctcccctgt | ccgactccat | cttggccgag | aagacagtaa | ctgtgctgga | 660 |
| tgacaaagta | tctgtgacag | acttagctgt | ccaggtggtg | gctgggctgt | ctgtcaccct | 720 |
| acacccatc | tcagagaaca | caaggccac | ctcagctgtg | gccatggcag | aagagctgct | 780 |
| acgtgcccca | aaaaggaag | ctataatcag | cacatggctc | cagttcagtg | atggctcagt | 840 |
| gacaccctg | gatatctacg | actccaagga | cttctccttg | actgccatct | ctttggacga | 900 |
| ggctgtcgtg | tccatccccc | aacccctctc | gccttggtgg | cccaccgtgg | tagctgaagg | 960 |
| agaaggccag | ggcccactgc | tccgggtcga | tatgtccatt | gccgaagcct | gtcagaaatc | 1020 |
| caagcgcaag | agtgtgctgg | ctgttggcat | tggccacgtg | ggggtcaagt | ttggatggga | 1080 |
| tgacgctgac | tccagccaga | ctggagaaaa | ggatgaggag | gagatcaaga | accatgccag | 1140 |
| tgaccgtcgg | cagaagattc | aggacctgga | acgcccaggc | caggatgaac | tataccatgg | 1200 |
| caactttcct | ggggatcgtg | aagaaggagc | gctgagtgct | accaccacta | ccaagtccct | 1260 |
| gctggataac | aacgtgggga | agagtggcag | gcgggacggg | gctaggctac | acagcatacc | 1320 |
| cattgacttc | accaatttcc | cggcccatgt | ggacctcccc | aaggccaaga | ccaggggcac | 1380 |
| actggaggag | aatggtctca | tgcagacagc | ccatggcctg | agtgacctag | agattgggat | 1440 |
| gtatgccctc | ctaggtgtct | tctgcctggc | catccttgtc | tttctcatta | actgcgccac | 1500 |
| ctttgccttc | aagtacaggc | acaaacaggt | gcctctggaa | ggccaggcat | ccatgaccca | 1560 |
| ctctcatgac | tgggtctggc | tgggcaatga | ggcggagctc | ttggagaaca | accacttact | 1620 |
| tctcaacggt | ggctcccaaa | agcccacgca | gagccaggtt | cacaggccgc | caggctccgg | 1680 |
| gggacggcag | accagggagc | ccaggcagga | gcctgcaaac | tcacccacct | ccaagatgaa | 1740 |
| gaaggtcaag | tttgccacat | tcaccatccc | acctgaggaa | agctgccccca | cggtgaactc | 1800 |
| catcctcagt | ggggaagatg | atatcaagtg | ggtttgtcaa | gacctggacg | tgggcgcacc | 1860 |
| caaggaactc | agaacctacc | tggagaaatt | ccaagacagt | gtgtagcgct | ctggcctcct | 1920 |
| cgccaacttg | ggacagtagc | ctccttcccg | acctccctca | ccagagtagc | tgaacggaag | 1980 |
| gagctctcag | tggactgagt | gaggaaatct | ggggcccaca | gaataccagg | tagcaggtta | 2040 |
| gaagctggga | agggatgttt | ttatactaaa | gcagtttttt | ttgttttttg | tttttgttt | 2100 |

```
tttgtttttt ttagcagcaa aggatggtag gtttccagaa gtttgagtct ctgactcagc    2160
agcgaggcag agtggatccg aaagagaact gctcagacat gagagagtta ttttatgaat    2220
caaacgacac tgcagacaag ctaccaaaaa tatttgttaa aaaaaatata taaaaagacg    2280
aataaaaaaa acacacaaat gactgtcggt ttatatttct aataaggaa caaaatgtaa     2340 aaatagggct tgctaaaaga aggcctacat tttaattcag tctttatgct tctgaggaca    2400
gtccaggtct gttagccttc tgcccaagga gaggcacatc tgaacaatgg tcacctctta    2460
ggaagaatga gaattttaca ttggattcca ttatctctgt ttgcttccat gtttctttct    2520
aaggtcctaa gcctccattt gattcaatgt catgtttatt tctgaggacc aagtggtaca    2580
ttttcctaaa tgaaatgtaa attatatttc tattcattag atagcttttt ccccctcttt    2640
ttaagaagat catcaacgaa tccagtcttt acgttgtaac atc                      2683
```

<210> SEQ ID NO 21
<211> LENGTH: 5112
<212> TYPE: DNA
<213> ORGANISM: Rattus norvegicus
<220> FEATURE:
<221> NAME/KEY: CDS
<222> LOCATION: (1)..(5112)
<223> OTHER INFORMATION:

<400> SEQUENCE: 21

```
atg cgc aga ctt aac tgt ctc atg act ctg gat ctg ggg ctc tta aca      48
Met Arg Arg Leu Asn Cys Leu Met Thr Leu Asp Leu Gly Leu Leu Thr
 1               5                  10                  15 tta agt cca tcc cgg ggg tcc agc agg caa ttc ttt cag gct gca gac      96
Leu Ser Pro Ser Arg Gly Ser Ser Arg Gln Phe Phe Gln Ala Ala Asp
             20                  25                  30 gct gaa tcc aag tat cca gat gtc cac cat cca cca tct ctt att ctg     144
Ala Glu Ser Lys Tyr Pro Asp Val His His Pro Pro Ser Leu Ile Leu
         35                  40                  45 tgc cag ctg tgg act aac ccc cac ccc gct gtt tcc atc ctt act gcg     192
Cys Gln Leu Trp Thr Asn Pro His Pro Ala Val Ser Ile Leu Thr Ala
     50                  55                  60 ctg aga gtg ata gaa agc cga gga gtc atg gat aat gct cag aga ttc     240
Leu Arg Val Ile Glu Ser Arg Gly Val Met Asp Asn Ala Gln Arg Phe
 65                  70                  75                  80 tct tcc ttg cct cca tac ctg ccg gta agc ttc cgt gtc ctc aga gcc     288
Ser Ser Leu Pro Pro Tyr Leu Pro Val Ser Phe Arg Val Leu Arg Ala
                 85                  90                  95 gaa acc gcc ttt ttc cta agg gag gcc aac cct gac cca ttg cgg aat     336
Glu Thr Ala Phe Phe Leu Arg Glu Ala Asn Pro Asp Pro Leu Arg Asn
            100                 105                 110 gcc agc ctg cag tcc agg acg gag tct ttc ttc act tac aag gcc gag     384
Ala Ser Leu Gln Ser Arg Thr Glu Ser Phe Phe Thr Tyr Lys Ala Glu
        115                 120                 125 cag ccc ccg ata tta aat gtc agc tat ggg ccc tac tct gca gaa aag     432
Gln Pro Pro Ile Leu Asn Val Ser Tyr Gly Pro Tyr Ser Ala Glu Lys
    130                 135                 140 gtc atg cct ctg gac ttg atg ttg aac ccc aac ttt cta ggc cca acc     480
Val Met Pro Leu Asp Leu Met Leu Asn Pro Asn Phe Leu Gly Pro Thr
145                 150                 155                 160 aat aag ttt cct ttt gac tgg agg ctg aag gcc tac atc ctc caa gag     528
Asn Lys Phe Pro Phe Asp Trp Arg Leu Lys Ala Tyr Ile Leu Gln Glu
                165                 170                 175 aaa gtc tac ccg agc cat ccc aaa gtt cag gtg ctc ttc cac atc gtg     576
Lys Val Tyr Pro Ser His Pro Lys Val Gln Val Leu Phe His Ile Val
            180                 185                 190
```

```
ggc cga gac tgg gat aac cac agg gac gag aag cta ccc tgc ctt cgg      624
Gly Arg Asp Trp Asp Asn His Arg Asp Glu Lys Leu Pro Cys Leu Arg
            195                 200                 205 atc ttt gct ttc cga gat acc cgg gag gtt cga ggt agc tgc cgg ctg      672
Ile Phe Ala Phe Arg Asp Thr Arg Glu Val Arg Gly Ser Cys Arg Leu
210                 215                 220 ggc ggg gcc ttg ggg ctg tgc gtg gcc cag ctg gag atg ctg ccg ggc      720
Gly Gly Ala Leu Gly Leu Cys Val Ala Gln Leu Glu Met Leu Pro Gly
225                 230                 235                 240 tgg ttc aat ccc cca ccg gtg gtg tct ggg cgc agg agg ccc acg gag      768
Trp Phe Asn Pro Pro Pro Val Val Ser Gly Arg Arg Arg Pro Thr Glu
                245                 250                 255 cag tca gag ggg agt ccc gtg gaa ctg tat tat tct gta cag cca ggg      816
Gln Ser Glu Gly Ser Pro Val Glu Leu Tyr Tyr Ser Val Gln Pro Gly
            260                 265                 270 gat gag cga ggg gac tgc acc gga ggt gac acc agg aag gac aat gcc      864
Asp Glu Arg Gly Asp Cys Thr Gly Gly Asp Thr Arg Lys Asp Asn Ala
        275                 280                 285 att cgt cca gga aag gac gga cag gag gac agg aca tcc cac ctg cag      912
Ile Arg Pro Gly Lys Asp Gly Gln Glu Asp Arg Thr Ser His Leu Gln
290                 295                 300 aag att ggc tct att agc ctt tat cga acc cag gac agc acc cag ctc      960
Lys Ile Gly Ser Ile Ser Leu Tyr Arg Thr Gln Asp Ser Thr Gln Leu
305                 310                 315                 320 agc gaa ctg cga ctg gat ggg aat gtg gtc atc tgg ctg ccc tcc cag     1008
Ser Glu Leu Arg Leu Asp Gly Asn Val Val Ile Trp Leu Pro Ser Gln
                325                 330                 335 ccc gtc aag caa gga gac ata gtc acc gca tct gtc acc atc gcc aat     1056
Pro Val Lys Gln Gly Asp Ile Val Thr Ala Ser Val Thr Ile Ala Asn
            340                 345                 350 aac tct act gtg gac cat ttc atc cta agc aca ttt ggg ttc ctg gtt     1104
Asn Ser Thr Val Asp His Phe Ile Leu Ser Thr Phe Gly Phe Leu Val
        355                 360                 365 cct gga aaa gtc aat ctt ctg cat ttt gaa ttt ctg tgc ctc ttc acc     1152
Pro Gly Lys Val Asn Leu Leu His Phe Glu Phe Leu Cys Leu Phe Thr
370                 375                 380 cga cac ctc ggc aac gag aga gga cgg cac atc ttg cca agg cgc ctt     1200
Arg His Leu Gly Asn Glu Arg Gly Arg His Ile Leu Pro Arg Arg Leu
385                 390                 395                 400 tgc tgc gat tat cct act gtg ctg ctg gca agg caa gaa cat gaa tgt     1248
Cys Cys Asp Tyr Pro Thr Val Leu Leu Ala Arg Gln Glu His Glu Cys
                405                 410                 415 gct gtg ttc tgt gga gag ttg cag tac agc aaa gca gta gtg act gcc     1296
Ala Val Phe Cys Gly Glu Leu Gln Tyr Ser Lys Ala Val Val Thr Ala
            420                 425                 430 tct gtg tct agc ggc gag tgt aca gaa acc atg ggt att agg ttt cga     1344
Ser Val Ser Ser Gly Glu Cys Thr Glu Thr Met Gly Ile Arg Phe Arg
        435                 440                 445 tgc ttt tcg atg cct gtg cga atg ctc agg gag tgg gga aca atc cgg     1392
Cys Phe Ser Met Pro Val Arg Met Leu Arg Glu Trp Gly Thr Ile Arg
450                 455                 460 cat cct ggg aac ggg tat tgt aga att gcc tat cag tgc ggg tcc ata     1440
His Pro Gly Asn Gly Tyr Cys Arg Ile Ala Tyr Gln Cys Gly Ser Ile
465                 470                 475                 480 caa ttc tgt atc ctt ttg agg agt tct ccc atc agg acc gtt gat tgg     1488
Gln Phe Cys Ile Leu Leu Arg Ser Ser Pro Ile Arg Thr Val Asp Trp
                485                 490                 495 atg gtg gtc ttt gaa agt agg caa gga aca gga agc ttc cgt aat cgc     1536
Met Val Val Phe Glu Ser Arg Gln Gly Thr Gly Ser Phe Arg Asn Arg
            500                 505                 510
```

| | | | | | | | | | | | | | | | |
|---|---|---|---|---|---|---|---|---|---|---|---|---|---|---|---|
| tgg | cca | tca | cct | ttt | cac | aaa | gca | aca | gct | tgg | aag | cag | aca | gca | ggt | 1584 |
| Trp | Pro | Ser | Pro | Phe | His | Lys | Ala | Thr | Ala | Trp | Lys | Gln | Thr | Ala | Gly |
| | 515 | | | | 520 | | | | | 525 | | | | | |

```
tgg cca tca cct ttt cac aaa gca aca gct tgg aag cag aca gca ggt    1584
Trp Pro Ser Pro Phe His Lys Ala Thr Ala Trp Lys Gln Thr Ala Gly
    515                 520                 525 ggg aac tac agt tct gtt tct gac agt gaa gtc agt aag gct aca ctt    1632
Gly Asn Tyr Ser Ser Val Ser Asp Ser Glu Val Ser Lys Ala Thr Leu
530                 535                 540 aga agt tct cct aag cgg gcc ccg gca cac tac ctc tgt gtc ttc cgg    1680
Arg Ser Ser Pro Lys Arg Ala Pro Ala His Tyr Leu Cys Val Phe Arg
545                 550                 555                 560 atc acc gca gtg tgg tcc aat gac tcc agc tgc ggg gtc tct gtt aca    1728
Ile Thr Ala Val Trp Ser Asn Asp Ser Ser Cys Gly Val Ser Val Thr
                565                 570                 575 ata ctg ctc gtt ctt caa ata aat gat ctg tgg ggt gtc acc tgt cct    1776
Ile Leu Leu Val Leu Gln Ile Asn Asp Leu Trp Gly Val Thr Cys Pro
                580                 585                 590 gtg acc ctt cga cca cct gtg gga atc tgg gtc ttc atg ggt cac cgc    1824
Val Thr Leu Arg Pro Pro Val Gly Ile Trp Val Phe Met Gly His Arg
            595                 600                 605 tgt gaa acc agg gtc cga gaa aaa tgt gtc cac act ggt tta agg aag    1872
Cys Glu Thr Arg Val Arg Glu Lys Cys Val His Thr Gly Leu Arg Lys
610                 615                 620 aga gta gag aga aga atc aag ggg gag aaa aga caa ata cag att tgg    1920
Arg Val Glu Arg Arg Ile Lys Gly Glu Lys Arg Gln Ile Gln Ile Trp
625                 630                 635                 640 tca gag tgt aca gag gga cag gtg tgc agg gcg gaa cga tgc aga ctg    1968
Ser Glu Cys Thr Glu Gly Gln Val Cys Arg Ala Glu Arg Cys Arg Leu
                645                 650                 655 gat gac aca gag gag aac agg gag cag ttt ggt cct cta cgg gaa gga    2016
Asp Asp Thr Glu Glu Asn Arg Glu Gln Phe Gly Pro Leu Arg Glu Gly
                660                 665                 670 cag tca gac aga cct act gta tgg aag gga gga aac gtc cag gag ggg    2064
Gln Ser Asp Arg Pro Thr Val Trp Lys Gly Gly Asn Val Gln Glu Gly
            675                 680                 685 cgc cgg cgc aaa caa gtc cct gcc ccc aat gcc caa gcc cag gga aga    2112
Arg Arg Arg Lys Gln Val Pro Ala Pro Asn Ala Gln Ala Gln Gly Arg
690                 695                 700 gcc aag gta aag aag ggg gtg aac att ctg act gca cag acc agt gag    2160
Ala Lys Val Lys Lys Gly Val Asn Ile Leu Thr Ala Gln Thr Ser Glu
705                 710                 715                 720 cct cgg cag tgg gat gtg agg caa gag gtg ggc aac gga ggg aaa cac    2208
Pro Arg Gln Trp Asp Val Arg Gln Glu Val Gly Asn Gly Gly Lys His
                725                 730                 735 acc acc acc tcc gtg tcc tgc cag cgc ctg ggc cct ggg gca cga aat    2256
Thr Thr Thr Ser Val Ser Cys Gln Arg Leu Gly Pro Gly Ala Arg Asn
                740                 745                 750 agg tca act gca tca gca tcc ata gcc tta gca gag aag ctc ccc aga    2304
Arg Ser Thr Ala Ser Ala Ser Ile Ala Leu Ala Glu Lys Leu Pro Arg
            755                 760                 765 cct ctg agg aag act gac agt tat agc tct ccc atg cct gaa gct tcc    2352
Pro Leu Arg Lys Thr Asp Ser Tyr Ser Ser Pro Met Pro Glu Ala Ser
770                 775                 780 ccg ggc atg ggc acg gga gct ggc ctc cct gcc aac cgg gaa gaa gca    2400
Pro Gly Met Gly Thr Gly Ala Gly Leu Pro Ala Asn Arg Glu Glu Ala
785                 790                 795                 800 gac agc cct tat cag gat atg tgt acc aag cat tct tgc ttc aag gac    2448
Asp Ser Pro Tyr Gln Asp Met Cys Thr Lys His Ser Cys Phe Lys Asp
                805                 810                 815 aac ctc agt caa tta tct aag gat tct att ggc aca gac ccc cgc ccc    2496
Asn Leu Ser Gln Leu Ser Lys Asp Ser Ile Gly Thr Asp Pro Arg Pro
                820                 825                 830
```

```
cat ctt cgt gat ttg tgg ctg cct gca gga gcc tct ctg tgg gat gct      2544
His Leu Arg Asp Leu Trp Leu Pro Ala Gly Ala Ser Leu Trp Asp Ala
        835                 840                 845 ggc tgg tgg cag ttg gag aca cgg aga gtg ctt tgc gtc ttg cct ttg      2592
Gly Trp Trp Gln Leu Glu Thr Arg Arg Val Leu Cys Val Leu Pro Leu
850                 855                 860 gct ctt gca gtg tcc ctc ggt ctg gcg gtg ggt aat tgt tta agg cag      2640
Ala Leu Ala Val Ser Leu Gly Leu Ala Val Gly Asn Cys Leu Arg Gln
865                 870                 875                 880 ctg ata cct tca aag ctg gga aat ctg gtc tca gaa cac agg gat gtt      2688
Leu Ile Pro Ser Lys Leu Gly Asn Leu Val Ser Glu His Arg Asp Val
                885                 890                 895 tgc cgt tca ggg att atg ctg tgg ctc tct gga gac ctg aga ggc aga      2736
Cys Arg Ser Gly Ile Met Leu Trp Leu Ser Gly Asp Leu Arg Gly Arg
            900                 905                 910 gac ttc ttc cca aag tca ctt cac cag act cca gct tac cgt tgt gtt      2784
Asp Phe Phe Pro Lys Ser Leu His Gln Thr Pro Ala Tyr Arg Cys Val
        915                 920                 925 cct gtc aga agc agc aat tta ttc aat gag gtc atg cag atg aat ttc      2832
Pro Val Arg Ser Ser Asn Leu Phe Asn Glu Val Met Gln Met Asn Phe
930                 935                 940 gaa atc gcc agc ttc agc agc ctc tca ggg aca cag ccc atc acc tgg      2880
Glu Ile Ala Ser Phe Ser Ser Leu Ser Gly Thr Gln Pro Ile Thr Trp
945                 950                 955                 960 cag gtg gag tac ccg agg aag ggg acc aca gac atc gcc gtg tct gag      2928
Gln Val Glu Tyr Pro Arg Lys Gly Thr Thr Asp Ile Ala Val Ser Glu
                965                 970                 975 atc ttc atc agc cag aag gac ctg gtc gcc atc gtc ccc ctc gct atg      2976
Ile Phe Ile Ser Gln Lys Asp Leu Val Ala Ile Val Pro Leu Ala Met
        980                 985                 990 gac act gaa ctc ctg aac aca gcc atc ctc acg ggg aag acg gtg gcc      3024
Asp Thr Glu Leu Leu Asn Thr Ala Ile Leu Thr Gly Lys Thr Val Ala
            995                 1000                1005 atg ccc gtg agg gtg gtg tcg gtg gag gag aac tgc acc gtg aga          3069
Met Pro Val Arg Val Val Ser Val Glu Glu Asn Cys Thr Val Arg
1010                1015                1020 gac atc tca gag ctg gcg gag tgc aaa gcc atg gat gag aat gtc          3114
Asp Ile Ser Glu Leu Ala Glu Cys Lys Ala Met Asp Glu Asn Val
1025                1030                1035 atc aag gtc tca gac cac tgt gac tat gtc ttt gtc aac ggt aaa          3159
Ile Lys Val Ser Asp His Cys Asp Tyr Val Phe Val Asn Gly Lys
1040                1045                1050 gag atc aag ggc aag gtg gac tcg gtg gtg aat ttc acc tac cag          3204
Glu Ile Lys Gly Lys Val Asp Ser Val Val Asn Phe Thr Tyr Gln
1055                1060                1065 cac ctg agc gca ctg ctg cat gtc acc gtg tgg gtg cca cgg ctt          3249
His Leu Ser Ala Leu Leu His Val Thr Val Trp Val Pro Arg Leu
1070                1075                1080 ccc ctg cag atc gag gtc tct gac acg gaa ctg agc cag att aag          3294
Pro Leu Gln Ile Glu Val Ser Asp Thr Glu Leu Ser Gln Ile Lys
1085                1090                1095 ggc tgg cga gtc ccc atc gtg gcc agc aag agg ccc act cgg gac          3339
Gly Trp Arg Val Pro Ile Val Ala Ser Lys Arg Pro Thr Arg Asp
1100                1105                1110 agt gag gag gaa gaa gag gaa gaa cag aga ggc cgg ggt tgt gcc          3384
Ser Glu Glu Glu Glu Glu Glu Gln Arg Gly Arg Gly Cys Ala
1115                1120                1125 ctg cag ttc cag cat gcc aca gtg cgc gtc ctc acc cag ttt gta          3429
Leu Gln Phe Gln His Ala Thr Val Arg Val Leu Thr Gln Phe Val
1130                1135                1140
```

-continued

| | | |
|---|---|---|
| tca gaa agt gct ggg ccc tgg ggc cag ttg agc cac ctt ctc agt<br>Ser Glu Ser Ala Gly Pro Trp Gly Gln Leu Ser His Leu Leu Ser<br>　　1145　　　　　　　1150　　　　　　　1155 | 3474 | |
| cca gac tgg cag ttt gac atc acc cac ttg gtg gct gac ttc atg<br>Pro Asp Trp Gln Phe Asp Ile Thr His Leu Val Ala Asp Phe Met<br>1160　　　　　　　1165　　　　　　　1170 | 3519 | |
| aag ctg gag tcc cca cac atc gcc acc ttg cag gat agc agg gtc<br>Lys Leu Glu Ser Pro His Ile Ala Thr Leu Gln Asp Ser Arg Val<br>　1175　　　　　　　1180　　　　　　　1185 | 3564 | |
| ttg gtt ggg cgg gaa gtc gga atg acc act atc cag gtg ctg tcg<br>Leu Val Gly Arg Glu Val Gly Met Thr Thr Ile Gln Val Leu Ser<br>　　1190　　　　　　　1195　　　　　　　1200 | 3609 | |
| ccc ctg tcc gac tcc atc ttg gcc gag aag aca gta act gtg ctg<br>Pro Leu Ser Asp Ser Ile Leu Ala Glu Lys Thr Val Thr Val Leu<br>1205　　　　　　　1210　　　　　　　1215 | 3654 | |
| gac gac aaa gtg tcc gtg aca gac ttg gct gtg cag gtg gtg gct<br>Asp Asp Lys Val Ser Val Thr Asp Leu Ala Val Gln Val Val Ala<br>　1220　　　　　　　1225　　　　　　　1230 | 3699 | |
| ggg ctg tcc atc acc ctg cac ccc atc tca gag aac aac aag gcc<br>Gly Leu Ser Ile Thr Leu His Pro Ile Ser Glu Asn Asn Lys Ala<br>　　1235　　　　　　　1240　　　　　　　1245 | 3744 | |
| acc tca gcc gta gcc aca gca gag gaa ctg ctg cgt gcc ccc aaa<br>Thr Ser Ala Val Ala Thr Ala Glu Glu Leu Leu Arg Ala Pro Lys<br>1250　　　　　　　1255　　　　　　　1260 | 3789 | |
| cag gtc ctg atg gcc gtc agt tcc cct ttc ccc tac ttc ccc act<br>Gln Val Leu Met Ala Val Ser Ser Pro Phe Pro Tyr Phe Pro Thr<br>　1265　　　　　　　1270　　　　　　　1275 | 3834 | |
| ctc tcc cac aca cat agc ctg cct cat gct cat cca cca cca gca<br>Leu Ser His Thr His Ser Leu Pro His Ala His Pro Pro Pro Ala<br>　　1280　　　　　　　1285　　　　　　　1290 | 3879 | |
| gga gga atc aac gac cct aaa gga ggt tgt aac ttc atc acc agc<br>Gly Gly Ile Asn Asp Pro Lys Gly Gly Cys Asn Phe Ile Thr Ser<br>1295　　　　　　　1300　　　　　　　1305 | 3924 | |
| ccc ctg cta gga gag gtt cct gga gat aag gca cct ccc atg tgg<br>Pro Leu Leu Gly Glu Val Pro Gly Asp Lys Ala Pro Pro Met Trp<br>　1310　　　　　　　1315　　　　　　　1320 | 3969 | |
| ttc tta cag tct ctc tcc ctg cag gaa gct ata atc agc aca tgg<br>Phe Leu Gln Ser Leu Ser Leu Gln Glu Ala Ile Ile Ser Thr Trp<br>　　1325　　　　　　　1330　　　　　　　1335 | 4014 | |
| ctc cag ttc agt gat ggc tca gtg aca ccc ctg gac atc tat gac<br>Leu Gln Phe Ser Asp Gly Ser Val Thr Pro Leu Asp Ile Tyr Asp<br>1340　　　　　　　1345　　　　　　　1350 | 4059 | |
| acc aag gac ttc tcc ttg act gcc atc tct ttg gac gag gct gtc<br>Thr Lys Asp Phe Ser Leu Thr Ala Ile Ser Leu Asp Glu Ala Val<br>　1355　　　　　　　1360　　　　　　　1365 | 4104 | |
| atc tcc atc cca caa ccc ctc tcg cct tgg tgg ccc act gtg gta<br>Ile Ser Ile Pro Gln Pro Leu Ser Pro Trp Trp Pro Thr Val Val<br>　　1370　　　　　　　1375　　　　　　　1380 | 4149 | |
| gct gaa gga gag ggt cag ggc cca ctg ctc cgg gtc gat atg tcc<br>Ala Glu Gly Glu Gly Gln Gly Pro Leu Leu Arg Val Asp Met Ser<br>1385　　　　　　　1390　　　　　　　1395 | 4194 | |
| atc gct gag gcc tgt cag aaa tcc aag cgc aag agc gtg ctg gct<br>Ile Ala Glu Ala Cys Gln Lys Ser Lys Arg Lys Ser Val Leu Ala<br>　1400　　　　　　　1405　　　　　　　1410 | 4239 | |
| gtt ggc att ggc cac gtg ggg gtc aag ttt ggg tgg gaa gat gct<br>Val Gly Ile Gly His Val Gly Val Lys Phe Gly Trp Glu Asp Ala<br>　　1415　　　　　　　1420　　　　　　　1425 | 4284 | |
| gac tcc ggc cag act gga gaa aag gat gag gag gag atc aag aac<br>Asp Ser Gly Gln Thr Gly Glu Lys Asp Glu Glu Glu Ile Lys Asn<br>1430　　　　　　　1435　　　　　　　1440 | 4329 | |

| | | |
|---|---|---|
| cat gcc agc gat cgt cgg cag aag att cag gac ctg gaa cgc cca<br>His Ala Ser Asp Arg Arg Gln Lys Ile Gln Asp Leu Glu Arg Pro<br>1445                       1450                       1455 | | 4374 |
| ggg cca gat gaa cta cac cat ggc aac ttt ccc cgg gga tcg gaa<br>Gly Pro Asp Glu Leu His His Gly Asn Phe Pro Arg Gly Ser Glu<br>1460                       1465                       1470 | | 4419 |
| ggg ggg acc ggg gcc agg cta cac agc atc ccc ata gac ttc acc<br>Gly Gly Thr Gly Ala Arg Leu His Ser Ile Pro Ile Asp Phe Thr<br>1475                       1480                       1485 | | 4464 |
| aac ttc ccg gcc cat gtg gac ctc ccc aag gcc aag gcc ggg ggc<br>Asn Phe Pro Ala His Val Asp Leu Pro Lys Ala Lys Ala Gly Gly<br>1490                       1495                       1500 | | 4509 |
| aca ctg gag gag aat ggt ctg atg cag aca gcc cat ggc ctg agt<br>Thr Leu Glu Glu Asn Gly Leu Met Gln Thr Ala His Gly Leu Ser<br>1505                       1510                       1515 | | 4554 |
| gat cta gag att ggg atg tat gcc ctg ctg ggt gtt ttc tgc ctg<br>Asp Leu Glu Ile Gly Met Tyr Ala Leu Leu Gly Val Phe Cys Leu<br>1520                       1525                       1530 | | 4599 |
| gcc atc ctt gtc ttt ctc atc aac tgc gcc acc ttt gcc ttc aaa<br>Ala Ile Leu Val Phe Leu Ile Asn Cys Ala Thr Phe Ala Phe Lys<br>1535                       1540                       1545 | | 4644 |
| tac agg cac aaa cag gta cct cta gaa ggt cag gca tcc atg acc<br>Tyr Arg His Lys Gln Val Pro Leu Glu Gly Gln Ala Ser Met Thr<br>1550                       1555                       1560 | | 4689 |
| cac tct cat gac tgg gtc tgg ctg ggc aat gag gcg gag ctc ttg<br>His Ser His Asp Trp Val Trp Leu Gly Asn Glu Ala Glu Leu Leu<br>1565                       1570                       1575 | | 4734 |
| gag aac att ggg gac ttg tcc cca ccc caa gac gag cac acg acc<br>Glu Asn Ile Gly Asp Leu Ser Pro Pro Gln Asp Glu His Thr Thr<br>1580                       1585                       1590 | | 4779 |
| atc ata gac cga ggg ctg gga ggc ttc gag gag aac aac cac ttg<br>Ile Ile Asp Arg Gly Leu Gly Gly Phe Glu Glu Asn Asn His Leu<br>1595                       1600                       1605 | | 4824 |
| ttt ctc aat ggc ggc tcc caa aag cac atg cag agc cag gtc cac<br>Phe Leu Asn Gly Gly Ser Gln Lys His Met Gln Ser Gln Val His<br>1610                       1615                       1620 | | 4869 |
| agg cca cca gat tct ggg ggg tgg cag acc agg gag ccc agg cag<br>Arg Pro Pro Asp Ser Gly Gly Trp Gln Thr Arg Glu Pro Arg Gln<br>1625                       1630                       1635 | | 4914 |
| gaa cct gcg aac tcg ccc acc tcc aag atg aag aag gta aag ttt<br>Glu Pro Ala Asn Ser Pro Thr Ser Lys Met Lys Lys Val Lys Phe<br>1640                       1645                       1650 | | 4959 |
| gcc aca ttc acc atc cca cct gag gac agc tgc ccc aca gtg aac<br>Ala Thr Phe Thr Ile Pro Pro Glu Asp Ser Cys Pro Thr Val Asn<br>1655                       1660                       1665 | | 5004 |
| tcc atc cta agt ggg gaa gac gac gtc aag tgg gtt tgt caa gac<br>Ser Ile Leu Ser Gly Glu Asp Asp Val Lys Trp Val Cys Gln Asp<br>1670                       1675                       1680 | | 5049 |
| cta gac gtg ggc gca ccc aag gag ctc aga acc tac ctg gag aaa<br>Leu Asp Val Gly Ala Pro Lys Glu Leu Arg Thr Tyr Leu Glu Lys<br>1685                       1690                       1695 | | 5094 |
| ttc caa gac agc gtg tag<br>Phe Gln Asp Ser Val<br>        1700 | | 5112 |

```
<210> SEQ ID NO 22
<211> LENGTH: 1703
<212> TYPE: PRT
<213> ORGANISM: Rattus norvegicus

<400> SEQUENCE: 22
```

-continued

```
Met Arg Arg Leu Asn Cys Leu Met Thr Leu Asp Leu Gly Leu Leu Thr
1               5                   10                  15
Leu Ser Pro Ser Arg Gly Ser Ser Arg Gln Phe Phe Gln Ala Ala Asp
            20                  25                  30
Ala Glu Ser Lys Tyr Pro Asp Val His His Pro Pro Ser Leu Ile Leu
        35                  40                  45
Cys Gln Leu Trp Thr Asn Pro His Pro Ala Val Ser Ile Leu Thr Ala
    50                  55                  60
Leu Arg Val Ile Glu Ser Arg Gly Val Met Asp Asn Ala Gln Arg Phe
65                  70                  75                  80
Ser Ser Leu Pro Pro Tyr Leu Pro Val Ser Phe Arg Val Leu Arg Ala
                85                  90                  95
Glu Thr Ala Phe Phe Leu Arg Glu Ala Asn Pro Asp Pro Leu Arg Asn
            100                 105                 110
Ala Ser Leu Gln Ser Arg Thr Glu Ser Phe Phe Thr Tyr Lys Ala Glu
        115                 120                 125
Gln Pro Pro Ile Leu Asn Val Ser Tyr Gly Pro Tyr Ser Ala Glu Lys
    130                 135                 140
Val Met Pro Leu Asp Leu Met Leu Asn Pro Asn Phe Leu Gly Pro Thr
145                 150                 155                 160
Asn Lys Phe Pro Phe Asp Trp Arg Leu Lys Ala Tyr Ile Leu Gln Glu
                165                 170                 175
Lys Val Tyr Pro Ser His Pro Lys Val Gln Val Leu Phe His Ile Val
            180                 185                 190
Gly Arg Asp Trp Asp Asn His Arg Asp Glu Lys Leu Pro Cys Leu Arg
        195                 200                 205
Ile Phe Ala Phe Arg Asp Thr Arg Glu Val Arg Gly Ser Cys Arg Leu
    210                 215                 220
Gly Gly Ala Leu Gly Leu Cys Val Ala Gln Leu Glu Met Leu Pro Gly
225                 230                 235                 240
Trp Phe Asn Pro Pro Val Val Ser Gly Arg Arg Pro Thr Glu
                245                 250                 255
Gln Ser Glu Gly Ser Pro Val Glu Leu Tyr Tyr Ser Val Gln Pro Gly
            260                 265                 270
Asp Glu Arg Gly Asp Cys Thr Gly Gly Asp Thr Arg Lys Asp Asn Ala
        275                 280                 285
Ile Arg Pro Gly Lys Asp Gly Gln Glu Asp Arg Thr Ser His Leu Gln
    290                 295                 300
Lys Ile Gly Ser Ile Ser Leu Tyr Arg Thr Gln Asp Ser Thr Gln Leu
305                 310                 315                 320
Ser Glu Leu Arg Leu Asp Gly Asn Val Val Ile Trp Leu Pro Ser Gln
                325                 330                 335
Pro Val Lys Gln Gly Asp Ile Val Thr Ala Ser Val Thr Ile Ala Asn
            340                 345                 350
Asn Ser Thr Val Asp His Phe Ile Leu Ser Thr Phe Gly Phe Leu Val
        355                 360                 365
Pro Gly Lys Val Asn Leu Leu His Phe Glu Phe Leu Cys Leu Phe Thr
    370                 375                 380
Arg His Leu Gly Asn Glu Arg Gly Arg His Ile Leu Pro Arg Arg Leu
385                 390                 395                 400
Cys Cys Asp Tyr Pro Thr Val Leu Leu Ala Arg Gln Glu His Glu Cys
                405                 410                 415
Ala Val Phe Cys Gly Glu Leu Gln Tyr Ser Lys Ala Val Val Thr Ala
```

```
                    420             425             430
Ser Val Ser Ser Gly Glu Cys Thr Glu Thr Met Gly Ile Arg Phe Arg
        435                 440                 445
Cys Phe Ser Met Pro Val Arg Met Leu Arg Glu Trp Gly Thr Ile Arg
        450                 455                 460
His Pro Gly Asn Gly Tyr Cys Arg Ile Ala Tyr Gln Cys Gly Ser Ile
465                 470                 475                 480
Gln Phe Cys Ile Leu Leu Arg Ser Ser Pro Ile Arg Thr Val Asp Trp
                485                 490                 495
Met Val Val Phe Glu Ser Arg Gln Gly Thr Gly Ser Phe Arg Asn Arg
                500                 505                 510
Trp Pro Ser Pro Phe His Lys Ala Thr Ala Trp Lys Gln Thr Ala Gly
                515                 520                 525
Gly Asn Tyr Ser Ser Val Ser Asp Ser Glu Val Ser Lys Ala Thr Leu
        530                 535                 540
Arg Ser Ser Pro Lys Arg Ala Pro Ala His Tyr Leu Cys Val Phe Arg
545                 550                 555                 560
Ile Thr Ala Val Trp Ser Asn Asp Ser Ser Cys Gly Val Ser Val Thr
                565                 570                 575
Ile Leu Leu Val Leu Gln Ile Asn Asp Leu Trp Gly Val Thr Cys Pro
                580                 585                 590
Val Thr Leu Arg Pro Pro Val Gly Ile Trp Val Phe Met Gly His Arg
                595                 600                 605
Cys Glu Thr Arg Val Arg Glu Lys Cys Val His Thr Gly Leu Arg Lys
        610                 615                 620
Arg Val Glu Arg Arg Ile Lys Gly Glu Lys Arg Gln Ile Gln Ile Trp
625                 630                 635                 640
Ser Glu Cys Thr Glu Gly Gln Val Cys Arg Ala Glu Arg Cys Arg Leu
                645                 650                 655
Asp Asp Thr Glu Glu Asn Arg Glu Gln Phe Gly Pro Leu Arg Glu Gly
                660                 665                 670
Gln Ser Asp Arg Pro Thr Val Trp Lys Gly Gly Asn Val Gln Glu Gly
        675                 680                 685
Arg Arg Arg Lys Gln Val Pro Ala Pro Asn Ala Gln Ala Gln Gly Arg
690                 695                 700
Ala Lys Val Lys Lys Gly Val Asn Ile Leu Thr Ala Gln Thr Ser Glu
705                 710                 715                 720
Pro Arg Gln Trp Asp Val Arg Gln Glu Val Gly Asn Gly Gly Lys His
                725                 730                 735
Thr Thr Thr Ser Val Ser Cys Gln Arg Leu Gly Pro Gly Ala Arg Asn
                740                 745                 750
Arg Ser Thr Ala Ser Ala Ser Ile Ala Leu Ala Glu Lys Leu Pro Arg
        755                 760                 765
Pro Leu Arg Lys Thr Asp Ser Tyr Ser Ser Pro Met Pro Glu Ala Ser
        770                 775                 780
Pro Gly Met Gly Thr Gly Ala Gly Leu Pro Ala Asn Arg Glu Glu Ala
785                 790                 795                 800
Asp Ser Pro Tyr Gln Asp Met Cys Thr Lys His Ser Cys Phe Lys Asp
                805                 810                 815
Asn Leu Ser Gln Leu Ser Lys Asp Ser Ile Gly Thr Asp Pro Arg Pro
                820                 825                 830
His Leu Arg Asp Leu Trp Leu Pro Ala Gly Ala Ser Leu Trp Asp Ala
        835                 840                 845
```

-continued

```
Gly Trp Trp Gln Leu Glu Thr Arg Arg Val Leu Cys Val Leu Pro Leu
850                 855                 860

Ala Leu Ala Val Ser Leu Gly Leu Ala Val Gly Asn Cys Leu Arg Gln
865                 870                 875                 880

Leu Ile Pro Ser Lys Leu Gly Asn Leu Val Ser Glu His Arg Asp Val
                885                 890                 895

Cys Arg Ser Gly Ile Met Leu Trp Leu Ser Gly Asp Leu Arg Gly Arg
            900                 905                 910

Asp Phe Phe Pro Lys Ser Leu His Gln Thr Pro Ala Tyr Arg Cys Val
        915                 920                 925

Pro Val Arg Ser Ser Asn Leu Phe Asn Glu Val Met Gln Met Asn Phe
    930                 935                 940

Glu Ile Ala Ser Phe Ser Ser Leu Ser Gly Thr Gln Pro Ile Thr Trp
945                 950                 955                 960

Gln Val Glu Tyr Pro Arg Lys Gly Thr Thr Asp Ile Ala Val Ser Glu
                965                 970                 975

Ile Phe Ile Ser Gln Lys Asp Leu Val Ala Ile Val Pro Leu Ala Met
                980                 985                 990

Asp Thr Glu Leu Leu Asn Thr Ala Ile Leu Thr Gly Lys Thr Val Ala
            995                 1000                1005

Met Pro Val Arg Val Val Ser Val Glu Glu Asn Cys Thr Val Arg
    1010                1015                1020

Asp Ile Ser Glu Leu Ala Glu Cys Lys Ala Met Asp Glu Asn Val
    1025                1030                1035

Ile Lys Val Ser Asp His Cys Asp Tyr Val Phe Val Asn Gly Lys
    1040                1045                1050

Glu Ile Lys Gly Lys Val Asp Ser Val Val Asn Phe Thr Tyr Gln
    1055                1060                1065

His Leu Ser Ala Leu Leu His Val Thr Val Trp Val Pro Arg Leu
    1070                1075                1080

Pro Leu Gln Ile Glu Val Ser Asp Thr Glu Leu Ser Gln Ile Lys
    1085                1090                1095

Gly Trp Arg Val Pro Ile Val Ala Ser Lys Arg Pro Thr Arg Asp
    1100                1105                1110

Ser Glu Glu Glu Glu Glu Glu Gln Arg Gly Arg Gly Cys Ala
    1115                1120                1125

Leu Gln Phe Gln His Ala Thr Val Arg Val Leu Thr Gln Phe Val
    1130                1135                1140

Ser Glu Ser Ala Gly Pro Trp Gly Gln Leu Ser His Leu Leu Ser
    1145                1150                1155

Pro Asp Trp Gln Phe Asp Ile Thr His Leu Val Ala Asp Phe Met
    1160                1165                1170

Lys Leu Glu Ser Pro His Ile Ala Thr Leu Gln Asp Ser Arg Val
    1175                1180                1185

Leu Val Gly Arg Glu Val Gly Met Thr Thr Ile Gln Val Leu Ser
    1190                1195                1200

Pro Leu Ser Asp Ser Ile Leu Ala Glu Lys Thr Val Thr Val Leu
    1205                1210                1215

Asp Asp Lys Val Ser Val Thr Asp Leu Ala Val Gln Val Val Ala
    1220                1225                1230

Gly Leu Ser Ile Thr Leu His Pro Ile Ser Glu Asn Asn Lys Ala
    1235                1240                1245

Thr Ser Ala Val Ala Thr Ala Glu Glu Leu Leu Arg Ala Pro Lys
    1250                1255                1260
```

```
Gln Val Leu Met Ala Val Ser Ser Pro Phe Pro Tyr Phe Pro Thr
    1265            1270                1275
Leu Ser His Thr His Ser Leu Pro His Ala His Pro Pro Pro Ala
    1280            1285                1290
Gly Gly Ile Asn Asp Pro Lys Gly Gly Cys Asn Phe Ile Thr Ser
    1295            1300                1305
Pro Leu Leu Gly Glu Val Pro Gly Asp Lys Ala Pro Pro Met Trp
    1310            1315                1320
Phe Leu Gln Ser Leu Ser Leu Gln Glu Ala Ile Ile Ser Thr Trp
    1325            1330                1335
Leu Gln Phe Ser Asp Gly Ser Val Thr Pro Leu Asp Ile Tyr Asp
    1340            1345                1350
Thr Lys Asp Phe Ser Leu Thr Ala Ile Ser Leu Asp Glu Ala Val
    1355            1360                1365
Ile Ser Ile Pro Gln Pro Leu Ser Pro Trp Trp Pro Thr Val Val
    1370            1375                1380
Ala Glu Gly Glu Gly Gln Gly Pro Leu Leu Arg Val Asp Met Ser
    1385            1390                1395
Ile Ala Glu Ala Cys Gln Lys Ser Lys Arg Lys Ser Val Leu Ala
    1400            1405                1410
Val Gly Ile Gly His Val Gly Val Lys Phe Gly Trp Glu Asp Ala
    1415            1420                1425
Asp Ser Gly Gln Thr Gly Glu Lys Asp Glu Glu Ile Lys Asn
    1430            1435                1440
His Ala Ser Asp Arg Arg Gln Lys Ile Gln Asp Leu Glu Arg Pro
    1445            1450                1455
Gly Pro Asp Glu Leu His His Gly Asn Phe Pro Arg Gly Ser Glu
    1460            1465                1470
Gly Gly Thr Gly Ala Arg Leu His Ser Ile Pro Ile Asp Phe Thr
    1475            1480                1485
Asn Phe Pro Ala His Val Asp Leu Pro Lys Ala Lys Ala Gly Gly
    1490            1495                1500
Thr Leu Glu Glu Asn Gly Leu Met Gln Thr Ala His Gly Leu Ser
    1505            1510                1515
Asp Leu Glu Ile Gly Met Tyr Ala Leu Leu Gly Val Phe Cys Leu
    1520            1525                1530
Ala Ile Leu Val Phe Leu Ile Asn Cys Ala Thr Phe Ala Phe Lys
    1535            1540                1545
Tyr Arg His Lys Gln Val Pro Leu Glu Gly Gln Ala Ser Met Thr
    1550            1555                1560
His Ser His Asp Trp Val Trp Leu Gly Asn Glu Ala Glu Leu Leu
    1565            1570                1575
Glu Asn Ile Gly Asp Leu Ser Pro Pro Gln Asp Glu His Thr Thr
    1580            1585                1590
Ile Ile Asp Arg Gly Leu Gly Gly Phe Glu Glu Asn Asn His Leu
    1595            1600                1605
Phe Leu Asn Gly Gly Ser Gln Lys His Met Gln Ser Gln Val His
    1610            1615                1620
Arg Pro Pro Asp Ser Gly Gly Trp Gln Thr Arg Glu Pro Arg Gln
    1625            1630                1635
Glu Pro Ala Asn Ser Pro Thr Ser Lys Met Lys Lys Val Lys Phe
    1640            1645                1650
Ala Thr Phe Thr Ile Pro Pro Glu Asp Ser Cys Pro Thr Val Asn
```

| | | | |
|---|---|---|---|
| 1655 | | 1660 | 1665 |

Ser Ile Leu Ser Gly Glu Asp Asp Val Lys Trp Val Cys Gln Asp
1670            1675            1680

Leu Asp Val Gly Ala Pro Lys Glu Leu Arg Thr Tyr Leu Glu Lys
1685            1690            1695

Phe Gln Asp Ser Val
    1700

<210> SEQ ID NO 23
<211> LENGTH: 3908
<212> TYPE: DNA
<213> ORGANISM: Bos taurus
<220> FEATURE:
<221> NAME/KEY: CDS
<222> LOCATION: (1)..(3600)
<223> OTHER INFORMATION:

<400> SEQUENCE: 23

```
atg tgt gtt acc aac ttc tgg aga gtg ggc ttt gat gcc tta cag caa      48
Met Cys Val Thr Asn Phe Trp Arg Val Gly Phe Asp Ala Leu Gln Gln
1               5                   10                  15 cgg atc tca agg ctg gtc cca gac cac cag cag cag cat ccc ctg atc      96
Arg Ile Ser Arg Leu Val Pro Asp His Gln Gln Gln His Pro Leu Ile
            20                  25                  30 tcg gga gag ctt gtt aga aat ggg cat gct cca ccc tgc cct cta gac     144
Ser Gly Glu Leu Val Arg Asn Gly His Ala Pro Pro Cys Pro Leu Asp
        35                  40                  45 tct gga gaa agg gcg gca gtc cta tgt gca gaa gcc atc gtc aga aca     192
Ser Gly Glu Arg Ala Ala Val Leu Cys Ala Glu Ala Ile Val Arg Thr
    50                  55                  60 tct gag cca gcc cag gtc tgt tct gac acc cag agc ctg gaa ttc tgc     240
Ser Glu Pro Ala Gln Val Cys Ser Asp Thr Gln Ser Leu Glu Phe Cys
65                  70                  75                  80 tgt gca cgt gat ctg agg cag cca gcc agc cgg gtg gct ttt agg aag     288
Cys Ala Arg Asp Leu Arg Gln Pro Ala Ser Arg Val Ala Phe Arg Lys
                85                  90                  95 aat ctc aaa aac tca att tcc ggc agc ggc ttt gca gga gag ttc tct     336
Asn Leu Lys Asn Ser Ile Ser Gly Ser Gly Phe Ala Gly Glu Phe Ser
            100                 105                 110 gat gaa cag ctg atg gag gac aca ata tcc cca aca ctg aca gtg atc     384
Asp Glu Gln Leu Met Glu Asp Thr Ile Ser Pro Thr Leu Thr Val Ile
        115                 120                 125 gag ggc cgt ggg ctc aca gac aac atc cag cga ttt tcc tcc ctg ccc     432
Glu Gly Arg Gly Leu Thr Asp Asn Ile Gln Arg Phe Ser Ser Leu Pro
    130                 135                 140 cct tac ctg cct gtg acc tat cag gtg ctc aga gcc gag act tcc ttc     480
Pro Tyr Leu Pro Val Thr Tyr Gln Val Leu Arg Ala Glu Thr Ser Phe
145                 150                 155                 160 ttc ctg aag gaa acc aac cag gac ttg aca cgc aac tcc agc ctg cag     528
Phe Leu Lys Glu Thr Asn Gln Asp Leu Thr Arg Asn Ser Ser Leu Gln
                165                 170                 175 tcc cgg gtc gag tcc ttc ttc ctc tac aaa gcc aga cag ccg cca atc     576
Ser Arg Val Glu Ser Phe Phe Leu Tyr Lys Ala Arg Gln Pro Pro Ile
            180                 185                 190 tta aat gcc agc tat ggg cct ttc tcg gtg caa aag gtc gtg ccc ctg     624
Leu Asn Ala Ser Tyr Gly Pro Phe Ser Val Gln Lys Val Val Pro Leu
        195                 200                 205 gaa ttg atg tcg act tcc aac ttt tta ggt ccc acc gac aaa gtg agt     672
Glu Leu Met Ser Thr Ser Asn Phe Leu Gly Pro Thr Asp Lys Val Ser
    210                 215                 220 ttc aac tgg aag ctg aag gcg cac atc ctg cgg gac aag atc tac ctg     720
```

-continued

```
Phe Asn Trp Lys Leu Lys Ala His Ile Leu Arg Asp Lys Ile Tyr Leu
225                 230                 235                 240 agc cgg ccc cgc gtg cag gtg ctg ttc cac ctg gtg ggc cgg gac tgg     768
Ser Arg Pro Arg Val Gln Val Leu Phe His Leu Val Gly Arg Asp Trp
                245                 250                 255 gac gac ccc agc ccc gcg cag agc ctg ccc tgc ctg cgt gtg ttc gcc     816
Asp Asp Pro Ser Pro Ala Gln Ser Leu Pro Cys Leu Arg Val Phe Ala
                260                 265                 270 ttc cgg gag acc cgg gag gtg cgg ggc agc tgc cgg ctt cgg ggg gcc     864
Phe Arg Glu Thr Arg Glu Val Arg Gly Ser Cys Arg Leu Arg Gly Ala
            275                 280                 285 ctg ggg ctg tgc gtg gca cag ctg gag ctc cca gcc agc tgg ttt ggc     912
Leu Gly Leu Cys Val Ala Gln Leu Glu Leu Pro Ala Ser Trp Phe Gly
        290                 295                 300 acc ccc acc gtg gtg gcc ggg agg aag aag gcg ccg gag ccc ccc gag     960
Thr Pro Thr Val Val Ala Gly Arg Lys Lys Ala Pro Glu Pro Pro Glu
305                 310                 315                 320 ggc agc ccc gtg gag ctc tac tac gcc gtg cag ccc ggg gac gag cgt    1008
Gly Ser Pro Val Glu Leu Tyr Tyr Ala Val Gln Pro Gly Asp Glu Arg
                325                 330                 335 gga gac tgt tcc ggg ggc gat gtc cgc aag ggc aat gcc atc cgc ccc    1056
Gly Asp Cys Ser Gly Gly Asp Val Arg Lys Gly Asn Ala Ile Arg Pro
                340                 345                 350 ggc aag gat gga ctg cag gag agc acg tcc cac ctg cag agg atc agc    1104
Gly Lys Asp Gly Leu Gln Glu Ser Thr Ser His Leu Gln Arg Ile Ser
            355                 360                 365 gcc gtg ggc ctc tac cgc gct cag gac agc gcc cag ctc agc gag ctg    1152
Ala Val Gly Leu Tyr Arg Ala Gln Asp Ser Ala Gln Leu Ser Glu Leu
        370                 375                 380 cgt cta gac ggc aac gtg gcc atc tgg ctg ccc tcc agg ccc gtc aag    1200
Arg Leu Asp Gly Asn Val Ala Ile Trp Leu Pro Ser Arg Pro Val Lys
385                 390                 395                 400 cag gga gat gtg gtc act gcc tat gtc acc gtg gcc agc aat tcc acc    1248
Gln Gly Asp Val Val Thr Ala Tyr Val Thr Val Ala Ser Asn Ser Thr
                405                 410                 415 gtg gac ttc ttc atc ttg aga gcc aag gtg aag aag ggg gtg aac atc    1296
Val Asp Phe Phe Ile Leu Arg Ala Lys Val Lys Lys Gly Val Asn Ile
                420                 425                 430 ctg agc acg cgg acc agc gag cct cgg cag tgg gac gtc aag cag gag    1344
Leu Ser Thr Arg Thr Ser Glu Pro Arg Gln Trp Asp Val Lys Gln Glu
            435                 440                 445 atg ggg aac gga ggc aaa cac gcc acc acc gct gtg gtg tgc cag cga    1392
Met Gly Asn Gly Gly Lys His Ala Thr Thr Ala Val Val Cys Gln Arg
450                 455                 460 ctg gcg cca ggc gcg cgc aac aga agc agc agt tta ttc aat gag gtt    1440
Leu Ala Pro Gly Ala Arg Asn Arg Ser Ser Ser Leu Phe Asn Glu Val
465                 470                 475                 480 gtg cag atg aac ttt gaa atc gcc agc ttc agc agc ctc tca ggg agc    1488
Val Gln Met Asn Phe Glu Ile Ala Ser Phe Ser Ser Leu Ser Gly Ser
                485                 490                 495 cag ccc atc acc tgg caa gtg gaa tac cca cgg agg ggg acc acg gac    1536
Gln Pro Ile Thr Trp Gln Val Glu Tyr Pro Arg Arg Gly Thr Thr Asp
                500                 505                 510 atc gca gtg tca gag atc ttc atc agc cag aag gac ctg gtt ggc atc    1584
Ile Ala Val Ser Glu Ile Phe Ile Ser Gln Lys Asp Leu Val Gly Ile
            515                 520                 525 gtg ccc ttg gcc atg gac act gag atc ctg aac acc gcc atc ctc acg    1632
Val Pro Leu Ala Met Asp Thr Glu Ile Leu Asn Thr Ala Ile Leu Thr
        530                 535                 540 gga aag aca gtt gcc atg ccc atc aag gtg gtc acc gtg gag gag aac    1680
```

-continued

| | | | | | | | | | | | | | | | | |
|---|---|---|---|---|---|---|---|---|---|---|---|---|---|---|---|---|
| Gly | Lys | Thr | Val | Ala | Met | Pro | Ile | Lys | Val | Val | Thr | Val | Glu | Glu | Asn | |
| 545 | | | | | 550 | | | | | 555 | | | | | 560 | |

| agt | atc | gtg | aca | gat | atc | tcg | gag | tcc | gtg | gaa | tgc | aag | tcc | aca | gat | 1728 |
|---|---|---|---|---|---|---|---|---|---|---|---|---|---|---|---|---|
| Ser | Ile | Val | Thr | Asp | Ile | Ser | Glu | Ser | Val | Glu | Cys | Lys | Ser | Thr | Asp | |
| | | | | 565 | | | | | 570 | | | | | 575 | | |

| gag | gag | gtc | atc | aaa | gtg | tcc | gat | cat | tgt | gac | tat | gtc | ttt | gtc | aac | 1776 |
|---|---|---|---|---|---|---|---|---|---|---|---|---|---|---|---|---|
| Glu | Glu | Val | Ile | Lys | Val | Ser | Asp | His | Cys | Asp | Tyr | Val | Phe | Val | Asn | |
| | | | 580 | | | | | 585 | | | | | 590 | | | |

| ggc | aaa | gag | atg | aaa | ggc | aag | gtg | gat | gtg | gtg | gtg | aac | ttc | acg | tac | 1824 |
|---|---|---|---|---|---|---|---|---|---|---|---|---|---|---|---|---|
| Gly | Lys | Glu | Met | Lys | Gly | Lys | Val | Asp | Val | Val | Val | Asn | Phe | Thr | Tyr | |
| | | 595 | | | | | 600 | | | | | 605 | | | | |

| cag | cac | cta | agc | gcc | ccc | ctg | cat | gtc | act | gta | tgg | gtg | ccc | cga | ctg | 1872 |
|---|---|---|---|---|---|---|---|---|---|---|---|---|---|---|---|---|
| Gln | His | Leu | Ser | Ala | Pro | Leu | His | Val | Thr | Val | Trp | Val | Pro | Arg | Leu | |
| 610 | | | | | 615 | | | | | 620 | | | | | | |

| ccc | ctg | cag | atc | gag | gtc | tct | gac | acg | gag | ctg | agc | cag | att | aaa | ggc | 1920 |
|---|---|---|---|---|---|---|---|---|---|---|---|---|---|---|---|---|
| Pro | Leu | Gln | Ile | Glu | Val | Ser | Asp | Thr | Glu | Leu | Ser | Gln | Ile | Lys | Gly | |
| 625 | | | | | 630 | | | | | 635 | | | | | 640 | |

| tgg | agg | gtg | ccc | atc | gtg | gcc | agc | aag | agg | ccc | aca | cga | gac | agc | gag | 1968 |
|---|---|---|---|---|---|---|---|---|---|---|---|---|---|---|---|---|
| Trp | Arg | Val | Pro | Ile | Val | Ala | Ser | Lys | Arg | Pro | Thr | Arg | Asp | Ser | Glu | |
| | | | | 645 | | | | | 650 | | | | | 655 | | |

| gat | gag | gac | gag | gag | gag | cgg | cgg | ggc | cgg | ggc | tgc | gcc | ctc | cag | tac | 2016 |
|---|---|---|---|---|---|---|---|---|---|---|---|---|---|---|---|---|
| Asp | Glu | Asp | Glu | Glu | Glu | Arg | Arg | Gly | Arg | Gly | Cys | Ala | Leu | Gln | Tyr | |
| | | | 660 | | | | | 665 | | | | | 670 | | | |

| cag | cac | gcc | atg | gtg | cgg | gtc | ctc | acc | cag | ttt | gtg | tcc | gag | ggg | gct | 2064 |
|---|---|---|---|---|---|---|---|---|---|---|---|---|---|---|---|---|
| Gln | His | Ala | Met | Val | Arg | Val | Leu | Thr | Gln | Phe | Val | Ser | Glu | Gly | Ala | |
| | | 675 | | | | | 680 | | | | | 685 | | | | |

| ggc | ccc | tgg | ggc | cag | cca | agc | cac | ctg | ctc | agt | cca | gac | tgg | cag | ttc | 2112 |
|---|---|---|---|---|---|---|---|---|---|---|---|---|---|---|---|---|
| Gly | Pro | Trp | Gly | Gln | Pro | Ser | His | Leu | Leu | Ser | Pro | Asp | Trp | Gln | Phe | |
| 690 | | | | | 695 | | | | | 700 | | | | | | |

| gac | atc | acc | cac | ctg | gtt | gct | gac | ttc | atg | aag | ctg | gag | gaa | cca | cat | 2160 |
|---|---|---|---|---|---|---|---|---|---|---|---|---|---|---|---|---|
| Asp | Ile | Thr | His | Leu | Val | Ala | Asp | Phe | Met | Lys | Leu | Glu | Glu | Pro | His | |
| 705 | | | | | 710 | | | | | 715 | | | | | 720 | |

| gtg | gcc | act | ctc | cag | gac | agc | agg | atc | ctg | gtc | ggg | cgg | gaa | gtt | ggc | 2208 |
|---|---|---|---|---|---|---|---|---|---|---|---|---|---|---|---|---|
| Val | Ala | Thr | Leu | Gln | Asp | Ser | Arg | Ile | Leu | Val | Gly | Arg | Glu | Val | Gly | |
| | | | | 725 | | | | | 730 | | | | | 735 | | |

| atg | aca | acc | atc | cag | gtg | ctc | tcc | cct | ctg | tct | gac | tcc | atc | ctg | gct | 2256 |
|---|---|---|---|---|---|---|---|---|---|---|---|---|---|---|---|---|
| Met | Thr | Thr | Ile | Gln | Val | Leu | Ser | Pro | Leu | Ser | Asp | Ser | Ile | Leu | Ala | |
| | | | 740 | | | | | 745 | | | | | 750 | | | |

| gag | aag | acg | gtc | act | gtg | ttg | gac | gac | aaa | gtt | gcg | gtg | tca | gac | ctg | 2304 |
|---|---|---|---|---|---|---|---|---|---|---|---|---|---|---|---|---|
| Glu | Lys | Thr | Val | Thr | Val | Leu | Asp | Asp | Lys | Val | Ala | Val | Ser | Asp | Leu | |
| | | 755 | | | | | 760 | | | | | 765 | | | | |

| gcc | atc | cag | ctc | gtg | gct | ggg | ctg | tct | gtc | acc | ctc | cac | ccc | agc | acg | 2352 |
|---|---|---|---|---|---|---|---|---|---|---|---|---|---|---|---|---|
| Ala | Ile | Gln | Leu | Val | Ala | Gly | Leu | Ser | Val | Thr | Leu | His | Pro | Ser | Thr | |
| 770 | | | | | 775 | | | | | 780 | | | | | | |

| gag | aac | agc | agg | gct | atc | aca | gct | gtg | gcc | aca | gct | gag | gag | ctg | ctg | 2400 |
|---|---|---|---|---|---|---|---|---|---|---|---|---|---|---|---|---|
| Glu | Asn | Ser | Arg | Ala | Ile | Thr | Ala | Val | Ala | Thr | Ala | Glu | Glu | Leu | Leu | |
| 785 | | | | | 790 | | | | | 795 | | | | | 800 | |

| cgg | gcc | cct | aaa | cag | gaa | gct | gtg | gtc | agc | act | tgg | ctc | cag | ttc | agc | 2448 |
|---|---|---|---|---|---|---|---|---|---|---|---|---|---|---|---|---|
| Arg | Ala | Pro | Lys | Gln | Glu | Ala | Val | Val | Ser | Thr | Trp | Leu | Gln | Phe | Ser | |
| | | | | 805 | | | | | 810 | | | | | 815 | | |

| gat | ggc | tct | gtg | acg | ccc | ctg | gac | atc | tac | gac | acc | aag | gac | ttc | acc | 2496 |
|---|---|---|---|---|---|---|---|---|---|---|---|---|---|---|---|---|
| Asp | Gly | Ser | Val | Thr | Pro | Leu | Asp | Ile | Tyr | Asp | Thr | Lys | Asp | Phe | Thr | |
| | | | 820 | | | | | 825 | | | | | 830 | | | |

| ctg | aca | gcc | acc | tcc | ctg | gac | gag | gcc | atc | gtg | tcc | gtc | ccc | cag | ccc | 2544 |
|---|---|---|---|---|---|---|---|---|---|---|---|---|---|---|---|---|
| Leu | Thr | Ala | Thr | Ser | Leu | Asp | Glu | Ala | Ile | Val | Ser | Val | Pro | Gln | Pro | |
| | | 835 | | | | | 840 | | | | | 845 | | | | |

| cgc | tcg | ccc | agg | tgg | ccc | act | gtg | atg | gct | gaa | ggt | gaa | ggc | cag | gga | 2592 |
|---|---|---|---|---|---|---|---|---|---|---|---|---|---|---|---|---|
| Arg | Ser | Pro | Arg | Trp | Pro | Thr | Val | Met | Ala | Glu | Gly | Glu | Gly | Gln | Gly | |
| 850 | | | | | 855 | | | | | 860 | | | | | | |

| ccc | ctg | gtc | cga | gtg | gat | ctg | acc | atc | gca | gag | gcc | tgc | caa | aaa | tcc | 2640 |

```
            Pro Leu Val Arg Val Asp Leu Thr Ile Ala Glu Ala Cys Gln Lys Ser
            865                 870                 875                 880 aaa cgc aag agc gtc ctg gca gtc ggc gtg ggg agc gtc agg gtc aag         2688
Lys Arg Lys Ser Val Leu Ala Val Gly Val Gly Ser Val Arg Val Lys
                    885                 890                 895 ttc ggg cag aac gac gcg aac tcc agc cca ggt gtg gac tac gag gag         2736
Phe Gly Gln Asn Asp Ala Asn Ser Ser Pro Gly Val Asp Tyr Glu Glu
                900                 905                 910 ggt gag atc aag aac cac gcc agc gac cgg cgc cag aag gcc cag gaa         2784
Gly Glu Ile Lys Asn His Ala Ser Asp Arg Arg Gln Lys Ala Gln Glu
            915                 920                 925 gga ccc ttc tat ggc agc tcc tcc gcg gaa cgc gag gaa ggg gtc ctc         2832
Gly Pro Phe Tyr Gly Ser Ser Ser Ala Glu Arg Glu Glu Gly Val Leu
        930                 935                 940 cgg agg ggc aac ccc acg gcc aag tca ctg ctg gac aac aag gtg ggc         2880
Arg Arg Gly Asn Pro Thr Ala Lys Ser Leu Leu Asp Asn Lys Val Gly
945                 950                 955                 960 aag aac agc cgg ctg gac ggg ggc cgg ctg gcg ggg gag ggt cag ctg         2928
Lys Asn Ser Arg Leu Asp Gly Gly Arg Leu Ala Gly Glu Gly Gln Leu
                965                 970                 975 cag acc atc ccc atc gat ttc gcc aac ttc cca gca cag gtg gac ctg         2976
Gln Thr Ile Pro Ile Asp Phe Ala Asn Phe Pro Ala Gln Val Asp Leu
                980                 985                 990 ccc cag gcg ggg agc ggg cgc ggg    gcc agc gac ctg gtg   cag act ccc    3024
Pro Gln Ala Gly Ser Gly Arg Gly    Ala Ser Asp Leu Val   Gln Thr Pro
            995                 1000                1005 cgc  ggc  ctg  agt  gat  ctg  gag    atc  ggc  atg  tat  gcc    ctc  ctg  ggg   3069
Arg  Gly  Leu  Ser  Asp  Leu  Glu    Ile  Gly  Met  Tyr  Ala    Leu  Leu  Gly
     1010                 1015                 1020 gtc  ttc  tgc  ctg  gcc  atc  ctc    gtc  ttc  ctc  atc  aac    tgc  gcc  acc   3114
Val  Phe  Cys  Leu  Ala  Ile  Leu    Val  Phe  Leu  Ile  Asn    Cys  Ala  Thr
     1025                 1030                 1035 ttc  gcc  ctc  aag  tac  agg  cat    aag  cag  gtg  ccc  ctg    gaa  ggc  cag   3159
Phe  Ala  Leu  Lys  Tyr  Arg  His    Lys  Gln  Val  Pro  Leu    Glu  Gly  Gln
     1040                 1045                 1050 gcc  tcc  gtg  acc  cac  tcg  cat    gac  tgg  gtg  tgg  ctg    ggc  aac  gag   3204
Ala  Ser  Val  Thr  His  Ser  His    Asp  Trp  Val  Trp  Leu    Gly  Asn  Glu
     1055                 1060                 1065 gcg  gag  ctc  ctg  gag  aac  gtg    ggc  gac  agc  tct  ccg    ccg  cag  gac   3249
Ala  Glu  Leu  Leu  Glu  Asn  Val    Gly  Asp  Ser  Ser  Pro    Pro  Gln  Asp
     1070                 1075                 1080 gag  cac  acg  acc  atc  ata  gac    cgc  ggg  cca  ggg  ggc    ttc  gag  gag   3294
Glu  His  Thr  Thr  Ile  Ile  Asp    Arg  Gly  Pro  Gly  Gly    Phe  Glu  Glu
     1085                 1090                 1095 agc  aac  cgc  ctc  ctg  ctc  aac    gga  ggt  tcc  caa  aag    cag  ggg  cag   3339
Ser  Asn  Arg  Leu  Leu  Leu  Asn    Gly  Gly  Ser  Gln  Lys    Gln  Gly  Gln
     1100                 1105                 1110 agc  cag  atc  ccc  agg  ccg  gcc    gac  tct  ggg  ggc  aag    cag  ggc  agg   3384
Ser  Gln  Ile  Pro  Arg  Pro  Ala    Asp  Ser  Gly  Gly  Lys    Gln  Gly  Arg
     1115                 1120                 1125 gac  cag  aaa  cac  gag  ccc  ctg    cac  tcg  ccc  acc  tcc    aag  agg  aaa   3429
Asp  Gln  Lys  His  Glu  Pro  Leu    His  Ser  Pro  Thr  Ser    Lys  Arg  Lys
     1130                 1135                 1140 aag  gtg  aaa  ttc  acc  acc  ttc    acc  acc  atc  ccc  gcc    gac  gac  ggc   3474
Lys  Val  Lys  Phe  Thr  Thr  Phe    Thr  Thr  Ile  Pro  Ala    Asp  Asp  Gly
     1145                 1150                 1155 tgc  ccc  acc  gtc  aac  tcc  att    ctg  ggc  ggg  aca  gag    gag  gac  atc   3519
Cys  Pro  Thr  Val  Asn  Ser  Ile    Leu  Gly  Gly  Thr  Glu    Glu  Asp  Ile
     1160                 1165                 1170 aaa  tgg  gtg  tgc  cag  gac  gtg    ggc  gtg  ggt  gcc  ccc    aaa  gaa  ctc   3564
```

```
Lys Trp Val Cys Gln Asp Val Gly Val Gly Ala Pro Lys Glu Leu
1175                1180                1185 aga gac tat ctg gag aag ttc aag gac aac gtg tag gcccctctgg       3610
Arg Asp Tyr Leu Glu Lys Phe Lys Asp Asn Val
        1190            1195 tcgaaggacc agcgcctgga caccctcctt cagctccacg gtagatctgg ggctcaacag 3670
ggactctatg gggcccatct ttgaaactat tcatagttgg aagttctgaa gccggaaagg 3730
gacagttttg tgatcagagg ttgatgatgg cagactttct caagtcggaa ggaaaaaact 3790
ctgggaacgg agctgatgga gacattttaa ctgcgcaagg ccaaattagg aaggttattt 3850
tatgagtcaa aatataaccc agacaagcta ccaaaaagta tttgttaaaa aaaaaaa    3908

<210> SEQ ID NO 24
<211> LENGTH: 1199
<212> TYPE: PRT
<213> ORGANISM: Bos taurus

<400> SEQUENCE: 24

Met Cys Val Thr Asn Phe Trp Arg Val Gly Phe Asp Ala Leu Gln Gln
1               5                   10                  15

Arg Ile Ser Arg Leu Val Pro Asp His Gln Gln His Pro Leu Ile
            20                  25                  30

Ser Gly Glu Leu Val Arg Asn Gly His Ala Pro Pro Cys Pro Leu Asp
        35                  40                  45

Ser Gly Glu Arg Ala Ala Val Leu Cys Ala Glu Ala Ile Val Arg Thr
    50                  55                  60

Ser Glu Pro Ala Gln Val Cys Ser Asp Thr Gln Ser Leu Glu Phe Cys
65                  70                  75                  80

Cys Ala Arg Asp Leu Arg Gln Pro Ala Ser Arg Val Ala Phe Arg Lys
                85                  90                  95

Asn Leu Lys Asn Ser Ile Ser Gly Ser Gly Phe Ala Gly Glu Phe Ser
            100                 105                 110

Asp Glu Gln Leu Met Glu Asp Thr Ile Ser Pro Thr Leu Thr Val Ile
        115                 120                 125

Glu Gly Arg Gly Leu Thr Asp Asn Ile Gln Arg Phe Ser Ser Leu Pro
    130                 135                 140

Pro Tyr Leu Pro Val Thr Tyr Gln Val Leu Arg Ala Glu Thr Ser Phe
145                 150                 155                 160

Phe Leu Lys Glu Thr Asn Gln Asp Leu Thr Arg Asn Ser Ser Leu Gln
                165                 170                 175

Ser Arg Val Glu Ser Phe Phe Leu Tyr Lys Ala Arg Gln Pro Pro Ile
            180                 185                 190

Leu Asn Ala Ser Tyr Gly Pro Phe Ser Val Gln Lys Val Val Pro Leu
        195                 200                 205

Glu Leu Met Ser Thr Ser Asn Phe Leu Gly Pro Thr Asp Lys Val Ser
    210                 215                 220

Phe Asn Trp Lys Leu Lys Ala His Ile Leu Arg Asp Lys Ile Tyr Leu
225                 230                 235                 240

Ser Arg Pro Arg Val Gln Val Leu Phe His Leu Val Gly Arg Asp Trp
                245                 250                 255

Asp Asp Pro Ser Pro Ala Gln Ser Leu Pro Cys Leu Arg Val Phe Ala
            260                 265                 270

Phe Arg Glu Thr Arg Glu Val Arg Gly Ser Cys Arg Leu Arg Gly Ala
        275                 280                 285

Leu Gly Leu Cys Val Ala Gln Leu Glu Leu Pro Ala Ser Trp Phe Gly
```

```
                290                 295                 300
Thr Pro Thr Val Val Ala Gly Arg Lys Lys Ala Pro Glu Pro Glu
305                 310                 315                 320

Gly Ser Pro Val Glu Leu Tyr Tyr Ala Val Gln Pro Gly Asp Glu Arg
                325                 330                 335

Gly Asp Cys Ser Gly Gly Asp Val Arg Lys Gly Asn Ala Ile Arg Pro
                340                 345                 350

Gly Lys Asp Gly Leu Gln Glu Ser Thr Ser His Leu Gln Arg Ile Ser
                355                 360                 365

Ala Val Gly Leu Tyr Arg Ala Gln Asp Ser Ala Gln Leu Ser Glu Leu
                370                 375                 380

Arg Leu Asp Gly Asn Val Ala Ile Trp Leu Pro Ser Arg Pro Val Lys
385                 390                 395                 400

Gln Gly Asp Val Val Thr Ala Tyr Val Thr Val Ala Ser Asn Ser Thr
                405                 410                 415

Val Asp Phe Phe Ile Leu Arg Ala Lys Val Lys Lys Gly Val Asn Ile
                420                 425                 430

Leu Ser Thr Arg Thr Ser Glu Pro Arg Gln Trp Asp Val Lys Gln Glu
                435                 440                 445

Met Gly Asn Gly Gly Lys His Ala Thr Thr Ala Val Val Cys Gln Arg
                450                 455                 460

Leu Ala Pro Gly Ala Arg Asn Arg Ser Ser Leu Phe Asn Glu Val
465                 470                 475                 480

Val Gln Met Asn Phe Glu Ile Ala Ser Phe Ser Ser Leu Ser Gly Ser
                485                 490                 495

Gln Pro Ile Thr Trp Gln Val Glu Tyr Pro Arg Arg Gly Thr Thr Asp
                500                 505                 510

Ile Ala Val Ser Glu Ile Phe Ile Ser Gln Lys Asp Leu Val Gly Ile
                515                 520                 525

Val Pro Leu Ala Met Asp Thr Glu Ile Leu Asn Thr Ala Ile Leu Thr
                530                 535                 540

Gly Lys Thr Val Ala Met Pro Ile Lys Val Val Thr Val Glu Glu Asn
545                 550                 555                 560

Ser Ile Val Thr Asp Ile Ser Glu Ser Val Glu Cys Lys Ser Thr Asp
                565                 570                 575

Glu Glu Val Ile Lys Val Ser Asp His Cys Asp Tyr Val Phe Val Asn
                580                 585                 590

Gly Lys Glu Met Lys Gly Lys Val Asp Val Val Asn Phe Thr Tyr
                595                 600                 605

Gln His Leu Ser Ala Pro Leu His Val Thr Val Trp Val Pro Arg Leu
                610                 615                 620

Pro Leu Gln Ile Glu Val Ser Asp Thr Glu Leu Ser Gln Ile Lys Gly
625                 630                 635                 640

Trp Arg Val Pro Ile Val Ala Ser Lys Arg Pro Thr Arg Asp Ser Glu
                645                 650                 655

Asp Glu Asp Glu Glu Arg Arg Gly Arg Gly Cys Ala Leu Gln Tyr
                660                 665                 670

Gln His Ala Met Val Arg Val Leu Thr Gln Phe Val Ser Glu Gly Ala
                675                 680                 685

Gly Pro Trp Gly Gln Pro Ser His Leu Leu Ser Pro Asp Trp Gln Phe
                690                 695                 700

Asp Ile Thr His Leu Val Ala Asp Phe Met Lys Leu Glu Glu Pro His
705                 710                 715                 720
```

```
Val Ala Thr Leu Gln Asp Ser Arg Ile Leu Val Gly Arg Glu Val Gly
                725                 730                 735

Met Thr Thr Ile Gln Val Leu Ser Pro Leu Ser Asp Ser Ile Leu Ala
            740                 745                 750

Glu Lys Thr Val Thr Val Leu Asp Asp Lys Val Ala Val Ser Asp Leu
        755                 760                 765

Ala Ile Gln Leu Val Ala Gly Leu Ser Val Thr Leu His Pro Ser Thr
    770                 775                 780

Glu Asn Ser Arg Ala Ile Thr Ala Val Ala Thr Ala Glu Glu Leu Leu
785                 790                 795                 800

Arg Ala Pro Lys Gln Glu Ala Val Val Ser Thr Trp Leu Gln Phe Ser
            805                 810                 815

Asp Gly Ser Val Thr Pro Leu Asp Ile Tyr Asp Thr Lys Asp Phe Thr
        820                 825                 830

Leu Thr Ala Thr Ser Leu Asp Glu Ala Ile Val Ser Val Pro Gln Pro
    835                 840                 845

Arg Ser Pro Arg Trp Pro Thr Val Met Ala Glu Gly Glu Gly Gln Gly
850                 855                 860

Pro Leu Val Arg Val Asp Leu Thr Ile Ala Glu Ala Cys Gln Lys Ser
865                 870                 875                 880

Lys Arg Lys Ser Val Leu Ala Val Gly Val Gly Ser Val Arg Val Lys
            885                 890                 895

Phe Gly Gln Asn Asp Ala Asn Ser Ser Pro Gly Val Asp Tyr Glu Glu
        900                 905                 910

Gly Glu Ile Lys Asn His Ala Ser Asp Arg Arg Gln Lys Ala Gln Glu
    915                 920                 925

Gly Pro Phe Tyr Gly Ser Ser Ser Ala Glu Arg Glu Glu Gly Val Leu
930                 935                 940

Arg Arg Gly Asn Pro Thr Ala Lys Ser Leu Leu Asp Asn Lys Val Gly
945                 950                 955                 960

Lys Asn Ser Arg Leu Asp Gly Gly Arg Leu Ala Gly Glu Gly Gln Leu
            965                 970                 975

Gln Thr Ile Pro Ile Asp Phe Ala Asn Phe Pro Ala Gly Val Asp Leu
        980                 985                 990

Pro Gln Ala Gly Ser Gly Arg Gly Ala Ser Asp Leu Val Gln Thr Pro
    995                 1000                1005

Arg Gly Leu Ser Asp Leu Glu Ile Gly Met Tyr Ala Leu Leu Gly
    1010                1015                1020

Val Phe Cys Leu Ala Ile Leu Val Phe Leu Ile Asn Cys Ala Thr
    1025                1030                1035

Phe Ala Leu Lys Tyr Arg His Lys Gln Val Pro Leu Glu Gly Gln
    1040                1045                1050

Ala Ser Val Thr His Ser His Asp Trp Val Trp Leu Gly Asn Glu
    1055                1060                1065

Ala Glu Leu Leu Glu Asn Val Gly Asp Ser Ser Pro Pro Gln Asp
    1070                1075                1080

Glu His Thr Thr Ile Ile Asp Arg Gly Pro Gly Gly Phe Glu Glu
    1085                1090                1095

Ser Asn Arg Leu Leu Leu Asn Gly Gly Ser Gln Lys Gln Gly Gln
    1100                1105                1110

Ser Gln Ile Pro Arg Pro Ala Asp Ser Gly Gly Lys Gln Gly Arg
    1115                1120                1125

Asp Gln Lys His Glu Pro Leu His Ser Pro Thr Ser Lys Arg Lys
    1130                1135                1140
```

```
Lys Val Lys Phe Thr Thr Phe Thr Thr Ile Pro Ala Asp Asp Gly
    1145                1150                1155

Cys Pro Thr Val Asn Ser Ile Leu Gly Gly Thr Glu Glu Asp Ile
    1160                1165                1170

Lys Trp Val Cys Gln Asp Val Gly Val Gly Ala Pro Lys Glu Leu
    1175                1180                1185

Arg Asp Tyr Leu Glu Lys Phe Lys Asp Asn Val
    1190                1195

<210> SEQ ID NO 25
<211> LENGTH: 3527
<212> TYPE: DNA
<213> ORGANISM: Canis familiaris
<220> FEATURE:
<221> NAME/KEY: CDS
<222> LOCATION: (1)..(3270)
<223> OTHER INFORMATION:

<400> SEQUENCE: 25
```

| | | | | | | | | | | | | | | | | |
|---|---|---|---|---|---|---|---|---|---|---|---|---|---|---|---|---|
| atg | gcc | acc | atg | cta | ttc | gcc | aag | ctc | aac | ttc | agg | aac | ttg | atc | gag | 48 |
| Met | Ala | Thr | Met | Leu | Phe | Ala | Lys | Leu | Asn | Phe | Arg | Asn | Leu | Ile | Glu | |
| 1 | | | | 5 | | | | | 10 | | | | | 15 | | |
| ggc | cgg | ggg | atc | aca | gat | aat | gtg | cca | cgg | ttc | tct | tct | ctg | cca | ccc | 96 |
| Gly | Arg | Gly | Ile | Thr | Asp | Asn | Val | Pro | Arg | Phe | Ser | Ser | Leu | Pro | Pro | |
| | | | 20 | | | | | 25 | | | | | 30 | | | |
| ttc | ctg | cct | gtg | agc | tac | cac | atc | ctt | gga | gca | gag | acc | tcc | ttc | ttc | 144 |
| Phe | Leu | Pro | Val | Ser | Tyr | His | Ile | Leu | Gly | Ala | Glu | Thr | Ser | Phe | Phe | |
| | | 35 | | | | | 40 | | | | | 45 | | | | |
| ctg | aag | gag | gcc | aac | cag | gac | gtc | ctg | cgc | aac | tcc | agc | ctg | cac | acc | 192 |
| Leu | Lys | Glu | Ala | Asn | Gln | Asp | Val | Leu | Arg | Asn | Ser | Ser | Leu | His | Thr | |
| | 50 | | | | | 55 | | | | | 60 | | | | | |
| agg | gtg | gag | tcc | ttc | ttc | acc | tac | aag | gcc | aac | cgg | ccc | cca | gtg | ctc | 240 |
| Arg | Val | Glu | Ser | Phe | Phe | Thr | Tyr | Lys | Ala | Asn | Arg | Pro | Pro | Val | Leu | |
| 65 | | | | | 70 | | | | | 75 | | | | | 80 | |
| aac | gcc | agc | tac | ggg | ccc | ttc | tcc | atc | gag | cag | gtg | gtg | cct | cag | gac | 288 |
| Asn | Ala | Ser | Tyr | Gly | Pro | Phe | Ser | Ile | Glu | Gln | Val | Val | Pro | Gln | Asp | |
| | | | | 85 | | | | | 90 | | | | | 95 | | |
| ctc | ctg | ctg | ccc | tcc | agc | ccc | ttc | gga | gcc | acc | agc | aag | ctc | tcc | ctc | 336 |
| Leu | Leu | Leu | Pro | Ser | Ser | Pro | Phe | Gly | Ala | Thr | Ser | Lys | Leu | Ser | Leu | |
| | | | 100 | | | | | 105 | | | | | 110 | | | |
| aac | tgg | agg | ctg | agg | gcg | cac | atc | ctg | cgg | gac | aag | gtg | tac | ctg | agc | 384 |
| Asn | Trp | Arg | Leu | Arg | Ala | His | Ile | Leu | Arg | Asp | Lys | Val | Tyr | Leu | Ser | |
| | | 115 | | | | | 120 | | | | | 125 | | | | |
| cgg | ccc | cgg | gtg | cag | gtg | ctc | ttc | cac | ctg | ctg | ggc | cgg | gac | tgg | gcg | 432 |
| Arg | Pro | Arg | Val | Gln | Val | Leu | Phe | His | Leu | Leu | Gly | Arg | Asp | Trp | Ala | |
| | 130 | | | | | 135 | | | | | 140 | | | | | |
| gca | cag | agc | cct | ggc | gag | cgg | ctg | ccc | tgc | ctg | cgg | ctg | ttc | gcc | ttc | 480 |
| Ala | Gln | Ser | Pro | Gly | Glu | Arg | Leu | Pro | Cys | Leu | Arg | Leu | Phe | Ala | Phe | |
| 145 | | | | | 150 | | | | | 155 | | | | | 160 | |
| cgg | gag | acc | cgg | gag | gtg | cgg | gcc | ggc | tgc | cgg | ctg | cag | ggc | gcc | ctg | 528 |
| Arg | Glu | Thr | Arg | Glu | Val | Arg | Ala | Gly | Cys | Arg | Leu | Gln | Gly | Ala | Leu | |
| | | | | 165 | | | | | 170 | | | | | 175 | | |
| ggg | ctg | tgc | gtg | gcc | gaa | ctg | gag | ctg | ctg | gcc | gcc | tgg | ttc | ggg | ccc | 576 |
| Gly | Leu | Cys | Val | Ala | Glu | Leu | Glu | Leu | Leu | Ala | Ala | Trp | Phe | Gly | Pro | |
| | | | 180 | | | | | 185 | | | | | 190 | | | |
| ccc | acc | gtg | gtg | gcc | ggg | agg | aag | cgg | gcg | cct | ggg | ccg | ccc | gag | ggg | 624 |
| Pro | Thr | Val | Val | Ala | Gly | Arg | Lys | Arg | Ala | Pro | Gly | Pro | Pro | Glu | Gly | |
| | | 195 | | | | | 200 | | | | | 205 | | | | |
| agc | ccc | gtg | gag | ctc | tac | tac | tcc | gtg | cag | ccg | ggg | gat | gcg | cgc | ggg | 672 |
| Ser | Pro | Val | Glu | Leu | Tyr | Tyr | Ser | Val | Gln | Pro | Gly | Asp | Ala | Arg | Gly | |
| | 210 | | | | | 215 | | | | | 220 | | | | | |

```
gac tgt gcg ggc ggc ggc ggc gac gtc agg aag ggc aac gcc atc cgg       720
Asp Cys Ala Gly Gly Gly Gly Asp Val Arg Lys Gly Asn Ala Ile Arg
225                 230                 235                 240 cct ggg aag gac ggg ctg gat gag gcc gtg ccc cac ctg cag agg atc       768
Pro Gly Lys Asp Gly Leu Asp Glu Ala Val Pro His Leu Gln Arg Ile
                245                 250                 255 ggc gcc gtc agc ctc tac cgg gcc cag gac agc acc cag ctc agc gag       816
Gly Ala Val Ser Leu Tyr Arg Ala Gln Asp Ser Thr Gln Leu Ser Glu
            260                 265                 270 ctg cgt ttg gac agc aac gtg gtc atc tgg ctg ccc tcc cgg ccc gtc       864
Leu Arg Leu Asp Ser Asn Val Val Ile Trp Leu Pro Ser Arg Pro Val
        275                 280                 285 aag caa gga gat gtg gtc acc gcc tac gtc acc atc gcc agc aac tcc       912
Lys Gln Gly Asp Val Val Thr Ala Tyr Val Thr Ile Ala Ser Asn Ser
    290                 295                 300 act gtg gac ctt ttc atc ctg aga gcc aag gtg aag aag ggg gtg aac       960
Thr Val Asp Leu Phe Ile Leu Arg Ala Lys Val Lys Lys Gly Val Asn
305                 310                 315                 320 atc ctg ggc act cag acc agc gag ccc cgg cag tgg gat gtc aaa cag      1008
Ile Leu Gly Thr Gln Thr Ser Glu Pro Arg Gln Trp Asp Val Lys Gln
                325                 330                 335 gag atg ggg aat ggc gga aag cat gct acc acc acc gtg ctg tgc cag      1056
Glu Met Gly Asn Gly Gly Lys His Ala Thr Thr Thr Val Leu Cys Gln
            340                 345                 350 cgc ctg ggg tcc agc aca cgt aac aga agc agc agc ctg ttc agt gag      1104
Arg Leu Gly Ser Ser Thr Arg Asn Arg Ser Ser Ser Leu Phe Ser Glu
        355                 360                 365 gtt atg cag atg aac ttt gaa ata gcc agc ttc agc agc ctc tcg ggg      1152
Val Met Gln Met Asn Phe Glu Ile Ala Ser Phe Ser Ser Leu Ser Gly
    370                 375                 380 act cag ccc atc gcc tgg cag gtg gaa tat cca cgg aga gcg acc acc      1200
Thr Gln Pro Ile Ala Trp Gln Val Glu Tyr Pro Arg Arg Ala Thr Thr
385                 390                 395                 400 gac acc gct gtg tcc gag atc ttc atc agc cag aag gac ctg gct ggc      1248
Asp Thr Ala Val Ser Glu Ile Phe Ile Ser Gln Lys Asp Leu Ala Gly
                405                 410                 415 atc gtt cct cta gcc acg gac acg gaa att ctg aac act gcc atc ctc      1296
Ile Val Pro Leu Ala Thr Asp Thr Glu Ile Leu Asn Thr Ala Ile Leu
            420                 425                 430 acg gga aag aca gtg gtc ctg ccc atc aag gtg gtc tct gtg gag gag      1344
Thr Gly Lys Thr Val Val Leu Pro Ile Lys Val Val Ser Val Glu Glu
        435                 440                 445 aac agt gcc gtg atg gat atc tcc gag tcg gtg gag tgc aag tcc aca      1392
Asn Ser Ala Val Met Asp Ile Ser Glu Ser Val Glu Cys Lys Ser Thr
    450                 455                 460 gac gag gat gtc atc aag gtg tct gaa aga tgt gac tac gtc ttt gtc      1440
Asp Glu Asp Val Ile Lys Val Ser Glu Arg Cys Asp Tyr Val Phe Val
465                 470                 475                 480 aat ggc aaa gag atg aag ggc aag gtg gat gcg gtg gtg aac ttc acc      1488
Asn Gly Lys Glu Met Lys Gly Lys Val Asp Ala Val Val Asn Phe Thr
                485                 490                 495 tac cag cac ctg agt gcc tcc ctg cac atc acc gtg tgg gtg ccc cgg      1536
Tyr Gln His Leu Ser Ala Ser Leu His Ile Thr Val Trp Val Pro Arg
            500                 505                 510 cta ccc cta cag att gag gtc tct gac aca gag ctg agc cag atc aaa      1584
Leu Pro Leu Gln Ile Glu Val Ser Asp Thr Glu Leu Ser Gln Ile Lys
        515                 520                 525 ggc tgg agg gtc ccc att gtg tcc agt aag agg ccc act cga gag agc      1632
Gly Trp Arg Val Pro Ile Val Ser Ser Lys Arg Pro Thr Arg Glu Ser
    530                 535                 540
```

```
gag gat gaa gac gag gag gag cgg cgg ggc cga ggc tgt gcc ctg cag    1680
Glu Asp Glu Asp Glu Glu Glu Arg Arg Gly Arg Gly Cys Ala Leu Gln
545                 550                 555                 560 tac cag cac gcc acg gtg cgg gtc ctc acc cag ttc gtg tcg gag ggc    1728
Tyr Gln His Ala Thr Val Arg Val Leu Thr Gln Phe Val Ser Glu Gly
                565                 570                 575 gct ggc ccg tgg ggc cag ccg agc cac ctt ctc agt ccc gac tgg caa    1776
Ala Gly Pro Trp Gly Gln Pro Ser His Leu Leu Ser Pro Asp Trp Gln
            580                 585                 590 gtc gac atc acc cac ctg gtt gca gac ttc atg aag ctg gag gaa cct    1824
Val Asp Ile Thr His Leu Val Ala Asp Phe Met Lys Leu Glu Glu Pro
        595                 600                 605 cac gtg gcc aca ctc cag gac agc agg atc ctg gtc ggg cgg gag gtt    1872
His Val Ala Thr Leu Gln Asp Ser Arg Ile Leu Val Gly Arg Glu Val
    610                 615                 620 ggg atg acc acc atc cag gtg ttg tct cca ctc tct gac tcc atc ctg    1920
Gly Met Thr Thr Ile Gln Val Leu Ser Pro Leu Ser Asp Ser Ile Leu
625                 630                 635                 640 gca gag aag acg gtg acc gtg tta gat gac aag gta tcg gtg aca gac    1968
Ala Glu Lys Thr Val Thr Val Leu Asp Asp Lys Val Ser Val Thr Asp
                645                 650                 655 ttg gcc atc cag ctc gtg gct ggg ctg tct gtc acc ctc cac ccc agc    2016
Leu Ala Ile Gln Leu Val Ala Gly Leu Ser Val Thr Leu His Pro Ser
            660                 665                 670 acg gag aac agc aag gcc atc act gct gtg gcc aca gct gag gag ctg    2064
Thr Glu Asn Ser Lys Ala Ile Thr Ala Val Ala Thr Ala Glu Glu Leu
        675                 680                 685 ctg cgg acc ccc aaa cag gag gcc gtg gtc agc act tgg ctc cag ctc    2112
Leu Arg Thr Pro Lys Gln Glu Ala Val Val Ser Thr Trp Leu Gln Leu
    690                 695                 700 agc gac ggc tcc gcc acc ccc ctg gac atc tac gac acc aag gac ttc    2160
Ser Asp Gly Ser Ala Thr Pro Leu Asp Ile Tyr Asp Thr Lys Asp Phe
705                 710                 715                 720 acc ctg acc gcc acc tcc ctg aac gag gcc gtc gtg tcc acc ccc cag    2208
Thr Leu Thr Ala Thr Ser Leu Asn Glu Ala Val Val Ser Thr Pro Gln
                725                 730                 735 gcc cgc tct ccc aga tgg ccg gtg gtg atg gcc gaa ggg gaa ggc cag    2256
Ala Arg Ser Pro Arg Trp Pro Val Val Met Ala Glu Gly Glu Gly Gln
            740                 745                 750 ggg ccg ctg gtg cga gtg gac atg tcc atc gcc gag gcc tgc cag aag    2304
Gly Pro Leu Val Arg Val Asp Met Ser Ile Ala Glu Ala Cys Gln Lys
        755                 760                 765 tcc aag cgc aag agc gtc ctg gcc gtg ggt gtg ggc agc gtc agg gtc    2352
Ser Lys Arg Lys Ser Val Leu Ala Val Gly Val Gly Ser Val Arg Val
    770                 775                 780 aag ttt ggc cag ggc aac gcc gac tcc agc cgc ggc gcg gac ggc gac    2400
Lys Phe Gly Gln Gly Asn Ala Asp Ser Ser Arg Gly Ala Asp Gly Asp
785                 790                 795                 800 agt ggc gag atc aag aac cac gcc agc gac cgc cgg cag aag agc cag    2448
Ser Gly Glu Ile Lys Asn His Ala Ser Asp Arg Arg Gln Lys Ser Gln
                805                 810                 815 gag ccc gag ggg cac ctc caa ggc agc ccg ggg gag cgc gag gac ggc    2496
Glu Pro Glu Gly His Leu Gln Gly Ser Pro Gly Glu Arg Glu Asp Gly
            820                 825                 830 gcc ctg cag aga ggc gac agc acg gcc agg ccg ctc ctg gac aac agg    2544
Ala Leu Gln Arg Gly Asp Ser Thr Ala Arg Pro Leu Leu Asp Asn Arg
        835                 840                 845 gtg gtg aag agc ggc cgg ccg gac gcg ggc agg ccg tcc ggg ggg gac    2592
Val Val Lys Ser Gly Arg Pro Asp Ala Gly Arg Pro Ser Gly Gly Asp
    850                 855                 860
```

| | | |
|---|---|---|
| cag ctg cag aac atc ccc ctg gac ttc gcc aac ttc ccg gcg cag gtg<br>Gln Leu Gln Asn Ile Pro Leu Asp Phe Ala Asn Phe Pro Ala Gln Val<br>865                    870               875               880 | | 2640 |
| gag ctg ccc cgg gcg ggg ggc ctg ggg gcc agc gac ctg gtg cag<br>Glu Leu Pro Arg Ala Gly Gly Gly Leu Gly Ala Ser Asp Leu Val Gln<br>              885               890               895 | | 2688 |
| acg ccc cgg ggc ctg agc gac ctg gag atc ggc atg tac gcc ctg ctc<br>Thr Pro Arg Gly Leu Ser Asp Leu Glu Ile Gly Met Tyr Ala Leu Leu<br>          900               905              910 | | 2736 |
| ggc gtc ttc tgc ttg gcc atc ctt gtc ttc ctc atc aac tgc gcc acc<br>Gly Val Phe Cys Leu Ala Ile Leu Val Phe Leu Ile Asn Cys Ala Thr<br>          915               920              925 | | 2784 |
| ttc gcc ctc agg tac cgc cac aag cag gtg ccc ctg gaa ggc cag gcc<br>Phe Ala Leu Arg Tyr Arg His Lys Gln Val Pro Leu Glu Gly Gln Ala<br>930                    935               940 | | 2832 |
| tct gtg acc cac tcg cac gac tgg gtg tgg ctg ggc aac gag gcg gag<br>Ser Val Thr His Ser His Asp Trp Val Trp Leu Gly Asn Glu Ala Glu<br>945                    950               955               960 | | 2880 |
| ctc ctg gag cac gcg ggc gag ggg tcg cca ccg cag gac gag cac acg<br>Leu Leu Glu His Ala Gly Glu Gly Ser Pro Pro Gln Asp Glu His Thr<br>              965               970              975 | | 2928 |
| act gtc ctg gac cgc ggg ccg ggc ggc agc gac gac ggc agc cgg ctg<br>Thr Val Leu Asp Arg Gly Pro Gly Gly Ser Asp Asp Gly Ser Arg Leu<br>980                    985               990 | | 2976 |
| ctg ctc aac ggc ggc gcc cgg cag  cac gtg cag ggc cag  gtg cac cgg<br>Leu Leu Asn Gly Gly Ala Arg Gln  His Val Gln Gly Gln  Val His Arg<br>              995               1000              1005 | | 3024 |
| gcg ggc tcg gcg ggc agg ccg  gcc agg gac ccg aag  ctc gag ccc<br>Ala Gly Ser Ala Gly Arg Pro  Ala Arg Asp Pro Lys  Leu Glu Pro<br>     1010               1015               1020 | | 3069 |
| ctg cat tcg ccc acc tcc aaa  agg aag aaa gtg aag  ttc acc acc<br>Leu His Ser Pro Thr Ser Lys  Arg Lys Lys Val Lys  Phe Thr Thr<br>1025                   1030               1035 | | 3114 |
| ttc acc acc atc ccg ccc gac  gac ggc tgc ccc acc  gtg aac tcc<br>Phe Thr Thr Ile Pro Pro Asp  Asp Gly Cys Pro Thr  Val Asn Ser<br>     1040               1045               1050 | | 3159 |
| atc ctg ggg ggc ggc ggc ggc  gag gac atc aag tgg  gtg tgc cag<br>Ile Leu Gly Gly Gly Gly Gly  Glu Asp Ile Lys Trp  Val Cys Gln<br>     1055               1060               1065 | | 3204 |
| gac gtg tcc ccg ggc gcc ccc  aag gag ctc aga aac  tac ctg gag<br>Asp Val Ser Pro Gly Ala Pro  Lys Glu Leu Arg Asn  Tyr Leu Glu<br>1070                   1075               1080 | | 3249 |
| aaa ttc aag gac ccg gcc tag gccccgcgg ggcctggctc ctcgctcggc<br>Lys Phe Lys Asp Pro Ala<br>     1085 | | 3300 |
| tccagagtgg gctggccggg gcgtcggagg gtctggccga gcgggacgca ccggggccgg | | 3360 |
| cggaccgcgg aggcctccga gccgggaagg gctgtgtgcc tcttttgcag cagcgggttt | | 3420 |
| agcagccggt gacggtggag ttcccagtca gcggagcaaa ctccggcctg caccgtcgga | | 3480 |
| aagtgagtct atgagtcaaa atagaacaga caagctacca aaaatta | | 3527 |

<210> SEQ ID NO 26
<211> LENGTH: 1089
<212> TYPE: PRT
<213> ORGANISM: Canis familiaris

<400> SEQUENCE: 26

Met Ala Thr Met Leu Phe Ala Lys Leu Asn Phe Arg Asn Leu Ile Glu
1               5                   10                 15

-continued

```
Gly Arg Gly Ile Thr Asp Asn Val Pro Arg Phe Ser Ser Leu Pro Pro
             20                  25                  30

Phe Leu Pro Val Ser Tyr His Ile Leu Gly Ala Glu Thr Ser Phe Phe
             35                  40                  45

Leu Lys Glu Ala Asn Gln Asp Val Leu Arg Asn Ser Ser Leu His Thr
 50                  55                  60

Arg Val Glu Ser Phe Phe Thr Tyr Lys Ala Asn Arg Pro Pro Val Leu
 65                  70                  75                  80

Asn Ala Ser Tyr Gly Pro Phe Ser Ile Glu Gln Val Pro Gln Asp
             85                  90                  95

Leu Leu Leu Pro Ser Ser Pro Phe Gly Ala Thr Ser Lys Leu Ser Leu
             100                 105                 110

Asn Trp Arg Leu Arg Ala His Ile Leu Arg Asp Lys Val Tyr Leu Ser
             115                 120                 125

Arg Pro Arg Val Gln Val Leu Phe His Leu Leu Gly Arg Asp Trp Ala
             130                 135                 140

Ala Gln Ser Pro Gly Glu Arg Leu Pro Cys Leu Arg Leu Phe Ala Phe
145                 150                 155                 160

Arg Glu Thr Arg Glu Val Arg Ala Gly Cys Arg Leu Gln Gly Ala Leu
             165                 170                 175

Gly Leu Cys Val Ala Glu Leu Glu Leu Leu Ala Ala Trp Phe Gly Pro
             180                 185                 190

Pro Thr Val Val Ala Gly Arg Lys Arg Ala Pro Gly Pro Pro Glu Gly
             195                 200                 205

Ser Pro Val Glu Leu Tyr Tyr Ser Val Gln Pro Gly Asp Ala Arg Gly
             210                 215                 220

Asp Cys Ala Gly Gly Gly Gly Asp Val Arg Lys Gly Asn Ala Ile Arg
225                 230                 235                 240

Pro Gly Lys Asp Gly Leu Asp Glu Ala Val Pro His Leu Gln Arg Ile
             245                 250                 255

Gly Ala Val Ser Leu Tyr Arg Ala Gln Asp Ser Thr Gln Leu Ser Glu
             260                 265                 270

Leu Arg Leu Asp Ser Asn Val Val Ile Trp Leu Pro Ser Arg Pro Val
             275                 280                 285

Lys Gln Gly Asp Val Val Thr Ala Tyr Val Thr Ile Ala Ser Asn Ser
             290                 295                 300

Thr Val Asp Leu Phe Ile Leu Arg Ala Lys Val Lys Lys Gly Val Asn
305                 310                 315                 320

Ile Leu Gly Thr Gln Thr Ser Glu Pro Arg Gln Trp Asp Val Lys Gln
             325                 330                 335

Glu Met Gly Asn Gly Gly Lys His Ala Thr Thr Thr Val Leu Cys Gln
             340                 345                 350

Arg Leu Gly Ser Ser Thr Arg Asn Arg Ser Ser Leu Phe Ser Glu
             355                 360                 365

Val Met Gln Met Asn Phe Glu Ile Ala Ser Phe Ser Ser Leu Ser Gly
             370                 375                 380

Thr Gln Pro Ile Ala Trp Gln Val Glu Tyr Pro Arg Arg Ala Thr Thr
385                 390                 395                 400

Asp Thr Ala Val Ser Glu Ile Phe Ile Ser Gln Lys Asp Leu Ala Gly
             405                 410                 415

Ile Val Pro Leu Ala Thr Asp Thr Glu Ile Leu Asn Thr Ala Ile Leu
             420                 425                 430

Thr Gly Lys Thr Val Val Leu Pro Ile Lys Val Val Ser Val Glu Glu
             435                 440                 445
```

-continued

```
Asn Ser Ala Val Met Asp Ile Ser Glu Ser Val Glu Cys Lys Ser Thr
    450                 455                 460
Asp Glu Asp Val Ile Lys Val Ser Glu Arg Cys Asp Tyr Val Phe Val
465                 470                 475                 480
Asn Gly Lys Glu Met Lys Gly Lys Val Asp Ala Val Val Asn Phe Thr
                485                 490                 495
Tyr Gln His Leu Ser Ala Ser Leu His Ile Thr Val Trp Val Pro Arg
            500                 505                 510
Leu Pro Leu Gln Ile Glu Val Ser Asp Thr Glu Leu Ser Gln Ile Lys
        515                 520                 525
Gly Trp Arg Val Pro Ile Val Ser Ser Lys Arg Pro Thr Arg Glu Ser
    530                 535                 540
Glu Asp Glu Asp Glu Glu Arg Arg Gly Arg Gly Cys Ala Leu Gln
545                 550                 555                 560
Tyr Gln His Ala Thr Val Arg Val Leu Thr Gln Phe Val Ser Glu Gly
                565                 570                 575
Ala Gly Pro Trp Gly Gln Pro Ser His Leu Ser Pro Asp Trp Gln
            580                 585                 590
Val Asp Ile Thr His Leu Val Ala Asp Phe Met Lys Leu Glu Glu Pro
        595                 600                 605
His Val Ala Thr Leu Gln Asp Ser Arg Ile Leu Val Gly Arg Glu Val
    610                 615                 620
Gly Met Thr Thr Ile Gln Val Leu Ser Pro Leu Ser Asp Ser Ile Leu
625                 630                 635                 640
Ala Glu Lys Thr Val Thr Val Leu Asp Asp Lys Val Ser Val Thr Asp
                645                 650                 655
Leu Ala Ile Gln Leu Val Ala Gly Leu Ser Val Thr Leu His Pro Ser
            660                 665                 670
Thr Glu Asn Ser Lys Ala Ile Thr Ala Val Ala Thr Ala Glu Glu Leu
        675                 680                 685
Leu Arg Thr Pro Lys Gln Glu Ala Val Val Ser Thr Trp Leu Gln Leu
    690                 695                 700
Ser Asp Gly Ser Ala Thr Pro Leu Asp Ile Tyr Asp Thr Lys Asp Phe
705                 710                 715                 720
Thr Leu Thr Ala Thr Ser Leu Asn Glu Ala Val Val Ser Thr Pro Gln
                725                 730                 735
Ala Arg Ser Pro Arg Trp Pro Val Val Met Ala Glu Gly Glu Gly Gln
            740                 745                 750
Gly Pro Leu Val Arg Val Asp Met Ser Ile Ala Glu Ala Cys Gln Lys
        755                 760                 765
Ser Lys Arg Lys Ser Val Leu Ala Val Gly Val Gly Ser Val Arg Val
    770                 775                 780
Lys Phe Gly Gln Gly Asn Ala Asp Ser Ser Arg Gly Ala Asp Gly Asp
785                 790                 795                 800
Ser Gly Glu Ile Lys Asn His Ala Ser Asp Arg Arg Gln Lys Ser Gln
                805                 810                 815
Glu Pro Glu Gly His Leu Gln Gly Ser Pro Gly Glu Arg Glu Asp Gly
            820                 825                 830
Ala Leu Gln Arg Gly Asp Ser Thr Ala Arg Pro Leu Leu Asp Asn Arg
        835                 840                 845
Val Val Lys Ser Gly Arg Pro Asp Ala Gly Arg Pro Ser Gly Gly Asp
    850                 855                 860
Gln Leu Gln Asn Ile Pro Leu Asp Phe Ala Asn Phe Pro Ala Gln Val
```

```
                865                 870                 875                 880
Glu Leu Pro Arg Ala Gly Gly Leu Gly Ala Ser Asp Leu Val Gln
                    885                 890                 895
Thr Pro Arg Gly Leu Ser Asp Leu Glu Ile Gly Met Tyr Ala Leu Leu
                900                 905                 910
Gly Val Phe Cys Leu Ala Ile Leu Val Phe Leu Ile Asn Cys Ala Thr
                915                 920                 925
Phe Ala Leu Arg Tyr Arg His Lys Gln Val Pro Leu Glu Gly Gln Ala
                930                 935                 940
Ser Val Thr His Ser His Asp Trp Val Trp Leu Gly Asn Glu Ala Glu
945                 950                 955                 960
Leu Leu Glu His Ala Gly Glu Gly Ser Pro Gln Asp Glu His Thr
                    965                 970                 975
Thr Val Leu Asp Arg Gly Pro Gly Gly Ser Asp Asp Gly Ser Arg Leu
                980                 985                 990
Leu Leu Asn Gly Gly Ala Arg Gln His Val Gln Gly Gln Val His Arg
                995                 1000                1005
Ala Gly Ser Ala Gly Arg Pro Ala Arg Asp Pro Lys Leu Glu Pro
        1010                1015                1020
Leu His Ser Pro Thr Ser Lys Arg Lys Val Lys Phe Thr Thr
        1025                1030                1035
Phe Thr Thr Ile Pro Pro Asp Asp Gly Cys Pro Thr Val Asn Ser
        1040                1045                1050
Ile Leu Gly Gly Gly Gly Glu Asp Ile Lys Trp Val Cys Gln
        1055                1060                1065
Asp Val Ser Pro Gly Ala Pro Lys Glu Leu Arg Asn Tyr Leu Glu
        1070                1075                1080
Lys Phe Lys Asp Pro Ala
        1085

<210> SEQ ID NO 27
<211> LENGTH: 3144
<212> TYPE: DNA
<213> ORGANISM: Pan troglodytes
<220> FEATURE:
<221> NAME/KEY: CDS
<222> LOCATION: (1)..(3144)
<223> OTHER INFORMATION:

<400> SEQUENCE: 27 atg cag ctc ctg gac agc agc agt acc ggt acc cag tgg cag ata agg      48
Met Gln Leu Leu Asp Ser Ser Ser Thr Gly Thr Gln Trp Gln Ile Arg
1               5                   10                  15 aga atc agg agc agc agt tta ttc aat gag gtt gtg cag atg aac ttt      96
Arg Ile Arg Ser Ser Ser Leu Phe Asn Glu Val Val Gln Met Asn Phe
            20                  25                  30 gaa ata gcc agt ttc agc agc ctt tca ggg act cag ccc atc aca tgg     144
Glu Ile Ala Ser Phe Ser Ser Leu Ser Gly Thr Gln Pro Ile Thr Trp
        35                  40                  45 cag gtg gag tac cca cgg aag ggg acc aca gac atc gcc gtg tcc gag     192
Gln Val Glu Tyr Pro Arg Lys Gly Thr Thr Asp Ile Ala Val Ser Glu
    50                  55                  60 atc ttt gtc agc cag aag gac ctg gtg ggc atc gtt ccc ttg gct atg     240
Ile Phe Val Ser Gln Lys Asp Leu Val Gly Ile Val Pro Leu Ala Met
65                  70                  75                  80 cac cgg cat ccc agg cat tat ctt gtg aac att aat cct gtg acc atc     288
His Arg His Pro Arg His Tyr Leu Val Asn Ile Asn Pro Val Thr Ile
                85                  90                  95
```

```
att cgg aaa gcc cct gtg agc cct ggg tcc cct gtc ctg ctg cct tca    336
Ile Arg Lys Ala Pro Val Ser Pro Gly Ser Pro Val Leu Leu Pro Ser
            100                 105                 110 acc caa gac agc agt ctc atc tct gcc aga cac gat gct atc tgt gca    384
Thr Gln Asp Ser Ser Leu Ile Ser Ala Arg His Asp Ala Ile Cys Ala
        115                 120                 125 gtc agc ctc tcc atc gcc cat gct ccc tct ggg cgg tca tgc cca gag    432
Val Ser Leu Ser Ile Ala His Ala Pro Ser Gly Arg Ser Cys Pro Glu
    130                 135                 140 gct cgg gaa ctt ggc tgt gtc cac tcc cta gtc ccc acc ttc cag atc    480
Ala Arg Glu Leu Gly Cys Val His Ser Leu Val Pro Thr Phe Gln Ile
145                 150                 155                 160 act gct caa tat cta gtc gat ggc caa aac ata tct aca ttg aat aaa    528
Thr Ala Gln Tyr Leu Val Asp Gly Gln Asn Ile Ser Thr Leu Asn Lys
                165                 170                 175 tcc atg tcc agc atc tcc ctc aat aac act aag aca aca act gca gac    576
Ser Met Ser Ser Ile Ser Leu Asn Asn Thr Lys Thr Thr Thr Ala Asp
            180                 185                 190 atg tcc tcc cag tgt ccc tgt gag atc tgg agt gcg ttg ggt tgt gtc    624
Met Ser Ser Gln Cys Pro Cys Glu Ile Trp Ser Ala Leu Gly Cys Val
        195                 200                 205 cct caa aga gat ccc atc agt gtt gga tgt gag tgt gtt tac tgg agt    672
Pro Gln Arg Asp Pro Ile Ser Val Gly Cys Glu Cys Val Tyr Trp Ser
    210                 215                 220 cca tca gcg ctg gat gtg agt gtg ttt act gga gtc cat cag cgt tgg    720
Pro Ser Ala Leu Asp Val Ser Val Phe Thr Gly Val His Gln Arg Trp
225                 230                 235                 240 atg agt gtg ttt act gga gtc cat cag cgt tgg atg agt gtg ttt act    768
Met Ser Val Phe Thr Gly Val His Gln Arg Trp Met Ser Val Phe Thr
                245                 250                 255 gga gtc cat cag cgc tgg atg tac ccc aag aag acc cat gaa cac ctc    816
Gly Val His Gln Arg Trp Met Tyr Pro Lys Lys Thr His Glu His Leu
            260                 265                 270 ata gtc tct tca cat ctg cag ttg tct gca gcc caa gca cag ggc cct    864
Ile Val Ser Ser His Leu Gln Leu Ser Ala Ala Gln Ala Gln Gly Pro
        275                 280                 285 ggc ctc atc tcc aag gct ggc tct tca gac aac gac tcc atc cag ggt    912
Gly Leu Ile Ser Lys Ala Gly Ser Ser Asp Asn Asp Ser Ile Gln Gly
    290                 295                 300 cct gat gct cgg aac aca gag ttc tcg gag cca caa gga gca gga ttc    960
Pro Asp Ala Arg Asn Thr Glu Phe Ser Glu Pro Gln Gly Ala Gly Phe
305                 310                 315                 320 aca gaa gac aga gga caa tgc ctc cac gtg cgt ata agt gga gcg tgc   1008
Thr Glu Asp Arg Gly Gln Cys Leu His Val Arg Ile Ser Gly Ala Cys
                325                 330                 335 tcc ggg aaa cag ggg ccc agg aca gga ggc ctg cct ggt ggc cag cat   1056
Ser Gly Lys Gln Gly Pro Arg Thr Gly Gly Leu Pro Gly Gly Gln His
            340                 345                 350 ggc cac act tcc cag ccc ctg acc cgg gac act gaa att ctg aac acc   1104
Gly His Thr Ser Gln Pro Leu Thr Arg Asp Thr Glu Ile Leu Asn Thr
        355                 360                 365 gcc ata ctc aca gga aag aca gtt gcc atg cct atc aag gtg gtc tct   1152
Ala Ile Leu Thr Gly Lys Thr Val Ala Met Pro Ile Lys Val Val Ser
    370                 375                 380 gtg gag gag aac agt gcc gtg atg gac atc tca gag tcg gtg gag tgc   1200
Val Glu Glu Asn Ser Ala Val Met Asp Ile Ser Glu Ser Val Glu Cys
385                 390                 395                 400 aag tcc aca gac gag gac gtt atc aaa gtg tct gac cgc tgt gac tac   1248
Lys Ser Thr Asp Glu Asp Val Ile Lys Val Ser Asp Arg Cys Asp Tyr
                405                 410                 415
```

```
atc ttt gtc aat ggc aaa gag atc aaa gga aag atg gat gcg gtg gtg     1296
Ile Phe Val Asn Gly Lys Glu Ile Lys Gly Lys Met Asp Ala Val Val
            420                 425                 430 aac ttc aca tac cag tac ctg agc gcc ccc ctg cgt gtc acc gtg tgg     1344
Asn Phe Thr Tyr Gln Tyr Leu Ser Ala Pro Leu Arg Val Thr Val Trp
            435                 440                 445 gtg ccc cgg ctg ccc ctg cag atc gag gtc tct gac acg gag ctc agc     1392
Val Pro Arg Leu Pro Leu Gln Ile Glu Val Ser Asp Thr Glu Leu Ser
        450                 455                 460 cag ata aag ggc tgg agg gtc ccc att gtg acc aat aag agg cct act     1440
Gln Ile Lys Gly Trp Arg Val Pro Ile Val Thr Asn Lys Arg Pro Thr
465                 470                 475                 480 cgt gag agc gag gat gag gac gag gag gag cgg cgg ggc cgg ggc tgc     1488
Arg Glu Ser Glu Asp Glu Asp Glu Glu Glu Arg Arg Gly Arg Gly Cys
                485                 490                 495 gcg ctg cag tac cag cac gcc acc gtg cgg gtc ctc acc cag ttt gtg     1536
Ala Leu Gln Tyr Gln His Ala Thr Val Arg Val Leu Thr Gln Phe Val
            500                 505                 510 tcc gag ggc gcc ggt ccg tgg ggc cag ccg aac tac ctg ctt agt cct     1584
Ser Glu Gly Ala Gly Pro Trp Gly Gln Pro Asn Tyr Leu Leu Ser Pro
        515                 520                 525 aac tgg cag ttc gac atc act cac ctg gtg gca gac ttc atg aag ctg     1632
Asn Trp Gln Phe Asp Ile Thr His Leu Val Ala Asp Phe Met Lys Leu
530                 535                 540 gag gaa cct cac gtg gcc acc ctc cag gac agc cgg gtc ctg gtt ggg     1680
Glu Glu Pro His Val Ala Thr Leu Gln Asp Ser Arg Val Leu Val Gly
545                 550                 555                 560 cga gag gtt ggg atg acg acc atc cag gtg ttg tct cca ctg tct gac     1728
Arg Glu Val Gly Met Thr Thr Ile Gln Val Leu Ser Pro Leu Ser Asp
                565                 570                 575 tcc atc ctg gca gag aag aca ata acc gtg cta gat gac aaa gtg tcg     1776
Ser Ile Leu Ala Glu Lys Thr Ile Thr Val Leu Asp Asp Lys Val Ser
            580                 585                 590 gtg aca gac ttg gcc atc cag ctc gtg gct ggg ctg tct gtt gcc ctt     1824
Val Thr Asp Leu Ala Ile Gln Leu Val Ala Gly Leu Ser Val Ala Leu
        595                 600                 605 tac ccc aac gca gaa aac agc aag gcc ata aca gct gtg gtc aca gct     1872
Tyr Pro Asn Ala Glu Asn Ser Lys Ala Ile Thr Ala Val Val Thr Ala
610                 615                 620 gag gag gtg ctg cgg acc ccc aaa cag gca aag ctt aat tca ctg ggg     1920
Glu Glu Val Leu Arg Thr Pro Lys Gln Ala Lys Leu Asn Ser Leu Gly
625                 630                 635                 640 gca gtg cag gca gaa gag ggg agg ttc ctt tct gat gtc att ggt tct     1968
Ala Val Gln Ala Glu Glu Gly Arg Phe Leu Ser Asp Val Ile Gly Ser
                645                 650                 655 gac agt gtt tcc tgc cca tca acc ttt gtc atc agg ctg gat aca gac     2016
Asp Ser Val Ser Cys Pro Ser Thr Phe Val Ile Arg Leu Asp Thr Asp
            660                 665                 670 aac agc tca gcc acc tct cag gac gag gct gtc gtg tcc gtc ccc cag     2064
Asn Ser Ser Ala Thr Ser Gln Asp Glu Ala Val Val Ser Val Pro Gln
        675                 680                 685 ccc cgc tct ccc agg tgg ccc gtt gtg gtg gcc gaa ggg gaa ggc cag     2112
Pro Arg Ser Pro Arg Trp Pro Val Val Val Ala Glu Gly Glu Gly Gln
690                 695                 700 ggc cca ctg atc cga gtg gac atg acg atc gcc gag gcc tgc cag aaa     2160
Gly Pro Leu Ile Arg Val Asp Met Thr Ile Ala Glu Ala Cys Gln Lys
705                 710                 715                 720 tcc aaa cgc aag agc atc ctg gct gtg ggc gtc ggc aac gtc agg gtc     2208
Ser Lys Arg Lys Ser Ile Leu Ala Val Gly Val Gly Asn Val Arg Val
                725                 730                 735
```

```
aag ttc gga cag aac gat gct gac tcc agc ccc ggc agg gac tat gag    2256
Lys Phe Gly Gln Asn Asp Ala Asp Ser Ser Pro Gly Arg Asp Tyr Glu
        740                 745                 750 gaa gat gag atc aag aac cac gcc agc gac cgc cgg cag aag ggc cag    2304
Glu Asp Glu Ile Lys Asn His Ala Ser Asp Arg Arg Gln Lys Gly Gln
        755                 760                 765 cac cat gag cgc aca ggc cag gat ggg cac ctc tat ggc agc tct ccc    2352
His His Glu Arg Thr Gly Gln Asp Gly His Leu Tyr Gly Ser Ser Pro
        770                 775                 780 gtg gag cgt gag gaa ggg gct ctc cga aga gcc act acc acg gcc agg    2400
Val Glu Arg Glu Glu Gly Ala Leu Arg Arg Ala Thr Thr Thr Ala Arg
785                 790                 795                 800 tcc ctg ctg gac aac aaa gtg gtg aag aac agt cgg gca gac ggg ggc    2448
Ser Leu Leu Asp Asn Lys Val Val Lys Asn Ser Arg Ala Asp Gly Gly
                805                 810                 815 agg ctg gca gga gag ggg cag ctg cag aac atc ccc att gac ttc acc    2496
Arg Leu Ala Gly Glu Gly Gln Leu Gln Asn Ile Pro Ile Asp Phe Thr
        820                 825                 830 aac ttc ccg gcc cac gtg gac ctc ccc aag gcc ggg agt ggg ctg gag    2544
Asn Phe Pro Ala His Val Asp Leu Pro Lys Ala Gly Ser Gly Leu Glu
        835                 840                 845 gaa aac gac ctg gtg cag act ccg cgg ggc ctg agt gat ctg gag ata    2592
Glu Asn Asp Leu Val Gln Thr Pro Arg Gly Leu Ser Asp Leu Glu Ile
        850                 855                 860 ggg atg tac gcc ctc ctg ggg gtg ttc tgc ctg gcc atc ctc gtc ttc    2640
Gly Met Tyr Ala Leu Leu Gly Val Phe Cys Leu Ala Ile Leu Val Phe
865                 870                 875                 880 ctg atc aac tgc gcc acc ttt gcc ctg aag tac agg cac aag caa gtg    2688
Leu Ile Asn Cys Ala Thr Phe Ala Leu Lys Tyr Arg His Lys Gln Val
                885                 890                 895 ccc ctg gaa ggt cag gcc tcc atg acc cac tct cac gac tgg gtg tgg    2736
Pro Leu Glu Gly Gln Ala Ser Met Thr His Ser His Asp Trp Val Trp
        900                 905                 910 ctt ggc aat gag gcc gaa ctc ctg gag agc atg ggg gac gcg cca ccg    2784
Leu Gly Asn Glu Ala Glu Leu Leu Glu Ser Met Gly Asp Ala Pro Pro
        915                 920                 925 ccc cag gac gag cac acc acc atc ata gac cgc gga ccg ggg gcc tgc    2832
Pro Gln Asp Glu His Thr Thr Ile Ile Asp Arg Gly Pro Gly Ala Cys
930                 935                 940 gag gag agc aac cat ctc ctg ctc aat ggt ggc tcc cac aag cac gtg    2880
Glu Glu Ser Asn His Leu Leu Leu Asn Gly Gly Ser His Lys His Val
945                 950                 955                 960 cag agc cag att cac agg tca gcc gac tcc ggg ggg cgg cag ggc aga    2928
Gln Ser Gln Ile His Arg Ser Ala Asp Ser Gly Gly Arg Gln Gly Arg
                965                 970                 975 gaa cag aag cag gac ccc ctg cac tcg ccc acc tcc aag agg aag aag    2976
Glu Gln Lys Gln Asp Pro Leu His Ser Pro Thr Ser Lys Arg Lys Lys
        980                 985                 990 gtg aaa ttc acc acc ttt acc acc atc ccc ccg gac gac agc tgc ccc    3024
Val Lys Phe Thr Thr Phe Thr Thr Ile Pro Pro Asp Asp Ser Cys Pro
        995                 1000                1005 aca gtg aac tcc atc gtc agc agc aat gat gag gac atc aaa tgg         3069
Thr Val Asn Ser Ile Val Ser Ser Asn Asp Glu Asp Ile Lys Trp
        1010                1015                1020 gtg tgt caa gac atg gct gtg ggt gcc ccc aag gaa ctt aga aac         3114
Val Cys Gln Asp Met Ala Val Gly Ala Pro Lys Glu Leu Arg Asn
        1025                1030                1035 tat ctg gag aaa ctc aaa gat aag gct tag                             3144
Tyr Leu Glu Lys Leu Lys Asp Lys Ala
        1040                1045
```

<210> SEQ ID NO 28
<211> LENGTH: 1047
<212> TYPE: PRT
<213> ORGANISM: Pan troglodytes

<400> SEQUENCE: 28

```
Met Gln Leu Leu Asp Ser Ser Thr Gly Thr Gln Trp Gln Ile Arg
1               5                   10                  15

Arg Ile Arg Ser Ser Leu Phe Asn Glu Val Val Gln Met Asn Phe
                20                  25                  30

Glu Ile Ala Ser Phe Ser Ser Leu Ser Gly Thr Gln Pro Ile Thr Trp
                35                  40                  45

Gln Val Glu Tyr Pro Arg Lys Gly Thr Thr Asp Ile Ala Val Ser Glu
    50                  55                  60

Ile Phe Val Ser Gln Lys Asp Leu Val Gly Ile Val Pro Leu Ala Met
65                  70                  75                  80

His Arg His Pro Arg His Tyr Leu Val Asn Ile Asn Pro Val Thr Ile
                85                  90                  95

Ile Arg Lys Ala Pro Val Ser Pro Gly Ser Pro Val Leu Leu Pro Ser
                100                 105                 110

Thr Gln Asp Ser Ser Leu Ile Ser Ala Arg His Asp Ala Ile Cys Ala
                115                 120                 125

Val Ser Leu Ser Ile Ala His Ala Pro Ser Gly Arg Ser Cys Pro Glu
    130                 135                 140

Ala Arg Glu Leu Gly Cys Val His Ser Leu Val Pro Thr Phe Gln Ile
145                 150                 155                 160

Thr Ala Gln Tyr Leu Val Asp Gly Gln Asn Ile Ser Thr Leu Asn Lys
                165                 170                 175

Ser Met Ser Ser Ile Ser Leu Asn Asn Thr Lys Thr Thr Ala Asp
                180                 185                 190

Met Ser Ser Gln Cys Pro Cys Glu Ile Trp Ser Ala Leu Gly Cys Val
                195                 200                 205

Pro Gln Arg Asp Pro Ile Ser Val Gly Cys Glu Cys Val Tyr Trp Ser
    210                 215                 220

Pro Ser Ala Leu Asp Val Ser Val Phe Thr Gly Val His Gln Arg Trp
225                 230                 235                 240

Met Ser Val Phe Thr Gly Val His Gln Arg Trp Met Ser Val Phe Thr
                245                 250                 255

Gly Val His Gln Arg Trp Met Tyr Pro Lys Lys Thr His Glu His Leu
                260                 265                 270

Ile Val Ser Ser His Leu Gln Leu Ser Ala Ala Gln Ala Gln Gly Pro
                275                 280                 285

Gly Leu Ile Ser Lys Ala Gly Ser Ser Asp Asn Asp Ser Ile Gln Gly
    290                 295                 300

Pro Asp Ala Arg Asn Thr Glu Phe Ser Glu Pro Gln Gly Ala Gly Phe
305                 310                 315                 320

Thr Glu Asp Arg Gly Gln Cys Leu His Val Arg Ile Ser Gly Ala Cys
                325                 330                 335

Ser Gly Lys Gln Gly Pro Arg Thr Gly Gly Leu Pro Gly Gly Gln His
                340                 345                 350

Gly His Thr Ser Gln Pro Leu Thr Arg Asp Thr Glu Ile Leu Asn Thr
                355                 360                 365

Ala Ile Leu Thr Gly Lys Thr Val Ala Met Pro Ile Lys Val Val Ser
    370                 375                 380
```

```
Val Glu Glu Asn Ser Ala Val Met Asp Ile Ser Glu Ser Val Glu Cys
385                 390                 395                 400

Lys Ser Thr Asp Glu Asp Val Ile Lys Val Ser Asp Arg Cys Asp Tyr
            405                 410                 415

Ile Phe Val Asn Gly Lys Glu Ile Lys Gly Lys Met Asp Ala Val Val
            420                 425                 430

Asn Phe Thr Tyr Gln Tyr Leu Ser Ala Pro Leu Arg Val Thr Val Trp
            435                 440                 445

Val Pro Arg Leu Pro Leu Gln Ile Glu Val Ser Asp Thr Glu Leu Ser
450                 455                 460

Gln Ile Lys Gly Trp Arg Val Pro Ile Val Thr Asn Lys Arg Pro Thr
465                 470                 475                 480

Arg Glu Ser Glu Asp Glu Asp Glu Glu Arg Arg Gly Arg Gly Cys
                485                 490                 495

Ala Leu Gln Tyr Gln His Ala Thr Val Arg Val Leu Thr Gln Phe Val
            500                 505                 510

Ser Glu Gly Ala Gly Pro Trp Gly Gln Pro Asn Tyr Leu Leu Ser Pro
            515                 520                 525

Asn Trp Gln Phe Asp Ile Thr His Leu Val Ala Asp Phe Met Lys Leu
530                 535                 540

Glu Glu Pro His Val Ala Thr Leu Gln Asp Ser Arg Val Leu Val Gly
545                 550                 555                 560

Arg Glu Val Gly Met Thr Thr Ile Gln Val Leu Ser Pro Leu Ser Asp
                565                 570                 575

Ser Ile Leu Ala Glu Lys Thr Ile Thr Val Leu Asp Asp Lys Val Ser
            580                 585                 590

Val Thr Asp Leu Ala Ile Gln Leu Val Ala Gly Leu Ser Val Ala Leu
            595                 600                 605

Tyr Pro Asn Ala Glu Asn Ser Lys Ala Ile Thr Ala Val Val Thr Ala
            610                 615                 620

Glu Glu Val Leu Arg Thr Pro Lys Gln Ala Lys Leu Asn Ser Leu Gly
625                 630                 635                 640

Ala Val Gln Ala Glu Glu Gly Arg Phe Leu Ser Asp Val Ile Gly Ser
                645                 650                 655

Asp Ser Val Ser Cys Pro Ser Thr Phe Val Ile Arg Leu Asp Thr Asp
            660                 665                 670

Asn Ser Ser Ala Thr Ser Gln Asp Glu Ala Val Val Ser Val Pro Gln
            675                 680                 685

Pro Arg Ser Pro Arg Trp Pro Val Val Ala Gly Glu Gly Gln
690                 695                 700

Gly Pro Leu Ile Arg Val Asp Met Thr Ile Ala Glu Ala Cys Gln Lys
705                 710                 715                 720

Ser Lys Arg Lys Ser Ile Leu Ala Val Gly Val Gly Asn Val Arg Val
                725                 730                 735

Lys Phe Gly Gln Asn Asp Ala Asp Ser Ser Pro Gly Arg Asp Tyr Glu
            740                 745                 750

Glu Asp Glu Ile Lys Asn His Ala Ser Asp Arg Gln Lys Gly Gln
            755                 760                 765

His His Glu Arg Thr Gly Gln Asp Gly His Leu Tyr Gly Ser Ser Pro
770                 775                 780

Val Glu Arg Glu Glu Gly Ala Leu Arg Arg Ala Thr Thr Ala Arg
785                 790                 795                 800

Ser Leu Leu Asp Asn Lys Val Val Lys Asn Ser Arg Ala Asp Gly Gly
                805                 810                 815
```

-continued

Arg Leu Ala Gly Glu Gly Gln Leu Gln Asn Ile Pro Ile Asp Phe Thr
            820                 825                 830

Asn Phe Pro Ala His Val Asp Leu Pro Lys Ala Gly Ser Gly Leu Glu
        835                 840                 845

Glu Asn Asp Leu Val Gln Thr Pro Arg Gly Leu Ser Asp Leu Glu Ile
850                 855                 860

Gly Met Tyr Ala Leu Leu Gly Val Phe Cys Leu Ala Ile Leu Val Phe
865                 870                 875                 880

Leu Ile Asn Cys Ala Thr Phe Ala Leu Lys Tyr Arg His Lys Gln Val
                885                 890                 895

Pro Leu Glu Gly Gln Ala Ser Met Thr His Ser His Asp Trp Val Trp
            900                 905                 910

Leu Gly Asn Glu Ala Glu Leu Leu Glu Ser Met Gly Asp Ala Pro Pro
        915                 920                 925

Pro Gln Asp Glu His Thr Thr Ile Ile Asp Arg Gly Pro Gly Ala Cys
    930                 935                 940

Glu Glu Ser Asn His Leu Leu Leu Asn Gly Gly Ser His Lys His Val
945                 950                 955                 960

Gln Ser Gln Ile His Arg Ser Ala Asp Ser Gly Arg Gln Gly Arg
                965                 970                 975

Glu Gln Lys Gln Asp Pro Leu His Ser Pro Thr Ser Arg Lys Lys
            980                 985                 990

Val Lys Phe Thr Thr Phe Thr Thr  Ile Pro Pro Asp Asp  Ser Cys Pro
        995                 1000                1005

Thr Val  Asn Ser Ile Val Ser  Ser Asn Asp Glu Asp  Ile Lys Trp
   1010                1015                1020

Val Cys  Gln Asp Met Ala Val  Gly Ala Pro Lys Glu  Leu Arg Asn
   1025                1030                1035

Tyr Leu  Glu Lys Leu Lys Asp  Lys Ala
   1040                1045

<210> SEQ ID NO 29
<211> LENGTH: 26
<212> TYPE: DNA
<213> ORGANISM: Artificial
<220> FEATURE:
<223> OTHER INFORMATION: primer

<400> SEQUENCE: 29
cagctccaca acctacatca ttccgt                                    26

<210> SEQ ID NO 30
<211> LENGTH: 12
<212> TYPE: DNA
<213> ORGANISM: Artificial
<220> FEATURE:
<223> OTHER INFORMATION: primer

<400> SEQUENCE: 30
acggaatgat gt                                                   12

<210> SEQ ID NO 31
<211> LENGTH: 26
<212> TYPE: DNA
<213> ORGANISM: Artificial
<220> FEATURE:
<223> OTHER INFORMATION: primer

<400> SEQUENCE: 31

```
tagtctacca ctgctcgact gtaacg                                              26

<210> SEQ ID NO 32
<211> LENGTH: 26
<212> TYPE: DNA
<213> ORGANISM: Artificial
<220> FEATURE:
<223> OTHER INFORMATION: primer

<400> SEQUENCE: 32
cagagtgaac ccagtggaca tatctg                                              26

<210> SEQ ID NO 33
<211> LENGTH: 26
<212> TYPE: DNA
<213> ORGANISM: Artificial
<220> FEATURE:
<223> OTHER INFORMATION: primer

<400> SEQUENCE: 33
tggttcaggt gtggttccag aaccag                                              26

<210> SEQ ID NO 34
<211> LENGTH: 26
<212> TYPE: DNA
<213> ORGANISM: Artificial
<220> FEATURE:
<223> OTHER INFORMATION: primer

<400> SEQUENCE: 34
gagttgtaga cgctctgttc aatggc                                              26

<210> SEQ ID NO 35
<211> LENGTH: 26
<212> TYPE: DNA
<213> ORGANISM: Artificial
<220> FEATURE:
<223> OTHER INFORMATION: primer

<400> SEQUENCE: 35
accaggaagg acaatgccat tcgtcc                                              26

<210> SEQ ID NO 36
<211> LENGTH: 26
<212> TYPE: DNA
<213> ORGANISM: Artificial
<220> FEATURE:
<223> OTHER INFORMATION: primer

<400> SEQUENCE: 36
ccttcttcac cttggctctt aggatg                                              26

<210> SEQ ID NO 37
<211> LENGTH: 12
<212> TYPE: DNA
<213> ORGANISM: Artificial
<220> FEATURE:
<223> OTHER INFORMATION: primer

<400> SEQUENCE: 37
catcccagtc tc                                                             12

<210> SEQ ID NO 38
<211> LENGTH: 26
<212> TYPE: DNA
<213> ORGANISM: Artificial
<220> FEATURE:
```

<223> OTHER INFORMATION: primer

<400> SEQUENCE: 38
tggagaaggt tgtgcctctg gacttg                                      26

<210> SEQ ID NO 39
<211> LENGTH: 26
<212> TYPE: DNA
<213> ORGANISM: Artificial
<220> FEATURE:
<223> OTHER INFORMATION: primer

<400> SEQUENCE: 39
ctggttggct tccttgagga agaagg                                      26

<210> SEQ ID NO 40
<211> LENGTH: 26
<212> TYPE: DNA
<213> ORGANISM: Artificial
<220> FEATURE:
<223> OTHER INFORMATION: primer

<400> SEQUENCE: 40
tcctgcggga caaagtctac ctgagc                                      26

<210> SEQ ID NO 41
<211> LENGTH: 26
<212> TYPE: DNA
<213> ORGANISM: Artificial
<220> FEATURE:
<223> OTHER INFORMATION: primer

<400> SEQUENCE: 41
ctgaggatgt ggtagctcac aggtag                                      26

<210> SEQ ID NO 42
<211> LENGTH: 39
<212> TYPE: DNA
<213> ORGANISM: Artificial
<220> FEATURE:
<223> OTHER INFORMATION: primer

<400> SEQUENCE: 42
gaggtcgacg ccaccatgcg ctccgagggt gcggccccc                        39

<210> SEQ ID NO 43
<211> LENGTH: 26
<212> TYPE: DNA
<213> ORGANISM: Artificial
<220> FEATURE:
<223> OTHER INFORMATION: primer

<400> SEQUENCE: 43
gggtccatag ctggcattga gcactg                                      26

<210> SEQ ID NO 44
<211> LENGTH: 26
<212> TYPE: DNA
<213> ORGANISM: Artificial
<220> FEATURE:
<223> OTHER INFORMATION: primer

<400> SEQUENCE: 44
ctacctgtga gctaccacat cctcag                                      26

<210> SEQ ID NO 45

```
<211> LENGTH: 26
<212> TYPE: DNA
<213> ORGANISM: Artificial
<220> FEATURE:
<223> OTHER INFORMATION: primer

<400> SEQUENCE: 45
ttctctgcca ggatggagtc agacag                                          26

<210> SEQ ID NO 46
<211> LENGTH: 26
<212> TYPE: DNA
<213> ORGANISM: Artificial
<220> FEATURE:
<223> OTHER INFORMATION: primer

<400> SEQUENCE: 46
actggcagtt cgacatcact cacctg                                          26

<210> SEQ ID NO 47
<211> LENGTH: 35
<212> TYPE: DNA
<213> ORGANISM: Artificial
<220> FEATURE:
<223> OTHER INFORMATION: primer

<400> SEQUENCE: 47
gaggaattcc agtacaagga aggcatctgg gcagg                                35

<210> SEQ ID NO 48
<211> LENGTH: 26
<212> TYPE: DNA
<213> ORGANISM: Artificial
<220> FEATURE:
<223> OTHER INFORMATION: primer

<400> SEQUENCE: 48
agctgagcca ccttctcagt ccagac                                          26

<210> SEQ ID NO 49
<211> LENGTH: 26
<212> TYPE: DNA
<213> ORGANISM: Artificial
<220> FEATURE:
<223> OTHER INFORMATION: primer

<400> SEQUENCE: 49
ccacgtccag gtcttgacaa acccac                                          26

<210> SEQ ID NO 50
<211> LENGTH: 26
<212> TYPE: DNA
<213> ORGANISM: Artificial
<220> FEATURE:
<223> OTHER INFORMATION: primer

<400> SEQUENCE: 50
gacagtgaac ctttggtcac tgatgg                                          26

<210> SEQ ID NO 51
<211> LENGTH: 26
<212> TYPE: DNA
<213> ORGANISM: Artificial
<220> FEATURE:
<223> OTHER INFORMATION: primer

<400> SEQUENCE: 51
```

```
gccttcctgt cctgggatca gcttgg                                              26

<210> SEQ ID NO 52
<211> LENGTH: 26
<212> TYPE: DNA
<213> ORGANISM: Artificial
<220> FEATURE:
<223> OTHER INFORMATION: primer

<400> SEQUENCE: 52
tctgaggttg ccaggaagca gtctcc                                              26
```